United States Patent [19]
George et al.

[11] Patent Number: 5,880,102
[45] Date of Patent: Mar. 9, 1999

[54] ADENOVIRAL VECTOR SYSTEM

[75] Inventors: Samuel E. George; Michael A. Blazing, both of Chapel Hill, N.C.

[73] Assignee: Duke University, Durham, N.C.

[21] Appl. No.: 374,483

[22] Filed: Jan. 17, 1995

[51] Int. Cl.$^6$ ..................................................... A61K 35/00
[52] U.S. Cl. ........................ 514/44; 424/93.21; 435/325; 435/369; 435/353; 435/320.1; 435/235.1
[58] Field of Search ........................... 514/44; 435/320.1, 435/172.3, 239, 352, 353, 366, 325, 369, 235.1; 536/24.2; 935/22, 23, 32; 424/93.21

[56] References Cited

U.S. PATENT DOCUMENTS 5,428,070   6/1995   Cooke et al. ............................ 514/557

OTHER PUBLICATIONS

Bett et al., An efficient and flexible system for construction of adenovirus vectors with insertions or deletions in early regions 1 and 3, Proc. Nat. Acad. Sci. USA 91:8802–8806, 1994.

Hearing and Shenk, The adenovirus type 5 E 1 a transcriptional control region contains a duplicated enhancer element, Cell 33:695–702, 1983.

Massie et al., Construction of a helper–free recombinant adenovirus that expresses polyomavirus large T antigen, Mol. Cell. Biol. 6:2872–2883, 1986.

Zabner et al., Correction of cAMP–stimulated fluid secretion in cystic fibrosis airway epithelia: Efficiency of adenovirus–mediated gene transfer in vitro, Human Gene Therapy 5:585–593, 1994.

Gerard and Meidell, Adenovirus–mediated gene transfer, Trends Cardiovasc. Med. 3: 171–177, 1993.

Friedman et al., Cellular promoters incorporated into the adenovirus genome; Mol. Cell. Biol. 6: 3791–3797, 1986.

*Primary Examiner*—James Ketter
*Assistant Examiner*—Irem Yucel
*Attorney, Agent, or Firm*—Nixon & Vanderhye P.C

[57] ABSTRACT

The present invention relates, in general, to a gene transfer system and, in particular, to an adenoviral vector system suitable for use in gene transfer and gene therapy.

36 Claims, 108 Drawing Sheets

Origins of the E3 deleted IN340 adenovirus

This figure shows the overlap extension PCR strategy used to generate the E3 deletion. Arrows indicate PCR oligos.

Fig. 7

Sequence Range: 1 to 7104

| Enzyme | #Cuts | Positions | | | | | |
|---|---|---|---|---|---|---|---|
| AatI | 1 | 4278 | | | | | |
| AatII | 5 | 479 | 532 | 615 | 801 | 6332 | |
| AccI | 2 | 3324 | 4262 | | | | |
| AccII | 30 | 153 | 312 | 334 | 414 | 1969 | 2156 |
| | | 2323 | 2392 | 2605 | 2607 | 2609 | 3214 |
| | | 3729 | 3863 | 3929 | 3977 | 3994 | 4064 |
| | | 4097 | 4364 | 4366 | 4564 | 5145 | 5475 |
| | | 5968 | 6300 | 6400 | 6402 | 6505 | 7045 |
| Acc65I | 1 | 999 | | | | | |
| AccB7I | 2 | 1283 | 2668 | | | | |
| AciI | 91 | 153 | 171 | 191 | 216 | 412 | 440 |
| | | 452 | 466 | 633 | 724 | 757 | 861 |
| | | 882 | 1028 | 1072 | 1076 | 1856 | 1885 |
| | | 1967 | 2095 | 2098 | 2101 | 2227 | 2290 |
| | | 2293 | 2296 | 2305 | 2317 | 2321 | 2323 |
| | | 2355 | 2386 | 2390 | 2520 | 2609 | 2627 |
| | | 2755 | 2873 | 3126 | 3129 | 3214 | 3218 |
| | | 3235 | 3331 | 3411 | 3550 | 3567 | 3625 |
| | | 3668 | 3729 | 3739 | 3975 | 3977 | 4019 |
| | | 4095 | 4100 | 4109 | 4366 | 4376 | 4400 |
| | | 4443 | 4450 | 4471 | 4562 | 4590 | 4717 |
| | | 4736 | 4857 | 4967 | 5102 | 5111 | 5473 |
| | | 5564 | 5755 | 5801 | 5922 | 5966 | 6043 |
| | | 6152 | 6251 | 6298 | 6472 | 6511 | 6521 |
| | | 6547 | 6652 | 6655 | 6658 | 6807 | 6907 |
| | | 7045 | | | | | |
| AcsI | 5 | 1 | 76 | 1217 | 1745 | 3017 | |
| AcyI | 11 | 476 | 529 | 612 | 798 | 3063 | 4016 |
| | | 5947 | 6329 | 6683 | 6797 | 6818 | |
| AfaI | 14 | 318 | 573 | 598 | 653 | 686 | 737 |
| | | 894 | 1001 | 1845 | 2009 | 3752 | 5890 |
| | | 6566 | 7026 | | | | |
| AflII | 1 | 2030 | | | | | |
| AflIII | 3 | 223 | 332 | 4517 | | | |
| AgeI | 1 | 70 | | | | | |
| AhdI | 2 | 2627 | 5410 | | | | |
| AluI | 34 | 920 | 995 | 1007 | 1200 | 1529 | 1710 |
| | | 1934 | 2140 | 2373 | 2465 | 2745 | 2831 |
| | | 2881 | 3031 | 3373 | 3400 | 3470 | 3476 |
| | | 3679 | 3999 | 4056 | 4143 | 4296 | 4341 |
| | | 4459 | 4685 | 4775 | 4821 | 5078 | 5599 |
| | | 5699 | 5762 | 6441 | 6460 | | |
| AlwI | 19 | 1006 | 1019 | 1139 | 2479 | 2571 | 2768 |
| | | 3161 | 3324 | 3700 | 4298 | 5078 | 5164 |
| | | 5166 | 5262 | 5263 | 5726 | 6043 | 6047 |
| | | 6863 | | | | | |
| Alw21I | 12 | 922 | 1009 | 2112 | 2142 | 3010 | 3770 |
| | | 4145 | 4835 | 5996 | 6081 | 6578 | 6651 |
| Alw26I | 15 | 788 | 980 | 1845 | 2247 | 2271 | 2635 |
| | | 2719 | 3054 | 3611 | 4123 | 4308 | 5471 |
| | | 6247 | 6400 | 6442 | | | |
| Alw44I | 4 | 3006 | 4831 | 6077 | 6574 | | |
| AlwNI | 5 | 1873 | 2307 | 2465 | 2550 | 4933 | |
| Aor51HI | 3 | 2793 | 3908 | 6738 | | | |
| ApaI | 3 | 1101 | 3120 | 3426 | | | |
| ApaLI | 4 | 3006 | 4831 | 6077 | 6574 | | |
| ApoI | 5 | 1 | 76 | 1217 | 1745 | 3017 | |
| AseI | 7 | 361 | 966 | 1045 | 4324 | 4347 | 5582 |

Fig. 8

| | | | | | | | |
|---|---|---|---|---|---|---|---|
| AsnI | 7 | 7055<br>361 | 966 | 1045 | 4324 | 4347 | 5582 |
| AspI | 1 | 7055<br>2258 | | | | | |
| Asp700I | 2 | 1046 | 6009 | | | | |
| Asp718I | 1 | 999 | | | | | |
| AspEI | 2 | 2627 | 5410 | | | | |
| AspHI | 12 | 922 | 1009 | 2112 | 2142 | 3010 | 3770 |
| | | 4145 | 4835 | 5996 | 6081 | 6578 | 6651 |
| AvaI | 5 | 284 | 1079 | 2437 | 2617 | 4285 | |
| AvaII | 7 | 2621 | 2645 | 3670 | 3811 | 3889 | 5548 |
| | | 5770 | | | | | |
| AviII | 1 | 5632 | | | | | |
| BalI | 1 | 3869 | | | | | |
| BamHI | 1 | 1011 | | | | | |
| BanI | 9 | 819 | 999 | 2803 | 3224 | 4015 | 5358 |
| | | 6682 | 6796 | 6817 | | | |
| BanII | 11 | 922 | 1009 | 1101 | 2142 | 2199 | 2355 |
| | | 3120 | 3426 | 4145 | 6749 | 6763 | |
| BbeI | 4 | 4019 | 6686 | 6800 | 6821 | | |
| BbiII | 11 | 476 | 529 | 612 | 798 | 3063 | 4016 |
| | | 5947 | 6329 | 6683 | 6797 | 6818 | |
| BbsI | 2 | 1431 | 3909 | | | | |
| BbuI | 3 | 1088 | 2162 | 3638 | | | |
| BbvI | 31 | 291 | 1516 | 1719 | 2100 | 2103 | 2294 |
| | | 2295 | 2322 | 2382 | 2474 | 2739 | 3387 |
| | | 3409 | 3425 | 3457 | 3463 | 3485 | 3845 |
| | | 3896 | 4008 | 4328 | 4409 | 4427 | 4846 |
| | | 4936 | 4939 | 5145 | 5448 | 5839 | 6450 |
| | | 6632 | | | | | |
| BcnI | 19 | 285 | 286 | 2174 | 2438 | 2439 | 2618 |
| | | 2619 | 2964 | 3356 | 3446 | 3855 | 4081 |
| | | 4897 | 5593 | 5944 | 6445 | 6480 | 6698 |
| | | 6901 | | | | | |
| BcoI | 5 | 284 | 1079 | 2437 | 2617 | 4285 | |
| BfaI | 14 | 354 | 933 | 1018 | 1092 | 1126 | 1359 |
| | | 1584 | 1780 | 1823 | 1984 | 5012 | 5265 |
| | | 5600 | 6863 | | | | |
| BfrI | 1 | 2030 | | | | | |
| BglI | 5 | 444 | 566 | 637 | 2499 | 5530 | |
| BglII | 2 | 276 | 1825 | | | | |
| BmyI | 19 | 922 | 1009 | 1101 | 2112 | 2142 | 2199 |
| | | 2355 | 3010 | 3120 | 3426 | 3770 | 4145 |
| | | 4835 | 5996 | 6081 | 6578 | 6651 | 6749 |
| | | 6763 | | | | | |
| BpiI | 2 | 1431 | 3909 | | | | |
| BpmI | 2 | 2183 | 5480 | | | | |
| BpuAI | 2 | 1431 | 3909 | | | | |
| BsaI | 8 | 980 | 1845 | 2247 | 2635 | 3611 | 4123 |
| | | 4308 | 5471 | | | | |
| BsaAI | 2 | 694 | 2898 | | | | |
| BsaBI | 3 | 1060 | 1593 | 2562 | | | |
| BsaHI | 11 | 476 | 529 | 612 | 798 | 3063 | 4016 |
| | | 5947 | 6329 | 6683 | 6797 | 6818 | |
| BsaJI | 30 | 284 | 285 | 714 | 1431 | 1927 | 2166 |
| | | 2173 | 2321 | 2437 | 2617 | 2839 | 2851 |
| | | 2963 | 3120 | 3133 | 3257 | 3258 | 3355 |
| | | 3783 | 3799 | 3870 | 3951 | 3975 | 3987 |
| | | 4005 | 4080 | 4677 | 6696 | 6702 | 6900 |
| BsaMI | 5 | 1318 | 1682 | 1775 | 3092 | 4123 | |
| BsaOI | 7 | 1028 | 1076 | 2637 | 4433 | 4857 | 5780 |
| | | 5929 | | | | | |

Fig. 9

| | | | | | | | |
|---|---|---|---|---|---|---|---|
| BsaWI | 6 | 70 | 3002 | 4299 | 4723 | 4870 | 5701 |
| BseDI | 30 | 284 | 285 | 714 | 1431 | 1927 | 2166 |
| | | 2173 | 2321 | 2437 | 2617 | 2839 | 2851 |
| | | 2963 | 3120 | 3133 | 3257 | 3258 | 3355 |
| | | 3783 | 3799 | 3870 | 3951 | 3975 | 3987 |
| | | 4005 | 4080 | 4677 | 6696 | 6702 | 6900 |
| BseNI | 15 | 649 | 956 | 1031 | 1073 | 2777 | 3459 |
| | | 4925 | 4938 | 5050 | 5456 | 5574 | 5617 |
| | | 5886 | 6056 | 6625 | | | |
| BseRI | 4 | 1389 | 1944 | 3709 | 4025 | | |
| BsgI | 6 | 1515 | 1886 | 1946 | 2389 | 2999 | 4054 |
| Bsh1236I | 30 | 153 | 312 | 334 | 414 | 1969 | 2156 |
| | | 2323 | 2392 | 2605 | 2607 | 2609 | 3214 |
| | | 3729 | 3863 | 3929 | 3977 | 3994 | 4064 |
| | | 4097 | 4364 | 4366 | 4564 | 5145 | 5475 |
| | | 5968 | 6300 | 6400 | 6402 | 6505 | 7045 |
| Bsh1285I | 7 | 1028 | 1076 | 2637 | 4433 | 4857 | 5780 |
| | | 5929 | | | | | |
| Bsh1365I | 3 | 1060 | 1593 | 2562 | | | |
| BshNI | 9 | 819 | 999 | 2803 | 3224 | 4015 | 5358 |
| | | 6682 | 6796 | 6817 | | | |
| BsiEI | 7 | 1028 | 1076 | 2637 | 4433 | 4857 | 5780 |
| | | 5929 | | | | | |
| BsiHKAI | 12 | 922 | 1009 | 2112 | 2142 | 3010 | 3770 |
| | | 4145 | 4835 | 5996 | 6081 | 6578 | 6651 |
| BsiYI | 40 | 103 | 291 | 403 | 996 | 1283 | 1861 |
| | | 2172 | 2323 | 2668 | 2717 | 2718 | 2845 |
| | | 3125 | 3234 | 3259 | 3361 | 3444 | 3493 |
| | | 3494 | 3556 | 3680 | 3976 | 3981 | 4025 |
| | | 4080 | 4114 | 4218 | 4365 | 4539 | 4557 |
| | | 4723 | 5002 | 6450 | 6613 | 6631 | 6661 |
| | | 6703 | 6704 | 6900 | 6906 | | |
| BslI | 40 | 103 | 291 | 403 | 996 | 1283 | 1861 |
| | | 2172 | 2323 | 2668 | 2717 | 2718 | 2845 |
| | | 3125 | 3234 | 3259 | 3361 | 3444 | 3493 |
| | | 3494 | 3556 | 3680 | 3976 | 3981 | 4025 |
| | | 4080 | 4114 | 4218 | 4365 | 4539 | 4557 |
| | | 4723 | 5002 | 6450 | 6613 | 6631 | 6661 |
| | | 6703 | 6704 | 6900 | 6906 | | |
| BsmI | 5 | 1318 | 1682 | 1775 | 3092 | 4123 | |
| BsmAI | 15 | 788 | 980 | 1845 | 2247 | 2271 | 2635 |
| | | 2719 | 3054 | 3611 | 4123 | 4308 | 5471 |
| | | 6247 | 6400 | 6442 | | | |
| BsmBI | 4 | 2719 | 3054 | 6400 | 6442 | | |
| BsmFI | 8 | 529 | 680 | 848 | 2634 | 3503 | 3656 |
| | | 4240 | 6678 | | | | |
| BsoFI | 57 | 305 | 1028 | 1073 | 1076 | 1530 | 1708 |
| | | 2089 | 2092 | 2095 | 2098 | 2101 | 2284 |
| | | 2293 | 2296 | 2305 | 2308 | 2311 | 2371 |
| | | 2463 | 2753 | 3127 | 3130 | 3398 | 3401 |
| | | 3414 | 3471 | 3474 | 3477 | 3567 | 3740 |
| | | 3859 | 3910 | 3978 | 3997 | 4019 | 4100 |
| | | 4342 | 4423 | 4441 | 4444 | 4562 | 4717 |
| | | 4860 | 4925 | 4928 | 5134 | 5462 | 5801 |
| | | 5828 | 5923 | 6152 | 6439 | 6548 | 6621 |
| | | 6655 | 6658 | 7046 | | | |
| Bsp68I | 1 | 312 | | | | | |
| Bsp120I | 3 | 1097 | 3116 | 3422 | | | |
| Bsp143I | 30 | 276 | 1011 | 1131 | 1588 | 1825 | 1943 |
| | | 2471 | 2563 | 2773 | 3153 | 3186 | 3316 |
| | | 3367 | 3705 | 4290 | 5083 | 5158 | 5169 |
| | | 5177 | 5255 | 5267 | 5372 | 5713 | 5731 |

Fig. 10

| Enzyme | Count | | | | | | |
|---|---|---|---|---|---|---|---|
| Bsp143II | 10 | 5777 | 6035 | 6052 | 6088 | 6764 | 6855 |
| | | 2795 | 3563 | 3910 | 4019 | 4395 | 4765 |
| | | 6686 | 6740 | 6800 | 6821 | | |
| Bsp1286I | 19 | 922 | 1009 | 1101 | 2112 | 2142 | 2199 |
| | | 2355 | 3010 | 3120 | 3426 | 3770 | 4145 |
| | | 4835 | 5996 | 6081 | 6578 | 6651 | 6749 |
| | | 6763 | | | | | |
| Bsp1407I | 1 | 7024 | | | | | |
| BspCI | 1 | 5780 | | | | | |
| BspHI | 4 | 5237 | 6245 | 6350 | 6741 | | |
| BspMI | 4 | 2474 | 3336 | 3376 | 3696 | | |
| BspTI | 1 | 2030 | | | | | |
| BspWI | 52 | 213 | 301 | 444 | 566 | 598 | 637 |
| | | 730 | 754 | 1081 | 1502 | 1864 | 1873 |
| | | 1882 | 1913 | 2094 | 2097 | 2100 | 2137 |
| | | 2289 | 2292 | 2301 | 2304 | 2310 | 2316 |
| | | 2367 | 2415 | 2499 | 2613 | 3135 | 3224 |
| | | 3476 | 3566 | 3586 | 3745 | 3855 | 3883 |
| | | 3892 | 3991 | 4000 | 4027 | 4103 | 4108 |
| | | 4140 | 4389 | 4456 | 4570 | 5142 | 5530 |
| | | 6607 | 6794 | 6815 | 6826 | | |
| BsrI | 15 | 649 | 956 | 1031 | 1073 | 2777 | 3459 |
| | | 4925 | 4938 | 5050 | 5456 | 5574 | 5617 |
| | | 5886 | 6056 | 6625 | | | |
| BsrBI | 3 | 1078 | 4450 | 6251 | | | |
| BsrBRI | 3 | 1060 | 1593 | 2562 | | | |
| BsrDI | 3 | 3118 | 5471 | 5645 | | | |
| BsrFI | 8 | 70 | 267 | 3416 | 3912 | 4218 | 5490 |
| | | 6820 | 6829 | | | | |
| BsrGI | 1 | 7024 | | | | | |
| BssHII | 4 | 2603 | 2605 | 3861 | 3992 | | |
| BstI | 1 | 1011 | | | | | |
| Bst71I | 31 | 291 | 1516 | 1719 | 2100 | 2103 | 2294 |
| | | 2295 | 2322 | 2382 | 2474 | 2739 | 3387 |
| | | 3409 | 3425 | 3457 | 3463 | 3485 | 3845 |
| | | 3896 | 4008 | 4328 | 4409 | 4427 | 4846 |
| | | 4936 | 4939 | 5145 | 5448 | 5839 | 6450 |
| | | 6632 | | | | | |
| Bst98I | 1 | 2030 | | | | | |
| Bst1107I | 1 | 4263 | | | | | |
| BstD102I | 3 | 1078 | 4450 | 6251 | | | |
| BstEII | 1 | 3683 | | | | | |
| BstNI | 17 | 444 | 637 | 1862 | 2663 | 2840 | 3134 |
| | | 3179 | 3259 | 3665 | 3784 | 3871 | 3937 |
| | | 4136 | 4168 | 4545 | 4666 | 4679 | |
| BstOI | 17 | 444 | 637 | 1862 | 2663 | 2840 | 3134 |
| | | 3179 | 3259 | 3665 | 3784 | 3871 | 3937 |
| | | 4136 | 4168 | 4545 | 4666 | 4679 | |
| BstPI | 1 | 3683 | | | | | |
| BstUI | 30 | 153 | 312 | 334 | 414 | 1969 | 2156 |
| | | 2323 | 2392 | 2605 | 2607 | 2609 | 3214 |
| | | 3729 | 3863 | 3929 | 3977 | 3994 | 4064 |
| | | 4097 | 4364 | 4366 | 4564 | 5145 | 5475 |
| | | 5968 | 6300 | 6400 | 6402 | 6505 | 7045 |
| BstXI | 3 | 1038 | 1068 | 3107 | | | |
| BstYI | 12 | 276 | 1011 | 1131 | 1825 | 2471 | 5158 |
| | | 5169 | 5255 | 5267 | 6035 | 6052 | 6855 |
| BstZI | 2 | 1025 | 1073 | | | | |
| BsuRI | 38 | 283 | 323 | 438 | 631 | 1027 | 1075 |
| | | 1099 | 1940 | 1959 | 2172 | 2616 | 2849 |
| | | 3118 | 3132 | 3198 | 3256 | 3424 | 3501 |
| | | 3782 | 3869 | 3935 | 3985 | 4106 | 4149 |

Fig. 11

| | | | | | | | |
|---|---|---|---|---|---|---|---|
| | | 4278 | 4358 | 4532 | 4543 | 4561 | 4995 |
| | | 5453 | 5533 | 5800 | 6387 | 6641 | 6701 |
| | | 6709 | 6833 | | | | |
| Cac8I | 38 | 440 | 633 | 1086 | 1498 | 1957 | 1961 |
| | | 2160 | 2227 | 2321 | 2355 | 2359 | 2363 |
| | | 2390 | 2481 | 2605 | 2607 | 2829 | 2847 |
| | | 3216 | 3564 | 3636 | 3863 | 3867 | 3994 |
| | | 4001 | 4104 | 4339 | 4448 | 4534 | 4571 |
| | | 5131 | 5522 | 6535 | 6711 | 6759 | 6801 |
| | | 6831 | 6864 | | | | |
| CfoI | 42 | 153 | 267 | 304 | 1971 | 2158 | 2479 |
| | | 2605 | 2607 | 2609 | 2794 | 3214 | 3562 |
| | | 3807 | 3851 | 3863 | 3865 | 3879 | 3909 |
| | | 3929 | 3994 | 3996 | 4018 | 4064 | 4099 |
| | | 4366 | 4394 | 4427 | 4697 | 4764 | 4864 |
| | | 5038 | 5147 | 5540 | 5633 | 5970 | 6302 |
| | | 6402 | 6505 | 6685 | 6739 | 6799 | 6820 |
| CfrI | 9 | 1025 | 1073 | 3867 | 3933 | 4147 | 4356 |
| | | 5798 | 6699 | 6831 | | | |
| Cfr9I | 3 | 284 | 2437 | 2617 | | | |
| Cfr10I | 8 | 70 | 267 | 3416 | 3912 | 4218 | 5490 |
| | | 6820 | 6829 | | | | |
| Cfr13I | 30 | 282 | 321 | 437 | 630 | 1097 | 1098 |
| | | 1939 | 2170 | 2615 | 2621 | 2645 | 2848 |
| | | 3116 | 3117 | 3255 | 3422 | 3423 | 3499 |
| | | 3670 | 3780 | 3811 | 3889 | 3984 | 4105 |
| | | 5452 | 5531 | 5548 | 5770 | 6386 | 6707 |
| Cfr42I | 2 | 2324 | 3978 | | | | |
| Csp6I | 14 | 317 | 572 | 597 | 652 | 685 | 736 |
| | | 893 | 1000 | 1844 | 2008 | 3751 | 5889 |
| | | 6565 | 7025 | | | | |
| CviJI | 124 | 114 | 283 | 323 | 396 | 438 | 447 |
| | | 631 | 920 | 928 | 955 | 995 | 1007 |
| | | 1027 | 1075 | 1099 | 1200 | 1373 | 1529 |
| | | 1600 | 1710 | 1907 | 1934 | 1940 | 1959 |
| | | 1981 | 2029 | 2094 | 2140 | 2172 | 2197 |
| | | 2286 | 2304 | 2313 | 2353 | 2373 | 2409 |
| | | 2465 | 2502 | 2616 | 2710 | 2745 | 2831 |
| | | 2849 | 2881 | 2940 | 2952 | 3031 | 3118 |
| | | 3132 | 3198 | 3256 | 3373 | 3400 | 3416 |
| | | 3424 | 3470 | 3476 | 3501 | 3679 | 3742 |
| | | 3782 | 3858 | 3869 | 3886 | 3935 | 3969 |
| | | 3985 | 3999 | 4056 | 4106 | 4134 | 4143 |
| | | 4149 | 4218 | 4246 | 4278 | 4296 | 4337 |
| | | 4341 | 4358 | 4440 | 4459 | 4532 | 4543 |
| | | 4561 | 4587 | 4685 | 4775 | 4821 | 4826 |
| | | 4851 | 4930 | 4995 | 5006 | 5049 | 5078 |
| | | 5441 | 5453 | 5494 | 5520 | 5524 | 5533 |
| | | 5599 | 5689 | 5699 | 5762 | 5800 | 6387 |
| | | 6441 | 6460 | 6493 | 6533 | 6537 | 6623 |
| | | 6641 | 6701 | 6709 | 6747 | 6761 | 6833 |
| | | 6862 | 7001 | 7021 | 7048 | | |
| DdeI | 18 | 1203 | 1342 | 1454 | 1839 | 1935 | 1972 |
| | | 2349 | 2458 | 3032 | 3393 | 3489 | 4792 |
| | | 5201 | 5367 | 5907 | 6333 | 6568 | 6928 |
| DpnI | 30 | 278 | 1013 | 1133 | 1590 | 1827 | 1945 |
| | | 2473 | 2565 | 2775 | 3155 | 3188 | 3318 |
| | | 3369 | 3707 | 4292 | 5085 | 5160 | 5171 |
| | | 5179 | 5257 | 5269 | 5374 | 5715 | 5733 |
| | | 5779 | 6037 | 6054 | 6090 | 6766 | 6857 |
| DpnII | 30 | 276 | 1011 | 1131 | 1588 | 1825 | 1943 |
| | | 2471 | 2563 | 2773 | 3153 | 3186 | 3316 |

Fig. 12

| | | | | | | | |
|---|---|---|---|---|---|---|---|
| | | | 3367 | 3705 | 4290 | 5083 | 5158 | 5169 |
| | | | 5177 | 5255 | 5267 | 5372 | 5713 | 5731 |
| | | | 5777 | 6035 | 6052 | 6088 | 6764 | 6855 |
| DraI | 6 | 1196 | 1633 | 2526 | 5276 | 5295 | 5987 |
| DraII | 8 | 1097 | 1098 | 2645 | 2848 | 3811 | 4105 |
| | | 6386 | 6707 | | | | |
| DraIII | 2 | 1864 | 1952 | | | | |
| DrdI | 3 | 3955 | 4625 | 6494 | | | |
| DsaI | 8 | 714 | 2166 | 2321 | 3120 | 3799 | 3951 |
| | | 3975 | 6702 | | | | |
| DsaV | 36 | 283 | 284 | 442 | 635 | 1860 | 2172 |
| | | 2436 | 2437 | 2616 | 2617 | 2661 | 2838 |
| | | 2962 | 3132 | 3177 | 3257 | 3354 | 3444 |
| | | 3663 | 3782 | 3853 | 3869 | 3935 | 4079 |
| | | 4134 | 4166 | 4543 | 4664 | 4677 | 4895 |
| | | 5591 | 5942 | 6443 | 6478 | 6696 | 6899 |
| EaeI | 9 | 1025 | 1073 | 3867 | 3933 | 4147 | 4356 |
| | | 5798 | 6699 | 6831 | | | |
| EagI | 2 | 1025 | 1073 | | | | |
| Eam1104I | 3 | 1406 | 4401 | 6205 | | | |
| Eam1105I | 2 | 2627 | 5410 | | | | |
| EarI | 3 | 1406 | 4401 | 6205 | | | |
| Ecl136II | 4 | 920 | 1007 | 2140 | 4143 | | |
| EclHKI | 2 | 2627 | 5410 | | | | |
| EclXI | 2 | 1025 | 1073 | | | | |
| Eco24I | 11 | 922 | 1009 | 1101 | 2142 | 2199 | 2355 |
| | | 3120 | 3426 | 4145 | 6749 | 6763 | |
| Eco31I | 8 | 980 | 1845 | 2247 | 2635 | 3611 | 4123 |
| | | 4308 | 5471 | | | | |
| Eco32I | 1 | 1058 | | | | | |
| Eco47I | 7 | 2621 | 2645 | 3670 | 3811 | 3889 | 5548 |
| | | 5770 | | | | | |
| Eco47III | 3 | 2793 | 3908 | 6738 | | | |
| Eco52I | 2 | 1025 | 1073 | | | | |
| Eco57I | 7 | 1428 | 2284 | 2517 | 3923 | 5065 | 6077 |
| | | 6977 | | | | | |
| Eco64I | 9 | 819 | 999 | 2803 | 3224 | 4015 | 5358 |
| | | 6682 | 6796 | 6817 | | | |
| Eco88I | 5 | 284 | 1079 | 2437 | 2617 | 4285 | |
| Eco91I | 1 | 3683 | | | | | |
| Eco105I | 1 | 694 | | | | | |
| Eco130I | 7 | 714 | 1431 | 2166 | 2851 | 3951 | 3987 |
| | | 4005 | | | | | |
| Eco147I | 1 | 4278 | | | | | |
| Eco255I | 1 | 5890 | | | | | |
| EcoICRI | 4 | 920 | 1007 | 2140 | 4143 | | |
| EcoNI | 1 | 6611 | | | | | |
| EcoO65I | 1 | 3683 | | | | | |
| EcoO109I | 8 | 1097 | 1098 | 2645 | 2848 | 3811 | 4105 |
| | | 6386 | 6707 | | | | |
| EcoRI | 2 | 1 | 76 | | | | |
| EcoRII | 17 | 442 | 635 | 1860 | 2661 | 2838 | 3132 |
| | | 3177 | 3257 | 3663 | 3782 | 3869 | 3935 |
| | | 4134 | 4166 | 4543 | 4664 | 4677 | |
| EcoRV | 1 | 1058 | | | | | |
| EcoT14I | 7 | 714 | 1431 | 2166 | 2851 | 3951 | 3987 |
| | | 4005 | | | | | |
| EcoT22I | 3 | 1090 | 2916 | 3094 | | | |
| EheI | 4 | 4017 | 6684 | 6798 | 6819 | | |
| Esp3I | 4 | 2719 | 3054 | 6400 | 6442 | | |
| Esp1396I | 2 | 1283 | 2668 | | | | |
| FokI | 13 | 249 | 1932 | 2363 | 2699 | 2898 | 3194 |

Fig. 13

|        |    |      |      |      |      |      |      |
|--------|----|------|------|------|------|------|------|
|        |    | 3236 | 3470 | 4078 | 5376 | 5557 | 5844 |
|        |    | 6487 |      |      |      |      |      |
| FspI   | 1  | 5632 |      |      |      |      |      |
| GsuI   | 2  | 2183 | 5480 |      |      |      |      |
| HaeII  | 10 | 2795 | 3563 | 3910 | 4019 | 4395 | 4765 |
|        |    | 6686 | 6740 | 6800 | 6821 |      |      |
| HaeIII | 38 |  283 |  323 |  438 |  631 | 1027 | 1075 |
|        |    | 1099 | 1940 | 1959 | 2172 | 2616 | 2849 |
|        |    | 3118 | 3132 | 3198 | 3256 | 3424 | 3501 |
|        |    | 3782 | 3869 | 3935 | 3985 | 4106 | 4149 |
|        |    | 4278 | 4358 | 4532 | 4543 | 4561 | 4995 |
|        |    | 5453 | 5533 | 5800 | 6387 | 6641 | 6701 |
|        |    | 6709 | 6833 |      |      |      |      |
| HapII  | 33 |   71 |  268 |  285 | 2173 | 2438 | 2618 |
|        |    | 2963 | 3003 | 3253 | 3355 | 3417 | 3445 |
|        |    | 3854 | 3913 | 4080 | 4219 | 4300 | 4724 |
|        |    | 4871 | 4897 | 5087 | 5491 | 5525 | 5592 |
|        |    | 5702 | 5944 | 6445 | 6479 | 6698 | 6821 |
|        |    | 6830 | 6845 | 6900 |      |      |      |
| HgaI   | 10 |  880 | 2169 | 3071 | 3918 | 4628 | 5206 |
|        |    | 5936 | 6494 | 6595 | 6830 |      |      |
| HhaI   | 42 |  153 |  267 |  304 | 1971 | 2158 | 2479 |
|        |    | 2605 | 2607 | 2609 | 2794 | 3214 | 3562 |
|        |    | 3807 | 3851 | 3863 | 3865 | 3879 | 3909 |
|        |    | 3929 | 3994 | 3996 | 4018 | 4064 | 4099 |
|        |    | 4366 | 4394 | 4427 | 4697 | 4764 | 4864 |
|        |    | 5038 | 5147 | 5540 | 5633 | 5970 | 6302 |
|        |    | 6402 | 6505 | 6685 | 6739 | 6799 | 6820 |
| Hin1I  | 11 |  476 |  529 |  612 |  798 | 3063 | 4016 |
|        |    | 5947 | 6329 | 6683 | 6797 | 6818 |      |
| Hin6I  | 42 |  151 |  265 |  302 | 1969 | 2156 | 2477 |
|        |    | 2603 | 2605 | 2607 | 2792 | 3212 | 3560 |
|        |    | 3805 | 3849 | 3861 | 3863 | 3877 | 3907 |
|        |    | 3927 | 3992 | 3994 | 4016 | 4062 | 4097 |
|        |    | 4364 | 4392 | 4425 | 4695 | 4762 | 4862 |
|        |    | 5036 | 5145 | 5538 | 5631 | 5968 | 6300 |
|        |    | 6400 | 6503 | 6683 | 6737 | 6797 | 6818 |
| HinP1I | 42 |  151 |  265 |  302 | 1969 | 2156 | 2477 |
|        |    | 2603 | 2605 | 2607 | 2792 | 3212 | 3560 |
|        |    | 3805 | 3849 | 3861 | 3863 | 3877 | 3907 |
|        |    | 3927 | 3992 | 3994 | 4016 | 4062 | 4097 |
|        |    | 4364 | 4392 | 4425 | 4695 | 4762 | 4862 |
|        |    | 5036 | 5145 | 5538 | 5631 | 5968 | 6300 |
|        |    | 6400 | 6503 | 6683 | 6737 | 6797 | 6818 |
| HincII | 3  |  338 | 1694 | 2404 |      |      |      |
| HindII | 3  |  338 | 1694 | 2404 |      |      |      |
| HindIII| 1  |  993 |      |      |      |      |      |
| HinfI  | 21 |   54 |  764 |  973 | 1249 | 1273 | 1382 |
|        |    | 1465 | 2427 | 2547 | 2680 | 2968 | 3524 |
|        |    | 4076 | 4316 | 4352 | 4417 | 4492 | 4888 |
|        |    | 5405 | 6603 | 6953 |      |      |      |
| HpaI   | 1  | 1694 |      |      |      |      |      |
| HpaII  | 33 |   71 |  268 |  285 | 2173 | 2438 | 2618 |
|        |    | 2963 | 3003 | 3253 | 3355 | 3417 | 3445 |
|        |    | 3854 | 3913 | 4080 | 4219 | 4300 | 4724 |
|        |    | 4871 | 4897 | 5087 | 5491 | 5525 | 5592 |
|        |    | 5702 | 5944 | 6445 | 6479 | 6698 | 6821 |
|        |    | 6830 | 6845 | 6900 |      |      |      |
| HphI   | 19 |    1 |   85 |  186 |  730 | 1107 | 2689 |
|        |    | 3677 | 3850 | 4150 | 4246 | 5253 | 5480 |
|        |    | 5896 | 6102 | 6137 | 6421 | 6430 | 6790 |
|        |    | 6835 |      |      |      |      |      |

Fig. 14

| | | | | | | | |
|---|---|---|---|---|---|---|---|
| Hsp92I | 11 | 476 | 529 | 612 | 798 | 3063 | 4016 |
| | | 5947 | 6329 | 6683 | 6797 | 6818 | |
| Hsp92II | 33 | 53 | 227 | 658 | 718 | 1088 | 1472 |
| | | 1821 | 2108 | 2162 | 2170 | 2702 | 2752 |
| | | 2975 | 3028 | 3092 | 3323 | 3518 | 3533 |
| | | 3638 | 3793 | 3955 | 4182 | 4216 | 4521 |
| | | 5241 | 5732 | 5742 | 5820 | 5856 | 6249 |
| | | 6354 | 6438 | 6745 | | | |
| ItaI | 57 | 305 | 1028 | 1073 | 1076 | 1530 | 1708 |
| | | 2089 | 2092 | 2095 | 2098 | 2101 | 2284 |
| | | 2293 | 2296 | 2305 | 2308 | 2311 | 2371 |
| | | 2463 | 2753 | 3127 | 3130 | 3398 | 3401 |
| | | 3414 | 3471 | 3474 | 3477 | 3567 | 3740 |
| | | 3859 | 3910 | 3978 | 3997 | 4019 | 4100 |
| | | 4342 | 4423 | 4441 | 4444 | 4562 | 4717 |
| | | 4860 | 4925 | 4928 | 5134 | 5462 | 5801 |
| | | 5828 | 5923 | 6152 | 6439 | 6548 | 6621 |
| | | 6655 | 6658 | 7046 | | | |
| KasI | 4 | 4015 | 6682 | 6796 | 6817 | | |
| KpnI | 1 | 1003 | | | | | |
| KspI | 2 | 2324 | 3978 | | | | |
| Ksp632I | 3 | 1406 | 4401 | 6205 | | | |
| MaeI | 14 | 354 | 933 | 1018 | 1092 | 1126 | 1359 |
| | | 1584 | 1780 | 1823 | 1984 | 5012 | 5265 |
| | | 5600 | 6863 | | | | |
| MaeII | 17 | 10 | 146 | 178 | 252 | 476 | 488 |
| | | 529 | 612 | 693 | 798 | 2667 | 2897 |
| | | 3162 | 5220 | 5636 | 6009 | 6329 | |
| MaeIII | 29 | 142 | 174 | 248 | 415 | 502 | 851 |
| | | 1020 | 1113 | 1162 | 1719 | 1922 | 2330 |
| | | 2677 | 3070 | 3268 | 3683 | 3832 | 4234 |
| | | 4873 | 4936 | 5052 | 5335 | 5666 | 5724 |
| | | 5877 | 6065 | 6453 | 6916 | 7093 | |
| MamI | 3 | 1060 | 1593 | 2562 | | | |
| MboI | 30 | 276 | 1011 | 1131 | 1588 | 1825 | 1943 |
| | | 2471 | 2563 | 2773 | 3153 | 3186 | 3316 |
| | | 3367 | 3705 | 4290 | 5083 | 5158 | 5169 |
| | | 5177 | 5255 | 5267 | 5372 | 5713 | 5731 |
| | | 5777 | 6035 | 6052 | 6088 | 6764 | 6855 |
| MboII | 16 | 1358 | 1423 | 1436 | 2004 | 3062 | 3152 |
| | | 3353 | 3390 | 3909 | 4388 | 5179 | 5250 |
| | | 6005 | 6083 | 6192 | 6759 | | |
| McrI | 7 | 1028 | 1076 | 2637 | 4433 | 4857 | 5780 |
| | | 5929 | | | | | |
| MflI | 12 | 276 | 1011 | 1131 | 1825 | 2471 | 5158 |
| | | 5169 | 5255 | 5267 | 6035 | 6052 | 6855 |
| MluI | 1 | 332 | | | | | |
| MluNI | 1 | 3869 | | | | | |
| MnlI | 48 | 121 | 895 | 1088 | 1122 | 1318 | 1363 |
| | | 1410 | 1610 | 1650 | 1659 | 1834 | 1922 |
| | | 1930 | 1998 | 2297 | 2516 | 2521 | 2635 |
| | | 2719 | 2970 | 3085 | 3214 | 3284 | 3730 |
| | | 3824 | 3876 | 3982 | 4003 | 4006 | 4018 |
| | | 4038 | 4212 | 4268 | 4281 | 4294 | 4366 |
| | | 4416 | 4625 | 4699 | 4949 | 5349 | 5430 |
| | | 5577 | 5783 | 6377 | 6436 | 6631 | 6846 |
| Mph1103I | 3 | 1090 | 2916 | 3094 | | | |
| MscI | 1 | 3869 | | | | | |
| MseI | 28 | 361 | 966 | 1045 | 1195 | 1223 | 1239 |
| | | 1320 | 1632 | 1693 | 2031 | 2446 | 2525 |
| | | 2877 | 3462 | 3510 | 4324 | 4347 | 5223 |
| | | 5275 | 5280 | 5294 | 5347 | 5582 | 5621 |

Fig. 15

| | | | | | | | |
|---|---|---|---|---|---|---|---|
| | | 5986 | 6358 | 6539 | 7055 | | |
| MslI | 7 | 719 | 1120 | 3105 | 3170 | 5662 | 5821 |
| | | 6180 | | | | | |
| MspI | 33 | 71 | 268 | 285 | 2173 | 2438 | 2618 |
| | | 2963 | 3003 | 3253 | 3355 | 3417 | 3445 |
| | | 3854 | 3913 | 4080 | 4219 | 4300 | 4724 |
| | | 4871 | 4897 | 5087 | 5491 | 5525 | 5592 |
| | | 5702 | 5944 | 6445 | 6479 | 6698 | 6821 |
| | | 6830 | 6845 | 6900 | | | |
| MspA1I | 13 | 2307 | 2323 | 2465 | 2627 | 3373 | 3400 |
| | | 3476 | 3977 | 4341 | 4859 | 5104 | 6045 |
| | | 6511 | | | | | |
| MunI | 2 | 1681 | 2421 | | | | |
| MvaI | 17 | 444 | 637 | 1862 | 2663 | 2840 | 3134 |
| | | 3179 | 3259 | 3665 | 3784 | 3871 | 3937 |
| | | 4136 | 4168 | 4545 | 4666 | 4679 | |
| Mva1269I | 5 | 1318 | 1682 | 1775 | 3092 | 4123 | |
| MvnI | 30 | 153 | 312 | 334 | 414 | 1969 | 2156 |
| | | 2323 | 2392 | 2605 | 2607 | 2609 | 3214 |
| | | 3729 | 3863 | 3929 | 3977 | 3994 | 4064 |
| | | 4097 | 4364 | 4366 | 4564 | 5145 | 5475 |
| | | 5968 | 6300 | 6400 | 6402 | 6505 | 7045 |
| MwoI | 52 | 213 | 301 | 444 | 566 | 598 | 637 |
| | | 730 | 754 | 1081 | 1502 | 1864 | 1873 |
| | | 1882 | 1913 | 2094 | 2097 | 2100 | 2137 |
| | | 2289 | 2292 | 2301 | 2304 | 2310 | 2316 |
| | | 2367 | 2415 | 2499 | 2613 | 3135 | 3224 |
| | | 3476 | 3566 | 3586 | 3745 | 3855 | 3883 |
| | | 3892 | 3991 | 4000 | 4027 | 4103 | 4108 |
| | | 4140 | 4389 | 4456 | 4570 | 5142 | 5530 |
| | | 6607 | 6794 | 6815 | 6826 | | |
| NaeI | 1 | 6831 | | | | | |
| NarI | 4 | 4016 | 6683 | 6797 | 6818 | | |
| NciI | 19 | 285 | 286 | 2174 | 2438 | 2439 | 2618 |
| | | 2619 | 2964 | 3356 | 3446 | 3855 | 4081 |
| | | 4897 | 5593 | 5944 | 6445 | 6480 | 6698 |
| | | 6901 | | | | | |
| NcoI | 3 | 714 | 2166 | 3951 | | | |
| NdeI | 1 | 588 | | | | | |
| NdeII | 30 | 276 | 1011 | 1131 | 1588 | 1825 | 1943 |
| | | 2471 | 2563 | 2773 | 3153 | 3186 | 3316 |
| | | 3367 | 3705 | 4290 | 5083 | 5158 | 5169 |
| | | 5177 | 5255 | 5267 | 5372 | 5713 | 5731 |
| | | 5777 | 6035 | 6052 | 6088 | 6764 | 6855 |
| NgoAIV | 1 | 6829 | | | | | |
| NgoMI | 1 | 6829 | | | | | |
| NheI | 1 | 6862 | | | | | |
| NlaIII | 33 | 53 | 227 | 658 | 718 | 1088 | 1472 |
| | | 1821 | 2108 | 2162 | 2170 | 2702 | 2752 |
| | | 2975 | 3028 | 3092 | 3323 | 3518 | 3533 |
| | | 3638 | 3793 | 3955 | 4182 | 4216 | 4521 |
| | | 5241 | 5732 | 5742 | 5820 | 5856 | 6249 |
| | | 6354 | 6438 | 6745 | | | |
| NlaIV | 31 | 821 | 1001 | 1013 | 1099 | 1146 | 1902 |
| | | 2198 | 2622 | 2646 | 2805 | 3118 | 3226 |
| | | 3247 | 3390 | 3424 | 3500 | 3672 | 3812 |
| | | 4017 | 4107 | 4549 | 4588 | 5360 | 5454 |
| | | 5495 | 5706 | 6296 | 6684 | 6708 | 6798 |
| | | 6819 | | | | | |
| NotI | 1 | 1073 | | | | | |
| NruI | 1 | 312 | | | | | |
| NsiI | 3 | 1090 | 2916 | 3094 | | | |

Fig. 16

| | | | | | | |
|---|---|---|---|---|---|---|
| NspI | 8 | 227 | 1088 | 2162 | 3518 | 3533 | 3638 |
| | | 4521 | 6438 | | | | |
| NspBII | 13 | 2307 | 2323 | 2465 | 2627 | 3373 | 3400 |
| | | 3476 | 3977 | 4341 | 4859 | 5104 | 6045 |
| | | 6511 | | | | | |
| PaeI | 3 | 1088 | 2162 | 3638 | | | |
| PaeR7I | 2 | 1079 | 4285 | | | | |
| PalI | 38 | 283 | 323 | 438 | 631 | 1027 | 1075 |
| | | 1099 | 1940 | 1959 | 2172 | 2616 | 2849 |
| | | 3118 | 3132 | 3198 | 3256 | 3424 | 3501 |
| | | 3782 | 3869 | 3935 | 3985 | 4106 | 4149 |
| | | 4278 | 4358 | 4532 | 4543 | 4561 | 4995 |
| | | 5453 | 5533 | 5800 | 6387 | 6641 | 6701 |
| | | 6709 | 6833 | | | | |
| PflMI | 2 | 1283 | 2668 | | | | |
| PinAI | 1 | 70 | | | | | |
| PleI | 13 | 758 | 967 | 1376 | 1473 | 2541 | 2674 |
| | | 3518 | 4324 | 4411 | 4896 | 5399 | 6597 |
| | | 6947 | | | | | |
| Ppu10I | 3 | 1086 | 2912 | 3090 | | | |
| PpuMI | 2 | 2645 | 3811 | | | | |
| Psp5II | 2 | 2645 | 3811 | | | | |
| Psp1406I | 2 | 5636 | 6009 | | | | |
| PspAI | 3 | 284 | 2437 | 2617 | | | |
| PstI | 5 | 1055 | 2285 | 2312 | 2742 | 3475 | |
| PvuI | 1 | 5780 | | | | | |
| PvuII | 5 | 2465 | 3373 | 3400 | 3476 | 4341 | |
| RcaI | 4 | 5237 | 6245 | 6350 | 6741 | | |
| RsaI | 14 | 318 | 573 | 598 | 653 | 686 | 737 |
| | | 894 | 1001 | 1845 | 2009 | 3752 | 5890 |
| | | 6566 | 7026 | | | | |
| SacI | 4 | 922 | 1009 | 2142 | 4145 | | |
| SacII | 2 | 2324 | 3978 | | | | |
| SapI | 1 | 4401 | | | | | |
| Sau96I | 30 | 282 | 321 | 437 | 630 | 1097 | 1098 |
| | | 1939 | 2170 | 2615 | 2621 | 2645 | 2848 |
| | | 3116 | 3117 | 3255 | 3422 | 3423 | 3499 |
| | | 3670 | 3780 | 3811 | 3889 | 3984 | 4105 |
| | | 5452 | 5531 | 5548 | 5770 | 6386 | 6707 |
| Sau3AI | 30 | 276 | 1011 | 1131 | 1588 | 1825 | 1943 |
| | | 2471 | 2563 | 2773 | 3153 | 3186 | 3316 |
| | | 3367 | 3705 | 4290 | 5083 | 5158 | 5169 |
| | | 5177 | 5255 | 5267 | 5372 | 5713 | 5731 |
| | | 5777 | 6035 | 6052 | 6088 | 6764 | 6855 |
| ScaI | 1 | 5890 | | | | | |
| ScrFI | 36 | 285 | 286 | 444 | 637 | 1862 | 2174 |
| | | 2438 | 2439 | 2618 | 2619 | 2663 | 2840 |
| | | 2964 | 3134 | 3179 | 3259 | 3356 | 3446 |
| | | 3665 | 3784 | 3855 | 3871 | 3937 | 4081 |
| | | 4136 | 4168 | 4545 | 4666 | 4679 | 4897 |
| | | 5593 | 5944 | 6445 | 6480 | 6698 | 6901 |
| SduI | 19 | 922 | 1009 | 1101 | 2112 | 2142 | 2199 |
| | | 2355 | 3010 | 3120 | 3426 | 3770 | 4145 |
| | | 4835 | 5996 | 6081 | 6578 | 6651 | 6749 |
| | | 6763 | | | | | |
| SexAI | 2 | 1860 | 4166 | | | | |
| SfaNI | 18 | 711 | 1097 | 1747 | 1903 | 2901 | 2923 |
| | | 3708 | 4100 | 4179 | 4614 | 5666 | 5857 |
| | | 6106 | 6465 | 6559 | 6816 | 6828 | 6995 |
| SfcI | 13 | 979 | 1051 | 1107 | 1185 | 2281 | 2308 |
| | | 2738 | 3471 | 4309 | 4782 | 4973 | 5651 |
| | | 7100 | | | | | |

Fig. 17

| | | | | | | |
|---|---|---|---|---|---|---|
| SgrAI | 2 | 267 | 6820 | | | |
| SinI | 7 | 2621 | 2645 | 3670 | 3811 | 3889 | 5548 |
| | | 5770 | | | | |
| SmaI | 3 | 286 | 2439 | 2619 | | |
| SnaBI | 1 | 694 | | | | |
| SpeI | 2 | 353 | 1017 | | | |
| SphI | 3 | 1088 | 2162 | 3638 | | |
| SspI | 2 | 1562 | 6214 | | | |
| SspBI | 1 | 7024 | | | | |
| SstI | 4 | 922 | 1009 | 2142 | 4145 | |
| SstII | 2 | 2324 | 3978 | | | |
| StuI | 1 | 4278 | | | | |
| StyI | 7 | 714 | 1431 | 2166 | 2851 | 3951 | 3987 |
| | | 4005 | | | | |
| TaqI | 8 | 960 | 1080 | 3704 | 4286 | 4330 | 4617 |
| | | 6061 | 6584 | | | |
| TfiI | 8 | 54 | 1249 | 1273 | 2427 | 2968 | 4076 |
| | | 4352 | 4492 | | | |
| ThaI | 30 | 153 | 312 | 334 | 414 | 1969 | 2156 |
| | | 2323 | 2392 | 2605 | 2607 | 2609 | 3214 |
| | | 3729 | 3863 | 3929 | 3977 | 3994 | 4064 |
| | | 4097 | 4364 | 4366 | 4564 | 5145 | 5475 |
| | | 5968 | 6300 | 6400 | 6402 | 6505 | 7045 |
| Tru1I | 28 | 361 | 966 | 1045 | 1195 | 1223 | 1239 |
| | | 1320 | 1632 | 1693 | 2031 | 2446 | 2525 |
| | | 2877 | 3462 | 3510 | 4324 | 4347 | 5223 |
| | | 5275 | 5280 | 5294 | 5347 | 5582 | 5621 |
| | | 5986 | 6358 | 6539 | 7055 | | |
| Tru9I | 28 | 361 | 966 | 1045 | 1195 | 1223 | 1239 |
| | | 1320 | 1632 | 1693 | 2031 | 2446 | 2525 |
| | | 2877 | 3462 | 3510 | 4324 | 4347 | 5223 |
| | | 5275 | 5280 | 5294 | 5347 | 5582 | 5621 |
| | | 5986 | 6358 | 6539 | 7055 | | |
| Tsp45I | 16 | 142 | 174 | 248 | 1113 | 1162 | 1922 |
| | | 2330 | 2677 | 3070 | 3683 | 3832 | 4234 |
| | | 5666 | 5877 | 6453 | 7093 | | |
| Tsp509I | 23 | 1 | 21 | 40 | 76 | 372 | 963 |
| | | 1042 | 1046 | 1169 | 1217 | 1254 | 1448 |
| | | 1548 | 1681 | 1745 | 2421 | 3017 | 4325 |
| | | 5277 | 5583 | 5838 | 7014 | 7052 | |
| TspEI | 23 | 1 | 21 | 40 | 76 | 372 | 963 |
| | | 1042 | 1046 | 1169 | 1217 | 1254 | 1448 |
| | | 1548 | 1681 | 1745 | 2421 | 3017 | 4325 |
| | | 5277 | 5583 | 5838 | 7014 | 7052 | |
| TspRI | 9 | 1038 | 1310 | 2372 | 3001 | 4037 | 5209 |
| | | 5358 | 5463 | 5810 | | | |
| Tth111I | 1 | 2258 | | | | |
| TthHB8I | 8 | 960 | 1080 | 3704 | 4286 | 4330 | 4617 |
| | | 6061 | 6584 | | | |
| Van91I | 2 | 1283 | 2668 | | | |
| VspI | 7 | 361 | 966 | 1045 | 4324 | 4347 | 5582 |
| | | 7055 | | | | |
| XbaI | 2 | 1091 | 1822 | | | |
| XcmI | 2 | 2551 | 4142 | | | |
| XhoI | 2 | 1079 | 4285 | | | |
| XhoII | 12 | 276 | 1011 | 1131 | 1825 | 2471 | 5158 |
| | | 5169 | 5255 | 5267 | 6035 | 6052 | 6855 |
| XmaI | 3 | 284 | 2437 | 2617 | | |
| XmaIII | 2 | 1025 | 1073 | | | |
| XmnI | 2 | 1046 | 6009 | | | |
| XorII | 1 | 5780 | | | | |

Fig. 18

```
AccIII
AocI
AscI
AvrII
BanIII
BbrPI
BclI
BlnI
BlpI
Bpu1102I
BscI
BseAI
BsiMI
BsiWI
Bsp106I
Bsp119I
BspDI
BspEI
BspXI
BstBI
Bsu15I
Bsu36I
CelII
ClaI
CpoI
CspI
Csp45I
CvnI
Eco72I
Eco81I
FbaI
FseI
Kpn2I
LspI
MroI
NspV
PacI
Pfl23II
PmaCI
PmeI
PmlI
PshAI
RsrII
SalI
SfiI
SfuI
SgfI
SplI
SrfI
Sse8387I
SunI
SwaI
```

Fig. 19

```
              10         20         30         40         50         60
               *          *          *          *          *          *
     GAATTCTGAACGTGCAAAAAAAATTACCAATAATCCAGAAAATTATTATCATGGATTCTA 70         80         90        100        110        120
               *          *          *          *          *          *
     AAACGGATTACCGGTGAATTCATCATCAATAATATACCTTATTTTGGATTGAAGCCAATA 130        140        150        160        170        180
               *          *          *          *          *          *
     TGATAATGAGGGGGTGGAGTTTGTGACGTGGCGCGGGGCGTGGGAACGGGGCGGGTGACG 190        200        210        220        230        240
               *          *          *          *          *          *
     TAGTAGTGTGGCGGAAGTGTGATGTTGCAAGTGTGGCGGAACACATGTAAGCGACGGATG 250        260        270        280        290        300
               *          *          *          *          *          *
     TGGCAAAAGTGACGTTTTTGGTGTGCGCCGGTGTCAGATCTGGCCCGGGGTTAGGCGTTT 310        320        330        340        350        360
               *          *          *          *          *          *
     TGCGCTGCTTCGCGATGTACGGGCCAGATATACGCGTTGACATTGATTATTGACTAGTTA 370        380        390        400        410        420
               *          *          *          *          *          *
     TTAATAGTAATCAATTACGGGGTCATTAGTTCATAGCCCATATATGGAGTTCCGCGTTAC 430        440        450        460        470        480
               *          *          *          *          *          *
     ATAACTTACGGTAAATGGCCCGCCTGGCTGACCGCCCAACGACCCCCGCCCATTGACGTC 490        500        510        520        530        540
               *          *          *          *          *          *
     AATAATGACGTATGTTCCCATAGTAACGCCAATAGGGACTTTCCATTGACGTCAATGGGT 550        560        570        580        590        600
               *          *          *          *          *          *
     GGACTATTTACGGTAAACTGCCCACTTGGCAGTACATCAAGTGTATCATATGCCAAGTAC 610        620        630        640        650        660
               *          *          *          *          *          *
     GCCCCCTATTGACGTCAATGACGGTAAATGGCCCGCCTGGCATTATGCCCAGTACATGAC 670        680        690        700        710        720
               *          *          *          *          *          *
     CTTATGGGACTTTCCTACTTGGCAGTACATCTACGTATTAGTCATCGCTATTACCATGGT 730        740        750        760        770        780
               *          *          *          *          *          *
     GATGCGGTTTTGGCAGTACATCAATGGGCGTGGATAGCGGTTTGACTCACGGGGATTTCC 790        800        810        820        830        840
               *          *          *          *          *          *
     AAGTCTCCACCCCATTGACGTCAATGGGAGTTTGTTTTGGCACCAAAATCAACGGGACTT 850        860        870        880        890        900
```

Fig. 20

```
        *         *         *         *         *         *
TCCAAAATGTCGTAACAACTCCGCCCCATTGACGCAAATGGGCGGTAGGCGTGTACGGTG 910       920       930       940       950       960
        *         *         *         *         *         *
GGAGGTCTATATAAGCAGAGCTCTCTGGCTAACTAGAGAACCCACTGCTTACTGGCTTAT 970       980       990      1000      1010      1020
        *         *         *         *         *         *
CGAAATTAATACGACTCACTATAGGGAGACCCAAGCTTGGTACCGAGCTCGGATCCACTA 1030      1040      1050      1060      1070      1080
        *         *         *         *         *         *
GTAACGGCCGCCAGTGTGCTGGAATTAATTCTGCAGATATCCATCACACTGGCGGCCGCT 1090      1100      1110      1120      1130      1140
        *         *         *         *         *         *
CGAGCATGCATCTAGAGGGCCCTATTCTATAGTGTCACCTAAATGCTAGAGGATCTTTGT 1150      1160      1170      1180      1190      1200
        *         *         *         *         *         *
GAAGGAACCTTACTTCTGTGGTGTGACATAATTGGACAAACTACCTACAGAGATTTAAAG 1210      1220      1230      1240      1250      1260
        *         *         *         *         *         *
CTCTAAGGTAAATATAAAATTTTTAAGTGTATAATGTGTTAAACTACTGATTCTAATTGT 1270      1280      1290      1300      1310      1320
        *         *         *         *         *         *
TTGTGTATTTTAGATTCCAACCTATGGAACTGATGAATGGGAGCAGTGGTGGAATGCCTT 1330      1340      1350      1360      1370      1380
        *         *         *         *         *         *
TAATGAGGAAAACCTGTTTTGCTCAGAAGAAATGCCATCTAGTGATGATGAGGCTACTGC 1390      1400      1410      1420      1430      1440
        *         *         *         *         *         *
TGACTCTCAACATTCTACTCCTCCAAAAAAGAAGAGAAAGGTAGAAGACCCCAAGGACTT 1450      1460      1470      1480      1490      1500
        *         *         *         *         *         *
TCCTTCAGAATTGCTAAGTTTTTTGAGTCATGCTGTGTTTAGTAATAGAACTCTTGCTTG 1510      1520      1530      1540      1550      1560
        *         *         *         *         *         *
CTTTGCTATTTACACCACAAAGGAAAAAGCTGCACTGCTATACAAGAAAATTATGGAAAA 1570      1580      1590      1600      1610      1620
        *         *         *         *         *         *
ATATTTGATGTATAGTGCCTTGACTAGAGATCATAATCAGCCATACCACATTTGTAGAGG 1630      1640      1650      1660      1670      1680
        *         *         *         *         *         *
TTTTACTTGCTTTAAAAAACCTCCCACACCTCCCCCTGAACCTGAAACATAAAATGAATG 1690      1700      1710      1720      1730      1740
        *         *         *         *         *         *
```

Fig. 21

```
CAATTGTTGTTGTTAACTTGTTTATTGCAGCTTATAATGGTTACAAATAAAGCAATAGCA 1750        1760        1770        1780        1790        1800
         *           *           *           *           *           *
TCACAAATTTCACAAATAAAGCATTTTTTTCACTGCATTCTAGTTGTGGTTTGTCCAAAC 1810        1820        1830        1840        1850        1860
         *           *           *           *           *           *
TCATCAATGTATCTTATCATGTCTAGATCTGGAAGGTGCTGAGGTACGATGAGACCCGCA
                            GlyArgCys***GlyThrMetArgProAla>
                            ___RECOMBINATION SEQUENCE ___>

1870        1880        1890        1900        1910        1920
         *           *           *           *           *           *
CCAGGTGCAGACCCTGCGAGTGTGGCGGTAAACATATTAGGAACCAGCCTGTGATGCTGG
ProGlyAlaAspProAlaSerValAlaValAsnIleLeuGlyThrSerLeu***CysTrp>
_____RECOMBINATION SEQUENCE FROM AD 5 BP 3328-5594 _____>

1930        1940        1950        1960        1970        1980
         *           *           *           *           *           *
ATGTGACCGAGGAGCTGAGGCCCGATCACTTGGTGCTGGCCTGCACCCGCGCTGAGTTTG
Met***ProArgSer***GlyProIleThrTrpCysTrpProAlaProAlaLeuSerLeu>
_____RECOMBINATION SEQUENCE FROM AD 5 BP 3328-5594 _____>

1990        2000        2010        2020        2030        2040
         *           *           *           *           *           *
GCTCTAGCGATGAAGATACAGATTGAGGTACTGAAATGTGTGGGCGTGGCTTAAGGGTGG
AlaLeuAlaMetLysIleGlnIleGluValLeuLysCysValGlyValAla***GlyTrp>
_____RECOMBINATION SEQUENCE FROM AD 5 BP 3328-5594 _____>

2050        2060        2070        2080        2090        2100
         *           *           *           *           *           *
GAAAGAATATATAAGGTGGGGGTCTTATGTAGTTTTGTATCTGTTTTGCAGCAGCCGCCG
GluArgIleTyrLysValGlyValLeuCysSerPheValSerValLeuGlnGlnProPro>
_____RECOMBINATION SEQUENCE FROM AD 5 BP 3328-5594 _____>

2110        2120        2130        2140        2150        2160
         *           *           *           *           *           *
CCGCCATGAGCACCAACTCGTTTGATGGAAGCATTGTGAGCTCATATTTGACAACGCGCA
ProPro***AlaProThrArgLeuMetGluAlaLeu***AlaHisIle***GlnArgAla>
_____RECOMBINATION SEQUENCE FROM AD 5 BP 3328-5594 _____>

2170        2180        2190        2200        2210        2220
         *           *           *           *           *           *
TGCCCCCATGGGCCGGGGTGCGTCAGAATGTGATGGGCTCCAGCATTGATGGTCGCCCCG
CysProHisGlyProGlyCysValArgMet***TrpAlaProAlaLeuMetValAlaPro>
_____RECOMBINATION SEQUENCE FROM AD 5 BP 3328-5594 _____>

2230        2240        2250        2260        2270        2280
         *           *           *           *           *           *
TCCTGCCCGCAAACTCTACTACCTTGACCTACGAGACCGTGTCTGGAACGCCGTTGGAGA
SerCysProGlnThrLeuLeuPro***ProThrArgProCysLeuGluArgArgTrpArg>
_____RECOMBINATION SEQUENCE FROM AD 5 BP 3328-5594 _____>

2290        2300        2310        2320        2330        2340
         *           *           *           *           *           *
CTGCAGCCTCCGCCGCCGCTTCAGCCGCTGCAGCCACCGCCCGCGGGATTGTGACTGACT
```

Fig. 22

```
LeuGlnProProProProLeuGlnProLeuGlnProProProAlaGlyLeu***LeuThr>
_____RECOMBINATION SEQUENCE FROM AD 5 BP 3328-5594 _____>

2350      2360      2370      2380      2390      2400
         *         *         *         *         *         *
TTGCTTTCCTGAGCCCGCTTGCAAGCAGTGCAGCTTCCCGTTCATCCGCCCGCGATGACA
LeuLeuSer***AlaArgLeuGlnAlaValGlnLeuProValHisProProAlaMetThr>
_____RECOMBINATION SEQUENCE FROM AD 5 BP 3328-5594 _____>

2410      2420      2430      2440      2450      2460
         *         *         *         *         *         *
AGTTGACGGCTCTTTTGGCACAATTGGATTCTTTGACCCGGGAACTTAATGTCGTTTCTC
Ser***ArgLeuPheTrpHisAsnTrpIleLeu***ProGlyAsnLeuMetSerPheLeu>
_____RECOMBINATION SEQUENCE FROM AD 5 BP 3328-5594 _____>

2470      2480      2490      2500      2510      2520
         *         *         *         *         *         *
AGCAGCTGTTGGATCTGCGCCAGCAGGTTTCTGCCCTGAAGGCTTCCTCCCCTCCCAATG
SerSerCysTrpIleCysAlaSerArgPheLeuPro***ArgLeuProProLeuProMet>
_____RECOMBINATION SEQUENCE FROM AD 5 BP 3328-5594 _____>

2530      2540      2550      2560      2570      2580
         *         *         *         *         *         *
CGGTTTAAAACATAAATAAAAAACCAGACTCTGTTTGGATTTGGATCAAGCAAGTGTCTT
ArgPheLysThr***IleLysAsnGlnThrLeuPheGlyPheGlySerSerLysCysLeu>
_____RECOMBINATION SEQUENCE FROM AD 5 BP 3328-5594 _____>

2590      2600      2610      2620      2630      2640
         *         *         *         *         *         *
GCTGTCTTTATTTAGGGGTTTTGCGCGCGCGGTAGGCCCGGGACCAGCGGTCTCGGTCGT
AlaValPheIle***GlyPheCysAlaArgGlyArgProGlyThrSerGlyLeuGlyArg>
_____RECOMBINATION SEQUENCE FROM AD 5 BP 3328-5594 _____>

2650      2660      2670      2680      2690      2700
         *         *         *         *         *         *
TGAGGGTCCTGTGTATTTTTTCCAGGACGTGGTAAAGGTGACTCTGGATGTTCAGATACA
***GlySerCysValPhePheProGlyArgGlyLysGlyAspSerGlyCysSerAspThr>
_____RECOMBINATION SEQUENCE FROM AD 5 BP 3328-5594 _____>

2710      2720      2730      2740      2750      2760
         *         *         *         *         *         *
TGGGCATAAGCCCGTCTCTGGGGTGGAGGTAGCACCACTGCAGAGCTTCATGCTGCGGGG
TrpAla***AlaArgLeuTrpGlyGlyGlySerThrThrAlaGluLeuHisAlaAlaGly>
_____RECOMBINATION SEQUENCE FROM AD 5 BP 3328-5594 _____>

2770      2780      2790      2800      2810      2820
         *         *         *         *         *         *
TGGTGTTGTAGATGATCCAGTCGTAGCAGGAGCGCTGGGCGTGGTGCCTAAAAATGTCTT
TrpCysCysArg***SerSerArgSerArgSerAlaGlyArgGlyAla***LysCysLeu>
_____RECOMBINATION SEQUENCE FROM AD 5 BP 3328-5594 _____>

2830      2840      2850      2860      2870      2880
         *         *         *         *         *         *
TCAGTAGCAAGCTGATTGCCAGGGGCAGGCCCTTGGTGTAAGTGTTTACAAAGCGGTTAA
SerValAlaSer***LeuProGlyAlaGlyProTrpCysLysCysLeuGlnSerGly***>
_____RECOMBINATION SEQUENCE FROM AD 5 BP 3328-5594 _____>
```

Fig. 23

```
         2890      2900      2910      2920      2930      2940
           *         *         *         *         *         *
GCTGGGATGGGTGCATACGTGGGGATATGAGATGCATCTTGGACTGTATTTTTAGGTTGG
AlaGlyMetGlyAlaTyrValGlyIle***AspAlaSerTrpThrValPheLeuGlyTrp>
_____RECOMBINATION SEQUENCE FROM AD 5 BP 3328-5594 _____>

2950      2960      2970      2980      2990      3000
           *         *         *         *         *         *
CTATGTTCCCAGCCATATCCCTCCGGGGATTCATGTTGTGCAGAACCACCAGCACAGTGT
LeuCysSerGlnProTyrProSerGlyAspSerCysCysAlaGluProProAlaGlnCys>
_____RECOMBINATION SEQUENCE FROM AD 5 BP 3328-5594 _____>

3010      3020      3030      3040      3050      3060
           *         *         *         *         *         *
ATCCGGTGCACTTGGGAAATTTGTCATGTAGCTTAGAAGGAAATGCGTGGAAGAACTTGG
IleArgCysThrTrpGluIleCysHisValAla***LysGluMetArgGlyArgThrTrp>
_____RECOMBINATION SEQUENCE FROM AD 5 BP 3328-5594 _____>

3070      3080      3090      3100      3110      3120
           *         *         *         *         *         *
AGACGCCCTTGTGACCTCCAAGATTTTCCATGCATTCGTCCATAATGATGGCAATGGGCC
ArgArgProCysAspLeuGlnAspPheProCysIleArgPro******TrpGlnTrpAla>
_____RECOMBINATION SEQUENCE FROM AD 5 BP 3328-5594 _____>

3130      3140      3150      3160      3170      3180
           *         *         *         *         *         *
CACGGGCGGCGGCCTGGGCGAAGATATTTCTGGGATCACTAACGTCATAGTTGTGTTCCA
HisGlyArgArgProGlyArgArgTyrPheTrpAspHis***ArgHisSerCysValPro>
_____RECOMBINATION SEQUENCE FROM AD 5 BP 3328-5594 _____>

3190      3200      3210      3220      3230      3240
           *         *         *         *         *         *
GGATGAGATCGTCATAGGCCATTTTTACAAAGCGCGGGCGGAGGGTGCCAGACTGCGGTA
Gly***AspArgHisArgProPheLeuGlnSerAlaGlyGlyGlyCysGlnThrAlaVal>
_____RECOMBINATION SEQUENCE FROM AD 5 BP 3328-5594 _____>

3250      3260      3270      3280      3290      3300
           *         *         *         *         *         *
TAATGGTTCCATCCGGCCCAGGGGCGTAGTTACCCTCACAGATTTGCATTTCCCACGCTT
***TrpPheHisProAlaGlnGlyArgSerTyrProHisArgPheAlaPheProThrLeu>
_____RECOMBINATION SEQUENCE FROM AD 5 BP 3328-5594 _____>

3310      3320      3330      3340      3350      3360
           *         *         *         *         *         *
TGAGTTCAGATGGGGGGATCATGTCTACCTGCGGGGCGATGAAGAAAACGGTTTCCGGGG
*ValGlnMetGlyGlySerCysLeuProAlaGlyArg*ArgLysArgPheProGly>
_____RECOMBINATION SEQUENCE FROM AD 5 BP 3328-5594 _____>

3370      3380      3390      3400      3410      3420
           *         *         *         *         *         *
TAGGGGAGATCAGCTGGGAAGAAAGCAGGTTCCTGAGCAGCTGCGACTTACCGCAGCCGG
*GlyArgSerAlaGlyLysLysAlaGlySer*AlaAlaAlaThrTyrArgSerArg>
_____RECOMBINATION SEQUENCE FROM AD 5 BP 3328-5594 _____>

3430      3440      3450      3460      3470      3480
           *         *         *         *         *         *
TGGGCCCGTAAATCACACCTATTACCGGGTGCAACTGGTAGTTAAGAGAGCTGCAGCTGC
```

Fig. 24

```
TrpAlaArgLysSerHisLeuLeuProGlyAlaThrGlySer***GluSerCysSerCys>
_____RECOMBINATION SEQUENCE FROM AD 5 BP 3328-5594 _____>

3490      3500      3510      3520      3530      3540
          *         *         *         *         *         *
CGTCATCCCTGAGCAGGGGGGCCACTTCGTTAAGCATGTCCCTGACTCGCATGTTTTCCC
ArgHisPro***AlaGlyGlyProLeuArg***AlaCysPro***LeuAlaCysPhePro>
_____RECOMBINATION SEQUENCE FROM AD 5 BP 3328-5594 _____>

3550      3560      3570      3580      3590      3600
          *         *         *         *         *         *
TGACCAAATCCGCCAGAAGGCGCTCGCCGCCCAGCGATAGCAGTTCTTGCAAGGAAGCAA
***ProAsnProProGluGlyAlaArgArgProAlaIleAlaValLeuAlaArgLysGln>
_____RECOMBINATION SEQUENCE FROM AD 5 BP 3328-5594 _____>

3610      3620      3630      3640      3650      3660
          *         *         *         *         *         *
AGTTTTTCAACGGTTTGAGACCGTCCGCCGTAGGCATGCTTTTGAGCGTTTGACCAAGCA
SerPheSerThrVal***AspArgProPro***AlaCysPhe***AlaPheAspGlnAla>
_____RECOMBINATION SEQUENCE FROM AD 5 BP 3328-5594 _____>

3670      3680      3690      3700      3710      3720
          *         *         *         *         *         *
GTTCCAGGCGGTCCCACAGCTCGGTCACCTGCTCTACGGCATCTCGATCCAGCATATCTC
ValProGlyGlyProThrAlaArgSerProAlaLeuArgHisLeuAspProAlaTyrLeu>
_____RECOMBINATION SEQUENCE FROM AD 5 BP 3328-5594 _____>

3730      3740      3750      3760      3770      3780
          *         *         *         *         *         *
CTCGTTTCGCGGGTTGGGGCGGCTTTCGCTGTACGGCAGTAGTCGGTGCTCGTCCAGACG
LeuValSerArgValGlyAlaAlaPheAlaValArgGln***SerValLeuValGlnThr>
_____RECOMBINATION SEQUENCE FROM AD 5 BP 3328-5594 _____>

3790      3800      3810      3820      3830      3840
          *         *         *         *         *         *
GGCCAGGGTCATGTCTTTCCACGGGCGCAGGGTCCTCGTCAGCGTAGTCTGGGTCACGGT
GlyGlnGlyHisValPheProArgAlaGlnGlyProArgGlnArgSerLeuGlyHisGly>
_____RECOMBINATION SEQUENCE FROM AD 5 BP 3328-5594 _____>

3850      3860      3870      3880      3890      3900
          *         *         *         *         *         *
GAAGGGGTGCGCTCCGGGCTGCGCGCTGGCCAGGGTGCGCTTGAGGCTGGTCCTGCTGGT
GluGlyValArgSerGlyLeuArgAlaGlyGlnGlyAlaLeuGluAlaGlyProAlaGly>
_____RECOMBINATION SEQUENCE FROM AD 5 BP 3328-5594 _____>

3910      3920      3930      3940      3950      3960
          *         *         *         *         *         *
GCTGAAGCGCTGCCGGTCTTCGCCCTGCGCGTCGGCCAGGTAGCATTTGACCATGGTGTC
AlaGluAlaLeuProValPheAlaLeuArgValGlyGlnValAlaPheAspHisGlyVal>
_____RECOMBINATION SEQUENCE FROM AD 5 BP 3328-5594 _____>

3970      3980      3990      4000      4010      4020
          *         *         *         *         *         *
ATAGTCCAGCCCCTCCGCGGCGTGGCCCTTGGCGCGCAGCTTGCCCTTGGAGGAGGCGCC
IleValGlnProLeuArgGlyValAlaLeuGlyAlaGlnLeuAlaLeuGlyGlyGlyAla>
_____RECOMBINATION SEQUENCE FROM AD 5 BP 3328-5594 _____>
```

Fig. 25

```
              4030        4040        4050        4060        4070        4080
                *           *           *           *           *           *
     GCACGAGGGGCAGTGCAGACTTTTGAGGGCGTAGAGCTTGGGCGCGAGAAATACCGATTC
     AlaArgGlyAlaValGlnThrPheGluGlyValGluLeuGlyArgGluLysTyrArgPhe>
     _____RECOMBINATION SEQUENCE FROM AD 5 BP 3328-5594 _____>

4090        4100        4110        4120        4130        4140
                *           *           *           *           *           *
     CGGGGAGTAGGCATCCGCGCCGCAGGCCCCGCAGACGGTCTCGCATTCCACGAGCCAGGT
     ArgGlyValGlyIleArgAlaAlaGlyProAlaAspGlyLeuAlaPheHisGluProGly>
     _____RECOMBINATION SEQUENCE FROM AD 5 BP 3328-5594 _____>

4150        4160        4170        4180        4190        4200
                *           *           *           *           *           *
     GAGCTCTGGCCGTTCGGGGTCAAAAACCAGGTTTCCCCCATGCTTTTTGATGCGTTTCTT
     GluLeuTrpProPheGlyValLysAsnGlnValSerProMetLeuPheAspAlaPheLeu>
     _____RECOMBINATION SEQUENCE FROM AD 5 BP 3328-5594 _____>

4210        4220        4230        4240        4250        4260
                *           *           *           *           *           *
     ACCTCTGGTTTCCATGAGCCGGTGTCCACGCTCGGTGACGAAAAGGCTGTCCGTGTCCCC
     ThrSerGlyPheHisGluProValSerThrLeuGlyAspGluLysAlaValArgValPro>
     _____RECOMBINATION SEQUENCE FROM AD 5 BP 3328-5594 _____>

4270        4280        4290        4300        4310        4320
                *           *           *           *           *           *
     GTATACAGACTTGAGAGGCCTGTCCTCGAGGATCAGCTTCCGGTCTCCCTATAGTGAGTC
     ValTyrArgLeuGluArgProValLeuGlu>
     ____RECOMBINATION SEQUENCE ____>

4330        4340        4350        4360        4370        4380
                *           *           *           *           *           *
     GTATTAATTTCGATAAGCCAGCTGCATTAATGAATCGGCCAACGCGCGGGGAGAGGCGGT 4390        4400        4410        4420        4430        4440
                *           *           *           *           *           *
     TTGCGTATTGGGCGCTCTTCCGCTTCCTCGCTCACTGACTCGCTGCGCTCGGTCGTTCGG 4450        4460        4470        4480        4490        4500
                *           *           *           *           *           *
     CTGCGGCGAGCGGTATCAGCTCACTCAAAGGCGGTAATACGGTTATCCACAGAATCAGGG 4510        4520        4530        4540        4550        4560
                *           *           *           *           *           *
     GATAACGCAGGAAAGAACATGTGAGCAAAAGGCCAGCAAAAGGCCAGGAACCGTAAAAAG 4570        4580        4590        4600        4610        4620
                *           *           *           *           *           *
     GCCGCGTTGCTGGCGTTTTTCCATAGGCTCCGCCCCCCTGACGAGCATCACAAAAATCGA 4630        4640        4650        4660        4670        4680
                *           *           *           *           *           *
     CGCTCAAGTCAGAGGTGGCGAAACCCGACAGGACTATAAAGATACCAGGCGTTTCCCCCT 4690        4700        4710        4720        4730        4740
                *           *           *           *           *           *
     GGAAGCTCCCTCGTGCGCTCTCCTGTTCCGACCCTGCCGCTTACCGGATACCTGTCCGCC
```

Fig. 26

```
       4750      4760      4770      4780      4790      4800
         *         *         *         *         *         *
TTTCTCCCTTCGGGAAGCGTGGCGCTTTCTCATAGCTCACGCTGTAGGTATCTCAGTTCG 4810      4820      4830      4840      4850      4860
         *         *         *         *         *         *
GTGTAGGTCGTTCGCTCCAAGCTGGGCTGTGTGCACGAACCCCCCGTTCAGCCCGACCGC 4870      4880      4890      4900      4910      4920
         *         *         *         *         *         *
TGCGCCTTATCCGGTAACTATCGTCTTGAGTCCAACCCGGTAAGACACGACTTATCGCCA 4930      4940      4950      4960      4970      4980
         *         *         *         *         *         *
CTGGCAGCAGCCACTGGTAACAGGATTAGCAGAGCGAGGTATGTAGGCGGTGCTACAGAG 4990      5000      5010      5020      5030      5040
         *         *         *         *         *         *
TTCTTGAAGTGGTGGCCTAACTACGGCTACACTAGAAGGACAGTATTTGGTATCTGCGCT 5050      5060      5070      5080      5090      5100
         *         *         *         *         *         *
CTGCTGAAGCCAGTTACCTTCGGAAAAAGAGTTGGTAGCTCTTGATCCGGCAAACAAACC 5110      5120      5130      5140      5150      5160
         *         *         *         *         *         *
ACCGCTGGTAGCGGTGGTTTTTTTGTTTGCAAGCAGCAGATTACGCGCAGAAAAAAAGGA 5170      5180      5190      5200      5210      5220
         *         *         *         *         *         *
TCTCAAGAAGATCCTTTGATCTTTTCTACGGGGTCTGACGCTCAGTGGAACGAAAACTCA 5230      5240      5250      5260      5270      5280
         *         *         *         *         *         *
CGTTAAGGGATTTTGGTCATGAGATTATCAAAAAGGATCTTCACCTAGATCCTTTTAAAT 5290      5300      5310      5320      5330      5340
         *         *         *         *         *         *
TAAAAATGAAGTTTTAAATCAATCTAAAGTATATATGAGTAAACTTGGTCTGACAGTTAC 5350      5360      5370      5380      5390      5400
         *         *         *         *         *         *
CAATGCTTAATCAGTGAGGCACCTATCTCAGCGATCTGTCTATTTCGTTCATCCATAGTT 5410      5420      5430      5440      5450      5460
         *         *         *         *         *         *
GCCTGACTCCCCGTCGTGTAGATAACTACGATACGGGAGGGCTTACCATCTGGCCCCAGT 5470      5480      5490      5500      5510      5520
         *         *         *         *         *         *
GCTGCAATGATACCGCGAGACCCACGCTCACCGGCTCCAGATTTATCAGCAATAAACCAG 5530      5540      5550      5560      5570      5580
         *         *         *         *         *         *
CCAGCCGGAAGGGCCGAGCGCAGAAGTGGTCCTGCAACTTTATCCGCCTCCATCCAGTCT
```

Fig. 27

```
           5590      5600      5610      5620      5630      5640
             *         *         *         *         *         *
ATTAATTGTTGCCGGGAAGCTAGAGTAAGTAGTTCGCCAGTTAATAGTTTGCGCAACGTT 5650      5660      5670      5680      5690      5700
             *         *         *         *         *         *
GTTGCCATTGCTACAGGCATCGTGGTGTCACGCTCGTCGTTTGGTATGGCTTCATTCAGC 5710      5720      5730      5740      5750      5760
             *         *         *         *         *         *
TCCGGTTCCCAACGATCAAGGCGAGTTACATGATCCCCCATGTTGTGCAAAAAAGCGGTT 5770      5780      5790      5800      5810      5820
             *         *         *         *         *         *
AGCTCCTTCGGTCCTCCGATCGTTGTCAGAAGTAAGTTGGCCGCAGTGTTATCACTCATG 5830      5840      5850      5860      5870      5880
             *         *         *         *         *         *
GTTATGGCAGCACTGCATAATTCTCTTACTGTCATGCCATCCGTAAGATGCTTTTCTGTG 5890      5900      5910      5920      5930      5940
             *         *         *         *         *         *
ACTGGTGAGTACTCAACCAAGTCATTCTGAGAATAGTGTATGCGGCGACCGAGTTGCTCT 5950      5960      5970      5980      5990      6000
             *         *         *         *         *         *
TGCCCGGCGTCAATACGGGATAATACCGCGCCACATAGCAGAACTTTAAAAGTGCTCATC 6010      6020      6030      6040      6050      6060
             *         *         *         *         *         *
ATTGGAAAACGTTCTTCGGGGCGAAAACTCTCAAGGATCTTACCGCTGTTGAGATCCAGT 6070      6080      6090      6100      6110      6120
             *         *         *         *         *         *
TCGATGTAACCCACTCGTGCACCCAACTGATCTTCAGCATCTTTTACTTTCACCAGCGTT 6130      6140      6150      6160      6170      6180
             *         *         *         *         *         *
TCTGGGTGAGCAAAAACAGGAAGGCAAAATGCCGCAAAAAAGGGAATAAGGGCGACACGG 6190      6200      6210      6220      6230      6240
             *         *         *         *         *         *
AAATGTTGAATACTCATACTCTTCCTTTTTCAATATTATTGAAGCATTTATCAGGGTTAT 6250      6260      6270      6280      6290      6300
             *         *         *         *         *         *
TGTCTCATGAGCGGATACATATTTGAATGTATTTAGAAAAATAAACAAATAGGGGTTCCG 6310      6320      6330      6340      6350      6360
             *         *         *         *         *         *
CGCACATTTCCCCGAAAAGTGCCACCTGACGTCTAAGAAACCATTATTATCATGACATTA 6370      6380      6390      6400      6410      6420
             *         *         *         *         *         *
ACCTATAAAAATAGGCGTATCACGAGGCCCTTTCGTCTCGCGCGTTTCGGTGATGACGGT 6430      6440      6450      6460      6470      6480
```

Fig. 29

```
           10         20         30         40         50         60
            *          *          *          *          *          *
    GAATTCTGAACGTGCAAAAAAAATTACCAATAATCCAGAAAATTATTATCATGGATTCTA
    CTTAAGACTTGCACGTTTTTTTTAATGGTTATTAGGTCTTTTAATAATAGTACCTAAGAT 70         80         90        100        110        120
            *          *          *          *          *          *
    AAACGGATTACCGGTGAATTCATCATCAATAATATACCTTATTTTGGATTGAAGCCAATA
    TTTGCCTAATGGCCACTTAAGTAGTAGTTATTATATGGAATAAAACCTAACTTCGGTTAT
                     └─ Terminal repeat
          130        140        150        160        170        180
            *          *          *          *          *          *
    TGATAATGAGGGGGTGGAGTTTGTGACGTGGCGCGGGGCGTGGGAACGGGGCGGGTGACG
    ACTATTACTCCCCCACCTCAAACACTGCACCGCGCCCCGCACCCTTGCCCCGCCCACTGC 190        200        210        220        230        240
            *          *          *          *          *          *
    TAGTAGTGTGGCGGAAGTGTGATGTTGCAAGTGTGGCGGAACACATGTAAGCGACGGATG
    ATCATCACACCGCCTTCACACTACAACGTTCACACCGCCTTGTGTACATTCGCTGCCTAC 250        260        270        280        290        300
            *          *          *          *          *          *
    TGGCAAAAGTGACGTTTTGGTGTGCGCCGGTGTCAGATCCAGACATGATAAGATACATT
    ACCGTTTTCACTGCAAAAACCACACGCGGCCACAGTCTAGGTCTGTACTATTCTATGTAA
                                          └─ SV40 poly A
          310        320        330        340        350        360
            *          *          *          *          *          *
    GATGAGTTTGGACAAACCACAACTAGAATGCAGTGAAAAAAATGCTTTATTTGTGAAATT
    CTACTCAAACCTGTTTGGTGTTGATCTTACGTCACTTTTTTTACGAAATAAACACTTTAA 370        380        390        400        410        420
            *          *          *          *          *          *
    TGTGATGCTATTGCTTTATTTGTAACCATTATAAGCTGCAATAAACAGGATCTTATTTTT
    ACACTACGATAACGAAATAAACATTGGTAATATTCGACGTTATTTGTCCTAGAATAAAAA
                                                        ─<***LysGln
                                                        <_____

430        440        450        460        470        480
            *          *          *          *          *          *
    GACACCAGACCAACTGGTAATGGTAGCGACCGGCGCTCAGCTGGAATTCCGCCGATACTG
    CTGTGGTCTGGTTGACCATTACCATCGCTGGCCGCGAGTCGACCTTAAGGCGGCTATGAC
    <CysTrpValLeuGlnTyrHisTyrArgGlyAlaSerLeuGlnPheGluAlaSerValSer
    <_____GENE: LACZ _____

490        500        510        520        530        540
            *          *          *          *          *          *
    ACGGGCTCCAGGAGTCGTCGCCACCAATCCCCATATGGAAACCGTCGATATTCAGCCATG
    TGCCCGAGGTCCTCAGCAGCGGTGGTTAGGGGTATACCTTTGGCAGCTATAAGTCGGTAC
    <ProSerTrpSerAspAspGlyGlyIleGlyMetHisPheGlyAspIleAsnLeuTrpThr
    <_____GENE: LACZ _____

550        560        570        580        590        600
            *          *          *          *          *          *
    TGCCTTCTTCCGCGTGCAGCAGATGGCGATGGCTGGTTTCCATCAGTTGCTGTTGACTGT
    ACGGAAGAAGGCGCACGTCGTCTACCGCTACCGACCAAAGGTAGTCAACGACAACTGACA
    <GlyGluGluAlaHisLeuLeuHisArgHisSerThrGluMetLeuGlnGlnGlnSerTyr
    <_____GENE: LACZ _____
```

Fig. 30

```
              610          620         630         640         650         660
               *            *           *           *           *           *
        AGCGGCTGATGTTGAACTGGAAGTCGCCGCGCCACTGGTGTGGGCCATAATTCAATTCGC
        TCGCCGACTACAACTTGACCTTCAGCGGCGCGGTGACCACACCCGGTATTAAGTTAAGCG
       <ArgSerIleAsnPheGlnPheAspGlyArgTrpGlnHisProGlyTyrAsnLeuGluArg
       <_____GENE: LACZ _____

670          680         690         700         710         720
               *            *           *           *           *           *
        GCGTCCCGCAGCGCAGACCGTTTTCGCTCGGGAAGACGTACGGGGTATACATGTCTGACA
        CGCAGGGCGTCGCGTCTGGCAAAAGCGAGCCCTTCTGCATGCCCCATATGTACAGACTGT
       <ThrGlyCysArgLeuGlyAsnGluSerProPheValTyrProThrTyrMetAspSerLeu
       <_____GENE: LACZ _____

730          740         750         760         770         780
               *            *           *           *           *           *
        ATGGCAGATCCCAGCGGTCAAAACAGGCGGCAGTAAGGCGGTCGGGATAGTTTTCTTGCG
        TACCGTCTAGGGTCGCCAGTTTTGTCCGCCGTCATTCCGCCAGCCCTATCAAAAGAACGC
       <ProLeuAspTrpArgAspPheCysAlaAlaThrLeuArgAspProTyrAsnGluGlnPro
       <_____GENE: LACZ _____

790          800         810         820         830         840
               *            *           *           *           *           *
        GCCCTAATCCGAGCCAGTTTACCCGCTCTGCTACCTGCGCCAGCTGGCAGTTCAGGCCAA
        CGGGATTAGGCTCGGTCAAATGGGCGAGACGATGGACGCGGTCGACCGTCAAGTCCGGTT
       <GlyLeuGlyLeuTrpAsnValArgGluAlaValGlnAlaLeuGlnCysAsnLeuGlyIle
       <_____GENE: LACZ _____

850          860         870         880         890         900
               *            *           *           *           *           *
        TCCGCGCCGGATGCGGTGTATCGCTCGCCACTTCAACATCAACGGTAATCGCCATTTGAC
        AGGCGCGGCCTACGCCACATAGCGAGCGGTGAAGTTGTAGTTGCCATTAGCGGTAAACTG
       <ArgAlaProHisProThrAspSerAlaValGluValAspValThrIleAlaMetGlnGly
       <_____GENE: LACZ _____

910          920         930         940         950         960
               *            *           *           *           *           *
        CACTACCATCAATCCGGTAGGTTTTCCGGCTGATAAATAAGGTTTTCCCCTGATGCTGCC
        GTGATGGTAGTTAGGCCATCCAAAAGGCCGACTATTTATTCCAAAAGGGGACTACGACGG
       <SerGlyAspIleArgTyrThrLysArgSerIlePheLeuThrLysGlyGlnHisGlnTrp
       <_____GENE: LACZ _____

970          980         990        1000        1010        1020
               *            *           *           *           *           *
        ACGCGTGAGCGGTCGTAATCAGCACCGCATCAGCAAGTGTATCTGCCGTGCACTGCAACA
        TGCGCACTCGCCAGCATTAGTCGTGGCGTAGTCGTTCACATAGACGGCACGTGACGTTGT
       <AlaHisAlaThrThrIleLeuValAlaAspAlaLeuThrAspAlaThrCysGlnLeuLeu
       <_____GENE: LACZ _____

1030         1040        1050        1060        1070        1080
               *            *           *           *           *           *
        ACGCTGCTTCGGCCTGGTAATGGCCCGCCGCCTTCCAGCGTTCGACCCAGGCGTTAGGGT
        TGCGACGAAGCCGGACCATTACCGGGCGGCGGAAGGTCGCAAGCTGGGTCCGCAATCCCA
       <AlaAlaGluAlaGlnTyrHisGlyAlaAlaLysTrpArgGluValTrpAlaAsnProAsp
       <_____GENE: LACZ _____
```

Fig. 31

```
            1090      1100      1110      1120      1130      1140
              *         *         *         *         *         *
       CAATGCGGGTCGCTTCACTTACGCCAATGTCGTTATCCAGCGGTGCACGGGTGAACTGAT
       GTTACGCCCAGCGAAGTGAATGCGGTTACAGCAATAGGTCGCCACGTGCCCACTTGACTA
       <IleArgThrAlaGluSerValGlyIleAspAsnAspLeuProAlaArgThrPheGlnAsp
       <_____GENE: LACZ _____

1150      1160      1170      1180      1190      1200
              *         *         *         *         *         *
       CGCGCAGCGGCGTCAGCAGTTGTTTTTTATCGCCAATCCACATCTGTGAAAGAAAGCCTG
       GCGCGTCGCCGCAGTCGTCAACAAAAAATAGCGGTTAGGTGTAGACACTTTCTTTCGGAC
       <ArgLeuProThrLeuLeuGlnLysLysAspGlyIleTrpMetGlnSerLeuPheGlySer
       <_____GENE: LACZ _____

1210      1220      1230      1240      1250      1260
              *         *         *         *         *         *
       ACTGGCGGTTAAATTGCCAACGCTTATTACCCAGCTCGATGCAAAAATCCATTTCGCTGG
       TGACCGCCAATTTAACGGTTGCGAATAATGGGTCGAGCTACGTTTTTAGGTAAAGCGACC
       <GlnArgAsnPheGlnTrpArgLysAsnGlyLeuGluIleCysPheAspMetGluSerThr
       <_____GENE: LACZ _____

1270      1280      1290      1300      1310      1320
              *         *         *         *         *         *
       TGGTCAGATGCGGGATGGCGTGGGACGCGGCGGGGAGCGTCACACTGAGGTTTTCCGCCA
       ACCAGTCTACGCCCTACCGCACCCTGCGCCGCCCCTCGCAGTGTGACTCCAAAAGGCGGT
       <ThrLeuHisProIleAlaHisSerAlaAlaProLeuThrValSerLeuAsnGluAlaLeu
       <_____GENE: LACZ _____

1330      1340      1350      1360      1370      1380
              *         *         *         *         *         *
       GACGCCACTGCTGCCAGGCGCTGATGTGCCCGGCTTCTGACCATGCGGTCGCGTTCGGTT
       CTGCGGTGACGACGGTCCGCGACTACACGGGCCGAAGACTGGTACGCCAGCGCAAGCCAA
       <ArgTrpGlnGlnTrpAlaSerIleHisGlyAlaGluSerTrpAlaThrAlaAsnProGln
       <_____GENE: LACZ _____

1390      1400      1410      1420      1430      1440
              *         *         *         *         *         *
       GCACTACGCGTACTGTGAGCCAGAGTTGCCCGGCGCTCTCCGGCTGCGGTAGTTCAGGCA
       CGTGATGCGCATGACACTCGGTCTCAACGGGCCGCGAGAGGCCGACGCCATCAAGTCCGT
       <ValValArgValThrLeuTrpLeuGlnGlyAlaSerGluProGlnProLeuGluProLeu
       <_____GENE: LACZ _____

1450      1460      1470      1480      1490      1500
              *         *         *         *         *         *
       GTTCAATCAACTGTTTACCTTGTGGAGCGACATCCAGAGGCACTTCACCGCTTGCCAGCG
       CAAGTTAGTTGACAAATGGAACACCTCGCTGTAGGTCTCCGTGAAGTGGCGAACGGTCGC
       <GluIleLeuGlnLysGlyGlnProAlaValAspLeuProValGluGlySerAlaLeuPro
       <_____GENE: LACZ _____

1510      1520      1530      1540      1550      1560
              *         *         *         *         *         *
       GCTTACCATCCAGCGCCACCATCCAGTGCAGGAGCTCGTTATCGCTATGACGGAACAGGT
       CGAATGGTAGGTCGCGGTGGTAGGTCACGTCCTCGAGCAATAGCGATACTGCCTTGTCCA
       <LysGlyAspLeuAlaValMetTrpHisLeuLeuGluAsnAspSerHisArgPheLeuTyr
       <_____GENE: LACZ _____

```
         *         *         *         *         *         *
ATTCGCTGGTCACTTCGATGGTTTGCCCGGATAAACGGAACTGGAAAAACTGCTGCTGGT
TAAGCGACCAGTGAAGCTACCAAACGGGCCTATTTGCCTTGACCTTTTTGACGACGACCA
<GluSerThrValGluIleThrGlnGlySerLeuArgPheGlnPhePheGlnGlnGlnHis
<_____GENE: LACZ _____

1630      1640      1650      1660      1670      1680
         *         *         *         *         *         *
GTTTTGCTTCCGTCAGCGCTGGATGCGGCGTGCGGTCGGCAAAGACCAGACCGTTCATAC
CAAAACGAAGGCAGTCGCGACCTACGCCGCACGCCAGCCGTTTCTGGTCTGGCAAGTATG
<LysAlaGluThrLeuAlaProHisProThrArgAspAlaPheValLeuGlyAsnMetCys
<_____GENE: LACZ _____

1690      1700      1710      1720      1730      1740
         *         *         *         *         *         *
AGAACTGGCGATCGTTCGGCGTATCGCCAAAATCACCGCCGTAAGCCGACCACGGGTTGC
TCTTGACCGCTAGCAAGCCGCATAGCGGTTTTAGTGGCGGCATTCGGCTGGTGCCCAACG
<PheGlnArgAspAsnProThrAspGlyPheAspGlyGlyTyrAlaSerTrpProAsnGly
<_____GENE: LACZ _____

1750      1760      1770      1780      1790      1800
         *         *         *         *         *         *
CGTTTTCATCATATTTAATCAGCGACTGATCCACCCAGTCCCAGACGAAGCCGCCCTGTA
GCAAAAGTAGTATAAATTAGTCGCTGACTAGGTGGGTCAGGGTCTGCTTCGGCGGGACAT
<AsnGluAspTyrLysIleLeuSerGlnAspValTrpAspTrpValPheGlyGlyGlnLeu
<_____GENE: LACZ _____

1810      1820      1830      1840      1850      1860
         *         *         *         *         *         *
AACGGGGATACTGACGAAACGCCTGCCAGTATTTAGCGAAACCGCCAAGACTGTTACCCA
TTGCCCCTATGACTGCTTTGCGGACGGTCATAAATCGCTTTGGCGGTTCTGACAATGGGT
<ArgProTyrGlnArgPheAlaGlnTrpTyrLysAlaPheGlyGlyLeuSerAsnGlyMet
<_____GENE: LACZ _____

1870      1880      1890      1900      1910      1920
         *         *         *         *         *         *
TCGCGTGGGCGTATTCGCAAAGGATCAGCGGGCGCGTCTCTCCAGGTAGCGAAAGCCATT
AGCGCACCCGCATAAGCGTTTCCTAGTCGCCCGCGCAGAGAGGTCCATCGCTTTCGGTAA
<AlaHisAlaTyrGluCysLeuIleLeuProArgThrGluGlyProLeuSerLeuTrpLys
<_____GENE: LACZ _____

1930      1940      1950      1960      1970      1980
         *         *         *         *         *         *
TTTTGATGGACCATTTCGGCACAGCCGGGAAGGGCTGGTCTTCATCCACGCGCGCGTACA
AAAACTACCTGGTAAAGCCGTGTCGGCCCTTCCCGACCAGAAGTAGGTGCGCGCGCATGT
<LysIleSerTrpLysProValAlaProPheProGlnAspGluAspValArgAlaTyrMet
<_____GENE: LACZ _____

1990      2000      2010      2020      2030      2040
         *         *         *         *         *         *
TCGGGCAAATAATATCGGTGGCCGTGGTGTCGGCTCCGCCGCCTTCATACTGCACCGGGC
AGCCCGTTTATTATAGCCACCGGCACCACAGCCGAGGCGGCGGAAGTATGACGTGGCCCG
<ProCysIleIleAspThrAlaThrThrAspAlaGlyGlyGlyGluTyrGlnValProArg
<_____GENE: LACZ _____

```
GGGAAGGATCGACAGATTTGATCCAGCGATACAGCGCGTCGTGATTAGCGCCGTGGCCTG
CCCTTCCTAGCTGTCTAAACTAGGTCGCTATGTCGCGCAGCACTAATCGCGGCACCGGAC
<SerProAspValSerLysIleTrpArgTyrLeuAlaAspHisAsnAlaGlyHisGlySer
<_____GENE: LACZ _____

2110      2120      2130      2140      2150      2160
          *         *         *         *         *         *
ATTCATTCCCCAGCGACCAGATGATCACACTCGGGTGATTACGATCGCGCTGCACCATTC
TAAGTAAGGGGTCGCTGGTCTACTAGTGTGAGCCCACTAATGCTAGCGCGACGTGGTAAG
<GluAsnGlyLeuSerTrpIleIleValSerProHisAsnArgAspArgGlnValMetArg
<_____GENE: LACZ _____

2170      2180      2190      2200      2210      2220
          *         *         *         *         *         *
GCGTTACGCGTTCGCTCATCGCCGGTAGCCAGCGCGGATCATCGGTCAGACGATTCATTG
CGCAATGCGCAAGCGAGTAGCGGCCATCGGTCGCGCCTAGTAGCCAGTCTGCTAAGTAAC
<ThrValArgGluSerMetAlaProLeuTrpArgProAspAspThrLeuArgAsnMetPro
<_____GENE: LACZ _____

2230      2240      2250      2260      2270      2280
          *         *         *         *         *         *
GCACCATGCCGTGGGTTTCAATATTGGCTTCATCCACCACATACAGGCCGTAGCGGTCGC
CGTGGTACGGCACCCAAAGTTATAACCGAAGTAGGTGGTGTATGTCCGGCATCGCCAGCG
<ValMetGlyHisThrGluIleAsnAlaGluAspValValTyrLeuGlyTyrArgAspCys
<_____GENE: LACZ _____

2290      2300      2310      2320      2330      2340
          *         *         *         *         *         *
ACAGCGTGTACCACAGCGGATGGTTCGGATAATGCGAACAGCGCACGGCGTTAAAGTTGT
TGTCGCACATGGTGTCGCCTACCAAGCCTATTACGCTTGTCGCGTGCCGCAATTTCAACA
<LeuThrTyrTrpLeuProHisAsnProTyrHisSerCysArgValAlaAsnPheAsnAsn
<_____GENE: LACZ _____

2350      2360      2370      2380      2390      2400
          *         *         *         *         *         *
TCTGCTTCATCAGCAGGATATCCTGCACCATCGTCTGCTCATCCATGACCTGACCATGCA
AGACGAAGTAGTCGTCCTATAGGACGTGGTAGCAGACGAGTAGGTACTGGACTGGTACGT
<GlnLysMetLeuLeuIleAspGlnValMetThrGlnGluAspMetValGlnGlyHisLeu
<_____GENE: LACZ _____

2410      2420      2430      2440      2450      2460
          *         *         *         *         *         *
GAGGATGATGCTCGTGACGGTTAACGCCTCGAATCAGCAACGGCTTGCCGTTCAGCAGCA
CTCCTACTACGAGCACTGCCAATTGCGGAGCTTAGTCGTTGCCGAACGGCAAGTCGTCGT
<ProHisHisGluHisArgAsnValGlyArgIleLeuLeuProLysGlyAsnLeuLeuLeu
<_____GENE: LACZ _____

2470      2480      2490      2500      2510      2520
          *         *         *         *         *         *
GCAGACCATTTTCAATCCGCACCTCGCGGAAACCGACATCGCAGGCTTCTGCTTCAATCA
CGTCTGGTAAAAGTTAGGCGTGGAGCGCCTTTGGCTGTAGCGTCCGAAGACGAAGTTAGT
<LeuGlyAsnGluIleArgValGluArgPheGlyValAspCysAlaGluAlaGluIleLeu
<_____GENE: LACZ _____

2530      2540      2550      2560      2570      2580
          *         *         *         *         *         *
GCGTGCCGTCGGCGGTGTGCAGTTCAACCACCGCACGATAGAGATTCGGGATTTCGGCGC
```

Fig. 34

```
CGCACGGCAGCCGCCACACGTCAAGTTGGTGGCGTGCTATCTCTAAGCCCTAAAGCCGCG
<ThrGlyAspAlaThrHisLeuGluValValAlaArgTyrLeuAsnProIleGluAlaSer
<_____GENE: LACZ_____

2590       2600       2610       2620       2630       2640
          *          *          *          *          *          *
TCCACAGTTTCGGGTTTTCGACGTTCAGACGTAGTGTGACGCGATCGGCATAACCACCAC
AGGTGTCAAAGCCCAAAAGCTGCAAGTCTGCATCACACTGCGCTAGCCGTATTGGTGGTG
<TrpLeuLysProAsnGluValAsnLeuArgLeuThrValArgAspAlaTyrGlyGlyArg
<_____GENE: LACZ_____

2650       2660       2670       2680       2690       2700
          *          *          *          *          *          *
GCTCATCGATAATTTCACCGCCGAAAGGCGCGGTGCCGCTGGCGACCTGCGTTTCACCCT
CGAGTAGCTATTAAAGTGGCGGCTTTCCGCGCCACGGCGACCGCTGGACGCAAAGTGGGA
<GluAspIleIleGluGlyGlyPheProAlaThrGlySerAlaValGlnThrGluGlyGln
<_____GENE: LACZ_____

2710       2720       2730       2740       2750       2760
          *          *          *          *          *          *
GCCATAAAGAAACTGTTACCCGTAGGTAGTCACGCAACTCGCCGCACATCTGAACTTCAG
CGGTATTTCTTTGACAATGGGCATCCATCAGTGCGTTGAGCGGCGTGTAGACTTGAAGTC
<TrpLeuSerValThrValArgLeuTyrAspArgLeuGluGlyCysMetGlnValGluAla
<_____GENE: LACZ_____

2770       2780       2790       2800       2810       2820
          *          *          *          *          *          *
CCTCCAGTACAGCGCGGCTGAAATCATCATTAAAGCGAGTGGCAACATGGAAATCGCTGA
GGAGGTCATGTCGCGCCGACTTTAGTAGTAATTTCGCTCACCGTTGTACCTTTAGCGACT
<GluLeuValAlaArgSerPheAspAspAsnPheArgThrAlaValHisPheAspSerIle
<_____GENE: LACZ_____

2830       2840       2850       2860       2870       2880
          *          *          *          *          *          *
TTTGTGTAGTCGGTTTATGCAGCAACGAGACGTCACGGAAAATGCCGCTCATCCGCCACA
AAACACATCAGCCAAATACGTCGTTGCTCTGCAGTGCCTTTTACGGCGAGTAGGCGGTGT
<GlnThrThrProLysHisLeuLeuSerValAspArgPheIleGlySerMetArgTrpMet
<_____GENE: LACZ_____

2890       2900       2910       2920       2930       2940
          *          *          *          *          *          *
TATCCTGATCTTCCAGATAACTGCCGTCACTCCAACGCAGCACCATCACCGCGAGGCGGT
ATAGGACTAGAAGGTCTATTGACGGCAGTGAGGTTGCGTCGTGGTAGTGGCGCTCCGCCA
<AspGlnAspGluLeuTyrSerGlyAspSerTrpArgLeuValMetValAlaLeuArgAsn
<_____GENE: LACZ_____

2950       2960       2970       2980       2990       3000
          *          *          *          *          *          *
TTTCTCCGGCGCGTAAAAATGCGCTCAGGTCAAATTCAGACGGCAAACGACTGTCCTGGC
AAAGAGGCCGCGCATTTTTACGCGAGTCCAGTTTAAGTCTGCCGTTTGCTGACAGGACCG
<GluGlyAlaArgLeuPheAlaSerLeuAspPheGluSerProLeuArgSerAspGlnGly
<_____GENE: LACZ_____

3010       3020       3030       3040       3050       3060
          *          *          *          *          *          *
CGTAACCGACCCAGCGCCCGTTGCACCACAGATGAAACGCCGAGTTAACGCCATCAAAAA
GCATTGGCTGGGTCGCGGGCAACGTGGTGTCTACTTTGCGGCTCAATTGCGGTAGTTTTT
```

Fig. 35

```
<TyrGlyValTrpArgGlyAsnCysTrpLeuHisPheAlaSerAsnValGlyAspPheIle
<_____GENE: LACZ _____

3070      3080      3090      3100      3110      3120
        *         *         *         *         *         *
TAATTCGCGTCTGGCCTTCCTGTAGCCAGCTTTCATCAACATTAAATGTGAGCGAGTAAC
ATTAAGCGCAGACCGGAAGGACATCGGTCGAAAGTAGTTGTAATTTACACTCGCTCATTG
<IleArgThrGlnGlyGluGlnLeuTrpSerGluAspValAsnPheThrLeuSerTyrCys
<_____GENE: LACZ _____

3130      3140      3150      3160      3170      3180
        *         *         *         *         *         *
AACCCGTCGGATTCTCCGTGGGAACAAACGGCGGATTGACCGTAATGGGATAGGTTACGT
TTGGGCAGCCTAAGAGGCACCCTTGTTTGCCGCCTAACTGGCATTACCCTATCCAATGCA
<GlyThrProAsnGluThrProValPheProProAsnValThrIleProTyrThrValAsn
<_____GENE: LACZ _____

3190      3200      3210      3220      3230      3240
        *         *         *         *         *         *
TGGTGTAGATGGGCGCATCGTAACCGTGCATCTGCCAGTTTGAGGGGACGACGACAGTAT
ACCACATCTACCCGCGTAGCATTGGCACGTAGACGGTCAAACTCCCCTGCTGCTGTCATA
<ThrTyrIleProAlaAspTyrGlyHisMetGlnTrpAsnSerProValValValThrAsp
<_____GENE: LACZ _____

3250      3260      3270      3280      3290      3300
        *         *         *         *         *         *
CGGCCTCAGGAAGATCGCACTCCAGCCAGCTTTCCGGCACCGCTTCTGGTGCCGGAAACC
GCCGGAGTCCTTCTAGCGTGAGGTCGGTCGAAAGGCCGTGGCGAAGACCACGGCCTTTGG
<AlaGluProLeuAspCysGluLeuTrpSerGluProValAlaGluProAlaProPheTrp
<_____GENE: LACZ _____

3310      3320      3330      3340      3350      3360
        *         *         *         *         *         *
AGGCAAAGCGCCATTCGCCATTCAGGCTGCGCAACTGTTGGGAAGGGCGATCGGTGCGGG
TCCGTTTCGCGGTAAGCGGTAAGTCCGACGCGTTGACAACCCTTCCCGCTAGCCACGCCC
<AlaPheArgTrpGluGlyAsnLeuSerArgLeuGlnGlnSerProArgAspThrArgAla
<_____GENE: LACZ _____

3370      3380      3390      3400      3410      3420
        *         *         *         *         *         *
CCTCTTCGCTATTACGCCAGCTGGCGAAAGGGGGATGTGCTGCAAGGCGATTAAGTTGGG
GGAGAAGCGATAATGCGGTCGACCGCTTTCCCCCTACACGACGTTCCGCTAATTCAACCC
<GluGluSerAsnArgTrpSerAlaPheProProHisAlaAlaLeuArgAsnLeuGlnThr
<_____GENE: LACZ _____

3430      3440      3450      3460      3470      3480
        *         *         *         *         * HIII    *
TAACGCCAGGGTTTTCCCAGTCACGACGTTGTAAAACGACGGCCAGTGCCAAGCTTGGAC
ATTGCGGTCCCAAAAGGGTCAGTGCTGCAACATTTTGCTGCCGGTCACGGTTCGAACCTG
<ValGlyProAsnGluTrpAspArgArgGlnLeuValVal                Nuc loc
<_____GENE: LACZ _____

3490      3500      3510      3520      3530      3540
        *         *         *         *         *         *
TCAAAAAACTTAGCAATTCTGAAGGAAAGTCCTTGGGGTCTTCTACCTTTCTCTTCTTTT
AGTTTTTTGAATCGTTAAGACTTCCTTTCAGGAACCCCAGAAGATGGAAAGAGAAGAAAA
```

Fig. 36

```
          3550        3560        3570        3580        3590        3600
            *           *           *           *           *           *
       TTGCGGAATTCCGGAAAACTTTATCCATCTTTGCAAAGCTTGGGTCTCCCTATAGTGAGT
       AACGCCTTAAGGCCTTTTGAAATAGGTAGAAACGTTTCGAACCCAGAGGGATATCACTCA
                       Nuc loc
          3610        3620        3630        3640        3650        3660
            *           *           *  Start codon *           *           *
       CGTATTAATTTCGATAAGCCAGTAAGCAGTGGGTTCTCTAGTTAGCCAGAGAGCTCTGCT
       GCATAATTAAAGCTATTCGGTCATTCGTCACCCAAGAGATCAATCGGTCTCTCGAGACGA 3670        3680        3690        3700        3710        3720
            *           *           *           *           *           *
       TATATAGACCTCCCACCGTACACGCCTACCGCCCATTTGCGTCAATGGGGCGGAGTTGTT
       ATATATCTGGAGGGTGGCATGTGCGGATGGCGGGTAAACGCAGTTACCCCGCCTCAACAA 3730        3740        3750        3760        3770        3780
            *           *           *           *           *           *
       ACGACATTTTGGAAAGTCCCGTTGATTTTGGTGCCAAAACAAACTCCCATTGACGTCAAT
       TGCTGTAAAACCTTTCAGGGCAACTAAAACCACGGTTTTGTTTGAGGGTAACTGCAGTTA 3790        3800        3810        3820        3830        3840
            *           *           *           *           *           *
       GGGGTGGAGACTTGGAAATCCCCGTGAGTCAAACCGCTATCCACGCCCATTGATGTACTG
       CCCCACCTCTGAACCTTTAGGGGCACTCAGTTTGGCGATAGGTGCGGGTAACTACATGAC 3850        3860        3870        3880        3890        3900
            *           *           *           *           *           *
       CCAAAACCGCATCACCATGGTAATAGCGATGACTAATACGTAGATGTACTGCCAAGTAGG
       GGTTTTGGCGTAGTGGTACCATTATCGCTACTGATTATGCATCTACATGACGGTTCATCC 3910        3920        3930        3940        3950        3960
            *           *           *           *           *           *
       AAAGTCCCATAAGGTCATGTACTGGGCATAATGCCAGGCGGGCCATTTACCGTCATTGAC
       TTTCAGGGTATTCCAGTACATGACCCGTATTACGGTCCGCCCGGTAAATGGCAGTAACTG 3970        3980        3990        4000        4010        4020
            *           *           *           *           *           *
       GTCAATAGGGGCGTACTTGGCATATGATACACTTGATGTACTGCCAAGTGGGCAGTTTA
       CAGTTATCCCCCGCATGAACCGTATACTATGTGAACTACATGACGGTTCACCCGTCAAAT 4030        4040        4050        4060        4070        4080
            *           *           *           *           *           *
       CCGTAAATAGTCCACCCATTGACGTCAATGGAAAGTCCCTATTGGCGTTACTATGGGAAC
       GGCATTTATCAGGTGGGTAACTGCAGTTACCTTTCAGGGATAACCGCAATGATACCCTTG 4090        4100        4110        4120        4130        4140
            *           *           *           *           *           *
       ATACGTCATTATTGACGTCAATGGGCGGGGGTCGTTGGGCGGTCAGCCAGGCGGGCCATT
       TATGCAGTAATAACTGCAGTTACCCGCCCCCAGCAACCCGCCAGTCGGTCCGCCCGGTAA 4150        4160        4170        4180        4190        4200
            *           *           *           *           *           *
       TACCGTAAGTTATGTAACGCGGAACTCCATATATGGGCTATGAACTAATGACCCCGTAAT
       ATGGCATTCAATACATTGCGCCTTGAGGTATATACCCGATACTTGATTACTGGGGCATTA 4210        4220        4230        4240        4250        4260
            *           *           *           *           *           *
```

Fig. 37

```
TGATTACTATTAATAACTAGTCAATAATCAATGTCAACGCGTATATCTGGCCCGTACATC
ACTAATGATAATTATTGATCAGTTATTAGTTACAGTTGCGCATATAGACCGGGCATGTAG 4270      4280      4290      4300      4310      4320
          *         *         *         *   ┌─Cla─┐  *         *
GCGAAGCAGCGCAAAACGCCTAACCCCGGGCCAGATCTGACATCGATTACGCCAAGCTTG
CGCTTCGTCGCGTTTTGCGGATTGGGGCCCGGTCTAGACTGTAGCTAATGCGGTTCGAAC
                                         └─      ─┘

4330      4340      4350      4360      4370      4380
          *         *       ┌─ * ─┐┌─Pac *─┐       *         *
CATGCCTGCAGGTTTAAACAGTCGACTCTAGACTTAATTAAGGATCTGGAAGGTGCTGAG
GTACGGACGTCCAAATTTGTCAGCTGAGATCTGAATTAATTCCTAGACCTTCCACGACTC
                        └─Xba─┘└─       ─┘       GlyArgCys***>
                                                 ─────────────>

4390      4400      4410      4420      4430      4440
          *         *         *         *         *         *
GTACGATGAGACCCGCACCAGGTGCAGACCCTGCGAGTGTGGCGGTAAACATATTAGGAA
CATGCTACTCTGGGCGTGGTCCACGTCTGGGACGCTCACACCGCCATTTGTATAATCCTT
GlyThrMetArgProAlaProGlyAlaAspProAlaSerValAlaValAsnIleLeuGly>
_____VIRAL RECOMBINATION SITE BP 3325-5792 FROM AD 5_____>

4450      4460      4470      4480      4490      4500
          *         *         *         *         *         *
CCAGCCTGTGATGCTGGATGTGACCGAGGAGCTGAGGCCCCGATCACTTGGTGCTGGCCTG
GGTCGGACACTACGACCTACACTGGCTCCTCGACTCCGGGCTAGTGAACCACGACCGGAC
ThrSerLeu***CysTrpMet***ProArgSer***GlyProIleThrTrpCysTrpPro>
_____VIRAL RECOMBINATION SITE BP 3325-5792 FROM AD 5_____>

4510      4520      4530      4540      4550      4560
          *         *         *         *         *         *
CACCCGCGCTGAGTTTGGCTCTAGCGATGAAGATACAGATTGAGGTACTGAAATGTGTGG
GTGGGCGCGACTCAAACCGAGATCGCTACTTCTATGTCTAACTCCATGACTTTACACACC
AlaProAlaLeuSerLeuAlaLeuAlaMetLysIleGlnIleGluValLeuLysCysVal>
_____VIRAL RECOMBINATION SITE BP 3325-5792 FROM AD 5_____>

4570      4580      4590      4600      4610      4620
          *         *         *         *         *         *
GCGTGGCTTAAGGGTGGGAAAGAATATATAAGGTGGGGGTCTTATGTAGTTTTGTATCTG
CGCACCGAATTCCCACCCTTTCTTATATATTCCACCCCCAGAATACATCAAAACATAGAC
GlyValAla***GlyTrpGluArgIleTyrLysValGlyValLeuCysSerPheValSer>
_____VIRAL RECOMBINATION SITE BP 3325-5792 FROM AD 5_____>

4630      4640      4650      4660      4670      4680
          *         *         *         *         *         *
TTTTGCAGCAGCCGCCGCCGCCATGAGCACCAACTCGTTTGATGGAAGCATTGTGAGCTC
AAAACGTCGTCGGCGGCGGCGGTACTCGTGGTTGAGCAAACTACCTTCGTAACACTCGAG
ValLeuGlnGlnProProProPro***AlaProThrArgLeuMetGluAlaLeu***Ala>
_____VIRAL RECOMBINATION SITE BP 3325-5792 FROM AD 5_____>

4690      4700      4710      4720      4730      4740
          *         *         *         *         *         *
ATATTTGACAACGCGCATGCCCCCATGGGCCGGGGTGCGTCAGAATGTGATGGGCTCCAG
TATAAACTGTTGCGCGTACGGGGGTACCCGGCCCCACGCAGTCTTACACTACCCGAGGTC
HisIle***GlnArgAlaCysProHisGlyProGlyCysValArgMet***TrpAlaPro>
_____VIRAL RECOMBINATION SITE BP 3325-5792 FROM AD 5_____>
```

Fig. 38

```
              4750      4760      4770      4780      4790      4800
                *         *         *         *         *         *
         CATTGATGGTCGCCCCGTCCTGCCCGCAAACTCTACTACCTTGACCTACGAGACCGTGTC
         GTAACTACCAGCGGGGCAGGACGGGCGTTTGAGATGATGGAACTGGATGCTCTGGCACAG
         AlaLeuMetValAlaProSerCysProGlnThrLeuLeuPro***ProThrArgProCys>
         _____VIRAL RECOMBINATION SITE BP 3325-5792 FROM AD 5_____>

4810      4820      4830      4840      4850      4860
                *         *         *         *         *         *
         TGGAACGCCGTTGGAGACTGCAGCCTCCGCCGCCGCTTCAGCCGCTGCAGCCACCGCCCG
         ACCTTGCGGCAACCTCTGACGTCGGAGGCGGCGGCGAAGTCGGCGACGTCGGTGGCGGGC
         LeuGluArgArgTrpArgLeuGlnProProProProLeuGlnProLeuGlnProProPro>
         _____VIRAL RECOMBINATION SITE BP 3325-5792 FROM AD 5_____>

4870      4880      4890      4900      4910      4920
                *         *         *         *         *         *
         CGGGATTGTGACTGACTTTGCTTTCCTGAGCCCGCTTGCAAGCAGTGCAGCTTCCCGTTC
         GCCCTAACACTGACTGAAACGAAAGGACTCGGGCGAACGTTCGTCACGTCGAAGGGCAAG
         AlaGlyLeu***LeuThrLeuLeuSer***AlaArgLeuGlnAlaValGlnLeuProVal>
         _____VIRAL RECOMBINATION SITE BP 3325-5792 FROM AD 5_____>

4930      4940      4950      4960      4970      4980
                *         *         *         *         *         *
         ATCCGCCCGCGATGACAAGTTGACGGCTCTTTTGGCACAATTGGATTCTTTGACCCGGGA
         TAGGCGGGCGCTACTGTTCAACTGCCGAGAAAACCGTGTTAACCTAAGAAACTGGGCCCT
         HisProProAlaMetThrSer***ArgLeuPheTrpHisAsnTrpIleLeu***ProGly>
         _____VIRAL RECOMBINATION SITE BP 3325-5792 FROM AD 5_____>

4990      5000      5010      5020      5030      5040
                *         *         *         *         *         *
         ACTTAATGTCGTTTCTCAGCAGCTGTTGGATCTGCGCCAGCAGGTTTCTGCCCTGAAGGC
         TGAATTACAGCAAAGAGTCGTCGACAACCTAGACGCGGTCGTCCAAAGACGGGACTTCCG
         AsnLeuMetSerPheLeuSerSerCysTrpIleCysAlaSerArgPheLeuPro***Arg>
         _____VIRAL RECOMBINATION SITE BP 3325-5792 FROM AD 5_____>

5050      5060      5070      5080      5090      5100
                *         *         *         *         *         *
         TTCCTCCCCTCCCAATGCGGTTTAAAACATAAATAAAAAACCAGACTCTGTTTGGATTTG
         AAGGAGGGGAGGGTTACGCCAAATTTTGTATTTATTTTTTGGTCTGAGACAAACCTAAAC
         LeuProProLeuProMetArgPheLysThr***IleLysAsnGlnThrLeuPheGlyPhe>
         _____VIRAL RECOMBINATION SITE BP 3325-5792 FROM AD 5_____>

5110      5120      5130      5140      5150      5160
                *         *         *         *         *         *
         GATCAAGCAAGTGTCTTGCTGTCTTTATTTAGGGGTTTTGCGCGCGCGGTAGGCCCGGGA
         CTAGTTCGTTCACAGAACGACAGAAATAAATCCCCAAAACGCGCGCGCCATCCGGGCCCT
         GlySerSerLysCysLeuAlaValPheIle***GlyPheCysAlaArgGlyArgProGly>
         _____VIRAL RECOMBINATION SITE BP 3325-5792 FROM AD 5_____>

5170      5180      5190      5200      5210      5220
                *         *         *         *         *         *
         CCAGCGGTCTCGGTCGTTGAGGGTCCTGTGTATTTTTTCCAGGACGTGGTAAAGGTGACT
         GGTCGCCAGAGCCAGCAACTCCCAGGACACATAAAAAAGGTCCTGCACCATTTCCACTGA
         ThrSerGlyLeuGlyArg***GlySerCysValPhePheProGlyArgGlyLysGlyAsp>
         _____VIRAL RECOMBINATION SITE BP 3325-5792 FROM AD 5_____>

```
        *         *         *         *         *         *
CTGGATGTTCAGATACATGGGCATAAGCCCGTCTCTGGGGTGGAGGTAGCACCACTGCAG
GACCTACAAGTCTATGTACCCGTATTCGGGCAGAGACCCCACCTCCATCGTGGTGACGTC
SerGlyCysSerAspThrTrpAla***AlaArgLeuTrpGlyGlyGlySerThrThrAla>
_____VIRAL RECOMBINATION SITE BP 3325-5792 FROM AD 5_____>

5290      5300      5310      5320      5330      5340
        *         *         *         *         *         *
AGCTTCATGCTGCGGGGTGGTGTTGTAGATGATCCAGTCGTAGCAGGAGCGCTGGGCGTG
TCGAAGTACGACGCCCCACCACAACATCTACTAGGTCAGCATCGTCCTCGCGACCCGCAC
GluLeuHisAlaAlaGlyTrpCysCysArg***SerSerArgSerArgSerAlaGlyArg>
_____VIRAL RECOMBINATION SITE BP 3325-5792 FROM AD 5_____>

5350      5360      5370      5380      5390      5400
        *         *         *         *         *         *
GTGCCTAAAAATGTCTTTCAGTAGCAAGCTGATTGCCAGGGGCAGGCCCTTGGTGTAAGT
CACGGATTTTTACAGAAAGTCATCGTTCGACTAACGGTCCCCGTCCGGGAACCACATTCA
GlyAla***LysCysLeuSerValAlaSer***LeuProGlyAlaGlyProTrpCysLys>
_____VIRAL RECOMBINATION SITE BP 3325-5792 FROM AD 5_____>

5410      5420      5430      5440      5450      5460
        *         *         *         *         *         *
GTTTACAAAGCGGTTAAGCTGGGATGGGTGCATACGTGGGGATATGAGATGCATCTTGGA
CAAATGTTTCGCCAATTCGACCCTACCCACGTATGCACCCCTATACTCTACGTAGAACCT
CysLeuGlnSerGly***AlaGlyMetGlyAlaTyrValGlyIle***AspAlaSerTrp>
_____VIRAL RECOMBINATION SITE BP 3325-5792 FROM AD 5_____>

5470      5480      5490      5500      5510      5520
        *         *         *         *         *         *
CTGTATTTTTAGGTTGGCTATGTTCCCAGCCATATCCCTCCGGGGATTCATGTTGTGCAG
GACATAAAAATCCAACCGATACAAGGGTCGGTATAGGGAGGCCCCTAAGTACAACACGTC
ThrValPheLeuGlyTrpLeuCysSerGlnProTyrProSerGlyAspSerCysCysAla>
_____VIRAL RECOMBINATION SITE BP 3325-5792 FROM AD 5_____>

5530      5540      5550      5560      5570      5580
        *         *         *         *         *         *
AACCACCAGCACAGTGTATCCGGTGCACTTGGGAAATTTGTCATGTAGCTTAGAAGGAAA
TTGGTGGTCGTGTCACATAGGCCACGTGAACCCTTTAAACAGTACATCGAATCTTCCTTT
GluProProAlaGlnCysIleArgCysThrTrpGluIleCysHisValAla***LysGlu>
_____VIRAL RECOMBINATION SITE BP 3325-5792 FROM AD 5_____>

5590      5600      5610      5620      5630      5640
        *         *         *         *         *         *
TGCGTGGAAGAACTTGGAGACGCCCTTGTGACCTCCAAGATTTTCCATGCATTCGTCCAT
ACGCACCTTCTTGAACCTCTGCGGGAACACTGGAGGTTCTAAAAGGTACGTAAGCAGGTA
MetArgGlyArgThrTrpArgArgProCysAspLeuGlnAspPheProCysIleArgPro>
_____VIRAL RECOMBINATION SITE BP 3325-5792 FROM AD 5_____>

5650      5660      5670      5680      5690      5700
        *         *         *         *         *         *
AATGATGGCAATGGGCCCACGGGCGGCGGCCTGGGCGAAGATATTTCTGGGATCACTAAC
TTACTACCGTTACCCGGGTGCCCGCCGCCGGACCCGCTTCTATAAAGACCCTAGTGATTG
******TrpGlnTrpAlaHisGlyArgArgProGlyArgArgTyrPheTrpAspHis***>
_____VIRAL RECOMBINATION SITE BP 3325-5792 FROM AD 5_____>

```
GTCATAGTTGTGTTCCAGGATGAGATCGTCATAGGCCATTTTTACAAAGCGCGGGCGGAG
CAGTATCAACACAAGGTCCTACTCTAGCAGTATCCGGTAAAAATGTTTCGCGCCCGCCTC
ArgHisSerCysValProGly***AspArgHisArgProPheLeuGlnSerAlaGlyGly>
_____VIRAL RECOMBINATION SITE BP 3325-5792 FROM AD 5_____>

5770      5780      5790      5800      5810      5820
          *         *         *         *         *         *
GGTGCCAGACTGCGGTATAATGGTTCCATCCGGCCCAGGGGCGTAGTTACCCTCACAGAT
CCACGGTCTGACGCCATATTACCAAGGTAGGCCGGGTCCCCGCATCAATGGGAGTGTCTA
GlyCysGlnThrAlaVal***TrpPheHisProAlaGlnGlyArgSerTyrProHisArg>
_____VIRAL RECOMBINATION SITE BP 3325-5792 FROM AD 5_____>

5830      5840      5850      5860      5870      5880
          *         *         *         *         *         *
TTGCATTTCCCACGCTTTGAGTTCAGATGGGGGGATCATGTCTACCTGCGGGGCGATGAA
AACGTAAAGGGTGCGAAACTCAAGTCTACCCCCCTAGTACAGATGGACGCCCCGCTACTT
PheAlaPheProThrLeu***ValGlnMetGlyGlySerCysLeuProAlaGlyArg***>
_____VIRAL RECOMBINATION SITE BP 3325-5792 FROM AD 5_____>

5890      5900      5910      5920      5930      5940
          *         *         *         *         *         *
GAAAACGGTTTCCGGGGTAGGGGAGATCAGCTGGGAAGAAAGCAGGTTCCTGAGCAGCTG
CTTTTGCCAAAGGCCCCATCCCCTCTAGTCGACCCTTCTTTCGTCCAAGGACTCGTCGAC
ArgLysArgPheProGly***GlyArgSerAlaGlyLysLysAlaGlySer***AlaAla>
_____VIRAL RECOMBINATION SITE BP 3325-5792 FROM AD 5_____>

5950      5960      5970      5980      5990      6000
          *         *         *         *         *         *
CGACTTACCGCAGCCGGTGGGCCCGTAAATCACACCTATTACCGGGTGCAACTGGTAGTT
GCTGAATGGCGTCGGCCACCCGGGCATTTAGTGTGGATAATGGCCCACGTTGACCATCAA
AlaThrTyrArgSerArgTrpAlaArgLysSerHisLeuLeuProGlyAlaThrGlySer>
_____VIRAL RECOMBINATION SITE BP 3325-5792 FROM AD 5_____>

6010      6020      6030      6040      6050      6060
          *         *         *         *         *         *
AAGAGAGCTGCAGCTGCCGTCATCCCTGAGCAGGGGGGCCACTTCGTTAAGCATGTCCCT
TTCTCTCGACGTCGACGGCAGTAGGGACTCGTCCCCCCGGTGAAGCAATTCGTACAGGGA
*GluSerCysSerCysArgHisPro*AlaGlyGlyProLeuArg***AlaCysPro>
_____VIRAL RECOMBINATION SITE BP 3325-5792 FROM AD 5_____>

6070      6080      6090      6100      6110      6120
          *         *         *         *         *         *
GACTCGCATGTTTTCCCTGACCAAATCCGCCAGAAGGCGCTCGCCGCCCAGCGATAGCAG
CTGAGCGTACAAAAGGGACTGGTTTAGGCGGTCTTCCGCGAGCGGCGGGTCGCTATCGTC
*LeuAlaCysPhePro*ProAsnProProGluGlyAlaArgArgProAlaIleAla>
_____VIRAL RECOMBINATION SITE BP 3325-5792 FROM AD 5_____>

6130      6140      6150      6160      6170      6180
          *         *         *         *         *         *
TTCTTGCAAGGAAGCAAAGTTTTTCAACGGTTTGAGACCGTCCGCCGTAGGCATGCTTTT
AAGAACGTTCCTTCGTTTCAAAAAGTTGCCAAACTCTGGCAGCGGCATCCGTACGAAAA
ValLeuAlaArgLysGlnSerPheSerThrVal***AspArgProPro***AlaCysPhe>
_____VIRAL RECOMBINATION SITE BP 3325-5792 FROM AD 5_____>

6190      6200      6210      6220      6230      6240
          *         *         *         *         *         *
GAGCGTTTGACCAAGCAGTTCCAGGCGGTCCCACAGCTCGGTCACCTGCTCTACGGCATC
```

Fig. 41

```
           CTCGCAAACTGGTTCGTCAAGGTCCGCCAGGGTGTCGAGCCAGTGGACGAGATGCCGTAG
           ***AlaPheAspGlnAlaValProGlyGlyProThrAlaArgSerProAlaLeuArgHis>
              _____VIRAL RECOMBINATION SITE BP 3325-5792 FROM AD 5_____>

6250      6260      6270      6280      6290      6300
                 *         *         *         *         *         *
           TCGATCCAGCATATCTCCTCGTTTCGCGGGTTGGGGCGGCTTTCGCTGTACGGCAGTAGT
           AGCTAGGTCGTATAGAGGAGCAAAGCGCCCAACCCCGCCGAAAGCGACATGCCGTCATCA
           LeuAspProAlaTyrLeuLeuValSerArgValGlyAlaAlaPheAlaValArgGln***>
              _____VIRAL RECOMBINATION SITE BP 3325-5792 FROM AD 5_____>

6310      6320      6330      6340      6350      6360
                 *         *         *         *         *         *
           CGGTGCTCGTCCAGACGGGCCAGGGTCATGTCTTTCCACGGGCGCAGGGTCCTCGTCAGC
           GCCACGAGCAGGTCTGCCCGGTCCCAGTACAGAAAGGTGCCCGCGTCCCAGGAGCAGTCG
           SerValLeuValGlnThrGlyGlnGlyHisValPheProArgAlaGlnGlyProArgGln>
              _____VIRAL RECOMBINATION SITE BP 3325-5792 FROM AD 5_____>

6370      6380      6390      6400      6410      6420
                 *         *         *         *         *         *
           GTAGTCTGGGTCACGGTGAAGGGGTGCGCTCCGGGCTGCGCGCTGGCCAGGGTGCGCTTG
           CATCAGACCCAGTGCCACTTCCCCACGCGAGGCCCGACGCGCGACCGGTCCCACGCGAAC
           ArgSerLeuGlyHisGlyGluGlyValArgSerGlyLeuArgAlaGlyGlnGlyAlaLeu>
              _____VIRAL RECOMBINATION SITE BP 3325-5792 FROM AD 5_____>

6430      6440      6450      6460      6470      6480
                 *         *         *         *         *         *
           AGGCTGGTCCTGCTGGTGCTGAAGCGCTGCCGGTCTTCGCCCTGCGCGTCGGCCAGGTAG
           TCCGACCAGGACGACCACGACTTCGCGACGGCCAGAAGCGGGACGCGCAGCCGGTCCATC
           GluAlaGlyProAlaGlyAlaGluAlaLeuProValPheAlaLeuArgValGlyGlnVal>
              _____VIRAL RECOMBINATION SITE BP 3325-5792 FROM AD 5_____>

6490      6500      6510      6520      6530      6540
                 *         *         *         *         *         *
           CATTTGACCATGGTGTCATAGTCCAGCCCCTCCGCGGCGTGGCCCTTGGCGCGCAGCTTG
           GTAAACTGGTACCACAGTATCAGGTCGGGGAGGCGCCGCACCGGGAACCGCGCGTCGAAC
           AlaPheAspHisGlyValIleValGlnProLeuArgGlyValAlaLeuGlyAlaGlnLeu>
              _____VIRAL RECOMBINATION SITE BP 3325-5792 FROM AD 5_____>

6550      6560      6570      6580      6590      6600
                 *         *         *         *         *         *
           CCCTTGGAGGAGGCGCCGCACGAGGGGCAGTGCAGACTTTTGAGGGCGTAGAGCTTGGGC
           GGGAACCTCCTCCGCGGCGTGCTCCCCGTCACGTCTGAAAACTCCCGCATCTCGAACCCG
           AlaLeuGlyGlyGlyAlaAlaArgGlyAlaValGlnThrPheGluGlyValGluLeuGly>
              _____VIRAL RECOMBINATION SITE BP 3325-5792 FROM AD 5_____>

6610      6620      6630      6640      6650      6660
                 *         *         *         *         *         *
           GCGAGAAATACCGATTCCGGGGAGTAGGCATCCGCGCCGCAGGCCCCGCAGACGGTCTCG
           CGCTCTTTATGGCTAAGGCCCCTCATCCGTAGGCGCGGCGTCCGGGGCGTCTGCCAGAGC
           ArgGluLysTyrArgPheArgGlyValGlyIleArgAlaAlaGlyProAlaAspGlyLeu>
              _____VIRAL RECOMBINATION SITE BP 3325-5792 FROM AD 5_____>

6670      6680      6690      6700      6710      6720
                 *         *         *         *         *         *
           CATTCCACGAGCCAGGTGAGCTCTGGCCGTTCGGGGTCAAAAACCAGGTTTCCCCCATGC
           GTAAGGTGCTCGGTCCACTCGAGACCGGCAAGCCCCAGTTTTTGGTCCAAAGGGGGTACG
```

Fig. 42

```
AlaPheHisGluProGlyGluLeuTrpProPheGlyValLysAsnGlnValSerProMet>
_____VIRAL RECOMBINATION SITE BP 3325-5792 FROM AD 5_____>

6730       6740       6750       6760       6770       6780
         *          *          *          *          *          *
TTTTTGATGCGTTTCTTACCTCTGGTTTCCATGAGCCGGTGTCCACGCTCGGTGACGAAA
AAAAACTACGCAAAGAATGGAGACCAAAGGTACTCGGCCACAGGTGCGAGCCACTGCTTT
LeuPheAspAlaPheLeuThrSerGlyPheHisGluProValSerThrLeuGlyAspGlu>
_____VIRAL RECOMBINATION SITE BP 3325-5792 FROM AD 5_____>

6790       6800       6810       6820       6830       6840
         *          *          *          *          *          *
AGGCTGTCCGTGTCCCCGTATACAGACTTGAGAGGCCTGTCCTCGAGGATCAGCTTCCGG
TCCGACAGGCACAGGGGCATATGTCTGAACTCTCCGGACAGGAGCTCCTAGTCGAAGGCC
LysAlaValArgValProValTyrArgLeuGluArgProValLeuGlu>
___VIRAL RECOMBINATION SITE BP 3325-5792 FR____>

6850       6860       6870       6880       6890       6900
         *          *          *          *          *          *
TCTCCCTATAGTGAGTCGTATTAATTTCGATAAGCCAGCTGCATTAATGAATCGGCCAAC
AGAGGGATATCACTCAGCATAATTAAAGCTATTCGGTCGACGTAATTACTTAGCCGGTTG 6910       6920       6930       6940       6950       6960
         *          *          *          *          *          *
GCGCGGGGAGAGGCGGTTTGCGTATTGGGCGCTCTTCCGCTTCCTCGCTCACTGACTCGC
CGCGCCCCTCTCCGCCAAACGCATAACCCGCGAGAAGGCGAAGGAGCGAGTGACTGAGCG 6970       6980       6990       7000       7010       7020
         *          *          *          *          *          *
TGCGCTCGGTCGTTCGGCTGCGGCGAGCGGTATCAGCTCACTCAAAGGCGGTAATACGGT
ACGCGAGCCAGCAAGCCGACGCCGCTCGCCATAGTCGAGTGAGTTTCCGCCATTATGCCA 7030       7040       7050       7060       7070       7080
         *          *          *          *          *          *
TATCCACAGAATCAGGGGATAACGCAGGAAAGAACATGTGAGCAAAAGGCCAGCAAAAGG
ATAGGTGTCTTAGTCCCCTATTGCGTCCTTTCTTGTACACTCGTTTTCCGGTCGTTTTCC 7090       7100       7110       7120       7130       7140
         *          *          *          *          *          *
CCAGGAACCGTAAAAAGGCCGCGTTGCTGGCGTTTTTCCATAGGCTCCGCCCCCCTGACG
GGTCCTTGGCATTTTTCCGGCGCAACGACCGCAAAAAGGTATCCGAGGCGGGGGGACTGC 7150       7160       7170       7180       7190       7200
         *          *          *          *          *          *
AGCATCACAAAAATCGACGCTCAAGTCAGAGGTGGCGAAACCCGACAGGACTATAAAGAT
TCGTAGTGTTTTTAGCTGCGAGTTCAGTCTCCACCGCTTTGGGCTGTCCTGATATTTCTA 7210       7220       7230       7240       7250       7260
         *          *          *          *          *          *
ACCAGGCGTTTCCCCCTGGAAGCTCCCTCGTGCGCTCTCCTGTTCCGACCCTGCCGCTTA
TGGTCCGCAAAGGGGGACCTTCGAGGGAGCACGCGAGAGGACAAGGCTGGGACGGCGAAT 7270       7280       7290       7300       7310       7320
         *          *          *          *          *          *
CCGGATACCTGTCCGCCTTTCTCCCTTCGGGAAGCGTGGCGCTTTCTCATAGCTCACGCT
GGCCTATGGACAGGCGGAAAGAGGGAAGCCCTTCGCACCGCGAAAGAGTATCGAGTGCGA
```

Fig. 43

```
         7330      7340      7350      7360      7370      7380
           *         *         *         *         *         *
GTAGGTATCTCAGTTCGGTGTAGGTCGTTCGCTCCAAGCTGGGCTGTGTGCACGAACCCC
CATCCATAGAGTCAAGCCACATCCAGCAAGCGAGGTTCGACCCGACACACGTGCTTGGGG 7390      7400      7410      7420      7430      7440
           *         *         *         *         *         *
CCGTTCAGCCCGACCGCTGCGCCTTATCCGGTAACTATCGTCTTGAGTCCAACCCGGTAA
GGCAAGTCGGGCTGGCGACGCGGAATAGGCCATTGATAGCAGAACTCAGGTTGGGCCATT 7450      7460      7470      7480      7490      7500
           *         *         *         *         *         *
GACACGACTTATCGCCACTGGCAGCAGCCACTGGTAACAGGATTAGCAGAGCGAGGTATG
CTGTGCTGAATAGCGGTGACCGTCGTCGGTGACCATTGTCCTAATCGTCTCGCTCCATAC 7510      7520      7530      7540      7550      7560
           *         *         *         *         *         *
TAGGCGGTGCTACAGAGTTCTTGAAGTGGTGGCCTAACTACGGCTACACTAGAAGGACAG
ATCCGCCACGATGTCTCAAGAACTTCACCACCGGATTGATGCCGATGTGATCTTCCTGTC 7570      7580      7590      7600      7610      7620
           *         *         *         *         *         *
TATTTGGTATCTGCGCTCTGCTGAAGCCAGTTACCTTCGGAAAAAGAGTTGGTAGCTCTT
ATAAACCATAGACGCGAGACGACTTCGGTCAATGGAAGCCTTTTTCTCAACCATCGAGAA 7630      7640      7650      7660      7670      7680
           *         *         *         *         *         *
GATCCGGCAAACAAACCACCGCTGGTAGCGGTGGTTTTTTTGTTTGCAAGCAGCAGATTA
CTAGGCCGTTTGTTTGGTGGCGACCATCGCCACCAAAAAAACAAACGTTCGTCGTCTAAT 7690      7700      7710      7720      7730      7740
           *         *         *         *         *         *
CGCGCAGAAAAAAGGATCTCAAGAAGATCCTTTGATCTTTTCTACGGGGTCTGACGCTC
GCGCGTCTTTTTTTCCTAGAGTTCTTCTAGGAAACTAGAAAAGATGCCCCAGACTGCGAG 7750      7760      7770      7780      7790      7800
           *         *         *         *         *         *
AGTGGAACGAAAACTCACGTTAAGGGATTTTGGTCATGAGATTATCAAAAAGGATCTTCA
TCACCTTGCTTTTGAGTGCAATTCCCTAAAACCAGTACTCTAATAGTTTTTCCTAGAAGT 7810      7820      7830      7840      7850      7860
           *         *         *         *         *         *
CCTAGATCCTTTTAAATTAAAAATGAAGTTTTAAATCAATCTAAAGTATATATGAGTAAA
GGATCTAGGAAAATTTAATTTTTACTTCAAAATTTAGTTAGATTTCATATATACTCATTT 7870      7880      7890      7900      7910      7920
           *         *         *         *         *         *
CTTGGTCTGACAGTTACCAATGCTTAATCAGTGAGGCACCTATCTCAGCGATCTGTCTAT
GAACCAGACTGTCAATGGTTACGAATTAGTCACTCCGTGGATAGAGTCGCTAGACAGATA 7930      7940      7950      7960      7970      7980
           *         *         *         *         *         *
TTCGTTCATCCATAGTTGCCTGACTCCCCGTCGTGTAGATAACTACGATACGGGAGGGCT
AAGCAAGTAGGTATCAACGGACTGAGGGGCAGCACATCTATTGATGCTATGCCCTCCCGA 7990      8000      8010      8020      8030      8040
           *         *         *         *         *         *
```

Fig. 44

```
TACCATCTGGCCCCAGTGCTGCAATGATACCGCGAGACCCACGCTCACCGGCTCCAGATT
ATGGTAGACCGGGGTCACGACGTTACTATGGCGCTCTGGGTGCGAGTGGCCGAGGTCTAA 8050      8060      8070      8080      8090      8100
           *         *         *         *         *         *
TATCAGCAATAAACCAGCCAGCCGGAAGGGCCGAGCGCAGAAGTGGTCCTGCAACTTTAT
ATAGTCGTTATTTGGTCGGTCGGCCTTCCCGGCTCGCGTCTTCACCAGGACGTTGAAATA 8110      8120      8130      8140      8150      8160
           *         *         *         *         *         *
CCGCCTCCATCCAGTCTATTAATTGTTGCCGGGAAGCTAGAGTAAGTAGTTCGCCAGTTA
GGCGGAGGTAGGTCAGATAATTAACAACGGCCCTTCGATCTCATTCATCAAGCGGTCAAT 8170      8180      8190      8200      8210      8220
           *         *         *         *         *         *
ATAGTTTGCGCAACGTTGTTGCCATTGCTACAGGCATCGTGGTGTCACGCTCGTCGTTTG
TATCAAACGCGTTGCAACAACGGTAACGATGTCCGTAGCACCACAGTGCGAGCAGCAAAC 8230      8240      8250      8260      8270      8280
           *         *         *         *         *         *
GTATGGCTTCATTCAGCTCCGGTTCCCAACGATCAAGGCGAGTTACATGATCCCCCATGT
CATACCGAAGTAAGTCGAGGCCAAGGGTTGCTAGTTCCGCTCAATGTACTAGGGGGTACA 8290      8300      8310      8320      8330      8340
           *         *         *         *         *         *
TGTGCAAAAAAGCGGTTAGCTCCTTCGGTCCTCCGATCGTTGTCAGAAGTAAGTTGGCCG
ACACGTTTTTTCGCCAATCGAGGAAGCCAGGAGGCTAGCAACAGTCTTCATTCAACCGGC 8350      8360      8370      8380      8390      8400
           *         *         *         *         *         *
CAGTGTTATCACTCATGGTTATGGCAGCACTGCATAATTCTCTTACTGTCATGCCATCCG
GTCACAATAGTGAGTACCAATACCGTCGTGACGTATTAAGAGAATGACAGTACGGTAGGC 8410      8420      8430      8440      8450      8460
           *         *         *         *         *         *
TAAGATGCTTTTCTGTGACTGGTGAGTACTCAACCAAGTCATTCTGAGAATAGTGTATGC
ATTCTACGAAAAGACACTGACCACTCATGAGTTGGTTCAGTAAGACTCTTATCACATACG 8470      8480      8490      8500      8510      8520
           *         *         *         *         *         *
GGCGACCGAGTTGCTCTTGCCCGGCGTCAATACGGGATAATACCGCGCCACATAGCAGAA
CCGCTGGCTCAACGAGAACGGGCCGCAGTTATGCCCTATTATGGCGCGGTGTATCGTCTT 8530      8540      8550      8560      8570      8580
           *         *         *         *         *         *
CTTTAAAAGTGCTCATCATTGGAAAACGTTCTTCGGGGCGAAAACTCTCAAGGATCTTAC
GAAATTTTCACGAGTAGTAACCTTTTGCAAGAAGCCCCGCTTTTGAGAGTTCCTAGAATG 8590      8600      8610      8620      8630      8640
           *         *         *         *         *         *
CGCTGTTGAGATCCAGTTCGATGTAACCCACTCGTGCACCCAACTGATCTTCAGCATCTT
GCGACAACTCTAGGTCAAGCTACATTGGGTGAGCACGTGGGTTGACTAGAAGTCGTAGAA 8650      8660      8670      8680      8690      8700
           *         *         *         *         *         *
TTACTTTCACCAGCGTTTCTGGGTGAGCAAAAACAGGAAGGCAAAATGCCGCAAAAAAGG
AATGAAAGTGGTCGCAAAGACCCACTCGTTTTTGTCCTTCCGTTTTACGGCGTTTTTTCC
```

Fig. 45

```
           8710        8720        8730        8740        8750        8760
             *           *           *           *           *           *
GAATAAGGGCGACACGGAAATGTTGAATACTCATACTCTTCCTTTTTCAATATTATTGAA
CTTATTCCCGCTGTGCCTTTACAACTTATGAGTATGAGAAGGAAAAAGTTATAATAACTT 8770        8780        8790        8800        8810        8820
             *           *           *           *           *           *
GCATTTATCAGGGTTATTGTCTCATGAGCGGATACATATTTGAATGTATTTAGAAAAATA
CGTAAATAGTCCCAATAACAGAGTACTCGCCTATGTATAAACTTACATAAATCTTTTTAT 8830        8840        8850        8860        8870        8880
             *           *           *           *           *           *
AACAAATAGGGGTTCCGCGCACATTTCCCCGAAAAGTGCCACCTGACGTCTAAGAAACCA
TTGTTTATCCCCAAGGCGCGTGTAAAGGGGCTTTTCACGGTGGACTGCAGATTCTTTGGT 8890        8900        8910        8920        8930        8940
             *           *           *           *           *           *
TTATTATCATGACATTAACCTATAAAAATAGGCGTATCACGAGGCCCTTTCGTCTCGCGC
AATAATAGTACTGTAATTGGATATTTTTATCCGCATAGTGCTCCGGGAAAGCAGAGCGCG 8950        8960        8970        8980        8990        9000
             *           *           *           *           *           *
GTTTCGGTGATGACGGTGAAAACCTCTGACACATGCAGCTCCCGGAGACGGTCACAGCTT
CAAAGCCACTACTGCCACTTTTGGAGACTGTGTACGTCGAGGGCCTCTGCCAGTGTCGAA 9010        9020        9030        9040        9050        9060
             *           *           *           *           *           *
GTCTGTAAGCGGATGCCGGGAGCAGACAAGCCCGTCAGGGCGCGTCAGCGGGTGTTGGCG
CAGACATTCGCCTACGGCCCTCGTCTGTTCGGGCAGTCCCGCGCAGTCGCCCACAACCGC 9070        9080        9090        9100        9110        9120
             *           *           *           *           *           *
GGTGTCGGGGCTGGCTTAACTATGCGGCATCAGAGCAGATTGTACTGAGAGTGCACCATA
CCACAGCCCCGACCGAATTGATACGCCGTAGTCTCGTCTAACATGACTCTCACGTGGTAT 9130        9140        9150        9160        9170        9180
             *           *           *           *           *           *
TCGACGCTCTCCCTTATGCGACTCCTGCATTAGGAAGCAGCCCAGTAGTAGGTTGAGGCC
AGCTGCGAGAGGGAATACGCTGAGGACGTAATCCTTCGTCGGGTCATCATCCAACTCCGG 9190        9200        9210        9220        9230        9240
             *           *           *           *           *           *
GTTGAGCACCGCCGCCGCAAGGAATGGTGCAAGGAGATGGCGCCCAACAGTCCCCCGGCC
CAACTCGTGGCGGCGGCGTTCCTTACCACGTTCCTCTACCGCGGGTTGTCAGGGGGCCGG 9250        9260        9270        9280        9290        9300
             *           *           *           *           *           *
ACGGGGCCTGCCACCATACCCACGCCGAAACAAGCGCTCATGAGCCCGAAGTGGCGAGCC
TGCCCCGGACGGTGGTATGGGTGCGGCTTTGTTCGCGAGTACTCGGGCTTCACCGCTCGG 9310        9320        9330        9340        9350        9360
             *           *           *           *           *           *
CGATCTTCCCCATCGGTGATGTCGGCGATATAGGCGCCAGCAACCGCACCTGTGGCGCCG
GCTAGAAGGGGTAGCCACTACAGCCGCTATATCCGCGGTCGTTGGCGTGGACACCGCGGC 9370        9380        9390        9400        9410        9420
```

Fig. 46

```
         *         *         *         *         *         *
GTGATGCCGGCCACGATGCGTCCGGCGTAGAGGATCTGGCTAGCGATGACCCTGCTGATT
CACTACGGCCGGTGCTACGCAGGCCGCATCTCCTAGACCGATCGCTACTGGGACGACTAA 9430      9440      9450      9460      9470      9480
         *         *         *         *         *         *
GGTTCGCTGACCATTTCCGGGGTGCGGAACGGCGTTACCAGAAACTCAGAAGGTTCGTCC
CCAAGCGACTGGTAAAGGCCCCACGCCTTGCCGCAATGGTCTTTGAGTCTTCCAAGCAGG 9490      9500      9510      9520      9530      9540
         *         *         *         *         *         *
AACCAAACCGACTCTGACGGCAGTTTACGAGAGAGATGATAGGGTCTGCTTCAGTAAGCC
TTGGTTTGGCTGAGACTGCCGTCAAATGCTCTCTCTACTATCCCAGACGAAGTCATTCGG 9550      9560      9570      9580      9590      9600
         *         *         *         *         *         *
AGATGCTACACAATTAGGCTTGTACATATTGTCGTTAGAACGCGGCTACAATTAATACAT
TCTACGATGTGTTAATCCGAACATGTATAACAGCAATCTTGCGCCGATGTTAATTATGTA 9610      9620      9630      9640
         *         *         *         *
AACCTTATGTATCATACACATACGATTTAGGTGACACTATA
TTGGAATACATAGTATGTGTATGCTAAATCCACTGTGATAT
```

```
Sequence Range: 1 to 34413

10        20        30        40        50        60
           *         *         *         *         *         *
CATCATCAATAATATACCTTATTTTGGATTGAAGCCAATATGATAATGAGGGGGTGGAGT 70        80        90       100       110       120
           *         *         *         *         *         *
TTGTGACGTGGCGCGGGGCGTGGGAACGGGGCGGGTGACGTAGTAGTGTGGCGGAAGTGT 130       140       150       160       170       180
           *         *         *         *         *         *
GATGTTGCAAGTGTGGCGGAACACATGTAAGCGACGGATGTGGCAAAAGTGACGTTTTTG 190       200       210       220       230       240
           *         *         *         *         *         *
GTGTGCGCCGGTGTCAGATCCAGACATGATAAGATACATTGATGAGTTTGGACAAACCAC 250       260       270       280       290       300
           *         *         *         *         *         *
AACTAGAATGCAGTGAAAAAAATGCTTTATTTGTGAAATTTGTGATGCTATTGCTTTATT 310       320       330       340       350       360
           *         *         *         *         *         *
TGTAACCATTATAAGCTGCAATAAACAGGATCTTATTTTTGACACCAGACCAACTGGTAA
                                    <***LysGlnCysTrpValLeuGlnTyr
                                    <_____GENE: LACZ_____

370       380       390       400       410       420
           *         *         *         *         *         *
TGGTAGCGACCGGCGCTCAGCTGGAATTCCGCCGATACTGACGGGCTCCAGGAGTCGTCG
<HisTyrArgGlyAlaSerLeuGlnPheGluAlaSerValSerProSerTrpSerAspAsp
<_____GENE: LACZ_____

430       440       450       460       470       480
           *         *         *         *         *         *
CCACCAATCCCCATATGGAAACCGTCGATATTCAGCCATGTGCCTTCTTCCGCGTGCAGC
<GlyGlyIleGlyMetHisPheGlyAspIleAsnLeuTrpThrGlyGluGluAlaHisLeu
<_____GENE: LACZ_____

490       500       510       520       530       540
           *         *         *         *         *         *
AGATGGCGATGGCTGGTTTCCATCAGTTGCTGTTGACTGTAGCGGCTGATGTTGAACTGG
LeuHisArgHisSerThrGluMetLeuGlnGlnGlnSerTyrArgSerIleAsnPheGln
<_____GENE: LACZ_____
```

*Fig. 49*

```
              550         560         570         580         590         600
               *           *           *           *           *           *
         AAGTCGCCGCGCCACTGGTGTGGGCCATAATTCAATTCGCGCGTCCCGCAGCGCAGACCG
         <PheAspGlyArgTrpGlnHisProGlyTyrAsnLeuGluArgThrGlyCysArgLeuGly
          <_____GENE: LACZ _____

610         620         630         640         650         660
               *           *           *           *           *           *
         TTTTCGCTCGGGAAGACGTACGGGGTATACATGTCTGACAATGGCAGATCCCAGCGGTCA
         <AsnGluSerProPheValTyrProThrTyrMetAspSerLeuProLeuAspTrpArgAsp
          <_____GENE: LACZ _____

670         680         690         700         710         720
               *           *           *           *           *           *
         AAACAGGCGGCAGTAAGGCGGTCGGGATAGTTTTCTTGCGGCCCTAATCCGAGCCAGTTT
         <PheCysAlaAlaThrLeuArgAspProTyrAsnGluGlnProGlyLeuGlyLeuTrpAsn
          <_____GENE: LACZ _____

730         740         750         760         770         780
               *           *           *           *           *           *
         ACCCGCTCTGCTACCTGCGCCAGCTGGCAGTTCAGGCCAATCCGCGCCGGATGCGGTGTA
         <ValArgGluAlaValGlnAlaLeuGlnCysAsnLeuGlyIleArgAlaProHisProThr
          <_____GENE: LACZ _____

790         800         810         820         830         840
               *           *           *           *           *           *
         TCGCTCGCCACTTCAACATCAACGGTAATCGCCATTTGACCACTACCATCAATCCGGTAG
         <AspSerAlaValGluValAspValThrIleAlaMetGlnGlySerGlyAspIleArgTyr
          <_____GENE: LACZ _____

850         860         870         880         890         900
               *           *           *           *           *           *
         GTTTTCCGGCTGATAAATAAGGTTTTCCCCTGATGCTGCCACGCGTGAGCGGTCGTAATC
         <ThrLysArgSerIlePheLeuThrLysGlyGlnHisGlnTrpAlaHisAlaThrThrIle
          <_____GENE: LACZ _____

910         920         930         940         950         960
               *           *           *           *           *           *
         AGCACCGCATCAGCAAGTGTATCTGCCGTGCACTGCAACAACGCTGCTTCGGCCTGGTAA
         <LeuValAlaAspAlaLeuThrAspAlaThrCysGlnLeuLeuAlaAlaGluAlaGlnTyr
          <_____GENE: LACZ _____

970         980         990        1000        1010        1020
               *           *           *           *           *           *
         TGGCCCGCCGCCTTCCAGCGTTCGACCCAGGCGTTAGGGTCAATGCGGGTCGCTTCACTT
         <HisGlyAlaAlaLysTrpArgGluValTrpAlaAsnProAspIleArgThrAlaGluSer
```

*Fig. 50*

```
<_____GENE: LACZ _____

1030       1040       1050       1060       1070       1080
         *          *          *          *          *          *
     ACGCCAATGTCGTTATCCAGCGGTGCACGGGTGAACTGATCGCGCAGCGGCGTCAGCAGT
    <ValGlyIleAspAsnAspLeuProAlaArgThrPheGlnAspArgLeuProThrLeuLeu
       <_____GENE: LACZ _____

1090       1100       1110       1120       1130       1140
         *          *          *          *          *          *
     TGTTTTTTATCGCCAATCCACATCTGTGAAAGAAAGCCTGACTGGCGGTTAAATTGCCAA
    <GlnLysLysAspGlyIleTrpMetGlnSerLeuPheGlySerGlnArgAsnPheGlnTrp
       <_____GENE: LACZ _____

1150       1160       1170       1180       1190       1200
         *          *          *          *          *          *
     CGCTTATTACCCAGCTCGATGCAAAAATCCATTTCGCTGGTGGTCAGATGCGGGATGGCG
    <ArgLysAsnGlyLeuGluIleCysPheAspMetGluSerThrThrLeuHisProIleAla
       <_____GENE: LACZ _____

1210       1220       1230       1240       1250       1260
         *          *          *          *          *          *
     TGGGACGCGGCGGGGAGCGTCACACTGAGGTTTTCCGCCAGACGCCACTGCTGCCAGGCG
    <HisSerAlaAlaProLeuThrValSerLeuAsnGluAlaLeuArgTrpGlnGlnTrpAla
       <_____GENE: LACZ _____

1270       1280       1290       1300       1310       1320
         *          *          *          *          *          *
     CTGATGTGCCCGGCTTCTGACCATGCGGTCGCGTTCGGTTGCACTACGCGTACTGTGAGC
    <SerIleHisGlyAlaGluSerTrpAlaThrAlaAsnProGlnValValArgValThrLeu
       <_____GENE: LACZ _____

1330       1340       1350       1360       1370       1380
         *          *          *          *          *          *
     CAGAGTTGCCCGGCGCTCTCCGGCTGCGGTAGTTCAGGCAGTTCAATCAACTGTTTACCT
    <TrpLeuGlnGlyAlaSerGluProGlnProLeuGluProLeuGluIleLeuGlnLysGly
       <_____GENE: LACZ _____

1390       1400       1410       1420       1430       1440
         *          *          *          *          *          *
     TGTGGAGCGACATCCAGAGGCACTTCACCGCTTGCCAGCGGCTTACCATCCAGCGCCACC
    <GlnProAlaValAspLeuProValGluGlySerAlaLeuProLysGlyAspLeuAlaVal
       <_____GENE: LACZ _____

```
ATCCAGTGCAGGAGCTCGTTATCGCTATGACGGAACAGGTATTCGCTGGTCACTTCGATG
<MetTrpHisLeuLeuGluAsnAspSerHisArgPheLeuTyrGluSerThrValGluIle
 <_____GENE: LACZ_____

1510       1520       1530       1540       1550       1560
          *          *          *          *          *          *
GTTTGCCCGGATAAACGGAACTGGAAAAACTGCTGCTGGTGTTTTGCTTCCGTCAGCGCT
<ThrGlnGlySerLeuArgPheGlnPhePheGlnGlnGlnHisLysAlaGluThrLeuAla
 <_____GENE: LACZ_____

1570       1580       1590       1600       1610       1620
          *          *          *          *          *          *
GGATGCGGCGTGCGGTCGGCAAAGACCAGACCGTTCATACAGAACTGGCGATCGTTCGGC
<ProHisProThrArgAspAlaPheValLeuGlyAsnMetCysPheGlnArgAspAsnPro
 <_____GENE: LACZ_____

1630       1640       1650       1660       1670       1680
          *          *          *          *          *          *
GTATCGCCAAAATCACCGCCGTAAGCCGACCACGGGTTGCCGTTTTCATCATATTTAATC
<ThrAspGlyPheAspGlyGlyTyrAlaSerTrpProAsnGlyAsnGluAspTyrLysIle
 <_____GENE: LACZ_____

1690       1700       1710       1720       1730       1740
          *          *          *          *          *          *
AGCGACTGATCCACCCAGTCCCAGACGAAGCCGCCCTGTAAACGGGGATACTGACGAAAC
<LeuSerGlnAspValTrpAspTrpValPheGlyGlyGlnLeuArgProTyrGlnArgPhe
 <_____GENE: LACZ_____

1750       1760       1770       1780       1790       1800
          *          *          *          *          *          *
GCCTGCCAGTATTTAGCGAAACCGCCAAGACTGTTACCCATCGCGTGGGCGTATTCGCAA
<AlaGlnTrpTyrLysAlaPheGlyGlyLeuSerAsnGlyMetAlaHisAlaTyrGluCys
 <_____GENE: LACZ_____

1810       1820       1830       1840       1850       1860
          *          *          *          *          *          *
AGGATCAGCGGGCGCGTCTCTCCAGGTAGCGAAAGCCATTTTTTGATGGACCATTTCGGC
<LeuIleLeuProArgThrGluGlyProLeuSerLeuTrpLysLysIleSerTrpLysPro
 <_____GENE: LACZ_____

1870       1880       1890       1900       1910       1920
          *          *          *          *          *          *
ACAGCCGGGAAGGGCTGGTCTTCATCCACGCGCGCGTACATCGGGCAAATAATATCGGTG
 ValAlaProPheProGlnAspGluAspValArgAlaTyrMetProCysIleIleAspThr
 <_____GENE: LACZ_____
```

*Fig. 52*

```
        1930        1940        1950        1960        1970        1980
          *           *           *           *           *           *
     GCCGTGGTGTCGGCTCCGCCGCCTTCATACTGCACCGGGCGGGAAGGATCGACAGATTTG
     <AlaThrThrAspAlaGlyGlyGlyGluTyrGlnValProArgSerProAspValSerLys
        <_____GENE: LACZ _____

1990        2000        2010        2020        2030        2040
          *           *           *           *           *           *
     ATCCAGCGATACAGCGCGTCGTGATTAGCGCCGTGGCCTGATTCATTCCCCAGCGACCAG
     <IleTrpArgTyrLeuAlaAspHisAsnAlaGlyHisGlySerGluAsnGlyLeuSerTrp
        <_____GENE: LACZ _____

2050        2060        2070        2080        2090        2100
          *           *           *           *           *           *
     ATGATCACACTCGGGTGATTACGATCGCGCTGCACCATTCGCGTTACGCGTTCGCTCATC
     <IleIleValSerProHisAsnArgAspArgGlnValMetArgThrValArgGluSerMet
        <_____GENE: LACZ _____

2110        2120        2130        2140        2150        2160
          *           *           *           *           *           *
     GCCGGTAGCCAGCGCGGATCATCGGTCAGACGATTCATTGGCACCATGCCGTGGGTTTCA
     <AlaProLeuTrpArgProAspAspThrLeuArgAsnMetProValMetGlyHisThrGlu
        <_____GENE: LACZ _____

2170        2180        2190        2200        2210        2220
          *           *           *           *           *           *
     ATATTGGCTTCATCCACCACATACAGGCCGTAGCGGTCGCACAGCGTGTACCACAGCGGA
     <IleAsnAlaGluAspValValTyrLeuGlyTyrArgAspCysLeuThrTyrTrpLeuPro
        <_____GENE: LACZ _____

2230        2240        2250        2260        2270        2280
          *           *           *           *           *           *
     TGGTTCGGATAATGCGAACAGCGCACGGCGTTAAAGTTGTTCTGCTTCATCAGCAGGATA
     <HisAsnProTyrHisSerCysArgValAlaAsnPheAsnAsnGlnLysMetLeuLeuIle
        <_____GENE: LACZ _____

2290        2300        2310        2320        2330        2340
          *           *           *           *           *           *
     TCCTGCACCATCGTCTGCTCATCCATGACCTGACCATGCAGAGGATGATGCTCGTGACGG
     <AspGlnValMetThrGlnGluAspMetValGlnGlyHisLeuProHisHisGluHisArg
        <_____GENE: LACZ _____

2350        2360        2370        2380        2390        2400
          *           *           *           *           *           *
     TTAACGCCTCGAATCAGCAACGGCTTGCCGTTCAGCAGCAGCAGACCATTTTCAATCCGC
     <AsnValGlyArgIleLeuLeuProLysGlyAsnLeuLeuLeuLeuGlyAsnGluIleArg
```

*Fig. 53*

<_____GENE: LACZ _____

```
         2410        2420        2430        2440        2450        2460
           *           *           *           *           *           *
       ACCTCGCGGAAACCGACATCGCAGGCTTCTGCTTCAATCAGCGTGCCGTCGGCGGTGTGC
       <ValGluArgPheGlyValAspCysAlaGluAlaGluIleLeuThrGlyAspAlaThrHis
       <_____GENE: LACZ _____

2470        2480        2490        2500        2510        2520
           *           *           *           *           *           *
       AGTTCAACCACCGCACGATAGAGATTCGGGATTTCGGCGCTCCACAGTTTCGGGTTTTCG
       <LeuGluValValAlaArgTyrLeuAsnProIleGluAlaSerTrpLeuLysProAsnGlu
       <_____GENE: LACZ _____

2530        2540        2550        2560        2570        2580
           *           *           *           *           *           *
       ACGTTCAGACGTAGTGTGACGCGATCGGCATAACCACCACGCTCATCGATAATTTCACCG
       <ValAsnLeuArgLeuThrValArgAspAlaTyrGlyGlyArgGluAspIleIleGluGly
       <_____GENE: LACZ _____

2590        2600        2610        2620        2630        2640
           *           *           *           *           *           *
       CCGAAAGGCGCGGTGCCGCTGGCGACCTGCGTTTCACCCTGCCATAAAGAAACTGTTACC
       <GlyPheProAlaThrGlySerAlaValGlnThrGluGlyGlnTrpLeuSerValThrVal
       <_____GENE: LACZ _____

2650        2660        2670        2680        2690        2700
           *           *           *           *           *           *
       CGTAGGTAGTCACGCAACTCGCCGCACATCTGAACTTCAGCCTCCAGTACAGCGCGGCTG
       <ArgLeuTyrAspArgLeuGluGlyCysMetGlnValGluAlaGluLeuValAlaArgSer
       <_____GENE: LACZ _____

2710        2720        2730        2740        2750        2760
           *           *           *           *           *           *
       AAATCATCATTAAAGCGAGTGGCAACATGGAAATCGCTGATTTGTGTAGTCGGTTTATGC
       <PheAspAspAsnPheArgThrAlaValHisPheAspSerIleGlnThrThrProLysHis
       <_____GENE: LACZ _____

2770        2780        2790        2800        2810        2820
           *           *           *           *           *           *
       AGCAACGAGACGTCACGGAAAATGCCGCTCATCCGCCACATATCCTGATCTTCCAGATAA
       <LeuLeuSerValAspArgPheIleGlySerMetArgTrpMetAspGlnAspGluLeuTyr
       <_____GENE: LACZ _____

```
            CTGCCGTCACTCCAACGCAGCACCATCACCGCGAGGCGGTTTTCTCCGGCGCGTAAAAAT
           <SerGlyAspSerTrpArgLeuValMetValAlaLeuArgAsnGluGlyAlaArgLeuPhe
           <_____GENE: LACZ_____

2890      2900      2910      2920      2930      2940
               *         *         *         *         *         *
            GCGCTCAGGTCAAATTCAGACGGCAAACGACTGTCCTGGCCGTAACCGACCCAGCGCCCG
           <AlaSerLeuAspPheGluSerProLeuArgSerAspGlnGlyTyrGlyValTrpArgGly
           <_____GENE: LACZ_____

2950      2960      2970      2980      2990      3000
               *         *         *         *         *         *
            TTGCACCACAGATGAAACGCCGAGTTAACGCCATCAAAAATAATTCGCGTCTGGCCTTCC
           <AsnCysTrpLeuHisPheAlaSerAsnValGlyAspPheIleIleArgThrGlnGlyGlu
           <_____GENE: LACZ_____

3010      3020      3030      3040      3050      3060
               *         *         *         *         *         *
            TGTAGCCAGCTTTCATCAACATTAAATGTGAGCGAGTAACAACCCGTCGGATTCTCCGTG
           <GlnLeuTrpSerGluAspValAsnPheThrLeuSerTyrCysGlyThrProAsnGluThr
           <_____GENE: LACZ_____

3070      3080      3090      3100      3110      3120
               *         *         *         *         *         *
            GGAACAAACGGCGGATTGACCGTAATGGGATAGGTTACGTTGGTGTAGATGGGCGCATCG
           <ProValPheProProAsnValThrIleProTyrThrValAsnThrTyrIleProAlaAsp
           <_____GENE: LACZ_____

3130      3140      3150      3160      3170      3180
               *         *         *         *         *         *
            TAACCGTGCATCTGCCAGTTTGAGGGGACGACGACAGTATCGGCCTCAGGAAGATCGCAC
           <TyrGlyHisMetGlnTrpAsnSerProValValValThrAspAlaGluProLeuAspCys
           <_____GENE: LACZ_____

3190      3200      3210      3220      3230      3240
               *         *         *         *         *         *
            TCCAGCCAGCTTTCCGGCACCGCTTCTGGTGCCGGAAACCAGGCAAAGCGCCATTCGCCA
           <GluLeuTrpSerGluProValAlaGluProAlaProPheTrpAlaPheArgTrpGluGly
           <_____GENE: LACZ_____

3250      3260      3270      3280      3290      3300
               *         *         *         *         *         *
            TTCAGGCTGCGCAACTGTTGGGAAGGGCGATCGGTGCGGGCCTCTTCGCTATTACGCCAG
           <AsnLeuSerArgLeuGlnGlnSerProArgAspThrArgAlaGluGluSerAsnArgTrp
           <_____GENE: LACZ_____
```

*Fig. 55*

```
        3310       3320       3330       3340       3350       3360
          *          *          *          *          *          *
    CTGGCGAAAGGGGGATGTGCTGCAAGGCGATTAAGTTGGGTAACGCCAGGGTTTTCCCAG
    <SerAlaPheProProHisAlaAlaLeuArgAsnLeuGlnThrValGlyProAsnGluTrp
    <_____GENE: LACZ _____

3370       3380       3390       3400       3410       3420
          *          *          *       ⌐HIII⌐          *          *
    TCACGACGTTGTAAAACGACGGCCAGTGCCAAGCTTGGACTCAAAAAACTTAGCAATTCT
    <AspArgArgGlnLeuValVal              L    ⌐
    <____GENE: LACZ _____.                           _____ Nuc loc
```

```
        3430       3440       3450       3460       3470       3480
          *          *          *          *          *          *
    GAAGGAAAGTCCTTGGGGTCTTCTACCTTTCTCTTCTTTTTTGCGGAATTCCGGAAAACT
```

```
Start
codon   3490       3500       3510       3520       3530       3540
          *          *          *          *          *          *
    TTATCCATCTTTGCAAAGCTTGGGTCTCCCTATAGTGAGTCGTATTAATTTCGATAAGCC
                      L    ⌐

3550       3560       3570       3580       3590       3600
          *          *          *          *          *          *
    AGTAAGCAGTGGGTTCTCTAGTTAGCCAGAGAGCTCTGCTTATATAGACCTCCCACCGTA 3610       3620       3630       3640       3650       3660
          *          *          *          *          *          *
    CACGCCTACCGCCCATTTGCGTCAATGGGGCGGAGTTGTTACGACATTTTGGAAAGTCCC 3670       3680       3690       3700       3710       3720
          *          *          *          *          *          *
    GTTGATTTTGGTGCCAAAACAAACTCCCATTGACGTCAATGGGGTGGAGACTTGGAAATC 3730       3740       3750       3760       3770       3780
          *          *          *          *          *          *
    CCCGTGAGTCAAACCGCTATCCACGCCCATTGATGTACTGCCAAAACCGCATCACCATGG 3790       3800       3810       3820       3830       3840
          *          *          *          *          *          *
    TAATAGCGATGACTAATACGTAGATGTACTGCCAAGTAGGAAAGTCCCATAAGGTCATGT 3850       3860       3870       3880       3890       3900
          *          *          *          *          *          *
    ACTGGGCATAATGCCAGGCGGGCCATTTACCGTCATTGACGTCAATAGGGGGCGTACTTG 3910       3920       3930       3940       3950       3960
          *          *          *          *          *          *
```

*Fig. 56*

```
GCATATGATACACTTGATGTACTGCCAAGTGGGCAGTTTACCGTAAATAGTCCACCCATT
     3970      3980      3990      4000      4010      4020
       *         *         *         *         *         *
GACGTCAATGGAAAGTCCCTATTGGCGTTACTATGGGAACATACGTCATTATTGACGTCA
     4030      4040      4050      4060      4070      4080
       *         *         *         *         *         *
ATGGGCGGGGGTCGTTGGGCGGTCAGCCAGGCGGGCCATTTACCGTAAGTTATGTAACGC
     4090      4100      4110      4120      4130      4140
       *         *         *         *         *         *
GGAACTCCATATATGGGCTATGAACTAATGACCCCGTAATTGATTACTATTAATAACTAG
     4150      4160      4170      4180      4190      4200
       *         *         *         *         *         *
TCAATAATCAATGTCAACGCGTATATCTGGCCCGTACATCGCGAAGCAGCGCAAAACGCC
     4210      4220      4230      4240      4250      4260
       *         *     ┌ClaI┐     *         *         *
TAACCCCGGGCCAGATCTGACATCGATTACGCCAAGCTTGCATGCCTGCAGGTTTAAACA
                      └────┘
     4270    Xba 4280 Pac  4290      4300      4310      4320
       *    ┌───┐ ┌───┐      *         *         *         *
GTCGACTCTAGACTTAATTAAGGATCTGGAAGGTGCTGAGGTACGATGAGACCCGCACCA
     └ ┘ └───┘ └───┘
     4330      4340      4350      4360      4370      4380
       *         *         *         *         *         *
GGTGCAGACCCTGCGAGTGTGGCGGTAAACATATTAGGAACCAGCCTGTGATGCTGGATG
     4390      4400      4410      4420      4430      4440
       *         *         *         *         *         *
TGACCGAGGAGCTGAGGCCCGATCACTTGGTGCTGGCCTGCACCCGCGCTGAGTTTGGCT
     4450      4460      4470      4480      4490      4500
       *         *         *         *         *         *
CTAGCGATGAAGATACAGATTGAGGTACTGAAATGTGTGGGCGTGGCTTAAGGGTGGGAA
     4510      4520      4530      4540      4550      4560
       *         *         *         *         *         *
AGAATATATAAGGTGGGGGTCTTATGTAGTTTTGTATCTGTTTTGCAGCAGCCGCCGCCG
     4570      4580      4590      4600      4610      4620
       *         *         *         *         *         *
CCATGAGCACCAACTCGTTTGATGGAAGCATTGTGAGCTCATATTTGACAACGCGCATGC
```

*Fig. 57*

```
         4630        4640        4650        4660        4670        4680
           *           *           *           *           *           *
CCCCATGGGCCGGGGTGCGTCAGAATGTGATGGGCTCCAGCATTGATGGTCGCCCCGTCC 4690        4700        4710        4720        4730        4740
           *           *           *           *           *           *
TGCCCGCAAACTCTACTACCTTGACCTACGAGACCGTGTCTGGAACGCCGTTGGAGACTG 4750        4760        4770        4780        4790        4800
           *           *           *           *           *           *
CAGCCTCCGCCGCCGCTTCAGCCGCTGCAGCCACCGCCCGCGGGATTGTGACTGACTTTG 4810        4820        4830        4840        4850        4860
           *           *           *           *           *           *
CTTTCCTGAGCCCGCTTGCAAGCAGTGCAGCTTCCCGTTCATCCGCCCGCGATGACAAGT 4870        4880        4890        4900        4910        4920
           *           *           *           *           *           *
TGACGGCTCTTTTGGCACAATTGGATTCTTTGACCCGGGAACTTAATGTCGTTTCTCAGC 4930        4940        4950        4960        4970        4980
           *           *           *           *           *           *
AGCTGTTGGATCTGCGCCAGCAGGTTTCTGCCCTGAAGGCTTCCTCCCCTCCCAATGCGG 4990        5000        5010        5020        5030        5040
           *           *           *           *           *           *
TTTAAAACATAAATAAAAAACCAGACTCTGTTTGGATTTGGATCAAGCAAGTGTCTTGCT 5050        5060        5070        5080        5090        5100
           *           *           *           *           *           *
GTCTTTATTTAGGGGTTTTGCGCGCGCGGTAGGCCCGGGACCAGCGGTCTCGGTCGTTGA 5110        5120        5130        5140        5150        5160
           *           *           *           *           *           *
GGGTCCTGTGTATTTTTTCCAGGACGTGGTAAAGGTGACTCTGGATGTTCAGATACATGG 5170        5180        5190        5200        5210        5220
           *           *           *           *           *           *
GCATAAGCCCGTCTCTGGGGTGGAGGTAGCACCACTGCAGAGCTTCATGCTGCGGGGTGG 5230        5240        5250        5260        5270        5280
           *           *           *           *           *           *
TGTTGTAGATGATCCAGTCGTAGCAGGAGCGCTGGGCGTGGTGCCTAAAAATGTCTTTCA 5290        5300        5310        5320        5330        5340
           *           *           *           *           *           *
```

*Fig. 58*

```
GGTGTAAGTGTTTACAAAGCGGTTAAGCTGGGATGGGTGCATACGTGGGGATATGAGATG 5350        5360        5370        5380        5390        5400
      *           *           *           *           *           *
CATCTTGGACTGTATTTTTAGGTTGGCTATGTTCCCAGCCATATCCCTCCGGGGATTCAT 5410        5420        5430        5440        5450        5460
      *           *           *           *           *           *
GTTGTGCAGAACCACCAGCACAGTGTATCCGGTGCACTTGGGAAATTTGTCATGTAGCTT 5470        5480        5490        5500        5510        5520
      *           *           *           *           *           *
AGAAGGAAATGCGTGGAAGAACTTGGAGACGCCCTTGTGACCTCCAAGATTTTCCATGCA 5530        5540        5550        5560        5570        5580
      *           *           *           *           *           *
TTCGTCCATAATGATGGCAATGGGCCCACGGGCGGCGGCCTGGGCGAAGATATTTCTGGG 5590        5600        5610        5620        5630        5640
      *           *           *           *           *           *
ATCACTAACGTCATAGTTGTGTTCCAGGATGAGATCGTCATAGGCCATTTTTACAAAGCG 5650        5660        5670        5680        5690        5700
      *           *           *           *           *           *
CGGGCGGAGGGTGCCAGACTGCGGTATAATGGTTCCATCCGGCCCAGGGGCGTAGTTACC 5710        5720        5730        5740        5750        5760
      *           *           *           *           *           *
CTCACAGATTTGCATTTCCCACGCTTTGAGTTCAGATGGGGGGATCATGTCTACCTGCGG 5770        5780        5790        5800        5810        5820
      *           *           *           *           *           *
GGCGATGAAGAAAACGGTTTCCGGGGTAGGGGAGATCAGCTGGGAAGAAAGCAGGTTCCT 5830        5840        5850        5860        5870        5880
      *           *           *           *           *           *
GAGCAGCTGCGACTTACCGCAGCCGGTGGGCCCGTAAATCACACCTATTACCGGGTGCAA 5890        5900        5910        5920        5930        5940
      *           *           *           *           *           *
CTGGTAGTTAAGAGAGCTGCAGCTGCCGTCATCCCTGAGCAGGGGGCCACTTCGTTAAG 5950        5960        5970        5980        5990        6000
      *           *           *           *           *           *
CATGTCCCTGACTCGCATGTTTTCCCTGACCAAATCCGCCAGAAGGCGCTCGCCGCCCAG
```

*Fig. 59*

```
      6010        6020        6030        6040        6050        6060
        *           *           *           *           *           *
CGATAGCAGTTCTTGCAAGGAAGCAAAGTTTTTCAACGGTTTGAGACCGTCCGCCGTAGG 6070        6080        6090        6100        6110        6120
        *           *           *           *           *           *
CATGCTTTTGAGCGTTTGACCAAGCAGTTCCAGGCGGTCCCACAGCTCGGTCACCTGCTC 6130        6140        6150        6160        6170        6180
        *           *           *           *           *           *
TACGGCATCTCGATCCAGCATATCTCCTCGTTTCGCGGGTTGGGGCGGCTTTCGCTGTAC 6190        6200        6210        6220        6230        6240
        *           *           *           *           *           *
GGCAGTAGTCGGTGCTCGTCCAGACGGGCCAGGGTCATGTCTTTCCACGGGCGCAGGGTC 6250        6260        6270        6280        6290        6300
        *           *           *           *           *           *
CTCGTCAGCGTAGTCTGGGTCACGGTGAAGGGGTGCGCTCCGGGCTGCGCGCTGGCCAGG 6310        6320        6330        6340        6350        6360
        *           *           *           *           *           *
GTGCGCTTGAGGCTGGTCCTGCTGGTGCTGAAGCGCTGCCGGTCTTCGCCCTGCGCGTCG 6370        6380        6390        6400        6410        6420
        *           *           *           *           *           *
GCCAGGTAGCATTTGACCATGGTGTCATAGTCCAGCCCCTCCGCGGCGTGGCCCTTGGCG 6430        6440        6450        6460        6470        6480
        *           *           *           *           *           *
CGCAGCTTGCCCTTGGAGGAGGCGCCGCACGAGGGGCAGTGCAGACTTTTGAGGGCGTAG 6490        6500        6510        6520        6530        6540
        *           *           *           *           *           *
AGCTTGGGCGCGAGAAATACCGATTCCGGGGAGTAGGCATCCGCGCCGCAGGCCCCGCAG 6550        6560        6570        6580        6590        6600
        *           *           *           *           *           *
ACGGTCTCGCATTCCACGAGCCAGGTGAGCTCTGGCCGTTCGGGGTCAAAAACCAGGTTT 6610        6620        6630        6640        6650        6660
        *           *           *           *           *           *
CCCCCATGCTTTTTGATGCGTTTCTTACCTCTGGTTTCCATGAGCCGGTGTCCACGCTCG 6670        6680        6690        6700        6710        6720
        *           *           *           *           *           *
```

*Fig. 60*

```
GTGACGAAAAGGCTGTCCGTGTCCCGTATACAGACTTGAGAGGCCTGTCCTCGAGCGGT
     6730      6740      6750      6760      6770      6780
      *         *         *         *         *         *
GTTCCGCGGTCCTCCTCGTATAGAAACTCGGACCACTCTGAGACAAAGGCTCGCGTCCAG
     6790      6800      6810      6820      6830      6840
      *         *         *         *         *         *
GCCAGCACGAAGGAGGCTAAGTGGGAGGGGTAGCGGTCGTTGTCCACTAGGGGGTCCACT
     6850      6860      6870      6880      6890      6900
      *         *         *         *         *         *
CGCTCCAGGGTGTGAAGACACATGTCGCCCTCTTCGGCATCAAGGAAGGTGATTGGTTTG
     6910      6920      6930      6940      6950      6960
      *         *         *         *         *         *
TAGGTGTAGGCCACGTGACCGGGTGTTCCTGAAGGGGGGCTATAAAAGGGGGTGGGGGCG
     6970      6980      6990      7000      7010      7020
      *         *         *         *         *         *
CGTTCGTCCTCACTCTCTTCCGCATCGCTGTCTGCGAGGGCCAGCTGTTGGGGTGAGTAC
     7030      7040      7050      7060      7070      7080
      *         *         *         *         *         *
TCCCTCTGAAAAGCGGGCATGACTTCTGCGCTAAGATTGTCAGTTTCCAAAAACGAGGAG
     7090      7100      7110      7120      7130      7140
      *         *         *         *         *         *
GATTTGATATTCACCTGGCCCGCGGTGATGCCTTTGAGGGTGGCCGCATCCATCTGGTCA
     7150      7160      7170      7180      7190      7200
      *         *         *         *         *         *
GAAAAGACAATCTTTTTGTTGTCAAGCTTGGTGGCAAACGACCCGTAGAGGGCGTTGGAC
     7210      7220      7230      7240      7250      7260
      *         *         *         *         *         *
AGCAACTTGGCGATGGAGCGCAGGGTTTGGTTTTTGTCGCGATCGGCGCGCTCCTTGGCC
     7270      7280      7290      7300      7310      7320
      *         *         *         *         *         *
GCGATGTTTAGCTGCACGTATTCGCGCGCAACGCACCGCCATTCGGGAAAGACGGTGGTG
     7330      7340      7350      7360      7370      7380
      *         *         *         *         *         *
CGCTCGTCGGGCACCAGGTGCACGCGCCAACCGCGGTTGTGCAGGGTGACAAGGTCAACG
```

*Fig. 61*

```
         7390        7400        7410        7420        7430        7440
            *           *           *           *           *           *
CTGGTGGCTACCTCTCCGCGTAGGCGCTCGTTGGTCCAGCAGAGGCGGCCGCCCTTGCGC 7450        7460        7470        7480        7490        7500
            *           *           *           *           *           *
GAGCAGAATGGCGGTAGGGGGTCTAGCTGCGTCTCGTCCGGGGGGTCTGCGTCCACGGTA 7510        7520        7530        7540        7550        7560
            *           *           *           *           *           *
AAGACCCCGGGCAGCAGGCGCGCGTCGAAGTAGTCTATCTTGCATCCTTGCAAGTCTAGC 7570        7580        7590        7600        7610        7620
            *           *           *           *           *           *
GCCTGCTGCCATGCGCGGGCGGCAAGCGCGCGCTCGTATGGGTTGAGTGGGGGACCCCAT 7630        7640        7650        7660        7670        7680
            *           *           *           *           *           *
GGCATGGGGTGGGTGAGCGCGGAGGCGTACATGCCGCAAATGTCGTAAACGTAGAGGGGC 7690        7700        7710        7720        7730        7740
            *           *           *           *           *           *
TCTCTGAGTATTCCAAGATATGTAGGGTAGCATCTTCCACCGCGGATGCTGGCGCGCACG 7750        7760        7770        7780        7790        7800
            *           *           *           *           *           *
TAATCGTATAGTTCGTGCGAGGGAGCGAGGAGGTCGGGACCGAGGTTGCTACGGGCGGGC 7810        7820        7830        7840        7850        7860
            *           *           *           *           *           *
TGCTCTGCTCGGAAGACTATCTGCCTGAAGATGGCATGTGAGTTGGATGATATGGTTGGA 7870        7880        7890        7900        7910        7920
            *           *           *           *           *           *
CGCTGGAAGACGTTGAAGCTGGCGTCTGTGAGACCTACCGCGTCACGCACGAAGGAGGCG 7930        7940        7950        7960        7970        7980
            *           *           *           *           *           *
TAGGAGTCGCGCAGCTTGTTGACCAGCTCGGCGGTGACCTGCACGTCTAGGGCGCAGTAG 7990        8000        8010        8020        8030        8040
            *           *           *           *           *           *
TCCAGGGTTTCCTTGATGATGTCATACTTATCCTGTCCCTTTTTTTTCCACAGCTCGCGG 8050        8060        8070        8080        8090        8100
            *           *           *           *           *           *
```

*Fig. 62*

```
TTGAGGACAAACTCTTCGCGGTCTTTCCAGTACTCTTGGATCGGAAACCCGTCGGCCTCC 8110      8120      8130      8140      8150      8160
        *         *         *         *         *         *
GAACGGTAAGAGCCTAGCATGTAGAACTGGTTGACGGCCTGGTAGGCGCAGCATCCCTTT 8170      8180      8190      8200      8210      8220
        *         *         *         *         *         *
TCTACGGGTAGCGCGTATGCCTGCGCGGCCTTCCGGAGCGAGGTGTGGGTGAGCGCAAAG 8230      8240      8250      8260      8270      8280
        *         *         *         *         *         *
GTGTCCCTGACCATGACTTTGAGGTACTGGTATTTGAAGTCAGTGTCGTCGCATCCGCCC 8290      8300      8310      8320      8330      8340
        *         *         *         *         *         *
TGCTCCCAGAGCAAAAAGTCCGTGCGCTTTTTGGAACGCGGATTTGGCAGGGCGAAGGTG 8350      8360      8370      8380      8390      8400
        *         *         *         *         *         *
ACATCGTTGAAGAGTATCTTTCCCGCGCGAGGCATAAAGTTGCGTGTGATGCGGAAGGGT 8410      8420      8430      8440      8450      8460
        *         *         *         *         *         *
CCCGGCACCTCGGAACGGTTGTTAATTACCTGGGCGGCGAGCACGATCTCGTCAAAGCCG 8470      8480      8490      8500      8510      8520
        *         *         *         *         *         *
TTGATGTTGTGGCCCACAATGTAAAGTTCCAAGAAGCGCGGGATGCCCTTGATGGAAGGC 8530      8540      8550      8560      8570      8580
        *         *         *         *         *         *
AATTTTTTAAGTTCCTCGTAGGTGAGCTCTTCAGGGGAGCTGAGCCCGTGCTCTGAAAGG 8590      8600      8610      8620      8630      8640
        *         *         *         *         *         *
GCCCAGTCTGCAAGATGAGGGTTGGAAGCGACGAATGAGCTCCACAGGTCACGGGCCATT 8650      8660      8670      8680      8690      8700
        *         *         *         *         *         *
AGCATTTGCAGGTGGTCGCGAAAGGTCCTAAACTGGCGACCTATGGCCATTTTTTCTGGG 8710      8720      8730      8740      8750      8760
        *         *         *         *         *         *
GTGATGCAGTAGAAGGTAAGCGGGTCTTGTTCCCAGCGGTCCCATCCAAGGTTCGCGGCT
```

*Fig. 63*

```
      8770        8780        8790        8800        8810        8820
       *           *           *           *           *           *
AGGTCTCGCGCGGCAGTCACTAGAGGCTCATCTCCGCCGAACTTCATGACCAGCATGAAG 8830        8840        8850        8860        8870        8880
       *           *           *           *           *           *
GGCACGAGCTGCTTCCCAAAGGCCCCCATCCAAGTATAGGTCTCTACATCGTAGGTGACA 8890        8900        8910        8920        8930        8940
       *           *           *           *           *           *
AAGAGACGCTCGGTGCGAGGATGCGAGCCGATCGGGAAGAACTGGATCTCCCGCCACCAA 8950        8960        8970        8980        8990        9000
       *           *           *           *           *           *
TTGGAGGAGTGGCTATTGATGTGGTGAAAGTAGAAGTCCCTGCGACGGGCCGAACACTCG 9010        9020        9030        9040        9050        9060
       *           *           *           *           *           *
TGCTGGCTTTTGTAAAAACGTGCGCAGTACTGGCAGCGGTGCACGGGCTGTACATCCTGC 9070        9080        9090        9100        9110        9120
       *           *           *           *           *           *
ACGAGGTTGACCTGACGACCGCGCACAAGGAAGCAGAGTGGGAATTTGAGCCCCTCGCCT 9130        9140        9150        9160        9170        9180
       *           *           *           *           *           *
GGCGGGTTTGGCTGGTGGTCTTCTACTTCGGCTGCTTGTCCTTGACCGTCTGGCTGCTCG 9190        9200        9210        9220        9230        9240
       *           *           *           *           *           *
AGGGGAGTTACGGTGGATCGGACCACCACGCCGCGCGAGCCCAAAGTCCAGATGTCCGCG 9250        9260        9270        9280        9290        9300
       *           *           *           *           *           *
CGCGGCGGTCGGAGCTTGATGACAACATCGCGCAGATGGGAGCTGTCCATGGTCTGGAGC 9310        9320        9330        9340        9350        9360
       *           *           *           *           *           *
TCCCGCGGCGTCAGGTCAGGCGGGAGCTCCTGCAGGTTTACCTCGCATAGACGGGTCAGG 9370        9380        9390        9400        9410        9420
       *           *           *           *           *           *
GCGCGGGCTAGATCCAGGTGATACCTAATTTCCAGGGGCTGGTTGGTGGCGGCGTCGATG 9430        9440        9450        9460        9470        9480
       *           *           *           *           *           *
```

*Fig. 64*

```
GCTTGCAAGAGGCCGCATCCCCGCGGCGCGACTACGGTACCGCGCGGCGGGCGGTGGGCC 9490      9500      9510      9520      9530      9540
          *         *         *         *         *         *
GCGGGGGTGTCCTTGGATGATGCATCTAAAAGCGGTGACGCGGGCGAGCCCCCGGAGGTA 9550      9560      9570      9580      9590      9600
          *         *         *         *         *         *
GGGGGGGCTCCGGACCCGCCGGGAGAGGGGGCAGGGGCACGTCGGCGCCGCGCGCGGGCA 9610      9620      9630      9640      9650      9660
          *         *         *         *         *         *
GGAGCTGGTGCTGCGCGCGTAGGTTGCTGGCGAACGCGACGACGCGGCGGTTGATCTCCT 9670      9680      9690      9700      9710      9720
          *         *         *         *         *         *
GAATCTGGCGCCTCTGCGTGAAGACGACGGGCCCGGTGAGCTTGAGCCTGAAAGAGAGTT 9730      9740      9750      9760      9770      9780
          *         *         *         *         *         *
CGACAGAATCAATTTCGGTGTCGTTGACGGCGGCCTGGCGCAAAATCTCCTGCACGTCTC 9790      9800      9810      9820      9830      9840
          *         *         *         *         *         *
CTGAGTTGTCTTGATAGGCGATCTCGGCCATGAACTGCTCGATCTCTTCCTCCTGGAGAT 9850      9860      9870      9880      9890      9900
          *         *         *         *         *         *
CTCCGCGTCCGGCTCGCTCCACGGTGGCGGCGAGGTCGTTGGAAATGCGGGCCATGAGCT 9910      9920      9930      9940      9950      9960
          *         *         *         *         *         *
GCGAGAAGGCGTTGAGGCCTCCCTCGTTCCAGACGCGGCTGTAGACCACGCCCCCTTCGG 9970      9980      9990     10000     10010     10020
          *         *         *         *         *         *
CATCGCGGGCGCGCATGACCACCTGCGCGAGATTGAGCTCCACGTGCCGGGCGAAGACGG 10030     10040     10050     10060     10070     10080
          *         *         *         *         *         *
CGTAGTTTCGCAGGCGCTGAAAGAGGTAGTTGAGGGTGGTGGCGGTGTGTTCTGCCACGA 10090     10100     10110     10120     10130     10140
          *         *         *         *         *         *
AGAAGTACATAACCCAGCGTCGCAACGTGGATTCGTTGATATCCCCCAAGGCCTCAAGGC
```

*Fig. 65*

```
          10150     10160     10170     10180     10190     10200
            *         *         *         *         *         *
     GCTCCATGGCCTCGTAGAAGTCCACGGCGAAGTTGAAAAACTGGGAGTTGCGCGCCGACA 10210     10220     10230     10240     10250     10260
            *         *         *         *         *         *
     CGGTTAACTCCTCCTCCAGAAGACGGATGAGCTCGGCGACAGTGTCGCGCACCTCGCGCT 10270     10280     10290     10300     10310     10320
            *         *         *         *         *         *
     CAAAGGCTACAGGGGCCTCTTCTTCTTCTTCAATCTCCTCTTCCATAAGGGCCTCCCCTT 10330     10340     10350     10360     10370     10380
            *         *         *         *         *         *
     CTTCTTCTTCTGGCGGCGGTGGGGGAGGGGGGACACGGCGGCGACGACGGCGCACCGGGA 10390     10400     10410     10420     10430     10440
            *         *         *         *         *         *
     GGCGGTCGACAAAGCGCTCGATCATCTCCCCGCGGCGACGGCGCATGGTCTCGGTGACGG 10450     10460     10470     10480     10490     10500
            *         *         *         *         *         *
     CGCGGCCGTTCTCGCGGGGGCGCAGTTGGAAGACGCCGCCCGTCATGTCCCGGTTATGGG 10510     10520     10530     10540     10550     10560
            *         *         *         *         *         *
     TTGGCGGGGGGCTGCCATGCGGCAGGGATACGGCGCTAACGATGCATCTCAACAATTGTT 10570     10580     10590     10600     10610     10620
            *         *         *         *         *         *
     GTGTAGGTACTCCGCCGCCGAGGGACCTGAGCGAGTCCGCATCGACCGGATCGGAAAACC 10630     10640     10650     10660     10670     10680
            *         *         *         *         *         *
     TCTCGAGAAAGGCGTCTAACCAGTCACAGTCGCAAGGTAGGCTGAGCACCGTGGCGGGCG 10690     10700     10710     10720     10730     10740
            *         *         *         *         *         *
     GCAGCGGGCGGCGGTCGGGGTTGTTTCTGGCGGAGGTGCTGCTGATGATGTAATTAAAGT 10750     10760     10770     10780     10790     10800
            *         *         *         *         *         *
     AGGCGGTCTTGAGACGGCGGATGGTCGACAGAAGCACCATGTCCTTGGGTCCGGCCTGCT 10810     10820     10830     10840     10850     10860
            *         *         *         *         *         *
```

*Fig. 66*

```
GAATGCGCAGGCGGTCGGCCATGCCCCAGGCTTCGTTTTGACATCGGCGCAGGTCTTTGT
    10870     10880     10890     10900     10910     10920
       *         *         *         *         *         *
AGTAGTCTTGCATGAGCCTTTCTACCGGCACTTCTTCTTCTCCTTCCTCTTGTCCTGCAT
    10930     10940     10950     10960     10970     10980
       *         *         *         *         *         *
CTCTTGCATCTATCGCTGCGGCGGCGGCGGAGTTTGGCCGTAGGTGGCGCCCTCTTCCTC
    10990     11000     11010     11020     11030     11040
       *         *         *         *         *         *
CCATGCGTGTGACCCCGAAGCCCCTCATCGGCTGAAGCAGGGCTAGGTCGGCGACAACGC
    11050     11060     11070     11080     11090     11100
       *         *         *         *         *         *
GCTCGGCTAATATGGCCTGCTGCACCTGCGTGAGGGTAGACTGGAAGTCATCCATGTCCA
    11110     11120     11130     11140     11150     11160
       *         *         *         *         *         *
CAAAGCGGTGGTATGCGCCCGTGTTGATGGTGTAAGTGCAGTTGGCCATAACGGACCAGT
    11170     11180     11190     11200     11210     11220
       *         *         *         *         *         *
TAACGGTCTGGTGACCCGGCTGCGAGAGCTCGGTGTACCTGAGACGCGAGTAAGCCCTCG
    11230     11240     11250     11260     11270     11280
       *         *         *         *         *         *
AGTCAAATACGTAGTCGTTGCAAGTCCGCACCAGGTACTGGTATCCCACCAAAAAGTGCG
    11290     11300     11310     11320     11330     11340
       *         *         *         *         *         *
GCGGCGGCTGGCGGTAGAGGGGCCAGCGTAGGGTGGCCGGGGCTCCGGGGGCGAGATCTT
    11350     11360     11370     11380     11390     11400
       *         *         *         *         *         *
CCAACATAAGGCGATGATATCCGTAGATGTACCTGGACATCCAGGTGATGCCGGCGGCGG
    11410     11420     11430     11440     11450     11460
       *         *         *         *         *         *
TGGTGGAGGCGCGCGGAAAGTCGCGGACGCGGTTCCAGATGTTGCGCAGCGGCAAAAAGT
    11470     11480     11490     11500     11510     11520
       *         *         *         *         *         *
GCTCCATGGTCGGGACGCTCTGGCCGGTCAGGCGCGCGCAATCGTTGACGCACTAGACCG
```

*Fig. 67*

```
      11530      11540      11550      11560      11570      11580
        *          *          *          *          *          *
TGCAAAAGGAGAGCCTGTAAGCGGGCACTCTTCCGTGGTCTGGTGGATAAATTCGCAAGG 11590      11600      11610      11620      11630      11640
        *          *          *          *          *          *
GTATCATGGCGGACGACCGGGGTTCGAGCCCCGTATCCGGCCGTCCGCCGTGATCCATGC 11650      11660      11670      11680      11690      11700
        *          *          *          *          *          *
GGTTACCGCCCGCGTGTCGAACCCAGGTGTGCGACGTCAGACAACGGGGGAGTGCTCCTT 11710      11720      11730      11740      11750      11760
        *          *          *          *          *          *
TTGGCTTCCTTCCAGGCGCGGCGGCTGCTGCGCTAGCTTTTTTGGCCACTGGCCGCGCGC 11770      11780      11790      11800      11810      11820
        *          *          *          *          *          *
AGCGTAAGCGGTTAGGCTGGAAAGCGAAAGCATTAAGTGGCTCGCTCCCTGTAGCCGGAG 11830      11840      11850      11860      11870      11880
        *          *          *          *          *          *
GGTTATTTTCCAAGGGTTGAGTCGCGGGACCCCCGGTTCGAGTCTCGGACCGGCCGGACT 11890      11900      11910      11920      11930      11940
        *          *          *          *          *          *
GCGGCGAACGGGGGTTTGCCTCCCCGTCATGCAAGACCCCGCTTGCAAATTCCTCCGGAA 11950      11960      11970      11980      11990      12000
        *          *          *          *          *          *
ACAGGGACGAGCCCCTTTTTTGCTTTTCCCAGATGCATCCGGTGCTGCGGCAGATGCGCC 12010      12020      12030      12040      12050      12060
        *          *          *          *          *          *
CCCCTCCTCAGCAGCGGCAAGAGCAAGAGCAGCGGCAGACATGCAGGGCACCCTCCCCTC 12070      12080      12090      12100      12110      12120
        *          *          *          *          *          *
CTCCTACCGCGTCAGGAGGGGCGACATCCGCGGTTGACGCGGCAGCAGATGGTGATTACG 12130      12140      12150      12160      12170      12180
        *          *          *          *          *          *
AACCCCCGCGGCGCCGGGCCCGGCACTACCTGGACTTGGAGGAGGGCGAGGGCCTGGCGC 12190      12200      12210      12220      12230      12240
        *          *          *          *          *          *
```

*Fig. 68*

```
GGCTAGGAGCGCCCTCTCCTGAGCGGTACCCAAGGGTGCAGCTGAAGCGTGATACGCGTG
      12250     12260     12270     12280     12290     12300
        *         *         *         *         *         *
AGGCGTACGTGCCGCGGCAGAACCTGTTTCGCGACCGCGAGGGAGAGGAGCCCGAGGAGA
      12310     12320     12330     12340     12350     12360
        *         *         *         *         *         *
TGCGGGATCGAAAGTTCCACGCAGGGCGCGAGCTGCGGCATGGCCTGAATCGCGAGCGGT
      12370     12380     12390     12400     12410     12420
        *         *         *         *         *         *
TGCTGCGCGAGGAGGACTTTGAGCCCGACGCGCGAACCGGGATTAGTCCCGCGCGCGCAC
      12430     12440     12450     12460     12470     12480
        *         *         *         *         *         *
ACGTGGCGGCCGCCGACCTGGTAACCGCATACGAGCAGACGGTGAACCAGGAGATTAACT
      12490     12500     12510     12520     12530     12540
        *         *         *         *         *         *
TTCAAAAAGCTTTAACAACCACGTGCGTACGCTTGTGGCGCGCGAGGAGGTGGCTATAG
      12550     12560     12570     12580     12590     12600
        *         *         *         *         *         *
GACTGATGCATCTGTGGGACTTTGTAAGCGCGCTGGAGCAAAACCCAAATAGCAAGCCGC
      12610     12620     12630     12640     12650     12660
        *         *         *         *         *         *
TCATGGCGCAGCTGTTCCTTATAGTGCAGCACAGCAGGGACAACGAGGCATTCAGGGATG
      12670     12680     12690     12700     12710     12720
        *         *         *         *         *         *
CGCTGCTAAACATAGTAGAGCCCGAGGGCCGCTGGCTGCTCGATTTGATAAACATCCTGC
      12730     12740     12750     12760     12770     12780
        *         *         *         *         *         *
AGAGCATAGTGGTGCAGGAGCGCAGCTTGAGCCTGGCTGACAAGGTGGCCGCCATCAACT
      12790     12800     12810     12820     12830     12840
        *         *         *         *         *         *
ATTCCATGCTTAGCCTGGGCAAGTTTTACGCCCGCAAGATATACCATACCCCTTACGTTC
      12850     12860     12870     12880     12890     12900
        *         *         *         *         *         *
CCATAGACAAGGAGGTAAAGATCGAGGGGTTCTACATGCGCATGGCGCTGAAGGTGCTTA
```

*Fig. 69*

```
12910     12920     12930     12940     12950     12960
   *         *         *         *         *         *
CCTTGAGCGACGACCTGGGCGTTTATCGCAACGAGCGCATCCACAAGGCCGTGAGCGTGA 12970     12980     12990     13000     13010     13020
   *         *         *         *         *         *
GCCGGCGGCGCGAGCTCAGCGACCGCGAGCTGATGCACAGCCTGCAAAGGGCCCTGGCTG 13030     13040     13050     13060     13070     13080
   *         *         *         *         *         *
GCACGGGCAGCGGCGATAGAGAGGCCGAGTCCTACTTTGACGCGGGCGCTGACCTGCGCT 13090     13100     13110     13120     13130     13140
   *         *         *         *         *         *
GGGCCCCAAGCCGACGCGCCCTGGAGGCAGCTGGGGCCGGACCTGGGCTGGCGGTGGCAC 13150     13160     13170     13180     13190     13200
   *         *         *         *         *         *
CCGCGCGCTGGCAACGTCGGCGGCGTGGAGGAATATGACGAGGACGATGAGTACGAGC 13210     13220     13230     13240     13250     13260
   *         *         *         *         *         *
CAGAGGACGGCGAGTACTAAGCGGTGATGTTTCTGATCAGATGATGCAAGACGCAACGGA 13270     13280     13290     13300     13310     13320
   *         *         *         *         *         *
CCCGGCGGTGCGGGCGGCGCTGCAGAGCCAGCCGTCCGGCCTTAACTCCACGGACGACTG 13330     13340     13350     13360     13370     13380
   *         *         *         *         *         *
GCGCCAGGTCATGGACCGCATCATGTCGCTGACTGCGCGCAATCCTGACGCGTTCCGGCA 13390     13400     13410     13420     13430     13440
   *         *         *         *         *         *
GCAGCCGCAGGCCAACCGGCTCTCCGCAATTCTGGAAGCGGTGGTCCCGGCGCGCGCAAA 13450     13460     13470     13480     13490     13500
   *         *         *         *         *         *
CCCCACGCACGAGAAGGTGCTGGCGATCGTAAACGCGCTGGCCGAAAACAGGGCCATCCG 13510     13520     13530     13540     13550     13560
   *         *         *         *         *         *
GCCCGACGAGGCCGGCCTGGTCTACGACGCGCTGCTTCAGCGCGTGGCTCGTTACAACAG 13570     13580     13590     13600     13610     13620
   *         *         *         *         *         *
```

*Fig. 70*

```
CGGCAACGTGCAGACCAACCTGGACCGGCTGGTGGGGATGTGCGCGAGGCCGTGGCGCA 13630     13640     13650     13660     13670     13680
         *         *         *         *         *         *
GCGTGAGCGCGCGCAGCAGCAGGGCAACCTGGGCTCCATGGTTGCACTAAACGCCTTCCT 13690     13700     13710     13720     13730     13740
         *         *         *         *         *         *
GAGTACACAGCCCGCCAACGTGCCGCGGGGACAGGAGGACTACACCAACTTTGTGAGCGC 13750     13760     13770     13780     13790     13800
         *         *         *         *         *         *
ACTGCGGCTAATGGTGACTGAGACACCGCAAAGTGAGGTGTACCAGTCTGGGCCAGACTA 13810     13820     13830     13840     13850     13860
         *         *         *         *         *         *
TTTTTTCCAGACCAGTAGACAAGGCCTGCAGACCGTAAACCTGAGCCAGGCTTTCAAAAA 13870     13880     13890     13900     13910     13920
         *         *         *         *         *         *
CTTGCAGGGGCTGTGGGGGGTGCGGGCTCCCACAGGCGACCGCGCGACCGTGTCTAGCTT 13930     13940     13950     13960     13970     13980
         *         *         *         *         *         *
GCTGACGCCCAACTCGCGCCTGTTGCTGCTGCTAATAGCGCCCTTCACGGACAGTGGCAG 13990     14000     14010     14020     14030     14040
         *         *         *         *         *         *
CGTGTCCCGGGACACATACCTAGGTCACTTGCTGACACTGTACCGCGAGGCCATAGGTCA 14050     14060     14070     14080     14090     14100
         *         *         *         *         *         *
GGCGCATGTGGACGAGCATACTTTCCAGGAGATTACAAGTGTCAGCCGCGCGCTGGGGCA 14110     14120     14130     14140     14150     14160
         *         *         *         *         *         *
GGAGGACACGGGCAGCCTGGAGGCAACCCTAAACTACCTGCTGACCAACCGGCGGCAGAA 14170     14180     14190     14200     14210     14220
         *         *         *         *         *         *
GATCCCCTCGTTGCACAGTTTAAACAGCGAGGAGGAGCGCATTTTGCGCTACGTGCAGCA 14230     14240     14250     14260     14270     14280
         *         *         *         *         *         *
GAGCGTGAGCCTTAACCTGATGCGCGACGGGGTAACGCCCAGCGTGGCGCTGGACATGAC
```

*Fig. 71*

```
       14290       14300       14310       14320       14330       14340
          *           *           *           *           *           *
CGCGCGCAACATGGAACCGGGCATGTATGCCTCAAACCGGCCGTTTATCAACCGCCTAAT 14350       14360       14370       14380       14390       14400
          *           *           *           *           *           *
GGACTACTTGCATCGCGCGGCCGCCGTGAACCCCGAGTATTTCACCAATGCCATCTTGAA 14410       14420       14430       14440       14450       14460
          *           *           *           *           *           *
CCCGCACTGGCTACCGCCCCTGGTTTCTACACCGGGGGATTCGAGGTGCCCGAGGGTAA 14470       14480       14490       14500       14510       14520
          *           *           *           *           *           *
CGATGGATTCCTCTGGGACGACATAGACGACAGCGTGTTTTCCCCGCAACCGCAGACCCT 14530       14540       14550       14560       14570       14580
          *           *           *           *           *           *
GCTAGAGTTGCAACAGCGCGAGCAGGCAGAGGCGGCGCTGCGAAAGGAAAGCTTCCGCAG 14590       14600       14610       14620       14630       14640
          *           *           *           *           *           *
GCCAAGCAGCTTGTCCGATCTAGGCGCTGCGGCCCCGCGGTCAGATGCTAGTAGCCCATT 14650       14660       14670       14680       14690       14700
          *           *           *           *           *           *
TCCAAGCTTGATAGGGTCTCTTACCAGCACTCGCACCACCCGCCCGCGCCTGCTGGGCGA 14710       14720       14730       14740       14750       14760
          *           *           *           *           *           *
GGAGGAGTACCTAAACAACTCGCTGCTGCAGCCGCAGCGCGAAAAAAACCTGCCTCCGGC 14770       14780       14790       14800       14810       14820
          *           *           *           *           *           *
ATTTCCCAACAACGGGATAGAGAGCCTAGTGGACAAGATGAGTAGATGGAAGACGTACGC 14830       14840       14850       14860       14870       14880
          *           *           *           *           *           *
GCAGGAGCACAGGGACGTGCCAGGCCCGCGCCCGCCCACCCGTCGTCAAAGGCACGACCG 14890       14900       14910       14920       14930       14940
          *           *           *           *           *           *
TCAGCGGGGTCTGGTGTGGGAGGACGATGACTCGGCAGACGACAGCAGCGTCCTGGATTT 14950       14960       14970       14980       14990       15000
          *           *           *           *           *           *
```

*Fig. 72*

```
GGGAGGGAGTGGCAACCCGTTTGCGCACCTTCGCCCCAGGCTGGGGAGAATGTTTTAAAA
    15010     15020     15030     15040     15050     15060
      *         *         *         *         *         *
AAAAAAAAGCATGATGCAAAATAAAAAACTCACCAAGGCCATGGCACCGAGCGTTGGTTT
    15070     15080     15090     15100     15110     15120
      *         *         *         *         *         *
TCTTGTATTCCCCTTAGTATGCGGCGCGCGGCGATGTATGAGGAAGGTCCTCCTCCCTCC
    15130     15140     15150     15160     15170     15180
      *         *         *         *         *         *
TACGAGAGTGTGGTGAGCGCGGCGCCAGTGGCGGCGGCGCTGGGTTCTCCCTTCGATGCT
    15190     15200     15210     15220     15230     15240
      *         *         *         *         *         *
CCCCTGGACCCGCCGTTTGTGCCTCCGCGGTACCTGCGGCCTACCGGGGGAGAAACAGC
    15250     15260     15270     15280     15290     15300
      *         *         *         *         *         *
ATCCGTTACTCTGAGTTGGCACCCCTATTCGACACCACCCGTGTGTACCTGGTGGACAAC
    15310     15320     15330     15340     15350     15360
      *         *         *         *         *         *
AAGTCAACGGATGTGGCATCCCTGAACTACCAGAACGACCACAGCAACTTTCTGACCACG
    15370     15380     15390     15400     15410     15420
      *         *         *         *         *         *
GTCATTCAAAACAATGACTACAGCCCGGGGGAGGCAAGCACACAGACCATCAATCTTGAC
    15430     15440     15450     15460     15470     15480
      *         *         *         *         *         *
GACCGGTCGCACTGGGGCGGCGACCTGAAAACCATCCTGCATACCAACATGCCAAATGTG
    15490     15500     15510     15520     15530     15540
      *         *         *         *         *         *
AACGAGTTCATGTTTACCAATAAGTTTAAGGCGCGGGTGATGGTGTCGCGCTTGCCTACT
    15550     15560     15570     15580     15590     15600
      *         *         *         *         *         *
AAGGACAATCAGGTGGAGCTGAAATACGAGTGGGTGGAGTTCACGCTGCCCGAGGGCAAC
    15610     15620     15630     15640     15650     15660
      *         *         *         *         *         *
TACTCCGAGACCATGACCATAGACCTTATGAACAACGCGATCGTGGAGCACTACTTGAAA
```

*Fig. 73*

```
          15670     15680     15690     15700     15710     15720
            *         *         *         *         *         *
GTGGGCAGACAGAACGGGGTTCTGGAAAGCGACATCGGGGTAAAGTTTGACACCCGCAAC 15730     15740     15750     15760     15770     15780
            *         *         *         *         *         *
TTCAGACTGGGGTTTGACCCCGTCACTGGTCTTGTCATGCCTGGGGTATATACAAACGAA 15790     15800     15810     15820     15830     15840
            *         *         *         *         *         *
GCCTTCCATCCAGACATCATTTTGCTGCCAGGATGCGGGGTGGACTTCACCCACAGCCGC 15850     15860     15870     15880     15890     15900
            *         *         *         *         *         *
CTGAGCAACTTGTTGGGCATCCGCAAGCGGCAACCCTTCCAGGAGGGCTTTAGGATCACC 15910     15920     15930     15940     15950     15960
            *         *         *         *         *         *
TACGATGATCTGGAGGGTGGTAACATTCCCGCACTGTTGGATGTGGACGCCTACCAGGCG 15970     15980     15990     16000     16010     16020
            *         *         *         *         *         *
AGCTTGAAAGATGACACCGAACAGGGCGGGGGTGGCGCAGGCGGCAGCAACAGCAGTGGC 16030     16040     16050     16060     16070     16080
            *         *         *         *         *         *
AGCGGCGCGGAAGAGAACTCCAACGCGGCAGCCGCGGCAATGCAGCCGGTGGAGGACATG 16090     16100     16110     16120     16130     16140
            *         *         *         *         *         *
AACGATCATGCCATTCGCGGCGACACCTTTGCCACACGGGCTGAGGAGAAGCGCGCTGAG 16150     16160     16170     16180     16190     16200
            *         *         *         *         *         *
GCCGAAGCAGCGGCCGAAGCTGCCGCCCCCGCTGCGCAACCCGAGGTCGAGAAGCCTCAG 16210     16220     16230     16240     16250     16260
            *         *         *         *         *         *
AAGAAACCGGTGATCAAACCCCTGACAGAGGACAGCAAGAAACGCAGTTACAACCTAATA 16270     16280     16290     16300     16310     16320
            *         *         *         *         *         *
AGCAATGACAGCACCTTCACCCAGTACCGCAGCTGGTACCTTGCATACAACTACGGCGAC 16330     16340     16350     16360     16370     16380
            *         *         *         *         *         *
```

*Fig. 74*

```
                CCTCAGACCGGAATCCGCTCATGGACCCTGCTTTGCACTCCTGACGTAACCTGCGGCTCG 16390     16400     16410     16420     16430     16440
                    *         *         *         *         *         *
                GAGCAGGTCTACTGGTCGTTGCCAGACATGATGCAAGACCCCGTGACCTTCCGCTCCACG 16450     16460     16470     16480     16490     16500
                    *         *         *         *         *         *
                CGCCAGATCAGCAACTTTCCGGTGGTGGGCGCCGAGCTGTTGCCCGTGCACTCCAAGAGC 16510     16520     16530     16540     16550     16560
                    *         *         *         *         *         *
                TTCTACAACGACCAGGCCGTCTACTCCCAACTCATCCGCCAGTTTACCTCTCTGACCCAC 16570     16580     16590     16600     16610     16620
                    *         *         *         *         *         *
                GTGTTCAATCGCTTTCCCGAGAACCAGATTTGGCGCGCCCGCCAGCCCCCACCATCACC 16630     16640     16650     16660     16670     16680
                    *         *         *         *         *         *
                ACCGTCAGTGAAAACGTTCCTGCTCTCACAGATCACGGGACGCTACCGCTGCGCAACAGC 16690     16700     16710     16720     16730     16740
                    *         *         *         *         *         *
                ATCGGAGGAGTCCAGCGAGTGACCATTACTGACGCCAGACGCCGCACCTGCCCCTACGTT 16750     16760     16770     16780     16790     16800
                    *         *         *         *         *         *
                TACAAGGCCCTGGGCATAGTCTCGCCGCGCGTCCTATCGAGCCGCACTTTTTGAGCAAGC 16810     16820     16830     16840     16850     16860
                    *         *         *         *         *         *
                ATGTCCATCCTTATATCGCCCAGCAATAACACAGGCTGGGGCCTGCGCTTCCCAAGCAAG 16870     16880     16890     16900     16910     16920
                    *         *         *         *         *         *
                ATGTTTGGCGGGGCCAAGAAGCGCTCCGACCAACACCCAGTGCGCGTGCGCGGGCACTAC 16930     16940     16950     16960     16970     16980
                    *         *         *         *         *         *
                CGCGCGCCCTGGGGCGCGCACAAACGCGGCCGCACTGGGCGCACCACCGTCGATGACGCC 16990     17000     17010     17020     17030     17040
                    *         *         *         *         *         *
                ATCGACGCGGTGGTGGAGGAGGCGCGCAACTACACGCCCACGCCGCCACCAGTGTCCACA
```

*Fig. 75*

```
       17050       17060       17070       17080       17090       17100
         *           *           *           *           *           *
GTGGACGCGGCCATTCAGACCGTGGTGCGCGGAGCCCGGCGCTATGCTAAAATGAAGAGA 17110       17120       17130       17140       17150       17160
         *           *           *           *           *           *
CGGCGGAGGCGCGTAGCACGTCGCCACCGCCGCCGACCCGGCACTGCCGCCCAACGCGCG 17170       17180       17190       17200       17210       17220
         *           *           *           *           *           *
GCGGCGGCCCTGCTTAACCGCGCACGTCGCACCGGCCGACGGGCGGCCATGCGGGCCGCT 17230       17240       17250       17260       17270       17280
         *           *           *           *           *           *
CGAAGGCTGGCCGCGGGTATTGTCACTGTGCCCCCCAGGTCCAGGCGACGAGCGGCCGCC 17290       17300       17310       17320       17330       17340
         *           *           *           *           *           *
GCAGCAGCCGCGGCCATTAGTGCTATGACTCAGGGTCGCAGGGCAACGTGTATTGGGTG 17350       17360       17370       17380       17390       17400
         *           *           *           *           *           *
CGCGACTCGGTTAGCGGCCTGCGCGTGCCCGTGCGCACCCGCCCCCCGCGCAACTAGATT 17410       17420       17430       17440       17450       17460
         *           *           *           *           *           *
GCAAGAAAAAACTACTTAGACTCGTACTGTTGTATGTATCCAGCGGCGGCGGCGCGCAAC 17470       17480       17490       17500       17510       17520
         *           *           *           *           *           *
GAAGCTATGTCCAAGCGCAAAATCAAAGAAGAGATGCTCCAGGTCATCGCGCCGGAGATC 17530       17540       17550       17560       17570       17580
         *           *           *           *           *           *
TATGGCCCCCCGAAGAAGGAAGAGCAGGATTACAAGCCCCGAAAGCTAAAGCGGGTCAAA 17590       17600       17610       17620       17630       17640
         *           *           *           *           *           *
AAGAAAAAGAAAGATGATGATGATGAACTTGACGACGAGGTGGAACTGCTGCACGCTACC 17650       17660       17670       17680       17690       17700
         *           *           *           *           *           *
GCGCCCAGGCGACGGGTACAGTGGAAAGGTCGACGCGTAAAACGTGTTTTGCGACCCGGC 17710       17720       17730       17740       17750       17760
         *           *           *           *           *           *
```

*Fig. 76*

```
ACCACCGTAGTCTTTACGCCCGGTGAGCGCTCCACCCGCACCTACAAGCGCGTGTATGAT 17770      17780      17790      17800      17810      17820
        *          *          *          *          *          *
GAGGTGTACGGCGACGAGGACCTGCTTGAGCAGGCCAACGAGCGCCTCGGGGAGTTTGCC 17830      17840      17850      17860      17870      17880
        *          *          *          *          *          *
TACGGAAAGCGGCATAAGGACATGCTGGCGTTGCCGCTGGACGAGGGCAACCCAACACCT 17890      17900      17910      17920      17930      17940
        *          *          *          *          *          *
AGCCTAAAGCCCGTAACACTGCAGCAGGTGCTGCCCGCGCTTGCACCGTCCGAAGAAAAG 17950      17960      17970      17980      17990      18000
        *          *          *          *          *          *
CGCGGCCTAAAGCGCGAGTCTGGTGACTTGGCACCCACCGTGCAGCTGATGGTACCCAAG 18010      18020      18030      18040      18050      18060
        *          *          *          *          *          *
CGCCAGCGACTGGAAGATGTCTTGGAAAAAATGACCGTGGAACCTGGGCTGGAGCCCGAG 18070      18080      18090      18100      18110      18120
        *          *          *          *          *          *
GTCCGCGTGCGGCCAATCAAGCAGGTGGCGCCGGGACTGGGCGTGCAGACCGTGGACGTT 18130      18140      18150      18160      18170      18180
        *          *          *          *          *          *
CAGATACCCACTACCAGTAGCACCAGTATTGCCACCGCCACAGAGGGCATGGAGACACAA 18190      18200      18210      18220      18230      18240
        *          *          *          *          *          *
ACGTCCCCGGTTGCCTCAGCGGTGGCGGATGCCGCGGTGCAGGCGGTCGCTGCGGCCGCG 18250      18260      18270      18280      18290      18300
        *          *          *          *          *          *
TCCAAGACCTCTACGGAGGTGCAAACGGACCCGTGGATGTTTCGCGTTTCAGCCCCCCGG 18310      18320      18330      18340      18350      18360
        *          *          *          *          *          *
CGCCCGCGCGGTTCGAGGAAGTACGGCGCCGCCAGCGCGCTACTGCCCGAATATGCCCTA 18370      18380      18390      18400      18410      18420
        *          *          *          *          *          *
CATCCTTCCATTGCGCCTACCCCCGGCTATCGTGGCTACACCTACCGCCCCAGAAGACGA
```

*Fig. 77*

```
        18430       18440       18450       18460       18470       18480
          *           *           *           *           *           *
GCAACTACCCGACGCCGAACCACCACTGGAACCCGCCGCCGCCGTCGCCGTCGCCAGCCC 18490       18500       18510       18520       18530       18540
          *           *           *           *           *           *
GTGCTGGCCCCGATTTCCGTGCGCAGGGTGGCTCGCGAAGGAGGCAGGACCCTGGTGCTG 18550       18560       18570       18580       18590       18600
          *           *           *           *           *           *
CCAACAGCGCGCTACCACCCCAGCATCGTTTAAAAGCCGGTCTTTGTGGTTCTTGCAGAT 18610       18620       18630       18640       18650       18660
          *           *           *           *           *           *
ATGGCCCTCACCTGCCGCCTCCGTTTCCCGGTGCCGGGATTCCGAGGAAGAATGCACCGT 18670       18680       18690       18700       18710       18720
          *           *           *           *           *           *
AGGAGGGGCATGGCCGGCCACGGCCTGACGGGCGGCATGCGTCGTGCGCACCACCGGCGG 18730       18740       18750       18760       18770       18780
          *           *           *           *           *           *
CGGCGCGCGTCGCACCGTCGCATGCGCGGCGGTATCCTGCCCCTCCTTATTCCACTGATC 18790       18800       18810       18820       18830       18840
          *           *           *           *           *           *
GCCGCGGCGATTGGCGCCGTGCCCGGAATTGCATCCGTGGCCTTGCAGGCGCAGAGACAC 18850       18860       18870       18880       18890       18900
          *           *           *           *           *           *
TGATTAAAAACAAGTTGCATGTGGAAAAATCAAAATAAAAAGTCTGGACTCTCACGCTCG 18910       18920       18930       18940       18950       18960
          *           *           *           *           *           *
CTTGGTCCTGTAACTATTTTGTAGAATGGAAGACATCAACTTTGCGTCTCTGGCCCCGCG 18970       18980       18990       19000       19010       19020
          *           *           *           *           *           *
ACACGGCTCGCGCCCGTTCATGGGAAACTGGCAAGATATCGGCACCAGCAATATGAGCGG 19030       19040       19050       19060       19070       19080
          *           *           *           *           *           *
TGGCGCCTTCAGCTGGGGCTCGCTGTGGAGCGGCATTAAAAATTTCGGTTCCACCGTTAA 19090       19100       19110       19120       19130       19140
          *           *           *           *           *           *
```

*Fig. 78*

```
GAACTATGGCAGCAAGGCCTGGAACAGCAGCACAGGCCAGATGCTGAGGGATAAGTTGAA 19150     19160     19170     19180     19190     19200
       *         *         *         *         *         *
AGAGCAAAATTTCCAACAAAAGGTGGTAGATGGCCTGGCCTCTGGCATTAGCGGGGTGGT 19210     19220     19230     19240     19250     19260
       *         *         *         *         *         *
GGACCTGGCCAACCAGGCAGTGCAAAATAAGATTAACAGTAAGCTTGATCCCCGCCCTCC 19270     19280     19290     19300     19310     19320
       *         *         *         *         *         *
CGTAGAGGAGCCTCCACCGGCCGTGGAGACAGTGTCTCCAGAGGGGCGTGGCGAAAAGCG 19330     19340     19350     19360     19370     19380
       *         *         *         *         *         *
TCCGCGCCCCGACAGGGAAGAAACTCTGGTGACGCAAATAGACGAGCCTCCCTCGTACGA 19390     19400     19410     19420     19430     19440
       *         *         *         *         *         *
GGAGGCACTAAAGCAAGGCCTGCCCACCACCCGTCCCATCGCGCCCATGGCTACCGGAGT 19450     19460     19470     19480     19490     19500
       *         *         *         *         *         *
GCTGGGCCAGCACACACCCGTAACGCTGGACCTGCCTCCCCCCGCCGACACCCAGCAGAA 19510     19520     19530     19540     19550     19560
       *         *         *         *         *         *
ACCTGTGCTGCCAGGCCCGACCGCCGTTGTTGTAACCCGTCCTAGCCGCGCGTCCCTGCG 19570     19580     19590     19600     19610     19620
       *         *         *         *         *         *
CCGCGCCGCCAGCGGTCCGCGATCGTTGCGGCCCGTAGCCAGTGGCAACTGGCAAAGCAC 19630     19640     19650     19660     19670     19680
       *         *         *         *         *         *
ACTGAACAGCATCGTGGGTCTGGGGGTGCAATCCCTGAAGCGCCGACGATGCTTCTGAAT 19690     19700     19710     19720     19730     19740
       *         *         *         *         *         *
AGCTAACGTGTCGTATGTGTGTCATGTATGCGTCCATGTCGCCGCCAGAGGAGCTGCTGA 19750     19760     19770     19780     19790     19800
       *         *         *         *         *         *
GCCGCCGCGCGCCCGCTTTCCAAGATGGCTACCCCTTCGATGATGCCGCAGTGGTCTTAC
```

*Fig. 79*

```
 19810      19820      19830      19840      19850      19860
   *          *          *          *          *          *
ATGCACATCTCGGGCCAGGACGCCTCGGAGTACCTGAGCCCCGGGCTGGTGCAGTTTGCC 19870      19880      19890      19900      19910      19920
   *          *          *          *          *          *
CGCGCCACCGAGACGTACTTCAGCCTGAATAACAAGTTTAGAAACCCCACGGTGGCGCCT 19930      19940      19950      19960      19970      19980
   *          *          *          *          *          *
ACGCACGACGTGACCACAGACCGGTCCCAGCGTTTGACGCTGCGGTTCATCCCTGTGGAC 19990      20000      20010      20020      20030      20040
   *          *          *          *          *          *
CGTGAGGATACTGCGTACTCGTACAAGGCGCGGTTCACCCTAGCTGTGGGTGATAACCGT 20050      20060      20070      20080      20090      20100
   *          *          *          *          *          *
GTGCTGGACATGGCTTCCACGTACTTTGACATCCGCGGCGTGCTGGACAGGGGCCCTACT 20110      20120      20130      20140      20150      20160
   *          *          *          *          *          *
TTTAAGCCCTACTCTGGCACTGCCTACAACGCCCTGGCTCCCAAGGGTGCCCCAAATCCT 20170      20180      20190      20200      20210      20220
   *          *          *          *          *          *
TGCGAATGGGATGAAGCTGCTACTGCTCTTGAAATAAACCTAGAAGAAGAGGACGATGAC 20230      20240      20250      20260      20270      20280
   *          *          *          *          *          *
AACGAAGACGAAGTAGACGAGCAAGCTGAGCAGCAAAAAACTCACGTATTTGGGCAGGCG 20290      20300      20310      20320      20330      20340
   *          *          *          *          *          *
CCTTATTCTGGTATAAATATTACAAAGGAGGGTATTCAAATAGGTGTCGAAGGTCAAACA 20350      20360      20370      20380      20390      20400
   *          *          *          *          *          *
CCTAAATATGCCGATAAAACATTTCAACCTGAACCTCAAATAGGAGAATCTCAGTGGTAC 20410      20420      20430      20440      20450      20460
   *          *          *          *          *          *
GAAACTGAAATTAATCATGCAGCTGGGAGAGTCCTTAAAAGACTACCCCAATGAAACCA 20470      20480      20490      20500      20510      20520
   *          *          *          *          *          *
```

*Fig. 80*

```
TGTTACGGTTCATATGCAAAACCCACAAATGAAAATGGAGGGCAAGGCATTCTTGTAAAG
     20530     20540     20550     20560     20570     20580
       *         *         *         *         *         *
CAACAAAATGGAAAGCTAGAAAGTCAAGTGGAAATGCAATTTTCTCAACTACTGAGGCG
     20590     20600     20610     20620     20630     20640
       *         *         *         *         *         *
ACCGCAGGCAATGGTGATAACTTGACTCCTAAAGTGGTATTGTACAGTGAAGATGTAGAT
     20650     20660     20670     20680     20690     20700
       *         *         *         *         *         *
ATAGAAACCCCAGACACTCATATTTCTTACATGCCCACTATTAAGGAAGGTAACTCACGA
     20710     20720     20730     20740     20750     20760
       *         *         *         *         *         *
GAACTAATGGGCCAACAATCTATGCCCAACAGGCCTAATTACATTGCTTTTAGGGACAAT
     20770     20780     20790     20800     20810     20820
       *         *         *         *         *         *
TTTATTGGTCTAATGTATTACAACAGCACGGGTAATATGGGTGTTCTGGCGGGCCAAGCA
     20830     20840     20850     20860     20870     20880
       *         *         *         *         *         *
TCGCAGTTGAATGCTGTTGTAGATTTGCAAGACAGAAACACAGAGCTTTCATACCAGCTT
     20890     20900     20910     20920     20930     20940
       *         *         *         *         *         *
TTGCTTGATTCCATTGGTGATAGAACCAGGTACTTTTCTATGTGGAATCAGGCTGTTGAC
     20950     20960     20970     20980     20990     21000
       *         *         *         *         *         *
AGCTATGATCCAGATGTTAGAATTATTGAAAATCATGGAACTGAAGATGAACTTCCAAAT
     21010     21020     21030     21040     21050     21060
       *         *         *         *         *         *
TACTGCTTTCCACTGGGAGGTGTGATTAATACAGAGACTCTTACCAAGGTAAAACCTAAA
     21070     21080     21090     21100     21110     21120
       *         *         *         *         *         *
ACAGGTCAGGAAAATGGATGGGAAAAGATGCTACAGAATTTTCAGATAAAAATGAAATA
     21130     21140     21150     21160     21170     21180
       *         *         *         *         *         *
AGAGTTGGAAATAATTTTGCCATGGAAATCAATCTAAATGCCAACCTGTGGAGAAATTTC
```

*Fig. 81*

```
       21190      21200      21210      21220      21230      21240
         *          *          *          *          *          *
   CTGTACTCCAACATAGCGCTGTATTTGCCCGACAAGCTAAAGTACAGTCCTTCCAACGTA 21250      21260      21270      21280      21290      21300
         *          *          *          *          *          *
   AAAATTTCTGATAACCCAAACACCTACGACTACATGAACAAGCGAGTGGTGGCTCCCGGG 21310      21320      21330      21340      21350      21360
         *          *          *          *          *          *
   TTAGTGGACTGCTACATTAACCTTGGAGCACGCTGGTCCCTTGACTATATGGACAACGTC 21370      21380      21390      21400      21410      21420
         *          *          *          *          *          *
   AACCCATTTAACCACCACCGCAATGCTGGCCTGCGCTACCGCTCAATGTTGCTGGGCAAT 21430      21440      21450      21460      21470      21480
         *          *          *          *          *          *
   GGTCGCTATGTGCCCTTCCACATCCAGGTGCCTCAGAAGTTCTTTGCCATTAAAAACCTC 21490      21500      21510      21520      21530      21540
         *          *          *          *          *          *
   CTTCTCCTGCCGGGCTCATACACCTACGAGTGGAACTTCAGGAAGGATGTTAACATGGTT 21550      21560      21570      21580      21590      21600
         *          *          *          *          *          *
   CTGCAGAGCTCCCTAGGAAATGACCTAAGGGTTGACGGAGCCAGCATTAAGTTTGATAGC 21610      21620      21630      21640      21650      21660
         *          *          *          *          *          *
   ATTTGCCTTTACGCCACCTTCTTCCCCATGGCCCACAACACCGCCTCCACGCTTGAGGCC 21670      21680      21690      21700      21710      21720
         *          *          *          *          *          *
   ATGCTTAGAAACGACACCAACGACCAGTCCTTTAACGACTATCTCTCCGCCGCCAACATG 21730      21740      21750      21760      21770      21780
         *          *          *          *          *          *
   CTCTACCCTATACCCGCCAACGCTACCAACGTGCCCATATCCATCCCCTCCCGCAACTGG 21790      21800      21810      21820      21830      21840
         *          *          *          *          *          *
   GCGGCTTTCCGCGGCTGGGCCTTCACGCGCCTTAAGACTAAGGAAACCCCATCACTGGGC 21850      21860      21870      21880      21890      21900
         *          *          *          *          *          *
```

*Fig. 82*

```
TCGGGCTACGACCCTTATTACACCTACTCTGGCTCTATACCCTACCTAGATGGAACCTTT 21910     21920     21930     21940     21950     21960
      *         *         *         *         *         *
TACCTCAACCACACCTTTAAGAAGGTGGCCATTACCTTTGACTCTTCTGTCAGCTGGCCT 21970     21980     21990     22000     22010     22020
      *         *         *         *         *         *
GGCAATGACCGCCTGCTTACCCCCAACGAGTTTGAAATTAAGCGCTCAGTTGACGGGGAG 22030     22040     22050     22060     22070     22080
      *         *         *         *         *         *
GGTTACAACGTTGCCCAGTGTAACATGACCAAAGACTGGTTCCTGGTACAAATGCTAGCT 22090     22100     22110     22120     22130     22140
      *         *         *         *         *         *
AACTACAACATTGGCTACCAGGGCTTCTATATCCCAGAGAGCTACAAGGACCGCATGTAC 22150     22160     22170     22180     22190     22200
      *         *         *         *         *         *
TCCTTCTTTAGAAACTTCCAGCCCATGAGCCGTCAGGTGGTGGATGATACTAAATACAAG 22210     22220     22230     22240     22250     22260
      *         *         *         *         *         *
GACTACCAACAGGTGGGCATCCTACACCAACACAACAACTCTGGATTTGTTGGCTACCTT 22270     22280     22290     22300     22310     22320
      *         *         *         *         *         *
GCCCCCACCATGCGCGAAGGACAGGCCTACCCTGCTAACTTCCCCTATCCGCTTATAGGC 22330     22340     22350     22360     22370     22380
      *         *         *         *         *         *
AAGACCGCAGTTGACAGCATTACCCAGAAAAAGTTTCTTTGCGATCGCACCCTTTGGCGC 22390     22400     22410     22420     22430     22440
      *         *         *         *         *         *
ATCCCATTCTCCAGTAACTTTATGTCCATGGGCGCACTCACAGACCTGGGCCAAAACCTT 22450     22460     22470     22480     22490     22500
      *         *         *         *         *         *
CTCTACGCCAACTCCGCCCACGCGCTAGACATGACTTTTGAGGTGGATCCCATGGACGAG 22510     22520     22530     22540     22550     22560
      *         *         *         *         *         *
CCCACCCTTCTTTATGTTTTGTTTGAAGTCTTTGACGTGGTCCGTGTGCACCGGCCGCAC
```

*Fig. 83*

```
        22570     22580     22590     22600     22610     22620
          *         *         *         *         *         *
CGCGGCGTCATCGAAACCGTGTACCTGCGCACGCCCTTCTCGGCCGGCAACGCCACAACA 22630     22640     22650     22660     22670     22680
          *         *         *         *         *         *
TAAAGAAGCAAGCAACATCAACAACAGCTGCCGCCATGGGCTCCAGTGAGCAGGAACTGA 22690     22700     22710     22720     22730     22740
          *         *         *         *         *         *
AAGCCATTGTCAAAGATCTTGGTTGTGGGCCATATTTTTTGGGCACCTATGACAAGCGCT 22750     22760     22770     22780     22790     22800
          *         *         *         *         *         *
TTCCAGGCTTTGTTTCTCCACACAAGCTCGCCTGCGCCATAGTCAATACGGCCGGTCGCG 22810     22820     22830     22840     22850     22860
          *         *         *         *         *         *
AGACTGGGGGCGTACACTGGATGGCCTTTGCCTGGAACCCGCACTCAAAAACATGCTACC 22870     22880     22890     22900     22910     22920
          *         *         *         *         *         *
TCTTTGAGCCCTTTGGCTTTTCTGACCAGCGACTCAAGCAGGTTTACCAGTTTGAGTACG 22930     22940     22950     22960     22970     22980
          *         *         *         *         *         *
AGTCACTCCTGCGCCGTAGCGCCATTGCTTCTTCCCCCGACCGCTGTATAACGCTGGAAA 22990     23000     23010     23020     23030     23040
          *         *         *         *         *         *
AGTCCACCCAAAGCGTACAGGGGCCCAACTCGGCCGCCTGTGGACTATTCTGCTGCATGT 23050     23060     23070     23080     23090     23100
          *         *         *         *         *         *
TTCTCCACGCCTTTGCCAACTGGCCCCAAACTCCCATGGATCACAACCCCACCATGAACC 23110     23120     23130     23140     23150     23160
          *         *         *         *         *         *
TTATTACCGGGGTACCCAACTCCATGCTCAACAGTCCCCAGGTACAGCCCACCCTGCGTC 23170     23180     23190     23200     23210     23220
          *         *         *         *         *         *
GCAACCAGGAACAGCTCTACAGCTTCCTGGAGCGCCACTCGCCCTACTTCCGCAGCCACA 23230     23240     23250     23260     23270     23280
          *         *         *         *         *         *
```

*Fig. 84*

```
GTGCGCAGATTAGGAGCGCCACTTCTTTTTGTCACTTGAAAAACATGTAAAAATAATGTA
    23290     23300     23310     23320     23330     23340
      *         *         *         *         *         *
CTAGAGACACTTTCAATAAAGGCAAATGCTTTTATTTGTACACTCTCGGGTGATTATTTA
    23350     23360     23370     23380     23390     23400
      *         *         *         *         *         *
CCCCCACCCTTGCCGTCTGCGCCGTTTAAAAATCAAAGGGGTTCTGCCGCGCATCGCTAT
    23410     23420     23430     23440     23450     23460
      *         *         *         *         *         *
GCGCCACTGGCAGGGACACGTTGCGATACTGGTGTTTAGTGCTCCACTTAAACTCAGGCA
    23470     23480     23490     23500     23510     23520
      *         *         *         *         *         *
CAACCATCCGCGGCAGCTCGGTGAAGTTTTCACTCCACAGGCTGCGCACCATCACCAACG
    23530     23540     23550     23560     23570     23580
      *         *         *         *         *         *
CGTTTAGCAGGTCGGGCGCCGATATCTTGAAGTCGCAGTTGGGGCCTCCGCCCTGCGCGC
    23590     23600     23610     23620     23630     23640
      *         *         *         *         *         *
GCGAGTTGCGATACACAGGGTTGCAGCACTGGAACACTATCAGCGCCGGGTGGTGCACGC
    23650     23660     23670     23680     23690     23700
      *         *         *         *         *         *
TGGCCAGCACGCTCTTGTCGGAGATCAGATCCGCGTCCAGGTCCTCCGCGTTGCTCAGGG
    23710     23720     23730     23740     23750     23760
      *         *         *         *         *         *
CGAACGGAGTCAACTTTGGTAGCTGCCTTCCCAAAAAGGGCGCGTGCCCAGGCTTTGAGT
    23770     23780     23790     23800     23810     23820
      *         *         *         *         *         *
TGCACTCGCACCGTAGTGGCATCAAAAGGTGACCGTGCCCGGTCTGGGCGTTAGGATACA
    23830     23840     23850     23860     23870     23880
      *         *         *         *         *         *
GCGCCTGCATAAAAGCCTTGATCTGCTTAAAAGCCACCTGAGCCTTTGCGCCTTCAGAGA
    23890     23900     23910     23920     23930     23940
      *         *         *         *         *         *
AGAACATGCCGCAAGACTTGCCGGAAAACTGATTGGCCGGACAGGCCGCGTCGTGCACGC
```

*Fig. 85*

```
   23950     23960     23970     23980     23990     24000
     *         *         *         *         *         *
AGCACCTTGCGTCGGTGTTGGAGATCTGCACCACATTTCGGCCCCACCGGTTCTTCACGA 24010     24020     24030     24040     24050     24060
     *         *         *         *         *         *
TCTTGGCCTTGCTAGACTGCTCCTTCAGCGCGCGCTGCCCGTTTTCGCTCGTCACATCCA 24070     24080     24090     24100     24110     24120
     *         *         *         *         *         *
TTTCAATCACGTGCTCCTTATTTATCATAATGCTTCCGTGTAGACACTTAAGCTCGCCTT 24130     24140     24150     24160     24170     24180
     *         *         *         *         *         *
CGATCTCAGCGCAGCGGTGCAGCCACAACGCGCAGCCCGTGGGCTCGTGATGCTTGTAGG 24190     24200     24210     24220     24230     24240
     *         *         *         *         *         *
TCACCTCTGCAAACGACTGCAGGTACGCCTGCAGGAATCGCCCCATCATCGTCACAAAGG 24250     24260     24270     24280     24290     24300
     *         *         *         *         *         *
TCTTGTTGCTGGTGAAGGTCAGCTGCAACCCGCGGTGCTCCTCGTTCAGCCAGGTCTTGC 24310     24320     24330     24340     24350     24360
     *         *         *         *         *         *
ATACGGCCGCCAGAGCTTCCACTTGGTCAGGCAGTAGTTTGAAGTTCGCCTTTAGATCGT 24370     24380     24390     24400     24410     24420
     *         *         *         *         *         *
TATCCACGTGGTACTTGTCCATCAGCGCGCGCGCAGCCTCCATGCCCTTCTCCCACGCAG 24430     24440     24450     24460     24470     24480
     *         *         *         *         *         *
ACACGATCGGCACACTCAGCGGGTTCATCACCGTAATTTCACTTTCCGCTTCGCTGGGCT 24490     24500     24510     24520     24530     24540
     *         *         *         *         *         *
CTTCCTCTTCCTCTTGCGTCCGCATACCACGCGCCACTGGGTCGTCTTCATTCAGCCGCC 24550     24560     24570     24580     24590     24600
     *         *         *         *         *         *
GCACTGTGCGCTTACCTCCTTTGCCATGCTTGATTAGCACCGGTGGGTTGCTGAAACCCA 24610     24620     24630     24640     24650     24660
     *         *         *         *         *         *
```

*Fig. 86*

```
CCATTTGTAGCGCCACATCTTCTCTTTCTTCCTCGCTGTCCACGATTACCTCTGGTGATG
    24670     24680     24690     24700     24710     24720
      *         *         *         *         *         *
GCGGGCGCTCGGGCTTGGGAGAAGGGCGCTTCTTTTCTTCTTGGGCGCAATGGCCAAAT
    24730     24740     24750     24760     24770     24780
      *         *         *         *         *         *
CCGCCGCCGAGGTCGATGGCCGCGGGCTGGGTGTGCGCGGCACCAGCGCGTCTTGTGATG
    24790     24800     24810     24820     24830     24840
      *         *         *         *         *         *
AGTCTTCCTCGTCCTCGGACTCGATACGCCGCCTCATCCGCTTTTTGGGGGCGCCCGGG
    24850     24860     24870     24880     24890     24900
      *         *         *         *         *         *
GAGGCGGCGGCGACGGGGACGGGGACGACACGTCCTCCATGGTTGGGGACGTCGCGCCG
    24910     24920     24930     24940     24950     24960
      *         *         *         *         *         *
CACCGCGTCCGCGCTCGGGGGTGGTTTCGCGCTGCTCCTCTTCCCGACTGGCCATTTCCT
    24970     24980     24990     25000     25010     25020
      *         *         *         *         *         *
TCTCCTATAGGCAGAAAAAGATCATGGAGTCAGTCGAGAAGAAGGACAGCCTAACCGCCC
    25030     25040     25050     25060     25070     25080
      *         *         *         *         *         *
CCTCTGAGTTCGCCACCACCGCCTCCACCGATGCCGCCAACGCGCCTACCACCTTCCCCG
    25090     25100     25110     25120     25130     25140
      *         *         *         *         *         *
TCGAGGCACCCCCGCTTGAGGAGGAGGAAGTGATTATCGAGCAGGACCCAGGTTTTGTAA
    25150     25160     25170     25180     25190     25200
      *         *         *         *         *         *
GCGAAGACGACGAGGACCGCTCAGTACCAACAGAGGATAAAAAGCAAGACCAGGACAACG
    25210     25220     25230     25240     25250     25260
      *         *         *         *         *         *
CAGAGGCAAACGAGGAACAAGTCGGGCGGGGGACGAAAGGCATGGCGACTACCTAGATG
    25270     25280     25290     25300     25310     25320
      *         *         *         *         *         *
TGGGAGACGACGTGCTGTTGAAGCATCTGCAGCGCCAGTGCGCCATTATCTGCGACGCGT
```

*Fig. 87*

```
       25330     25340     25350     25360     25370     25380
         *         *         *         *         *         *
    TGCAAGAGCGCAGCGATGTGCCCCTCGCCATAGCGGATGTCAGCCTTGCCTACGAACGCC 25390     25400     25410     25420     25430     25440
         *         *         *         *         *         *
    ACCTATTCTCACCGCGCGTACCCCCAAACGCCAAGAAAACGGCACATGCGAGCCCAACC 25450     25460     25470     25480     25490     25500
         *         *         *         *         *         *
    CGCGCCTCAACTTCTACCCCGTATTTGCCGTGCCAGAGGTGCTTGCCACCTATCACATCT 25510     25520     25530     25540     25550     25560
         *         *         *         *         *         *
    TTTTCCAAAACTGCAAGATACCCCTATCCTGCCGTGCCAACCGCAGCCGAGCGGACAAGC 25570     25580     25590     25600     25610     25620
         *         *         *         *         *         *
    AGCTGGCCTTGCGGCAGGGCGCTGTCATACCTGATATCGCCTCGCTCAACGAAGTGCCAA 25630     25640     25650     25660     25670     25680
         *         *         *         *         *         *
    AAATCTTTGAGGGTCTTGGACGCGACGAGAAGCGCGCGGCAAACGCTCTGCAACAGGAAA 25690     25700     25710     25720     25730     25740
         *         *         *         *         *         *
    ACAGCGAAAATGAAAGTCACTCTGGAGTGTTGGTGGAACTCGAGGGTGACAACGCGCGCC 25750     25760     25770     25780     25790     25800
         *         *         *         *         *         *
    TAGCCGTACTAAAACGCAGCATCGAGGTCACCCACTTTGCCTACCCGGCACTTAACCTAC 25810     25820     25830     25840     25850     25860
         *         *         *         *         *         *
    CCCCCAAGGTCATGAGCACAGTCATGAGTGAGCTGATCGTGCGCCGTGCGCAGCCCCTGG 25870     25880     25890     25900     25910     25920
         *         *         *         *         *         *
    AGAGGGATGCAAATTTGCAAGAACAAACAGAGGAGGGCCTACCCGCAGTTGGCGACGAGC 25930     25940     25950     25960     25970     25980
         *         *         *         *         *         *
    AGCTAGCGCGCTGGCTTCAAACGCGCGAGCCTGCCGACTTGGAGGAGCGACGCAAACTAA 25990     26000     26010     26020     26030     26040
         *         *         *         *         *         *
```

*Fig. 88*

```
TGATGGCCGCAGTGCTCGTTACCGTGGAGCTTGAGTGCATGCAGCGGTTCTTTGCTGACC
      26050     26060     26070     26080     26090     26100
        *         *         *         *         *         *
CGGAGATGCAGCGCAAGCTAGAGGAAACATTGCACTACACCTTTCGACAGGGCTACGTAC
      26110     26120     26130     26140     26150     26160
        *         *         *         *         *         *
GCCAGGCCTGCAAGATCTCCAACGTGGAGCTCTGCAACCTGGTCTCCTACCTTGGAATTT
      26170     26180     26190     26200     26210     26220
        *         *         *         *         *         *
TGCACGAAAACCGCCTTGGGCAAAACGTGCTTCATTCCACGCTCAAGGGCGAGGCGCGCC
      26230     26240     26250     26260     26270     26280
        *         *         *         *         *         *
GCGACTACGTCCGCGACTGCGTTTACTTATTTCTATGCTACACCTGGCAGACGGCCATGG
      26290     26300     26310     26320     26330     26340
        *         *         *         *         *         *
GCGTTTGGCAGCAGTGCTTGGAGGAGTGCAACCTCAAGGAGCTGCAGAAACTGCTAAAGC
      26350     26360     26370     26380     26390     26400
        *         *         *         *         *         *
AAAACTTGAAGGACCTATGGACGGCCTTCAACGAGCGCTCCGTGGCCGCGCACCTGGCGG
      26410     26420     26430     26440     26450     26460
        *         *         *         *         *         *
ACATCATTTTCCCCGAACGCCTGCTTAAAACCCTGCAACAGGGTCTGCCAGACTTCACCA
      26470     26480     26490     26500     26510     26520
        *         *         *         *         *         *
GTCAAAGCATGTTGCAGAACTTTAGGAACTTTATCCTAGAGCGCTCAGGAATCTTGCCCG
      26530     26540     26550     26560     26570     26580
        *         *         *         *         *         *
CCACCTGCTGTGCACTTCCTAGCGACTTTGTGCCCATTAAGTACCGCGAATGCCCTCCGC
      26590     26600     26610     26620     26630     26640
        *         *         *         *         *         *
CGCTTTGGGGCCACTGCTACCTTCTGCAGCTAGCCAACTACCTTGCCTACCACTCTGACA
      26650     26660     26670     26680     26690     26700
        *         *         *         *         *         *
TAATGGAAGACGTGAGCGGTGACGGTCTACTGGAGTGTCACTGTCGCTGCAACCTATGCA
```

*Fig. 89*

```
        26710     26720     26730     26740     26750     26760
          *         *         *         *         *         *
CCCCGCACCGCTCCCTGGTTTGCAATTCGCAGCTGCTTAACGAAAGTCAAATTATCGGTA 26770     26780     26790     26800     26810     26820
          *         *         *         *         *         *
CCTTTGAGCTGCAGGGTCCCTCGCCTGACGAAAAGTCCGCGGCTCCGGGGTTGAAACTCA 26830     26840     26850     26860     26870     26880
          *         *         *         *         *         *
CTCCGGGGCTGTGGACGTCGGCTTACCTTCGCAAATTTGTACCTGAGGACTACCACGCCC 26890     26900     26910     26920     26930     26940
          *         *         *         *         *         *
ACGAGATTAGGTTCTACGAAGACCAATCCCGCCCGCCAAATGCGGAGCTTACCGCCTGCG 26950     26960     26970     26980     26990     27000
          *         *         *         *         *         *
TCATTACCCAGGGCCACATTCTTGGCCAATTGCAAGCCATCAACAAAGCCCGCCAAGAGT 27010     27020     27030     27040     27050     27060
          *         *         *         *         *         *
TTCTGCTACGAAAGGGACGGGGGGTTTACTTGGACCCCCAGTCCGGCGAGGAGCTCAACC 27070     27080     27090     27100     27110     27120
          *         *         *         *         *         *
CAATCCCCCCGCCGCCGCAGCCCTATCAGCAGCAGCCGCGGGCCCTTGCTTCCCAGGATG 27130     27140     27150     27160     27170     27180
          *         *         *         *         *         *
GCACCCAAAAAGAAGCTGCAGCTGCCGCCGCCACCCACGGACGAGGAGGAATACTGGGAC 27190     27200     27210     27220     27230     27240
          *         *         *         *         *         *
AGTCAGGCAGAGGAGGTTTTGGACGAGGAGGAGGAGGACATGATGGAAGACTGGGAGAGC 27250     27260     27270     27280     27290     27300
          *         *         *         *         *         *
CTAGACGAGGAAGCTTCCGAGGTCGAAGAGGTGTCAGACGAAACACCGTCACCCTCGGTC 27310     27320     27330     27340     27350     27360
          *         *         *         *         *         *
GCATTCCCCTCGCCGGCGCCCCAGAAATCGGCAACCGGTTCCAGCATGGCTACAACCTCC 27370     27380     27390     27400     27410     27420
          *         *         *         *         *         *
```

*Fig. 90*

```
GCTCCTCAGGCGCCGCCGGCACTGCCCGTTCGCCGACCCAACCGTAGATGGGACACCACT 27430     27440     27450     27460     27470     27480
      *         *         *         *         *         *
GGAACCAGGGCCGGTAAGTCCAAGCAGCCGCCGCCGTTAGCCCAAGAGCAACAACAGCGC 27490     27500     27510     27520     27530     27540
      *         *         *         *         *         *
CAAGGCTACCGCTCATGGCGCGGGCACAAGAACGCCATAGTTGCTTGCTTGCAAGACTGT 27550     27560     27570     27580     27590     27600
      *         *         *         *         *         *
GGGGGCAACATCTCCTTCGCCCGCCGCTTTCTTCTCTACCATCACGGCGTGGCCTTCCCC 27610     27620     27630     27640     27650     27660
      *         *         *         *         *         *
CGTAACATCCTGCATTACTACCGTCATCTCTACAGCCCATACTGCACCGGCGGCAGCGGC 27670     27680     27690     27700     27710     27720
      *         *         *         *         *         *
AGCGGCAGCAACAGCAGCGGCCACACAGAAGCAAAGGCGACCGGATAGCAAGACTCTGAC 27730     27740     27750     27760     27770     27780
      *         *         *         *         *         *
AAAGCCCAAGAAATCCACAGCGGCGGCAGCAGCAGGAGGAGGAGCGCTGCGTCTGGCGCC 27790     27800     27810     27820     27830     27840
      *         *         *         *         *         *
CAACGAACCCGTATCGACCCGCGAGCTTAGAAACAGGATTTTTCCCACTCTGTATGCTAT 27850     27860     27870     27880     27890     27900
      *         *         *         *         *         *
ATTTCAACAGAGCAGGGGCCAAGAACAAGAGCTGAAAATAAAAAACAGGTCTCTGCGATC 27910     27920     27930     27940     27950     27960
      *         *         *         *         *         *
CCTCACCCGCAGCTGCCTGTATCACAAAAGCGAAGATCAGCTTCGGCGCACGCTGGAAGA 27970     27980     27990     28000     28010     28020
      *         *         *         *         *         *
CGCGGAGGCTCTCTTCAGTAAATACTGCGCGCTGACTCTTAAGGACTAGTTTCGCGCCCT 28030     28040     28050     28060     28070     28080
      *         *         *         *         *         *
TTCTCAAATTTAAGCGCGAAAACTACGTCATCTCCAGCGGCCACACCCGGCGCCAGCACC
```

*Fig. 91*

```
     28090        28100        28110        28120        28130        28140
       *            *            *            *            *            *
TGTCGTCAGCGCCATTATGAGCAAGGAAATTCCCACGCCCTACATGTGGAGTTACCAGCC 28150        28160        28170        28180        28190        28200
       *            *            *            *            *            *
ACAAATGGGACTTGCGGCTGGAGCTGCCCAAGACTACTCAACCCGAATAAACTACATGAG 28210        28220        28230        28240        28250        28260
       *            *            *            *            *            *
CGCGGGACCCCACATGATATCCCGGGTCAACGGAATCCGCGCCCACCGAAACCGAATTCT 28270        28280        28290        28300        28310        28320
       *            *            *            *            *            *
CTTGGAACAGGCGGCTATTACCACCACACCTCGTAATAACCTTAATCCCCGTAGTTGGCC 28330        28340        28350        28360        28370        28380
       *            *            *            *            *            *
CGCTGCCCTGGTGTACCAGGAAAGTCCCGCTCCCACCACTGTGGTACTTCCCAGAGACGC 28390        28400        28410        28420        28430        28440
       *            *            *            *            *            *
CCAGGCCGAAGTTCAGATGACTAACTCAGGGGCGCAGCTTGCGGGCGGCTTTCGTCACAG 28450        28460        28470        28480        28490        28500
       *            *            *            *            *            *
GGTGCGGTCGCCCGGGCAGGGTATAACTCACCTGACAATCAGAGGGCGAGGTATTCAGCT 28510        28520        28530        28540        28550        28560
       *            *            *            *            *            *
CAACGACGAGTCGGTGAGCTCCTCGCTTGGTCTCCGTCCGGACGGGACATTTCAGATCGG 28570        28580        28590        28600        28610        28620
       *            *            *            *            *            *
CGGCGCCGGCCGTCCTTCATTCACGCCTCGTCAGGCAATCCTAACTCTGCAGACCTCGTC 28630        28640        28650        28660        28670        28680
       *            *            *            *            *            *
CTCTGAGCCGCGCTCTGGAGGCATTGGAACTCTGCAATTTATTGAGGAGTTTGTGCCATC 28690        28700        28710        28720        28730        28740
       *            *            *            *            *            *
GGTCTACTTTAACCCCTTCTCGGGACCTCCCGGCCACTATCCGGATCAATTTATTCCTAA 28750        28760        28770        28780        28790        28800
       *            *            *            *            *            *
```

*Fig. 92*

```
CTTTGACGCGGTAAAGGACTCGGCGGACGGCTACGACTGAATGTTAAGTGGAGAGGCAGA 28810     28820     28830     28840     28850     28860
      *         *         *         *         *         *
GCAACTGCGCCTGAAACACCTGGTCCACTGTCGCCGCCACAAGTGCTTTGCCCGCGACTC 28870     28880     28890     28900     28910     28920
      *         *         *         *         *         *
CGGTGAGTTTTGCTACTTTGAATTGCCCGAGGATCATATCGAGGGCCCGGCGCACGGCGT 28930     28940     28950     28960     28970     28980
      *         *         *         *         *         *
CCGGCTTACCGCCCAGGGAGAGCTTGCCCGTAGCCTGATTCGGGAGTTTACCCAGCGCCC 28990     29000     29010     29020     29030     29040
      *         *         *         *         *         *
CCTGCTAGTTGAGCGGGACAGGGGACCCTGTGTTCTCACTGTGATTTGCAACTGTCCTAA 29050     29060     29070     29080     29090     29100
      *         *         *         *         *         *
CCTTGGATTACATCAAGATCTTTGTTGCCATCTCTGTGCTGAGTATAATAAATACAGAAA 29110     29120     29130     29140     29150     29160
      *         *         *         *         *         *
TTAAAATATACTGGGGCTCCTATCGCCATCCTGTAAACGCCACCGTCTTCACCCGCCCAA 29170     29180     29190     29200     29210     29220
      *         *         *         *         *         *
GCAAACCAAGGCTTCGAATCGCGACGCGTCAGTTTCCTCCTGTTCCTGTCCATCCGCACC
              BstBI
    29230     29240     29250     29260     29270     29280
      *         *         *         *         *         *
CACTATCTTCATGTTGTTGCAGATGAAGCGCGCAAGACCGTCTGAAGATACCTTCAACCC 29290     29300     29310     29320     29330     29340
      *         *         *         *         *         *
CGTGTATCCATATGACACGGAAACCGGTCCTCCAACTGTGCCTTTTCTTACTCCTCCCTT 29350     29360     29370     29380     29390     29400
      *         *         *         *         *         *
TGTATCCCCCAATGGGTTTCAAGAGAGTCCCCCTGGGGTACTCTCTTTGCGCCTATCCGA 29410     29420     29430     29440     29450     29460
      *         *         *         *         *         *
ACCTCTAGTTACCTCCAATGGCATGCTTGCGCTCAAAATGGGCAACGGCCTCTCTCTGGA
```

*Fig. 93*

```
         29470      29480      29490      29500      29510      29520
           *          *          *          *          *          *
    CGAGGCCGGCAACCTTACCTCCCAAAATGTAACCACTGTGAGCCCACCTCTCAAAAAAAC 29530      29540      29550      29560      29570      29580
           *          *          *          *          *          *
    CAAGTCAAACATAAACCTGGAAATATCTGCACCCCTCACAGTTACCTCAGAAGCCCTAAC 29590      29600      29610      29620      29630      29640
           *          *          *          *          *          *
    TGTGGCTGCCGCCGCACCTCTAATGGTCGCGGGCAACACACTCACCATGCAATCACAGGC 29650      29660      29670      29680      29690      29700
           *          *          *          *          *          *
    CCCGCTAACCGTGCACGACTCCAAACTTAGCATTGCCACCCAAGGACCCCTCACAGTGTC 29710      29720      29730      29740      29750      29760
           *          *          *          *          *          *
    AGAAGGAAAGCTAGCCCTGCAAACATCAGGCCCCCTCACCACCACCGATAGCAGTACCCT 29770      29780      29790      29800      29810      29820
           *          *          *          *          *          *
    TACTATCACTGCCTCACCCCCTCTAACTACTGCCACTGGTAGCTTGGGCATTGACTTGAA 29830      29840      29850      29860      29870      29880
           *          *          *          *          *          *
    AGAGCCCATTTATACACAAAATGGAAAACTAGGACTAAAGTACGGGGCTCCTTTGCATGT 29890      29900      29910      29920      29930      29940
           *          *          *          *          *          *
    AACAGACGACCTAAACACTTTGACCGTAGCAACTGGTCCAGGTGTGACTATTAATAATAC 29950      29960      29970      29980      29990      30000
           *          *          *          *          *          *
    TTCCTTGCAAACTAAAGTTACTGGAGCCTTGGGTTTTGATTCACAAGGCAATATGCAACT 30010      30020      30030      30040      30050      30060
           *          *          *          *          *          *
    TAATGTAGCAGGAGGACTAAGGATTGATTCTCAAAACAGACGCCTTATACTTGATGTTAG 30070      30080      30090      30100      30110      30120
           *          *          *          *          *          *
    TTATCCGTTTGATGCTCAAAACCAACTAAATCTAAGACTAGGACAGGGCCCTCTTTTTAT 30130      30140      30150      30160      30170      30180
           *          *          *          *          *          *
```

*Fig. 94*

```
AAACTCAGCCCACAACTTGGATATTAACTACAACAAAGGCCTTTACTTGTTTACAGCTTC 30190     30200     30210     30220     30230     30240
       *         *         *         *         *         *
AAACAATTCCAAAAAGCTTGAGGTTAACCTAAGCACTGCCAAGGGGTTGATGTTTGACGC 30250     30260     30270     30280     30290     30300
       *         *         *         *         *         *
TACAGCCATAGCCATTAATGCAGGAGATGGGCTTGAATTTGGTTCACCTAATGCACCAAA 30310     30320     30330     30340     30350     30360
       *         *         *         *         *         *
CACAAATCCCCTCAAAACAAAAATTGGCCATGGCCTAGAATTTGATTCAAACAAGGCTAT 30370     30380     30390     30400     30410     30420
       *         *         *         *         *         *
GGTTCCTAAACTAGGAACTGGCCTTAGTTTTGACAGCACAGGTGCCATTACAGTAGGAAA 30430     30440     30450     30460     30470     30480
       *         *         *         *         *         *
CAAAAATAATGATAAGCTAACTTTGTGGACCACACCAGCTCCATCTCCTAACTGTAGACT 30490     30500     30510     30520     30530     30540
       *         *         *         *         *         *
AAATGCAGAGAAGATGCTAAACTCACTTTGGTCTTAACAAAATGTGGCAGTCAAATACT 30550     30560     30570     30580     30590     30600
       *         *         *         *         *         *
TGCTACAGTTTCAGTTTTGGCTGTTAAAGGCAGTTTGGCTCCAATATCTGGAACAGTTCA 30610     30620     30630     30640     30650     30660
       *         *         *         *         *         *
AAGTGCTCATCTTATTATAAGATTTGACGAAAATGGAGTGCTACTAAACAATTCCTTCCT 30670     30680     30690     30700     30710     30720
       *         *         *         *         *         *
GGACCCAGAATATTGGAACTTTAGAAATGGAGATCTTACTGAAGGCACAGCCTATACAAA 30730     30740     30750     30760     30770     30780
       *         *         *         *         *         *
CGCTGTTGGATTTATGCCTAACCTATCAGCTTATCCAAAATCTCACGGTAAAACTGCCAA 30790     30800     30810     30820     30830     30840
       *         *         *         *         *         *
AAGTAACATTGTCAGTCAAGTTTACTTAAACGGAGACAAAACTAAACCTGTAACACTAAC
```

*Fig. 95*

```
30850     30860     30870     30880     30890     30900
  *         *         *         *         *         *
CATTACACTAAACGGTACACAGGAAACAGGAGACACAACTCCAAGTGCATACTCTATGTC 30910     30920     30930     30940     30950     30960
  *         *         *         *         *         *
ATTTTCATGGGACTGGTCTGGCCACAACTACATTAATGAAATATTTGCCACATCCTCTTA 30970     30980     30990     31000     31010     31020
  *         *         *         *         *         *
CACTTTTTCATACATTGCCCAAGAATAAAGAATCGTTTGTGTTATGTTTCAACGTGTTTA 31030     31040     31050     31060     31070     31080
  *         *         *         *         *         *
TTTTTCAATTGCAGAAAATTTCAAGTCATTTTTCATTCAGTAGTATAGCCCCACCACCAC 31090     31100     31110     31120     31130     31140
  *         *         *         *         *         *
ATAGCTTATACAGATCACCGTACCTTAATCAAACTCACAGAACCCTAGTATTCAACCTGC 31150     31160     31170     31180     31190     31200
  *         *         *         *         *         *
CACCTCCCTCCCAACACACAGAGTACACAGTCCTTTCTCCCCGGCTGGCCTTAAAAAGCA 31210     31220     31230     31240     31250     31260
  *         *         *         *         *         *
TCATATCATGGGTAACAGACATATTCTTAGGTGTTATATTCCACACGGTTTCCTGTCGAG 31270     31280     31290     31300     31310     31320
  *         *         *         *         *         *
CCAAACGCTCATCAGTGATATTAATAAACTCCCCGGGCAGCTCACTTAAGTTCATGTCGC 31330     31340     31350     31360     31370     31380
  *         *         *         *         *         *
TGTCCAGCTGCTGAGCCACAGGCTGCTGTCCAACTTGCGGTTGCTTAACGGGCGGCGAAG 31390     31400     31410     31420     31430     31440
  *         *         *         *         *         *
GAGAAGTCCACGCCTACATGGGGGTAGAGTCATAATCGTGCATCAGGATAGGGCGGTGGT 31450     31460     31470     31480     31490     31500
  *         *         *         *         *         *
GCTGCAGCAGCGCGCGAATAAACTGCTGCCGCCGCCGCTCCGTCCTGCAGGAATACAACA 31510     31520     31530     31540     31550     31560
  *         *         *         *         *         *
```

Fig. 96

```
TGGCAGTGGTCTCCTCAGCGATGATTCGCACCGCCCGCAGCATAAGGCGCCTTGTCCTCC
    31570     31580     31590     31600     31610     31620
      *         *         *         *         *         *
GGGCACAGCAGCGCACCCTGATCTCACTTAAATCAGCACAGTAACTGCAGCACAGCACCA
    31630     31640     31650     31660     31670     31680
      *         *         *         *         *         *
CAATATTGTTCAAAATCCCACAGTGCAAGGCGCTGTATCCAAAGCTCATGGCGGGGACCA
    31690     31700     31710     31720     31730     31740
      *         *         *         *         *         *
CAGAACCCACGTGGCCATCATACCACAAGCGCAGGTAGATTAAGTGGCGACCCCTCATAA
    31750     31760     31770     31780     31790     31800
      *         *         *         *         *         *
ACACGCTGGACATAAACATTACCTCTTTTGGCATGTTGTAATTCACCACCTCCCGGTACC
    31810     31820     31830     31840     31850     31860
      *         *         *         *         *         *
ATATAAACCTCTGATTAAACATGGCGCCATCCACCACCATCCTAAACCAGCTGGCCAAAA
    31870     31880     31890     31900     31910     31920
      *         *         *         *         *         *
CCTGCCCGCCGGCTATACACTGCAGGGAACCGGGACTGGAACAATGACAGTGGAGAGCCC
    31930     31940     31950     31960     31970     31980
      *         *         *         *         *         *
AGGACTCGTAACCATGGATCATCATGCTCGTCATGATATCAATGTTGGCACAACACAGGC
    31990     32000     32010     32020     32030     32040
      *         *         *         *         *         *
ACACGTGCATACACTTCCTCAGGATTACAAGCTCCTCCCGCGTTAGAACCATATCCCAGG
    32050     32060     32070     32080     32090     32100
      *         *         *         *         *         *
GAACAACCCATTCCTGAATCAGCGTAAATCCCACACTGCAGGGAAGACCTCGCACGTAAC
    32110     32120     32130     32140     32150     32160
      *         *         *         *         *         *
TCACGTTGTGCATTGTCAAAGTGTTACATTCGGGCAGCAGCGGATGATCCTCCAGTATGG
    32170     32180     32190     32200     32210     32220
      *         *         *         *         *         *
TAGCGCGGGTTTCTGTCTCAAAAGGAGGTAGACGATCCCTACTGTACGGAGTGCGCCGAG
```

*Fig. 97*

```
       32230     32240     32250     32260     32270     32280
         *         *         *         *         *         *
ACAACCGAGATCGTGTTGGTCGTAGTGTCATGCCAAATGGAACGCCGGACGTAGTCATAT 32290     32300     32310     32320     32330     32340
         *         *         *         *         *         *
TTCCTGAAGCAAAACCAGGTGCGGGCGTGACAAACAGATCTGCGTCTCCGGTCTCGCCGC 32350     32360     32370     32380     32390     32400
         *         *         *         *         *         *
TTAGATCGCTCTGTGTAGTAGTTGTAGTATATCCACTCTCTCAAAGCATCCAGGCGCCCC 32410     32420     32430     32440     32450     32460
         *         *         *         *         *         *
CTGGCTTCGGGTTCTATGTAAACTCCTTCATGCGCCGCTGCCCTGATAACATCCACCACC 32470     32480     32490     32500     32510     32520
         *         *         *         *         *         *
GCAGAATAAGCCACACCCAGCCAACCTACACATTCGTTCTGCGAGTCACACACGGGAGGA 32530     32540     32550     32560     32570     32580
         *         *         *         *         *         *
GCGGGAAGAGCTGGAAGAACCATGTTTTTTTTTTATTCCAAAGATTATCCAAAACCTC 32590     32600     32610     32620     32630     32640
         *         *         *         *         *         *
AAAATGAAGATCTATTAAGTGAACGCGCTCCCCTCCGGTGGCGTGGTCAAACTCTACAGC 32650     32660     32670     32680     32690     32700
         *         *         *         *         *         *
CAAAGAACAGATAATGGCATTTGTAAGATGTTGCACAATGGCTTCCAAAAGGCAAACGGC 32710     32720     32730     32740     32750     32760
         *         *         *         *         *         *
CCTCACGTCCAAGTGGACGTAAAGGCTAAACCCTTCAGGGTGAATCTCCTCTATAAACAT 32770     32780     32790     32800     32810     32820
         *         *         *         *         *         *
TCCAGCACCTTCAACCATGCCCAAATAATTCTCATCTCGCCACCTTCTCAATATATCTCT 32830     32840     32850     32860     32870     32880
         *         *         *         *         *         *
AAGCAAATCCCGAATATTAAGTCCGGCCATTGTAAAAATCTGCTCCAGAGCGCCCTCCAC 32890     32900     32910     32920     32930     32940
         *         *         *         *         *         *
```

*Fig. 98*

CTTCAGCCTCAAGCAGCGAATCATGATTGCAAAAATTCAGGTTCCTCACAGACCTGTATA

```
   32950     32960     32970     32980     32990     33000
     *         *         *         *         *         *
```
AGATTCAAAAGCGGAACATTAACAAAAATACCGCGATCCCGTAGGTCCCTTCGCAGGGCC

```
   33010     33020     33030     33040     33050     33060
     *         *         *         *         *         *
```
AGCTGAACATAATCGTGCAGGTCTGCACGGACCAGCGCGGCCACTTCCCCGCCAGGAACC

```
   33070     33080     33090     33100     33110     33120
     *         *         *         *         *         *
```
TTGACAAAAGAACCCACACTGATTATGACACGCATACTCGGAGCTATGCTAACCAGCGTA

```
   33130     33140     33150     33160     33170     33180
     *         *         *         *         *         *
```
GCCCCGATGTAAGCTTTGTTGCATGGGCGGCGATATAAAATGCAAGGTGCTGCTCAAAAA

```
   33190     33200     33210     33220     33230     33240
     *         *         *         *         *         *
```
ATCAGGCAAAGCCTCGCGCAAAAAAGAAAGCACATCGTAGTCATGCTCATGCAGATAAAG

```
   33250     33260     33270     33280     33290     33300
     *         *         *         *         *         *
```
GCAGGTAAGCTCCGGAACCACCACAGAAAAAGACACCATTTTTCTCTCAAACATGTCTGC

```
   33310     33320     33330     33340     33350     33360
     *         *         *         *         *         *
```
GGGTTTCTGCATAAACACAAAATAAAATAACAAAAAAACATTTAAACATTAGAAGCCTGT

```
   33370     33380     33390     33400     33410     33420
     *         *         *         *         *         *
```
CTTACAACAGGAAAAACAACCCTTATAAGCATAAGACGGACTACGGCCATGCCGGCGTGA

```
   33430     33440     33450     33460     33470     33480
     *         *         *         *         *         *
```
CCGTAAAAAACTGGTCACCGTGATTAAAAAGCACCACCGACAGCTCCTCGGTCATGTCC

```
   33490     33500     33510     33520     33530     33540
     *         *         *         *         *         *
```
GGAGTCATAATGTAAGACTCGGTAAACACATCAGGTTGATTCATCGGTCAGTGCTAAAAA

```
   33550     33560     33570     33580     33590     33600
     *         *         *         *         *         *
```
GCGACCGAAATAGCCCGGGGGAATACATACCCGCAGGCGTAGAGACAACATTACAGCCCC

*Fig. 99*

```
        33610     33620      33630      33640      33650      33660
          *         *          *          *          *          *
CATAGGAGGTATAACAAAATTAATAGGAGAGAAAAACACATAAACACCTGAAAAACCCTC 33670     33680      33690      33700      33710      33720
          *         *          *          *          *          *
CTGCCTAGGCAAAATAGCACCCTCCCGCTCCAGAACAACATACAGCGCTTCACAGCGGCA 33730     33740      33750      33760      33770      33780
          *         *          *          *          *          *
GCCTAACAGTCAGCCTTACCAGTAAAAAAGAAAACCTATTAAAAAAACACCACTCGACAC 33790     33800      33810      33820      33830      33840
          *         *          *          *          *          *
GGCACCAGCTCAATCAGTCACAGTGTAAAAAAGGGCCAAGTGCAGAGCGAGTATATATAG 33850     33860      33870      33880      33890      33900
          *         *          *          *          *          *
GACTAAAAAATGACGTAACGGTTAAAGTCCACAAAAAACACCCAGAAAACCGCACGCGAA 33910     33920      33930      33940      33950      33960
          *         *          *          *          *          *
CCTACGCCCAGAAACGAAAGCCAAAAAACCCACAACTTCCTCAAATCGTCACTTCCGTTT 33970     33980      33990      34000      34010      34020
          *         *          *          *          *          *
TCCCACGTTACGTAACTTCCCATTTTAAGAAAACTACAATTCCCAACACATACAAGTTAC 34030     34040      34050      34060      34070      34080
          *         *          *          *          *          *
TCCGCCCTAAACTAGACAAATATTACGCGCTATGAGTAACACAAAATTATTCAGATTTCA 34090     34100      34110      34120      34130      34140
          *         *          *          *          *          *
CTTCCTCTTATTCAGTTTTCCCGCGAAAATGGCCAAATCTTACTCGGTTACGCCCAAATT 34150     34160      34170      34180      34190      34200
          *         *          *          *          *          *
TACTACAACATCCGCCTAAAACCGCGCGAAAATTGTCACTTCCTGTGTACACCGGCGCAC 34210     34220      34230      34240      34250      34260
          *         *          *          *          *          *
ACCAAAAACGTCACTTTTGCCACATCCGTCGCTTACATGTGTTCCGCCACACTTGCAACA 34270     34280      34290      34300      34310      34320
          *         *          *          *          *          *
TCACACTTCCGCCACACTACTACGTCACCCGCCCCGTTCCCACGCCCCGCGCCACGTCAC 34330     34340      34350      34360      34370      34380
          *         *          *          *          *          *
AAACTCCACCCCCTCATTATCATATTGGCTTCAATCCAAAATAAGGTATATTATTGATGA
TG
```

*Fig. 100*

Fig. 107A
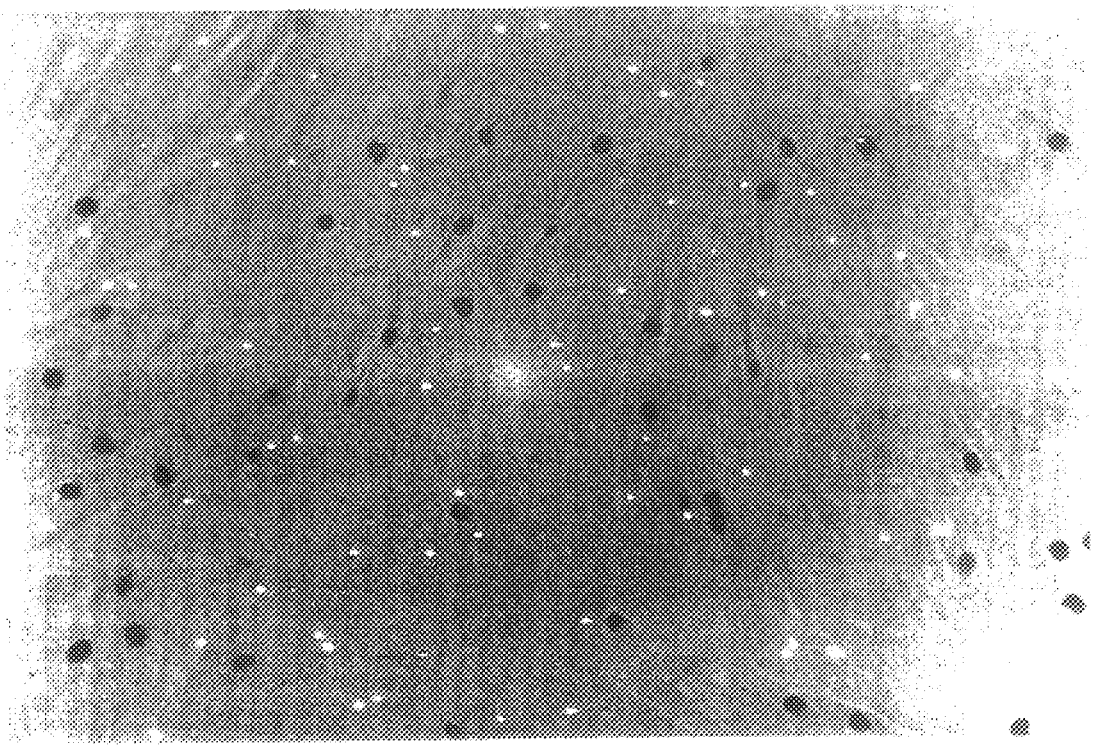
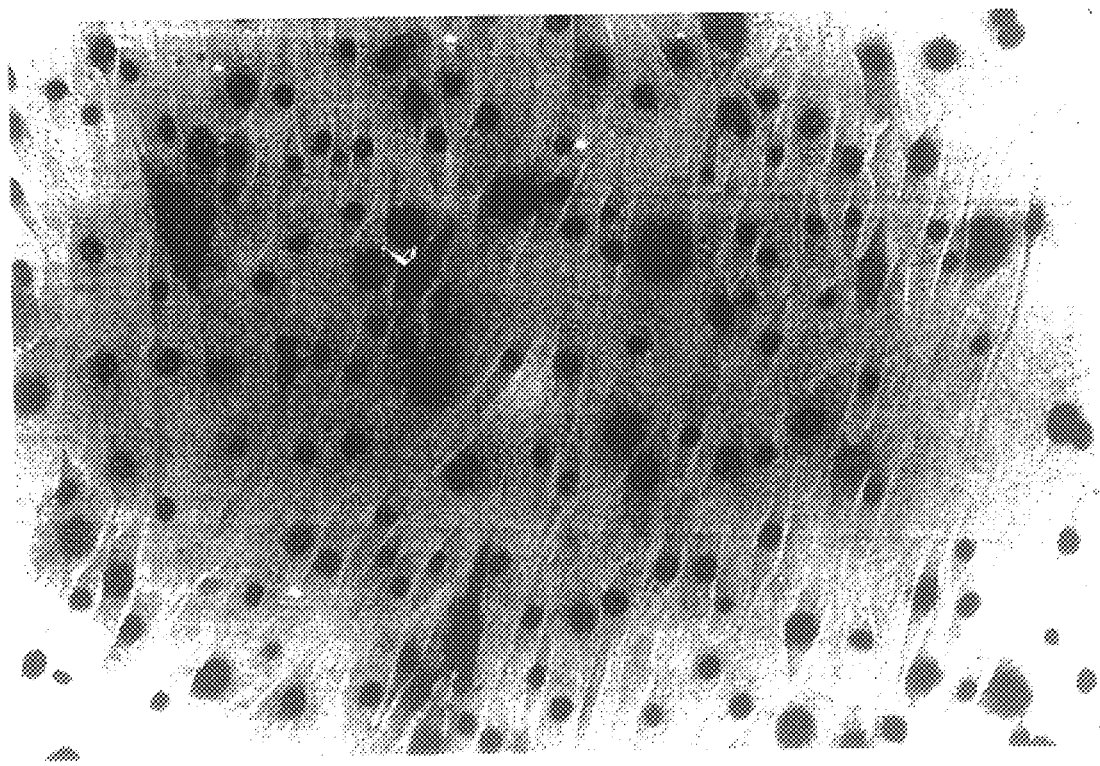
Fig. 107B

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 6420 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GAATTCTGAA  CGTGCAAAAA  AAATTACCAA  TAATCCAGAA  AATTATTATC  ATGGATTCTA     60

AAACGGATTA  CCGGTGAATT  CATCATCAAT  AATATACCTT  ATTTGGATT   GAAGCCAATA    120

TGATAATGAG  GGGGTGGAGT  TTGTGACGTG  GCGCGGGGCG  TGGGAACGGG  GCGGGTGACG    180

TAGTAGTGTG  GCGGAAGTGT  GATGTTGCAA  GTGTGGCGGA  ACACATGTAA  GCGACGGATG    240

TGGCAAAAGT  GACGTTTTTG  GTGTGCGCCG  GTGTCAGATC  TGGCCCGGGG  TTAGGCGTTT    300

TGCGCTGCTT  CGCGATGTAC  GGGCCAGATA  TACGCGTTGA  CATTGATTAT  TGACTAGTTA    360

TTAATAGTAA  TCAATTACGG  GGTCATTAGT  TCATAGCCCA  TATATGGAGT  TCCGCGTTAC    420

ATAACTTACG  GTAAATGGCC  CGCCTGGCTG  ACCGCCCAAC  GACCCCGCC   CATTGACGTC    480

AATAATGACG  TATGTTCCCA  TAGTAACGCC  AATAGGGACT  TTCCATTGAC  GTCAATGGGT    540

GGACTATTTA  CGGTAAACTG  CCCACTTGGC  AGTACATCAA  GTGTATCATA  TGCCAAGTAC    600

GCCCCCTATT  GACGTCAATG  ACGGTAAATG  GCCCGCCTGG  CATTATGCCC  AGTACATGAC    660

CTTATGGGAC  TTTCCTACTT  GGCAGTACAT  CTACGTATTA  GTCATCGCTA  TTACCATGGT    720

GATGCGGTTT  TGGCAGTACA  TCAATGGGCG  TGGATAGCGG  TTTGACTCAC  GGGGATTTCC    780

AAGTCTCCAC  CCCATTGACG  TCAATGGGAG  TTTGTTTTGG  CACCAAAATC  AACGGGACTT    840

TCCAAAATGT  CGTAACAACT  CCGCCCCATT  GACGCAAATG  GGCGGTAGGC  GTGTACGGTG    900

GGAGGTCTAT  ATAAGCAGAG  CTCTCTGGCT  AACTAGAGAA  CCCACTGCTT  ACTGGCTTAT    960
```

-continued

| | | | | | | |
|---|---|---|---|---|---|---|
| CGAAATTAAT | ACGACTCACT | ATAGGGAGAC | CCAAGCTTGG | TACCGAGCTC | GGATCCACTA | 1020 |
| GTAACGGCCG | CCAGTGTGCT | GGAATTAATT | CTGCAGATAT | CCATCACACT | GGCGGCCGCT | 1080 |
| CGAGCATGCA | TCTAGAGGGC | CCTATTCTAT | AGTGTCACCT | AAATGCTAGA | GGATCTTTGT | 1140 |
| GAAGGAACCT | TACTTCTGTG | GTGTGACATA | ATTGGACAAA | CTACCTACAG | AGATTTAAAG | 1200 |
| CTCTAAGGTA | AATATAAAAT | TTTTAAGTGT | ATAATGTGTT | AAACTACTGA | TTCTAATTGT | 1260 |
| TTGTGTATTT | TAGATTCCAA | CCTATGGAAC | TGATGAATGG | GAGCAGTGGT | GGAATGCCTT | 1320 |
| TAATGAGGAA | AACCTGTTTT | GCTCAGAAGA | AATGCCATCT | AGTGATGATG | AGGCTACTGC | 1380 |
| TGACTCTCAA | CATTCTACTC | CTCCAAAAAA | GAAGAGAAAG | GTAGAAGACC | CCAAGGACTT | 1440 |
| TCCTTCAGAA | TTGCTAAGTT | TTTTGAGTCA | TGCTGTGTTT | AGTAATAGAA | CTCTTGCTTG | 1500 |
| CTTTGCTATT | TACACCACAA | AGGAAAAAGC | TGCACTGCTA | TACAAGAAAA | TTATGGAAAA | 1560 |
| ATATTTGATG | TATAGTGCCT | TGACTAGAGA | TCATAATCAG | CCATACCACA | TTTGTAGAGG | 1620 |
| TTTTACTTGC | TTTAAAAAAC | CTCCCACACC | TCCCCCTGAA | CCTGAAACAT | AAAATGAATG | 1680 |
| CAATTGTTGT | TGTTAACTTG | TTTATTGCAG | CTTATAATGG | TTACAAATAA | AGCAATAGCA | 1740 |
| TCACAAATTT | CACAAATAAA | GCATTTTTT | CACTGCATTC | TAGTTGTGGT | TTGTCCAAAC | 1800 |
| TCATCAATGT | ATCTTATCAT | GTCTAGATCT | GGAAGGTGCT | GAGGTACGAT | GAGACCCGCA | 1860 |
| CCAGGTGCAG | ACCCTGCGAG | TGTGGCGGTA | AACATATTAG | GAACCAGCCT | GTGATGCTGG | 1920 |
| ATGTGACCGA | GGAGCTGAGG | CCCGATCACT | TGGTGCTGGC | CTGCACCCGC | GCTGAGTTTG | 1980 |
| GCTCTAGCGA | TGAAGATACA | GATTGAGGTA | CTGAAATGTG | TGGGCGTGGC | TTAAGGGTGG | 2040 |
| GAAAGAATAT | ATAAGGTGGG | GGTCTTATGT | AGTTTTGTAT | CTGTTTTGCA | GCAGCCGCCG | 2100 |
| CCGCCATGAG | CACCAACTCG | TTTGATGGAA | GCATTGTGAG | CTCATATTTG | ACAACGCGCA | 2160 |
| TGCCCCCATG | GGCCGGGGTG | CGTCAGAATG | TGATGGGCTC | CAGCATTGAT | GGTCGCCCCG | 2220 |
| TCCTGCCCGC | AAACTCTACT | ACCTTGACCT | ACGAGACGT | GTCTGGAACG | CCGTTGGAGA | 2280 |
| CTGCAGCCTC | CGCCGCCGCT | TCAGCCGCTG | CAGCCACCGC | CCGCGGGATT | GTGACTGACT | 2340 |
| TTGCTTTCCT | GAGCCCGCTT | GCAAGCAGTG | CAGCTTCCG | TTCATCCGCC | CGCGATGACA | 2400 |
| AGTTGACGGC | TCTTTTGGCA | CAATTGGATT | CTTTGACCCG | GAACTTAAT | GTCGTTTCTC | 2460 |
| AGCAGCTGTT | GGATCTGCGC | CAGCAGGTTT | CTGCCCTGAA | GGCTTCCTCC | CCTCCCAATG | 2520 |
| CGGTTTAAAA | CATAAATAAA | AAACCAGACT | CTGTTTGGAT | TTGGATCAAG | CAAGTGTCTT | 2580 |
| GCTGTCTTTA | TTTAGGGGTT | TTGCGCGCGC | GGTAGGCCCG | GGACCAGCGG | TCTCGGTCGT | 2640 |
| TGAGGGTCCT | GTGTATTTTT | TCCAGGACGT | GGTAAAGGTG | ACTCTGGATG | TTCAGATACA | 2700 |
| TGGGCATAAG | CCCGTCTCTG | GGGTGGAGGT | AGCACCACTG | CAGAGCTTCA | TGCTGCGGGG | 2760 |
| TGGTGTTGTA | GATGATCCAG | TCGTAGCAGG | AGCGCTGGGC | GTGGTGCCTA | AAAATGTCTT | 2820 |
| TCAGTAGCAA | GCTGATTGCC | AGGGGCAGGC | CCTTGGTGTA | AGTGTTTACA | AAGCGGTTAA | 2880 |
| GCTGGGATGG | GTGCATACGT | GGGGATATGA | GATGCATCTT | GGACTGTATT | TTTAGGTTGG | 2940 |
| CTATGTTCCC | AGCCATATCC | CTCCGGGGAT | TCATGTTGTG | CAGAACCACC | AGCACAGTGT | 3000 |
| ATCCGGTGCA | CTTGGGAAAT | TTGTCATGTA | GCTTAGAAGG | AAATGCGTGG | AAGAACTTGG | 3060 |
| AGACGCCCTT | GTGACCTCCA | AGATTTTCCA | TGCATTCGTC | CATAATGATG | GCAATGGGCC | 3120 |
| CACGGGCGGC | GGCCTGGGCG | AAGATATTTC | TGGGATCACT | AACGTCATAG | TTGTGTTCCA | 3180 |
| GGATGAGATC | GTCATAGGCC | ATTTTTACAA | AGCGCGGGCG | GAGGGTGCCA | GACTGCGGTA | 3240 |
| TAATGGTTCC | ATCCGGCCCA | GGGGCGTAGT | TACCCTCACA | GATTTGCATT | TCCCACGCTT | 3300 |
| TGAGTTCAGA | TGGGGGGATC | ATGTCTACCT | GCGGGGCGAT | GAAGAAAACG | GTTTCCGGGG | 3360 |

| | | | | | | |
|---|---|---|---|---|---|---|
| TAGGGGAGAT | CAGCTGGGAA | GAAAGCAGGT | TCCTGAGCAG | CTGCGACTTA | CCGCAGCCGG | 3420 |
| TGGGCCCGTA | AATCACACCT | ATTACCGGGT | GCAACTGGTA | GTTAAGAGAG | CTGCAGCTGC | 3480 |
| CGTCATCCCT | GAGCAGGGGG | GCCACTTCGT | TAAGCATGTC | CCTGACTCGC | ATGTTTTCCC | 3540 |
| TGACCAAATC | CGCCAGAAGG | CGCTCGCCGC | CCAGCGATAG | CAGTTCTTGC | AAGGAAGCAA | 3600 |
| AGTTTTTCAA | CGGTTTGAGA | CCGTCCGCCG | TAGGCATGCT | TTTGAGCGTT | TGACCAAGCA | 3660 |
| GTTCCAGGCG | GTCCCACAGC | TCGGTCACCT | GCTCTACGGC | ATCTCGATCC | AGCATATCTC | 3720 |
| CTCGTTTCGC | GGGTTGGGGC | GGCTTTCGCT | GTACGGCAGT | AGTCGGTGCT | CGTCCAGACG | 3780 |
| GGCCAGGGTC | ATGTCTTTCC | ACGGGCGCAG | GGTCCTCGTC | AGCGTAGTCT | GGGTCACGGT | 3840 |
| GAAGGGGTGC | GCTCCGGGCT | GCGCGCTGGC | CAGGGTGCGC | TTGAGGCTGG | TCCTGCTGGT | 3900 |
| GCTGAAGCGC | TGCCGGTCTT | CGCCCTGCGC | GTCGGCCAGG | TAGCATTTGA | CCATGGTGTC | 3960 |
| ATAGTCCAGC | CCCTCCGCGG | CGTGGCCCTT | GGCGCGCAGC | TTGCCCTTGG | AGGAGGCGCC | 4020 |
| GCACGAGGGG | CAGTGCAGAC | TTTTGAGGGC | GTAGAGCTTG | GGCGCGAGAA | ATACCGATTC | 4080 |
| CGGGGAGTAG | GCATCCGCGC | CGCAGGCCCC | GCAGACGGTC | TCGCATTCCA | CGAGCCAGGT | 4140 |
| GAGCTCTGGC | CGTTCGGGGT | CAAAAACCAG | GTTTCCCCCA | TGCTTTTTGA | TGCGTTTCTT | 4200 |
| ACCTCTGGTT | TCCATGAGCC | GGTGTCCACG | CTCGGTGACG | AAAAGGCTGT | CCGTGTCCCC | 4260 |
| GTATACAGAC | TTGAGAGGCC | TGTCCTCGAG | GATCAGCTTC | CGGTCTCCCT | ATAGTGAGTC | 4320 |
| GTATTAATTT | CGATAAGCCA | GCTGCATTAA | TGAATCGGCC | AACGCGCGGG | GAGAGGCGGT | 4380 |
| TTGCGTATTG | GGCGCTCTTC | CGCTTCCTCG | CTCACTGACT | CGCTGCGCTC | GGTCGTTCGG | 4440 |
| CTGCGGCGAG | CGGTATCAGC | TCACTCAAAG | GCGGTAATAC | GGTTATCCAC | AGAATCAGGG | 4500 |
| GATAACGCAG | GAAAGAACAT | GTGAGCAAAA | GGCCAGCAAA | AGGCCAGGAA | CCGTAAAAAG | 4560 |
| GCCGCGTTGC | TGGCGTTTTT | CCATAGGCTC | CGCCCCCCTG | ACGAGCATCA | CAAAAATCGA | 4620 |
| CGCTCAAGTC | AGAGGTGGCG | AAACCCGACA | GGACTATAAA | GATACCAGGC | GTTTCCCCCT | 4680 |
| GGAAGCTCCC | TCGTGCGCTC | TCCTGTTCCG | ACCCTGCCGC | TTACCGGATA | CCTGTCCGCC | 4740 |
| TTTCTCCCTT | CGGGAAGCGT | GGCGCTTTCT | CATAGCTCAC | GCTGTAGGTA | TCTCAGTTCG | 4800 |
| GTGTAGGTCG | TTCGCTCCAA | GCTGGGCTGT | GTGCACGAAC | CCCCCGTTCA | GCCCGACCGC | 4860 |
| TGCGCCTTAT | CCGGTAACTA | TCGTCTTGAG | TCCAACCCGG | TAAGACACGA | CTTATCGCCA | 4920 |
| CTGGCAGCAG | CCACTGGTAA | CAGGATTAGC | AGAGCGAGGT | ATGTAGGCGG | TGCTACAGAG | 4980 |
| TTCTTGAAGT | GGTGGCCTAA | CTACGGCTAC | ACTAGAAGGA | CAGTATTTGG | TATCTGCGCT | 5040 |
| CTGCTGAAGC | CAGTTACCTT | CGGAAAAAGA | GTTGGTAGCT | CTTGATCCGG | CAAACAAACC | 5100 |
| ACCGCTGGTA | GCGGTGGTTT | TTTTGTTTGC | AAGCAGCAGA | TTACGCGCAG | AAAAAAAGGA | 5160 |
| TCTCAAGAAG | ATCCTTTGAT | CTTTTCTACG | GGGTCTGACG | CTCAGTGGAA | CGAAAACTCA | 5220 |
| CGTTAAGGGA | TTTTGGTCAT | GAGATTATCA | AAAAGGATCT | TCACCTAGAT | CCTTTTAAAT | 5280 |
| TAAAAATGAA | GTTTTAAATC | AATCTAAAGT | ATATATGAGT | AAACTTGGTC | TGACAGTTAC | 5340 |
| CAATGCTTAA | TCAGTGAGGC | ACCTATCTCA | GCGATCTGTC | TATTTCGTTC | ATCCATAGTT | 5400 |
| GCCTGACTCC | CCGTCGTGTA | GATAACTACG | ATACGGGAGG | GCTTACCATC | TGGCCCCAGT | 5460 |
| GCTGCAATGA | TACCGCGAGA | CCCACGCTCA | CCGGCTCCAG | ATTTATCAGC | AATAAACCAG | 5520 |
| CCAGCCGGAA | GGGCCGAGCG | CAGAAGTGGT | CCTGCAACTT | TATCCGCCTC | CATCCAGTCT | 5580 |
| ATTAATTGTT | GCCGGGAAGC | TAGAGTAAGT | AGTTCGCCAG | TTAATAGTTT | GCGCAACGTT | 5640 |
| GTTGCCATTG | CTACAGGCAT | CGTGGTGTCA | CGCTCGTCGT | TTGGTATGGC | TTCATTCAGC | 5700 |
| TCCGGTTCCC | AACGATCAAG | GCGAGTTACA | TGATCCCCCA | TGTTGTGCAA | AAAAGCGGTT | 5760 |

```
AGCTCCTTCG  GTCCTCCGAT  CGTTGTCAGA  AGTAAGTTGG  CCGCAGTGTT  ATCACTCATG    5820

GTTATGGCAG  CACTGCATAA  TTCTCTTACT  GTCATGCCAT  CCGTAAGATG  CTTTTCTGTG    5880

ACTGGTGAGT  ACTCAACCAA  GTCATTCTGA  GAATAGTGTA  TGCGGCGACC  GAGTTGCTCT    5940

TGCCCGGCGT  CAATACGGGA  TAATACCGCG  CCACATAGCA  GAACTTTAAA  AGTGCTCATC    6000

ATTGGAAAAC  GTTCTTCGGG  GCGAAAACTC  TCAAGGATCT  TACCGCTGTT  GAGATCCAGT    6060

TCGATGTAAC  CCACTCGTGC  ACCCAACTGA  TCTTCAGCAT  CTTTTACTTT  CACCAGCGTT    6120

TCTGGGTGAG  CAAAAACAGG  AAGGCAAAAT  GCCGCAAAAA  AGGGAATAAG  GGCGACACGG    6180

AAATGTTGAA  TACTCATACT  CTTCCTTTTT  CAATATTATT  GAAGCATTTA  TCAGGGTTAT    6240

TGTCTCATGA  GCGGATACAT  ATTTGAATGT  ATTTAGAAAA  ATAAACAAAT  AGGGGTTCCG    6300

CGCACATTTC  CCCGAAAAGT  GCCACCTGAC  GTCTAAGAAA  CCATTATTAT  CATGACATTA    6360

ACCTATAAAA  ATAGGCGTAT  CACGAGGCCC  TTTCGTCTCG  CGCGTTTCGG  TGATGACGGT    6420
```

( 2 ) INFORMATION FOR SEQ ID NO:2:

( i ) SEQUENCE CHARACTERISTICS:
        ( A ) LENGTH: 820 amino acids
        ( B ) TYPE: amino acid
        ( D ) TOPOLOGY: linear ( i i ) MOLECULE TYPE: protein ( i x ) FEATURE:
        ( A ) NAME/KEY: CDS
        ( B ) LOCATION: 1831..4290
        ( D ) OTHER INFORMATION: /note= "Xaa = Ter"

( x i ) SEQUENCE DESCRIPTION: SEQ ID NO:2:

```
Gly  Arg  Cys  Xaa  Gly  Thr  Met  Arg  Pro  Ala  Pro  Gly  Ala  Asp  Pro  Ala
 1              5                        10                       15

Ser  Val  Ala  Val  Asn  Ile  Leu  Gly  Thr  Ser  Leu  Xaa  Cys  Trp  Met  Xaa
              20                        25                       30

Pro  Arg  Ser  Xaa  Gly  Pro  Ile  Thr  Trp  Cys  Trp  Pro  Ala  Pro  Ala  Leu
              35                        40                       45

Ser  Leu  Ala  Leu  Ala  Met  Lys  Ile  Gln  Ile  Glu  Val  Leu  Lys  Cys  Val
         50                        55                       60

Gly  Val  Ala  Xaa  Gly  Trp  Glu  Arg  Ile  Tyr  Lys  Val  Gly  Val  Leu  Cys
65                        70                       75                       80

Ser  Phe  Val  Ser  Val  Leu  Gln  Gln  Pro  Pro  Pro  Xaa  Ala  Pro  Thr
                   85                       90                       95

Arg  Leu  Met  Glu  Ala  Leu  Xaa  Ala  His  Ile  Xaa  Gln  Arg  Ala  Cys  Pro
                  100                      105                     110

His  Gly  Pro  Gly  Cys  Val  Arg  Met  Xaa  Trp  Ala  Pro  Ala  Leu  Met  Val
              115                      120                     125

Ala  Pro  Ser  Cys  Pro  Gln  Thr  Leu  Leu  Pro  Xaa  Pro  Thr  Arg  Pro  Cys
         130                      135                     140

Leu  Glu  Arg  Arg  Trp  Arg  Leu  Gln  Pro  Pro  Pro  Leu  Gln  Pro  Leu
145                      150                      155                     160

Gln  Pro  Pro  Pro  Ala  Gly  Leu  Xaa  Leu  Thr  Leu  Leu  Ser  Xaa  Ala  Arg
                   165                      170                     175

Leu  Gln  Ala  Val  Gln  Leu  Pro  Val  His  Pro  Pro  Ala  Met  Thr  Ser  Xaa
                   180                      185                     190

Arg  Leu  Phe  Trp  His  Asn  Trp  Ile  Leu  Xaa  Pro  Gly  Asn  Leu  Met  Ser
              195                      200                     205

Phe  Leu  Ser  Ser  Cys  Trp  Ile  Cys  Ala  Ser  Arg  Phe  Leu  Pro  Xaa  Arg
         210                      215                     220
```

```
Leu  Pro  Pro  Leu  Pro  Met  Arg  Phe  Lys  Thr  Xaa  Ile  Lys  Asn  Gln  Thr
225            		230                 235                           240

Leu  Phe  Gly  Phe  Gly  Ser  Ser  Lys  Cys  Leu  Ala  Val  Phe  Ile  Xaa  Gly
                    245                 250                      255

Phe  Cys  Ala  Arg  Gly  Arg  Pro  Gly  Thr  Ser  Gly  Leu  Gly  Arg  Xaa  Gly
               260                 265                           270

Ser  Cys  Val  Phe  Phe  Pro  Gly  Arg  Gly  Lys  Gly  Asp  Ser  Gly  Cys  Ser
          275                 280                      285

Asp  Thr  Trp  Ala  Xaa  Ala  Arg  Leu  Trp  Gly  Gly  Ser  Thr  Thr  Ala
     290                 295                      300

Glu  Leu  His  Ala  Ala  Gly  Trp  Cys  Cys  Arg  Xaa  Ser  Ser  Arg  Ser  Arg
305            	    310                 315                           320

Ser  Ala  Gly  Arg  Gly  Ala  Xaa  Lys  Cys  Leu  Ser  Val  Ala  Ser  Xaa  Leu
                    325                 330                      335

Pro  Gly  Ala  Gly  Pro  Trp  Cys  Lys  Cys  Leu  Gln  Ser  Gly  Xaa  Ala  Gly
               340                 345                           350

Met  Gly  Ala  Tyr  Val  Gly  Ile  Xaa  Asp  Ala  Ser  Trp  Thr  Val  Phe  Leu
          355                 360                      365

Gly  Trp  Leu  Cys  Ser  Gln  Pro  Tyr  Pro  Ser  Gly  Asp  Ser  Cys  Cys  Ala
     370                 375                      380

Glu  Pro  Pro  Ala  Gln  Cys  Ile  Arg  Cys  Thr  Trp  Glu  Ile  Cys  His  Val
385                      390                 395                           400

Ala  Xaa  Lys  Glu  Met  Arg  Gly  Arg  Thr  Trp  Arg  Arg  Pro  Cys  Asp  Leu
                    405                 410                      415

Gln  Asp  Phe  Pro  Cys  Ile  Arg  Pro  Xaa  Xaa  Trp  Gln  Trp  Ala  His  Gly
               420                 425                      430

Arg  Arg  Pro  Gly  Arg  Arg  Tyr  Phe  Trp  Asp  His  Xaa  Arg  His  Ser  Cys
               435                 440                      445

Val  Pro  Gly  Xaa  Asp  Arg  His  Arg  Pro  Phe  Leu  Gln  Ser  Ala  Gly  Gly
               450                 455                      460

Gly  Cys  Gln  Thr  Ala  Val  Xaa  Trp  Phe  His  Pro  Ala  Gln  Gly  Arg  Ser
465                      470                 475                           480

Tyr  Pro  His  Arg  Phe  Ala  Phe  Pro  Thr  Leu  Xaa  Val  Gln  Met  Gly  Gly
               485                 490                      495

Ser  Cys  Leu  Pro  Ala  Gly  Arg  Xaa  Arg  Lys  Arg  Phe  Pro  Gly  Xaa  Gly
               500                 505                      510

Arg  Ser  Ala  Gly  Lys  Lys  Ala  Gly  Ser  Xaa  Ala  Ala  Ala  Thr  Tyr  Arg
               515                 520                      525

Ser  Arg  Trp  Ala  Arg  Lys  Ser  His  Leu  Leu  Pro  Gly  Ala  Thr  Gly  Ser
530                      535                      540

Xaa  Glu  Ser  Cys  Ser  Cys  Arg  His  Pro  Xaa  Ala  Gly  Gly  Pro  Leu  Arg
545                      550                 555                           560

Xaa  Ala  Cys  Pro  Xaa  Leu  Ala  Cys  Phe  Pro  Xaa  Pro  Asn  Pro  Pro  Glu
                    565                 570                      575

Gly  Ala  Arg  Arg  Pro  Ala  Ile  Ala  Val  Leu  Ala  Arg  Lys  Gln  Ser  Phe
               580                 585                      590

Ser  Thr  Val  Xaa  Asp  Arg  Pro  Pro  Xaa  Ala  Cys  Phe  Xaa  Ala  Phe  Asp
          595                 600                      605

Gln  Ala  Val  Pro  Gly  Gly  Pro  Thr  Ala  Arg  Ser  Pro  Ala  Leu  Arg  His
     610                 615                      620

Leu  Asp  Pro  Ala  Tyr  Leu  Leu  Val  Ser  Arg  Val  Gly  Ala  Ala  Phe  Ala
625            	    630                 635                           640

Val  Arg  Gln  Xaa  Ser  Val  Leu  Val  Gln  Thr  Gly  Gln  Gly  His  Val  Phe
```

|     |     |     |     | 645 |     |     |     |     | 650 |     |     |     |     | 655 |     |
| --- | --- | --- | --- | --- | --- | --- | --- | --- | --- | --- | --- | --- | --- | --- | --- |
| Pro | Arg | Ala | Gln | Gly | Pro | Arg | Gln | Arg | Ser | Leu | Gly | His | Gly | Glu | Gly |
|     |     |     | 660 |     |     |     | 665 |     |     |     |     | 670 |     |     |     |
| Val | Arg | Ser | Gly | Leu | Arg | Ala | Gly | Gln | Gly | Ala | Leu | Glu | Ala | Gly | Pro |
|     |     | 675 |     |     |     |     | 680 |     |     |     |     | 685 |     |     |     |
| Ala | Gly | Ala | Glu | Ala | Leu | Pro | Val | Phe | Ala | Leu | Arg | Val | Gly | Gln | Val |
|     | 690 |     |     |     |     | 695 |     |     |     |     | 700 |     |     |     |     |
| Ala | Phe | Asp | His | Gly | Val | Ile | Val | Gln | Pro | Leu | Arg | Gly | Val | Ala | Leu |
| 705 |     |     |     |     | 710 |     |     |     |     | 715 |     |     |     |     | 720 |
| Gly | Ala | Gln | Leu | Ala | Leu | Gly | Gly | Gly | Ala | Ala | Arg | Gly | Ala | Val | Gln |
|     |     |     |     | 725 |     |     |     |     | 730 |     |     |     |     | 735 |     |
| Thr | Phe | Glu | Gly | Val | Glu | Leu | Gly | Arg | Glu | Lys | Tyr | Arg | Phe | Arg | Gly |
|     |     |     | 740 |     |     |     |     | 745 |     |     |     |     | 750 |     |     |
| Val | Gly | Ile | Arg | Ala | Ala | Gly | Pro | Ala | Asp | Gly | Leu | Ala | Phe | His | Glu |
|     |     | 755 |     |     |     |     | 760 |     |     |     |     | 765 |     |     |     |
| Pro | Gly | Glu | Leu | Trp | Pro | Phe | Gly | Val | Lys | Asn | Gln | Val | Ser | Pro | Met |
|     | 770 |     |     |     |     | 775 |     |     |     |     | 780 |     |     |     |     |
| Leu | Phe | Asp | Ala | Phe | Leu | Thr | Ser | Gly | Phe | His | Glu | Pro | Val | Ser | Thr |
| 785 |     |     |     |     | 790 |     |     |     |     | 795 |     |     |     |     | 800 |
| Leu | Gly | Asp | Glu | Lys | Ala | Val | Arg | Val | Pro | Val | Tyr | Arg | Leu | Glu | Arg |
|     |     |     |     | 805 |     |     |     |     | 810 |     |     |     |     | 815 |     |
| Pro | Val | Leu | Glu |     |     |     |     |     |     |     |     |     |     |     |     |
|     |     |     | 820 |     |     |     |     |     |     |     |     |     |     |     |     |

( 2 ) INFORMATION FOR SEQ ID NO:3:

( i ) SEQUENCE CHARACTERISTICS:
        ( A ) LENGTH: 9641 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
| --- | --- | --- | --- | --- | --- |
| GAATTCTGAA | CGTGCAAAAA | AAATTACCAA | TAATCCAGAA | AATTATTATC | ATGGATTCTA | 60 |
| AAACGGATTA | CCGGTGAATT | CATCATCAAT | AATATACCTT | ATTTTGGATT | GAAGCCAATA | 120 |
| TGATAATGAG | GGGGTGGAGT | TTGTGACGTG | GCGCGGGGCG | TGGGAACGGG | GCGGGTGACG | 180 |
| TAGTAGTGTG | GCGGAAGTGT | GATGTTGCAA | GTGTGGCGGA | ACACATGTAA | GCGACGGATG | 240 |
| TGGCAAAAGT | GACGTTTTTG | GTGTGCGCCG | GTGTCAGATC | CAGACATGAT | AAGATACATT | 300 |
| GATGAGTTTG | GACAAACCAC | AACTAGAATG | CAGTGAAAAA | AATGCTTTAT | TTGTGAAATT | 360 |
| TGTGATGCTA | TTGCTTTATT | TGTAACCATT | ATAAGCTGCA | ATAAACAGGA | TCTTATTTTT | 420 |
| GACACCAGAC | CAACTGGTAA | TGGTAGCGAC | CGGCGCTCAG | CTGGAATTCC | GCCGATACTG | 480 |
| ACGGGCTCCA | GGAGTCGTCG | CCACCAATCC | CCATATGGAA | ACCGTCGATA | TTCAGCCATG | 540 |
| TGCCTTCTTC | CGCGTGCAGC | AGATGGCGAT | GGCTGGTTTC | CATCAGTTGC | TGTTGACTGT | 600 |
| AGCGGCTGAT | GTTGAACTGG | AAGTCGCCGC | GCCACTGGTG | TGGGCCATAA | TTCAATTCGC | 660 |
| GCGTCCCGCA | GCGCAGACCG | TTTTCGCTCG | GGAAGACGTA | CGGGGTATAC | ATGTCTGACA | 720 |
| ATGGCAGATC | CCAGCGGTCA | AAACAGGCGG | CAGTAAGGCG | GTCGGGATAG | TTTTCTTGCG | 780 |
| GCCCTAATCC | GAGCCAGTTT | ACCCGCTCTG | CTACCTGCGC | CAGCTGGCAG | TTCAGGCCAA | 840 |
| TCCGCGCCGG | ATGCGGTGTA | TCGCTCGCCA | CTTCAACATC | AACGGTAATC | GCCATTTGAC | 900 |
| CACTACCATC | AATCCGGTAG | GTTTTCCGGC | TGATAAATAA | GGTTTTCCCC | TGATGCTGCC | 960 |

| | | | | | | |
|---|---|---|---|---|---|---|
| ACGCGTGAGC | GGTCGTAATC | AGCACCGCAT | CAGCAAGTGT | ATCTGCCGTG | CACTGCAACA | 1020 |
| ACGCTGCTTC | GGCCTGGTAA | TGGCCCGCCG | CCTTCCAGCG | TTCGACCCAG | GCGTTAGGGT | 1080 |
| CAATGCGGGT | CGCTTCACTT | ACGCCAATGT | CGTTATCCAG | CGGTGCACGG | GTGAACTGAT | 1140 |
| CGCGCAGCGG | CGTCAGCAGT | TGTTTTTTAT | CGCCAATCCA | CATCTGTGAA | AGAAAGCCTG | 1200 |
| ACTGGCGGTT | AAATTGCCAA | CGCTTATTAC | CCAGCTCGAT | GCAAAAATCC | ATTTCGCTGG | 1260 |
| TGGTCAGATG | CGGGATGGCG | TGGGACGCGG | CGGGGAGCGT | CACACTGAGG | TTTTCCGCCA | 1320 |
| GACGCCACTG | CTGCCAGGCG | CTGATGTGCC | CGGCTTCTGA | CCATGCGGTC | GCGTTCGGTT | 1380 |
| GCACTACGCG | TACTGTGAGC | CAGAGTTGCC | CGGCGCTCTC | CGGCTGCGGT | AGTTCAGGCA | 1440 |
| GTTCAATCAA | CTGTTTACCT | TGTGGAGCGA | CATCCAGAGG | CACTTCACCG | CTTGCCAGCG | 1500 |
| GCTTACCATC | CAGCGCCACC | ATCCAGTGCA | GGAGCTCGTT | ATCGCTATGA | CGGAACAGGT | 1560 |
| ATTCGCTGGT | CACTTCGATG | GTTTGCCCGG | ATAAACGGAA | CTGGAAAAAC | TGCTGCTGGT | 1620 |
| GTTTTGCTTC | CGTCAGCGCT | GGATGCGGCG | TGCGGTCGGC | AAAGACCAGA | CCGTTCATAC | 1680 |
| AGAACTGGCG | ATCGTTCGGC | GTATCGCCAA | AATCACCGCC | GTAAGCCGAC | CACGGGTTGC | 1740 |
| CGTTTTCATC | ATATTTAATC | AGCGACTGAT | CCACCCAGTC | CCAGACGAAG | CCGCCCTGTA | 1800 |
| AACGGGGATA | CTGACGAAAC | GCCTGCCAGT | ATTTAGCGAA | ACCGCCAAGA | CTGTTACCCA | 1860 |
| TCGCGTGGGC | GTATTCGCAA | AGGATCAGCG | GGCGCGTCTC | TCCAGGTAGC | GAAAGCCATT | 1920 |
| TTTTGATGGA | CCATTTCGGC | ACAGCCGGGA | AGGGCTGGTC | TTCATCCACG | CGCGCGTACA | 1980 |
| TCGGGCAAAT | AATATCGGTG | CCGTGGTGT | CGGCTCCGCC | GCCTTCATAC | TGCACCGGGC | 2040 |
| GGGAAGGATC | GACAGATTTG | ATCCAGCGAT | ACAGCGCGTC | GTGATTAGCG | CCGTGGCCTG | 2100 |
| ATTCATTCCC | CAGCGACCAG | ATGATCACAC | TCGGGTGATT | ACGATCGCGC | TGCACCATTC | 2160 |
| GCGTTACGCG | TTCGCTCATC | GCCGGTAGCC | AGCGCGGATC | ATCGGTCAGA | CGATTCATTG | 2220 |
| GCACCATGCC | GTGGGTTTCA | ATATTGGCTT | CATCCACCAC | ATACAGGCCG | TAGCGGTCGC | 2280 |
| ACAGCGTGTA | CCACAGCGGA | TGGTTCGGAT | AATGCGAACA | GCGCACGGCG | TTAAAGTTGT | 2340 |
| TCTGCTTCAT | CAGCAGGATA | TCCTGCACCA | TCGTCTGCTC | ATCCATGACC | TGACCATGCA | 2400 |
| GAGGATGATG | CTCGTGACGG | TTAACGCCTC | GAATCAGCAA | CGGCTTGCCG | TTCAGCAGCA | 2460 |
| GCAGACCATT | TTCAATCCGC | ACCTCGCGGA | AACCGACATC | GCAGGCTTCT | GCTTCAATCA | 2520 |
| GCGTGCCGTC | GGCGGTGTGC | AGTTCAACCA | CCGCACGATA | GAGATTCGGG | ATTTCGGCGC | 2580 |
| TCCACAGTTT | CGGGTTTTCG | ACGTTCAGAC | GTAGTGTGAC | GCGATCGGCA | TAACCACCAC | 2640 |
| GCTCATCGAT | AATTTCACCG | CCGAAAGGCG | CGGTGCCGCT | GGCGACCTGC | GTTTCACCCT | 2700 |
| GCCATAAAGA | AACTGTTACC | CGTAGGTAGT | CACGCAACTC | GCCGCACATC | TGAACTTCAG | 2760 |
| CCTCCAGTAC | AGCGCGGCTG | AAATCATCAT | TAAAGCGAGT | GGCAACATGG | AAATCGCTGA | 2820 |
| TTTGTGTAGT | CGGTTTATGC | AGCAACGAGA | CGTCACGGAA | AATGCCGCTC | ATCCGCCACA | 2880 |
| TATCCTGATC | TTCCAGATAA | CTGCCGTCAC | TCCAACGCAG | CACCATCACC | GCGAGGCGGT | 2940 |
| TTTCTCCGGC | GCGTAAAAAT | GCGCTCAGGT | CAAATTCAGA | CGGCAAACGA | CTGTCCTGGC | 3000 |
| CGTAACCGAC | CCAGCGCCCG | TTGCACCACA | GATGAAACGC | CGAGTTAACG | CCATCAAAAA | 3060 |
| TAATTCGCGT | CTGGCCTTCC | TGTAGCCAGC | TTTCATCAAC | ATTAAATGTG | AGCGAGTAAC | 3120 |
| AACCCGTCGG | ATTCTCCGTG | GGAACAAACG | GCGGATTGAC | CGTAATGGGA | TAGGTTACGT | 3180 |
| TGGTGTAGAT | GGGCGCATCG | TAACCGTGCA | TCTGCCAGTT | TGAGGGGACG | ACGACAGTAT | 3240 |
| CGGCCTCAGG | AAGATCGCAC | TCCAGCCAGC | TTTCCGGCAC | CGCTTCTGGT | GCCGGAAACC | 3300 |
| AGGCAAAGCG | CCATTCGCCA | TTCAGGCTGC | GCAACTGTTG | GGAAGGGCGA | TCGGTGCGGG | 3360 |

-continued

| | | | | | | |
|---|---|---|---|---|---|---|
| CCTCTTCGCT | ATTACGCCAG | CTGGCGAAAG | GGGGATGTGC | TGCAAGGCGA | TTAAGTTGGG | 3420 |
| TAACGCCAGG | GTTTTCCCAG | TCACGACGTT | GTAAAACGAC | GGCCAGTGCC | AAGCTTGGAC | 3480 |
| TCAAAAAACT | TAGCAATTCT | GAAGGAAAGT | CCTTGGGGTC | TTCTACCTTT | CTCTTCTTTT | 3540 |
| TTGCGGAATT | CCGGAAAACT | TTATCCATCT | TTGCAAAGCT | TGGGTCTCCC | TATAGTGAGT | 3600 |
| CGTATTAATT | TCGATAAGCC | AGTAAGCAGT | GGGTTCTCTA | GTTAGCCAGA | GAGCTCTGCT | 3660 |
| TATATAGACC | TCCCACCGTA | CACGCCTACC | GCCCATTTGC | GTCAATGGGG | CGGAGTTGTT | 3720 |
| ACGACATTTT | GGAAAGTCCC | GTTGATTTTG | GTGCCAAAAC | AAACTCCCAT | TGACGTCAAT | 3780 |
| GGGGTGGAGA | CTTGGAAATC | CCCGTGAGTC | AAACCGCTAT | CCACGCCCAT | TGATGTACTG | 3840 |
| CCAAAACCGC | ATCACCATGG | TAATAGCGAT | GACTAATACG | TAGATGTACT | GCCAAGTAGG | 3900 |
| AAAGTCCCAT | AAGGTCATGT | ACTGGGCATA | ATGCCAGGCG | GGCCATTTAC | CGTCATTGAC | 3960 |
| GTCAATAGGG | GGCGTACTTG | GCATATGATA | CACTTGATGT | ACTGCCAAGT | GGGCAGTTTA | 4020 |
| CCGTAAATAG | TCCACCCATT | GACGTCAATG | GAAAGTCCCT | ATTGGCGTTA | CTATGGGAAC | 4080 |
| ATACGTCATT | ATTGACGTCA | ATGGGCGGGG | GTCGTTGGGC | GGTCAGCCAG | GCGGGCCATT | 4140 |
| TACCGTAAGT | TATGTAACGC | GGAACTCCAT | ATATGGGCTA | TGAACTAATG | ACCCCGTAAT | 4200 |
| TGATTACTAT | TAATAACTAG | TCAATAATCA | ATGTCAACGC | GTATATCTGG | CCCGTACATC | 4260 |
| GCGAAGCAGC | GCAAAACGCC | TAACCCCGGG | CCAGATCTGA | CATCGATTAC | GCCAAGCTTG | 4320 |
| CATGCCTGCA | GGTTTAAACA | GTCGACTCTA | GACTTAATTA | AGGATCTGGA | AGGTGCTGAG | 4380 |
| GTACGATGAG | ACCCGCACCA | GGTGCAGACC | CTGCGAGTGT | GGCGGTAAAC | ATATTAGGAA | 4440 |
| CCAGCCTGTG | ATGCTGGATG | TGACCGAGGA | GCTGAGGCCC | GATCACTTGG | TGCTGGCCTG | 4500 |
| CACCCGCGCT | GAGTTTGGCT | CTAGCGATGA | AGATACAGAT | TGAGGTACTG | AAATGTGTGG | 4560 |
| GCGTGGCTTA | AGGGTGGGAA | AGAATATATA | AGGTGGGGGT | CTTATGTAGT | TTTGTATCTG | 4620 |
| TTTTGCAGCA | GCCGCCGCCG | CCATGAGCAC | CAACTCGTTT | GATGGAAGCA | TTGTGAGCTC | 4680 |
| ATATTTGACA | ACGCGCATGC | CCCCATGGGC | CGGGGTGCGT | CAGAATGTGA | TGGGCTCCAG | 4740 |
| CATTGATGGT | CGCCCCGTCC | TGCCCGCAAA | CTCTACTACC | TTGACCTACG | AGACCGTGTC | 4800 |
| TGGAACGCCG | TTGGAGACTG | CAGCCTCCGC | CGCCGCTTCA | GCCGCTGCAG | CCACCGCCCG | 4860 |
| CGGGATTGTG | ACTGACTTTG | CTTTCCTGAG | CCCGCTTGCA | AGCAGTGCAG | CTTCCCGTTC | 4920 |
| ATCCGCCCGC | GATGACAAGT | TGACGGCTCT | TTTGGCACAA | TTGGATTCTT | TGACCCGGGA | 4980 |
| ACTTAATGTC | GTTTCTCAGC | AGCTGTTGGA | TCTGCGCCAG | CAGGTTTCTG | CCCTGAAGGC | 5040 |
| TTCCTCCCCT | CCCAATGCGG | TTTAAAACAT | AAATAAAAAA | CCAGACTCTG | TTTGGATTTG | 5100 |
| GATCAAGCAA | GTGTCTTGCT | GTCTTTATTT | AGGGGTTTTG | CGCGCGCGGT | AGGCCCGGGA | 5160 |
| CCAGCGGTCT | CGGTCGTTGA | GGGTCCTGTG | TATTTTTTCC | AGGACGTGGT | AAAGGTGACT | 5220 |
| CTGGATGTTC | AGATACATGG | GCATAAGCCC | GTCTCTGGGG | TGGAGGTAGC | ACCACTGCAG | 5280 |
| AGCTTCATGC | TGCGGGGTGG | TGTTGTAGAT | GATCCAGTCG | TAGCAGGAGC | GCTGGGCGTG | 5340 |
| GTGCCTAAAA | ATGTCTTTCA | GTAGCAAGCT | GATTGCCAGG | GCAGGCCCT | TGGTGTAAGT | 5400 |
| GTTTACAAAG | CGGTTAAGCT | GGGATGGGTG | CATACGTGGG | GATATGAGAT | GCATCTTGGA | 5460 |
| CTGTATTTTT | AGGTTGGCTA | TGTTCCCAGC | CATATCCCTC | CGGGGATTCA | TGTTGTGCAG | 5520 |
| AACCACCAGC | ACAGTGTATC | CGGTGCACTT | GGGAAATTTG | TCATGTAGCT | TAGAAGGAAA | 5580 |
| TGCGTGGAAG | AACTTGGAGA | CGCCCTTGTG | ACCTCCAAGA | TTTTCCATGC | ATTCGTCCAT | 5640 |
| AATGATGGCA | ATGGGCCCAC | GGGCGGCGGC | CTGGGCGAAG | ATATTCTGG | GATCACTAAC | 5700 |
| GTCATAGTTG | TGTTCCAGGA | TGAGATCGTC | ATAGGCCATT | TTTACAAAGC | GCGGGCGGAG | 5760 |

| | | | | | | |
|---|---|---|---|---|---|---|
| GGTGCCAGAC | TGCGGTATAA | TGGTTCCATC | CGGCCCAGGG | GCGTAGTTAC | CCTCACAGAT | 5820 |
| TTGCATTTCC | CACGCTTTGA | GTTCAGATGG | GGGGATCATG | TCTACCTGCG | GGGCGATGAA | 5880 |
| GAAAACGGTT | TCCGGGGTAG | GGGAGATCAG | CTGGGAAGAA | AGCAGGTTCC | TGAGCAGCTG | 5940 |
| CGACTTACCG | CAGCCGGTGG | GCCCGTAAAT | CACACCTATT | ACCGGGTGCA | ACTGGTAGTT | 6000 |
| AAGAGAGCTG | CAGCTGCCGT | CATCCCTGAG | CAGGGGGGCC | ACTTCGTTAA | GCATGTCCCT | 6060 |
| GACTCGCATG | TTTTCCCTGA | CCAAATCCGC | CAGAAGGCGC | TCGCCGCCCA | GCGATAGCAG | 6120 |
| TTCTTGCAAG | GAAGCAAAGT | TTTTCAACGG | TTTGAGACCG | TCCGCCGTAG | GCATGCTTTT | 6180 |
| GAGCGTTTGA | CCAAGCAGTT | CCAGGCGGTC | CCACAGCTCG | GTCACCTGCT | CTACGGCATC | 6240 |
| TCGATCCAGC | ATATCTCCTC | GTTTCGCGGG | TTGGGGCGGC | TTTCGCTGTA | CGGCAGTAGT | 6300 |
| CGGTGCTCGT | CCAGACGGGC | CAGGGTCATG | TCTTTCCACG | GGCGCAGGGT | CCTCGTCAGC | 6360 |
| GTAGTCTGGG | TCACGGTGAA | GGGGTGCGCT | CCGGGCTGCG | CGCTGGCCAG | GGTGCGCTTG | 6420 |
| AGGCTGGTCC | TGCTGGTGCT | GAAGCGCTGC | CGGTCTTCGC | CCTGCGCGTC | GGCCAGGTAG | 6480 |
| CATTTGACCA | TGGTGTCATA | GTCCAGCCCC | TCCGCGGCGT | GGCCCTTGGC | GCGCAGCTTG | 6540 |
| CCCTTGGAGG | AGGCGCCGCA | CGAGGGGCAG | TGCAGACTTT | TGAGGGCGTA | GAGCTTGGGC | 6600 |
| GCGAGAAATA | CCGATTCCGG | GGAGTAGGCA | TCCGCGCCGC | AGGCCCCGCA | GACGGTCTCG | 6660 |
| CATTCCACGA | GCCAGGTGAG | CTCTGGCCGT | TCGGGGTCAA | AAACCAGGTT | TCCCCCATGC | 6720 |
| TTTTTGATGC | GTTTCTTACC | TCTGGTTTCC | ATGAGCGGT | GTCCACGCTC | GGTGACGAAA | 6780 |
| AGGCTGTCCG | TGTCCCCGTA | TACAGACTTG | AGAGGCCTGT | CCTCGAGGAT | CAGCTTCCGG | 6840 |
| TCTCCCTATA | GTGAGTCGTA | TTAATTTCGA | TAAGCCAGCT | GCATTAATGA | ATCGGCCAAC | 6900 |
| GCGCGGGGAG | AGGCGGTTTG | CGTATTGGGC | GCTCTTCCGC | TTCCTCGCTC | ACTGACTCGC | 6960 |
| TGCGCTCGGT | CGTTCGGCTG | CGGCGAGCGG | TATCAGCTCA | CTCAAAGGCG | GTAATACGGT | 7020 |
| TATCCACAGA | ATCAGGGGAT | AACGCAGGAA | AGAACATGTG | AGCAAAAGGC | CAGCAAAAGG | 7080 |
| CCAGGAACCG | TAAAAAGGCC | GCGTTGCTGG | CGTTTTTCCA | TAGGCTCCGC | CCCCCTGACG | 7140 |
| AGCATCACAA | AAATCGACGC | TCAAGTCAGA | GGTGGCGAAA | CCCGACAGGA | CTATAAAGAT | 7200 |
| ACCAGGCGTT | TCCCCCTGGA | AGCTCCCTCG | TGCGCTCTCC | TGTTCCGACC | CTGCCGCTTA | 7260 |
| CCGGATACCT | GTCCGCCTTT | CTCCCTTCGG | GAAGCGTGGC | GCTTTCTCAT | AGCTCACGCT | 7320 |
| GTAGGTATCT | CAGTTCGGTG | TAGGTCGTTC | GCTCCAAGCT | GGGCTGTGTG | CACGAACCCC | 7380 |
| CCGTTCAGCC | CGACCGCTGC | GCCTTATCCG | GTAACTATCG | TCTTGAGTCC | AACCCGGTAA | 7440 |
| GACACGACTT | ATCGCCACTG | GCAGCAGCCA | CTGGTAACAG | GATTAGCAGA | GCGAGGTATG | 7500 |
| TAGGCGGTGC | TACAGAGTTC | TTGAAGTGGT | GGCCTAACTA | CGGCTACACT | AGAAGGACAG | 7560 |
| TATTTGGTAT | CTGCGCTCTG | CTGAAGCCAG | TTACCTTCGG | AAAAAGAGTT | GGTAGCTCTT | 7620 |
| GATCCGGCAA | ACAAACCACC | GCTGGTAGCG | GTGGTTTTTT | TGTTTGCAAG | CAGCAGATTA | 7680 |
| CGCGCAGAAA | AAAGGATCT | CAAGAAGATC | CTTTGATCTT | TTCTACGGGG | TCTGACGCTC | 7740 |
| AGTGGAACGA | AAACTCACGT | TAAGGGATTT | TGGTCATGAG | ATTATCAAAA | AGGATCTTCA | 7800 |
| CCTAGATCCT | TTTAAATTAA | AAATGAAGTT | TTAAATCAAT | CTAAAGTATA | TATGAGTAAA | 7860 |
| CTTGGTCTGA | CAGTTACCAA | TGCTTAATCA | GTGAGGCACC | TATCTCAGCG | ATCTGTCTAT | 7920 |
| TTCGTTCATC | CATAGTTGCC | TGACTCCCCG | TCGTGTAGAT | AACTACGATA | CGGGAGGGCT | 7980 |
| TACCATCTGG | CCCCAGTGCT | GCAATGATAC | CGCGAGACCC | ACGCTCACCG | GCTCCAGATT | 8040 |
| TATCAGCAAT | AAACCAGCCA | GCCGGAAGGG | CCGAGCGCAG | AAGTGGTCCT | GCAACTTTAT | 8100 |
| CCGCCTCCAT | CCAGTCTATT | AATTGTTGCC | GGGAAGCTAG | AGTAAGTAGT | TCGCCAGTTA | 8160 |

| | | | | | |
|---|---|---|---|---|---|
| ATAGTTTGCG | CAACGTTGTT | GCCATTGCTA | CAGGCATCGT | GGTGTCACGC | TCGTCGTTTG | 8220 |
| GTATGGCTTC | ATTCAGCTCC | GGTTCCCAAC | GATCAAGGCG | AGTTACATGA | TCCCCCATGT | 8280 |
| TGTGCAAAAA | AGCGGTTAGC | TCCTTCGGTC | CTCCGATCGT | TGTCAGAAGT | AAGTTGGCCG | 8340 |
| CAGTGTTATC | ACTCATGGTT | ATGGCAGCAC | TGCATAATTC | TCTTACTGTC | ATGCCATCCG | 8400 |
| TAAGATGCTT | TTCTGTGACT | GGTGAGTACT | CAACCAAGTC | ATTCTGAGAA | TAGTGTATGC | 8460 |
| GGCGACCGAG | TTGCTCTTGC | CCGGCGTCAA | TACGGGATAA | TACCGCGCCA | CATAGCAGAA | 8520 |
| CTTTAAAAGT | GCTCATCATT | GGAAAACGTT | CTTCGGGGCG | AAAACTCTCA | AGGATCTTAC | 8580 |
| CGCTGTTGAG | ATCCAGTTCG | ATGTAACCCA | CTCGTGCACC | CAACTGATCT | TCAGCATCTT | 8640 |
| TTACTTTCAC | CAGCGTTTCT | GGGTGAGCAA | AAACAGGAAG | GCAAAATGCC | GCAAAAAAGG | 8700 |
| GAATAAGGGC | GACACGGAAA | TGTTGAATAC | TCATACTCTT | CCTTTTTCAA | TATTATTGAA | 8760 |
| GCATTTATCA | GGGTTATTGT | CTCATGAGCG | GATACATATT | TGAATGTATT | TAGAAAAATA | 8820 |
| AACAAATAGG | GGTTCCGCGC | ACATTTCCCC | GAAAAGTGCC | ACCTGACGTC | TAAGAAACCA | 8880 |
| TTATTATCAT | GACATTAACC | TATAAAAATA | GGCGTATCAC | GAGGCCCTTT | CGTCTCGCGC | 8940 |
| GTTTCGGTGA | TGACGGTGAA | AACCTCTGAC | ACATGCAGCT | CCCGGAGACG | GTCACAGCTT | 9000 |
| GTCTGTAAGC | GGATGCCGGG | AGCAGACAAG | CCCGTCAGGG | CGCGTCAGCG | GGTGTTGGCG | 9060 |
| GGTGTCGGGG | CTGGCTTAAC | TATGCGGCAT | CAGAGCAGAT | TGTACTGAGA | GTGCACCATA | 9120 |
| TCGACGCTCT | CCCTTATGCG | ACTCCTGCAT | TAGGAAGCAG | CCCAGTAGTA | GGTTGAGGCC | 9180 |
| GTTGAGCACC | GCCGCCGCAA | GGAATGGTGC | AAGGAGATGG | CGCCCAACAG | TCCCCCGGCC | 9240 |
| ACGGGGCCTG | CCACCATACC | CACGCCGAAA | CAAGCGCTCA | TGAGCCCGAA | GTGGCGAGCC | 9300 |
| CGATCTTCCC | CATCGGTGAT | GTCGGCGATA | TAGGCGCCAG | CAACCGCACC | TGTGGCGCCG | 9360 |
| GTGATGCCGG | CCACGATGCG | TCCGGCGTAG | AGGATCTGGC | TAGCGATGAC | CCTGCTGATT | 9420 |
| GGTTCGCTGA | CCATTTCCGG | GGTGCGGAAC | GGCGTTACCA | GAAACTCAGA | AGGTTCGTCC | 9480 |
| AACCAAACCG | ACTCTGACGG | CAGTTTACGA | GAGAGATGAT | AGGGTCTGCT | TCAGTAAGCC | 9540 |
| AGATGCTACA | CAATTAGGCT | TGTACATATT | GTCGTTAGAA | CGCGGCTACA | ATTAATACAT | 9600 |
| AACCTTATGT | ATCATACACA | TACGATTTAG | GTGACACTAT | A | | 9641 |

( 2 ) INFORMATION FOR SEQ ID NO:4:

( i ) SEQUENCE CHARACTERISTICS:
        ( A ) LENGTH: 1015 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

```
Lys Gln Cys Trp Val Leu Gln Tyr His Tyr Arg Gly Ala Ser Leu Gln
 1               5                  10                  15

Phe Glu Ala Ser Val Ser Pro Ser Trp Ser Asp Asp Gly Gly Ile Gly
                20                  25                  30

Met His Phe Gly Asp Ile Asn Leu Trp Thr Gly Glu Glu Ala His Leu
            35                  40                  45

Leu His Arg His Ser Thr Glu Met Leu Gln Gln Ser Tyr Arg Ser
        50                  55                  60

Ile Asn Phe Gln Phe Asp Gly Arg Trp Gln His Pro Gly Tyr Asn Leu
65                  70                  75                  80

Glu Arg Thr Gly Cys Arg Leu Gly Asn Glu Ser Pro Phe Val Tyr Pro
                85                  90                  95
```

```
Thr Tyr Met Asp Ser Leu Pro Leu Asp Trp Arg Asp Phe Cys Ala Ala
            100                 105                 110
Thr Leu Arg Asp Pro Tyr Asn Glu Gln Pro Gly Leu Gly Leu Trp Xaa
            115                 120                 125
Xaa Xaa Xaa Xaa Xaa Xaa Xaa Xaa Xaa Xaa Xaa Xaa Xaa Xaa Xaa Ala
130             135                             140
Pro His Pro Thr Asp Ser Ala Val Glu Val Asp Val Thr Ile Ala Met
145                 150                 155                 160
Gln Gly Ser Gly Asp Ile Arg Tyr Thr Lys Arg Ser Ile Phe Leu Thr
                165                 170                 175
Lys Gly Gln His Gln Trp Ala His Ala Thr Thr Ile Leu Val Ala Asp
                180                 185                 190
Ala Leu Thr Asp Ala Thr Cys Gln Leu Leu Ala Ala Glu Ala Gln Tyr
            195                 200                 205
His Gly Ala Ala Lys Trp Arg Glu Val Trp Ala Asn Pro Asp Ile Arg
210                 215                 220
Thr Ala Glu Ser Val Gly Ile Asp Asn Asp Leu Pro Ala Arg Thr Phe
225                 230                 235                 240
Gln Asp Arg Leu Pro Thr Leu Leu Gln Lys Lys Asp Gly Ile Trp Met
                245                 250                 255
Gln Ser Leu Phe Gly Ser Gln Arg Asn Phe Gln Trp Arg Lys Asn Gly
            260                 265                 270
Leu Glu Ile Cys Phe Asp Met Glu Ser Thr Thr Leu His Pro Ile Ala
            275                 280                 285
His Ser Ala Ala Pro Leu Thr Val Ser Leu Asn Glu Ala Leu Arg Trp
        290                 295                 300
Gln Gln Trp Ala Ser Ile His Gly Ala Glu Ser Trp Ala Thr Ala Asn
305                 310                 315                 320
Pro Gln Val Val Arg Val Thr Leu Trp Leu Gln Gly Ala Ser Glu Pro
                325                 330                 335
Gln Pro Leu Glu Pro Leu Glu Ile Leu Gln Lys Gly Gln Pro Ala Val
            340                 345                 350
Asp Leu Pro Val Glu Gly Ser Ala Leu Pro Lys Gly Asp Leu Ala Val
        355                 360                 365
Met Trp His Leu Leu Glu Asn Asp Ser His Arg Phe Leu Tyr Glu Ser
    370                 375                 380
Thr Val Glu Ile Thr Gln Gly Ser Leu Arg Phe Gln Phe Phe Gln Gln
385             390                 395                 400
Gln His Lys Ala Glu Thr Leu Ala Pro His Pro Thr Arg Asp Ala Phe
            405                 410                 415
Val Leu Gly Asn Met Cys Phe Gln Arg Asp Asn Pro Thr Asp Gly Phe
            420                 425                 430
Asp Gly Gly Tyr Ala Ser Trp Pro Asn Gly Asn Glu Asp Tyr Lys Ile
        435                 440                 445
Leu Ser Gln Asp Val Trp Asp Trp Val Phe Gly Gly Gln Leu Arg Pro
    450                 455                 460
Tyr Gln Arg Phe Ala Gln Trp Tyr Lys Ala Phe Gly Gly Leu Ser Asn
465                 470                 475                 480
Gly Met Ala His Ala Tyr Glu Cys Leu Ile Leu Pro Arg Thr Glu Gly
            485                 490                 495
Pro Leu Ser Leu Trp Lys Lys Ile Ser Trp Lys Pro Val Ala Pro Phe
            500                 505                 510
Pro Gln Asp Glu Asp Val Arg Ala Tyr Met Pro Cys Ile Ile Asp Thr
```

-continued

|     |     |     | 515 |     |     | 520 |     |     |     | 525 |     |     |     |
|---|---|---|---|---|---|---|---|---|---|---|---|---|---|
| Ala | Thr | Thr | Asp | Ala | Gly | Gly | Glu | Tyr | Gln | Val | Pro | Arg | Ser | Pro |
|     | 530 |     |     |     |     | 535 |     |     |     | 540 |     |     |     |
| Asp | Val | Ser | Lys | Ile | Trp | Arg | Tyr | Leu | Ala | Asp | His | Asn | Ala | Gly | His |
| 545 |     |     |     |     | 550 |     |     |     |     | 555 |     |     |     |     | 560 |
| Gly | Ser | Glu | Asn | Gly | Leu | Ser | Trp | Ile | Ile | Val | Ser | Pro | His | Asn | Arg |
|     |     |     |     | 565 |     |     |     |     | 570 |     |     |     |     | 575 |     |
| Asp | Arg | Gln | Val | Met | Arg | Thr | Val | Arg | Glu | Ser | Met | Ala | Pro | Leu | Trp |
|     |     |     | 580 |     |     |     |     | 585 |     |     |     |     | 590 |     |     |
| Arg | Pro | Asp | Asp | Thr | Leu | Arg | Asn | Met | Pro | Val | Met | Gly | His | Thr | Glu |
|     |     | 595 |     |     |     |     | 600 |     |     |     |     | 605 |     |     |     |
| Ile | Asn | Ala | Glu | Asp | Val | Val | Tyr | Leu | Gly | Tyr | Arg | Asp | Cys | Leu | Thr |
|     | 610 |     |     |     |     | 615 |     |     |     |     | 620 |     |     |     |     |
| Tyr | Trp | Leu | Pro | His | Asn | Pro | Tyr | His | Ser | Cys | Arg | Val | Ala | Asn | Phe |
| 625 |     |     |     |     | 630 |     |     |     |     | 635 |     |     |     |     | 640 |
| Asn | Asn | Gln | Lys | Met | Leu | Leu | Ile | Asp | Gln | Val | Met | Thr | Gln | Glu | Asp |
|     |     |     |     | 645 |     |     |     |     | 650 |     |     |     |     | 655 |     |
| Met | Val | Gln | Gly | His | Leu | Pro | His | His | Glu | His | Arg | Asn | Val | Gly | Arg |
|     |     |     | 660 |     |     |     |     | 665 |     |     |     |     | 670 |     |     |
| Ile | Leu | Leu | Pro | Lys | Gly | Asn | Leu | Leu | Leu | Gly | Asn | Glu | Ile | Arg |
|     |     | 675 |     |     |     |     | 680 |     |     |     |     | 685 |     |     |
| Val | Glu | Arg | Phe | Gly | Val | Asp | Cys | Ala | Glu | Ala | Glu | Ile | Leu | Thr | Gly |
|     | 690 |     |     |     |     | 695 |     |     |     |     | 700 |     |     |     |     |
| Asp | Ala | Thr | His | Leu | Glu | Val | Val | Ala | Arg | Tyr | Leu | Asn | Pro | Ile | Glu |
| 705 |     |     |     |     | 710 |     |     |     |     | 715 |     |     |     |     | 720 |
| Ala | Ser | Trp | Leu | Lys | Pro | Asn | Glu | Val | Asn | Leu | Arg | Leu | Thr | Val | Arg |
|     |     |     |     | 725 |     |     |     |     | 730 |     |     |     |     | 735 |     |
| Asp | Ala | Tyr | Gly | Gly | Arg | Glu | Asp | Ile | Ile | Glu | Gly | Gly | Phe | Pro | Ala |
|     |     |     | 740 |     |     |     |     | 745 |     |     |     |     | 750 |     |     |
| Thr | Gly | Ser | Ala | Val | Gln | Thr | Glu | Gly | Gln | Trp | Leu | Ser | Val | Thr | Val |
|     |     | 755 |     |     |     |     | 760 |     |     |     |     | 765 |     |     |     |
| Arg | Leu | Tyr | Asp | Arg | Leu | Glu | Gly | Cys | Met | Gln | Val | Glu | Ala | Glu | Leu |
|     | 770 |     |     |     |     | 775 |     |     |     |     | 780 |     |     |     |     |
| Val | Ala | Arg | Ser | Phe | Asp | Asp | Asn | Phe | Arg | Thr | Ala | Val | His | Phe | Asp |
| 785 |     |     |     |     | 790 |     |     |     |     | 795 |     |     |     |     | 800 |
| Ser | Ile | Gln | Thr | Thr | Pro | Lys | His | Leu | Leu | Ser | Val | Asp | Arg | Phe | Ile |
|     |     |     |     | 805 |     |     |     |     | 810 |     |     |     |     | 815 |     |
| Gly | Ser | Met | Arg | Trp | Met | Asp | Gln | Asp | Glu | Leu | Tyr | Ser | Gly | Asp | Ser |
|     |     |     | 820 |     |     |     |     | 825 |     |     |     |     | 830 |     |     |
| Trp | Arg | Leu | Val | Met | Val | Ala | Leu | Arg | Asn | Glu | Gly | Ala | Arg | Leu | Phe |
|     |     | 835 |     |     |     |     | 840 |     |     |     |     | 845 |     |     |     |
| Ala | Ser | Leu | Asp | Phe | Glu | Ser | Pro | Leu | Arg | Ser | Asp | Gln | Gly | Tyr | Gly |
|     | 850 |     |     |     |     | 855 |     |     |     |     | 860 |     |     |     |     |
| Val | Trp | Arg | Gly | Asn | Cys | Trp | Leu | His | Phe | Ala | Ser | Asn | Val | Gly | Asp |
| 865 |     |     |     |     | 870 |     |     |     |     | 875 |     |     |     |     | 880 |
| Phe | Ile | Ile | Arg | Thr | Gln | Gly | Glu | Gln | Leu | Trp | Ser | Glu | Asp | Val | Asn |
|     |     |     |     | 885 |     |     |     |     | 890 |     |     |     |     | 895 |     |
| Phe | Thr | Leu | Ser | Tyr | Cys | Gly | Thr | Pro | Asn | Glu | Thr | Pro | Val | Phe | Pro |
|     |     |     | 900 |     |     |     |     | 905 |     |     |     |     | 910 |     |     |
| Pro | Asn | Val | Thr | Ile | Pro | Tyr | Thr | Val | Asn | Thr | Tyr | Ile | Pro | Ala | Asp |
|     |     | 915 |     |     |     |     | 920 |     |     |     |     | 925 |     |     |     |
| Tyr | Gly | His | Met | Gln | Trp | Asn | Ser | Pro | Val | Val | Val | Thr | Asp | Ala | Glu |
|     | 930 |     |     |     |     | 935 |     |     |     |     | 940 |     |     |     |     |

-continued

```
Pro Leu Asp Cys Glu Leu Trp Ser Glu Pro Val Ala Glu Pro Ala Pro
945                 950                 955                 960

Phe Trp Ala Phe Arg Trp Glu Gly Asn Leu Ser Arg Leu Gln Gln Ser
                965                 970                 975

Pro Arg Asp Thr Arg Ala Glu Glu Ser Asn Arg Trp Ser Ala Phe Pro
            980                 985                 990

Pro His Ala Ala Leu Arg Asn Leu Gln Thr Val Gly Pro Asn Glu Trp
        995                1000                1005

Asp Arg Arg Gln Leu Val Val
        1010            1015
```

(2) INFORMATION FOR SEQ ID NO:5:

(i) SEQUENCE CHARACTERISTICS:
    (A) LENGTH: 820 amino acids
    (B) TYPE: amino acid
    (D) TOPOLOGY: linear (ii) MOLECULE TYPE: protein (ix) FEATURE:
    (A) NAME/KEY: CDS
    (B) LOCATION: 4368..6827

(xi) SEQUENCE DESCRIPTION: SEQ ID NO:5:

```
Gly Arg Cys Xaa Gly Thr Met Arg Pro Ala Pro Gly Ala Asp Pro Ala
1               5                  10                  15

Ser Val Ala Val Asn Ile Leu Gly Thr Ser Leu Xaa Cys Trp Met Xaa
            20                  25                  30

Pro Arg Ser Xaa Gly Pro Ile Thr Trp Cys Trp Pro Ala Pro Ala Leu
            35                  40                  45

Ser Leu Ala Leu Ala Met Lys Ile Gln Ile Glu Val Leu Lys Cys Val
        50                  55                  60

Gly Val Ala Xaa Gly Trp Glu Arg Ile Tyr Lys Val Gly Val Leu Cys
65                  70                  75                  80

Ser Phe Val Ser Val Leu Gln Gln Pro Pro Pro Xaa Ala Pro Thr
                85                  90                  95

Arg Leu Met Glu Ala Leu Xaa Ala His Ile Xaa Gln Arg Ala Cys Pro
                100                 105                 110

His Gly Pro Gly Cys Val Arg Met Xaa Trp Ala Pro Ala Leu Met Val
            115                 120                 125

Ala Pro Ser Cys Pro Gln Thr Leu Leu Pro Xaa Pro Thr Arg Pro Cys
130                 135                 140

Leu Glu Arg Arg Trp Arg Leu Gln Pro Pro Pro Leu Gln Pro Leu
145                 150                 155                 160

Gln Pro Pro Pro Ala Gly Leu Xaa Leu Thr Leu Leu Ser Xaa Ala Arg
                165                 170                 175

Leu Gln Ala Val Gln Leu Pro Val His Pro Pro Ala Met Thr Ser Xaa
            180                 185                 190

Arg Leu Phe Trp His Asn Trp Ile Leu Xaa Pro Gly Asn Leu Met Ser
            195                 200                 205

Phe Leu Ser Ser Cys Trp Ile Cys Ala Ser Arg Phe Leu Pro Xaa Arg
210                 215                 220

Leu Pro Pro Leu Pro Met Arg Phe Lys Thr Xaa Ile Lys Asn Gln Thr
225                 230                 235                 240

Leu Phe Gly Phe Gly Ser Ser Lys Cys Leu Ala Val Phe Ile Xaa Gly
                245                 250                 255

Phe Cys Ala Arg Gly Arg Pro Gly Thr Ser Gly Leu Gly Arg Xaa Gly
```

-continued

```
                    260                         265                         270

Ser   Cys   Val   Phe   Phe   Pro   Gly   Arg   Gly   Lys   Gly   Asp   Ser   Gly   Cys   Ser
            275                         280                         285

Asp   Thr   Trp   Ala   Xaa   Ala   Arg   Leu   Trp   Gly   Gly   Gly   Ser   Thr   Thr   Ala
      290                         295                         300

Glu   Leu   His   Ala   Ala   Gly   Trp   Cys   Cys   Arg   Xaa   Ser   Ser   Arg   Ser   Arg
305                         310                         315                               320

Ser   Ala   Gly   Arg   Gly   Ala   Xaa   Lys   Cys   Leu   Ser   Val   Ala   Ser   Xaa   Leu
                        325                         330                               335

Pro   Gly   Ala   Gly   Pro   Trp   Cys   Lys   Cys   Leu   Gln   Ser   Gly   Xaa   Ala   Gly
                  340                         345                         350

Met   Gly   Ala   Tyr   Val   Gly   Ile   Xaa   Asp   Ala   Ser   Trp   Thr   Val   Phe   Leu
            355                         360                         365

Gly   Trp   Leu   Cys   Ser   Gln   Pro   Tyr   Pro   Ser   Gly   Asp   Ser   Cys   Cys   Ala
      370                         375                         380

Glu   Pro   Pro   Ala   Gln   Cys   Ile   Arg   Cys   Thr   Trp   Glu   Ile   Cys   His   Val
385                         390                         395                               400

Ala   Xaa   Lys   Glu   Met   Arg   Gly   Arg   Thr   Trp   Arg   Arg   Pro   Cys   Asp   Leu
                        405                         410                               415

Gln   Asp   Phe   Pro   Cys   Ile   Arg   Pro   Xaa   Xaa   Trp   Gln   Trp   Ala   His   Gly
                  420                         425                         430

Arg   Arg   Pro   Gly   Arg   Arg   Tyr   Phe   Trp   Asp   His   Xaa   Arg   His   Ser   Cys
            435                         440                         445

Val   Pro   Gly   Xaa   Asp   Arg   His   Arg   Pro   Phe   Leu   Gln   Ser   Ala   Gly   Gly
            450                         455                         460

Gly   Cys   Gln   Thr   Ala   Val   Xaa   Trp   Phe   His   Pro   Ala   Gln   Gly   Arg   Ser
465                         470                         475                               480

Tyr   Pro   His   Arg   Phe   Ala   Phe   Pro   Thr   Leu   Xaa   Val   Gln   Met   Gly   Gly
                        485                         490                               495

Ser   Cys   Leu   Pro   Ala   Gly   Arg   Xaa   Arg   Lys   Arg   Phe   Pro   Gly   Xaa   Gly
                  500                         505                         510

Arg   Ser   Ala   Gly   Lys   Lys   Ala   Gly   Ser   Xaa   Ala   Ala   Ala   Thr   Tyr   Arg
            515                         520                         525

Ser   Arg   Trp   Ala   Arg   Lys   Ser   His   Leu   Leu   Pro   Gly   Ala   Thr   Gly   Ser
      530                         535                         540

Xaa   Glu   Ser   Cys   Ser   Cys   Arg   His   Pro   Xaa   Ala   Gly   Gly   Pro   Leu   Arg
545                         550                         555                               560

Xaa   Ala   Cys   Pro   Xaa   Leu   Ala   Cys   Phe   Pro   Xaa   Pro   Asn   Pro   Pro   Glu
                  565                         570                         575

Gly   Ala   Arg   Arg   Pro   Ala   Ile   Ala   Val   Leu   Ala   Arg   Lys   Gln   Ser   Phe
            580                         585                         590

Ser   Thr   Val   Xaa   Asp   Arg   Pro   Pro   Xaa   Ala   Cys   Phe   Xaa   Ala   Phe   Asp
                  595                         600                         605

Gln   Ala   Val   Pro   Gly   Gly   Pro   Thr   Ala   Arg   Ser   Pro   Ala   Leu   Arg   His
      610                         615                         620

Leu   Asp   Pro   Ala   Tyr   Leu   Leu   Val   Ser   Arg   Val   Gly   Ala   Ala   Phe   Ala
625                         630                         635                               640

Val   Arg   Gln   Xaa   Ser   Val   Leu   Val   Gln   Thr   Gly   Gln   Gly   His   Val   Phe
                  645                         650                         655

Pro   Arg   Ala   Gln   Gly   Pro   Arg   Gln   Arg   Ser   Leu   Gly   His   Gly   Glu   Gly
            660                         665                         670

Val   Arg   Ser   Gly   Leu   Arg   Ala   Gly   Gln   Gly   Ala   Leu   Glu   Ala   Gly   Pro
            675                         680                         685
```

| Ala | Gly | Ala | Glu | Ala | Leu | Pro | Val | Phe | Ala | Leu | Arg | Val | Gly | Gln | Val |
|---|---|---|---|---|---|---|---|---|---|---|---|---|---|---|---|
| | 690 | | | | | 695 | | | | 700 | | | | | |
| Ala | Phe | Asp | His | Gly | Val | Ile | Val | Gln | Pro | Leu | Arg | Gly | Val | Ala | Leu |
| 705 | | | | | 710 | | | | 715 | | | | | | 720 |
| Gly | Ala | Gln | Leu | Ala | Leu | Gly | Gly | Gly | Ala | Ala | Arg | Gly | Ala | Val | Gln |
| | | | | 725 | | | | | 730 | | | | | 735 | |
| Thr | Phe | Glu | Gly | Val | Glu | Leu | Gly | Arg | Glu | Lys | Tyr | Arg | Phe | Arg | Gly |
| | | | 740 | | | | | 745 | | | | | 750 | | |
| Val | Gly | Ile | Arg | Ala | Ala | Gly | Pro | Ala | Asp | Gly | Leu | Ala | Phe | His | Glu |
| | | 755 | | | | | 760 | | | | | 765 | | | |
| Pro | Gly | Glu | Leu | Trp | Pro | Phe | Gly | Val | Lys | Asn | Gln | Val | Ser | Pro | Met |
| | 770 | | | | | 775 | | | | | 780 | | | | |
| Leu | Phe | Asp | Ala | Phe | Leu | Thr | Ser | Gly | Phe | His | Glu | Pro | Val | Ser | Thr |
| 785 | | | | | 790 | | | | | 795 | | | | | 800 |
| Leu | Gly | Asp | Glu | Lys | Ala | Val | Arg | Val | Pro | Val | Tyr | Arg | Leu | Glu | Arg |
| | | | | 805 | | | | | 810 | | | | | 815 | |
| Pro | Val | Leu | Glu | | | | | | | | | | | | |
| | | | 820 | | | | | | | | | | | | |

( 2 ) INFORMATION FOR SEQ ID NO:6:

( i ) SEQUENCE CHARACTERISTICS:
        ( A ) LENGTH: 34382 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CATCATCAAT AATATACCTT ATTTTGGATT GAAGCCAATA TGATAATGAG GGGGTGGAGT         60
TTGTGACGTG GCGCGGGGCG TGGGAACGGG GCGGGTGACG TAGTAGTGTG GCGGAAGTGT        120
GATGTTGCAA GTGTGGCGGA ACACATGTAA GCGACGGATG TGGCAAAAGT GACGTTTTTG        180
GTGTGCGCCG GTGTCAGATC CAGACATGAT AAGATACATT GATGAGTTTG ACAAACCAC         240
AACTAGAATG CAGTGAAAAA AATGCTTTAT TTGTGAAATT TGTGATGCTA TTGCTTTATT        300
TGTAACCATT ATAAGCTGCA ATAAACAGGA TCTTATTTTT GACACCAGAC CAACTGGTAA        360
TGGTAGCGAC CGGCGCTCAG CTGGAATTCC GCCGATACTG ACGGGCTCCA GGAGTCGTCG        420
CCACCAATCC CCATATGGAA ACCGTCGATA TTCAGCCATG TGCCTTCTTC CGCGTGCAGC        480
AGATGGCGAT GGCTGGTTTC CATCAGTTGC TGTTGACTGT AGCGGCTGAT GTTGAACTGG        540
AAGTCGCCGC GCCACTGGTG TGGGCCATAA TTCAATTCGC GCGTCCCGCA GCGCAGACCG        600
TTTTCGCTCG GAAGACGTA  CGGGGTATAC ATGTCTGACA ATGGCAGATC CCAGCGGTCA        660
AAACAGGCGG CAGTAAGGCG GTCGGGATAG TTTTCTTGCG GCCCTAATCC GAGCCAGTTT        720
ACCCGCTCTG CTACCTGCGC CAGCTGGCAG TTCAGGCCAA TCCGCGCCGG ATGCGGTGTA        780
TCGCTCGCCA CTTCAACATC AACGGTAATC GCCATTTGAC CACTACCATC AATCCGGTAG        840
GTTTTCCGGC TGATAAATAA GGTTTTCCCC TGATGCTGCC ACGCGTGAGC GGTCGTAATC        900
AGCACCGCAT CAGCAAGTGT ATCTGCCGTG CACTGCAACA ACGCTGCTTC GGCCTGGTAA        960
TGGCCCGCCG CCTTCCAGCG TTCGACCCAG GCGTTAGGGT CAATGCGGGT CGCTTCACTT       1020
ACGCCAATGT CGTTATCCAG CGGTGCACGG GTGAACTGAT CGCGCAGCGG CGTCAGCAGT       1080
TGTTTTTTAT CGCCAATCCA CATCTGTGAA AGAAAGCCTG ACTGGCGGTT AAATTGCCAA       1140
CGCTTATTAC CCAGCTCGAT GCAAAAATCC ATTTCGCTGG TGGTCAGATG CGGGATGGCG       1200
```

-continued

| | | | | | | |
|---|---|---|---|---|---|---|
| TGGGACGCGG | CGGGGAGCGT | CACACTGAGG | TTTTCCGCCA | GACGCCACTG | CTGCCAGGCG | 1260 |
| CTGATGTGCC | CGGCTTCTGA | CCATGCGGTC | GCGTTCGGTT | GCACTACGCG | TACTGTGAGC | 1320 |
| CAGAGTTGCC | CGGCGCTCTC | CGGCTGCGGT | AGTTCAGGCA | GTTCAATCAA | CTGTTTACCT | 1380 |
| TGTGGAGCGA | CATCCAGAGG | CACTTCACCG | CTTGCCAGCG | GCTTACCATC | CAGCGCCACC | 1440 |
| ATCCAGTGCA | GGAGCTCGTT | ATCGCTATGA | CGGAACAGGT | ATTCGCTGGT | CACTTCGATG | 1500 |
| GTTTGCCCGG | ATAAACGGAA | CTGGAAAAAC | TGCTGCTGGT | GTTTTGCTTC | CGTCAGCGCT | 1560 |
| GGATGCGGCG | TGCGGTCGGC | AAAGACCAGA | CCGTTCATAC | AGAACTGGCG | ATCGTTCGGC | 1620 |
| GTATCGCCAA | AATCACCGCC | GTAAGCCGAC | CACGGGTTGC | CGTTTTCATC | ATATTTAATC | 1680 |
| AGCGACTGAT | CCACCCAGTC | CCAGACGAAG | CCGCCCTGTA | AACGGGGATA | CTGACGAAAC | 1740 |
| GCCTGCCAGT | ATTTAGCGAA | ACCGCCAAGA | CTGTTACCCA | TCGCGTGGGC | GTATTCGCAA | 1800 |
| AGGATCAGCG | GGCGCGTCTC | TCCAGGTAGC | GAAAGCCATT | TTTTGATGGA | CCATTTCGGC | 1860 |
| ACAGCCGGGA | AGGGCTGGTC | TTCATCCACG | CGCGCGTACA | TCGGGCAAAT | AATATCGGTG | 1920 |
| GCCGTGGTGT | CGGCTCCGCC | GCCTTCATAC | TGCACCGGGC | GGGAAGGATC | GACAGATTTG | 1980 |
| ATCCAGCGAT | ACAGCGCGTC | GTGATTAGCG | CCGTGGCCTG | ATTCATTCCC | CAGCGACCAG | 2040 |
| ATGATCACAC | TCGGGTGATT | ACGATCGCGC | TGCACCATTC | GCGTTACGCG | TTCGCTCATC | 2100 |
| GCCGGTAGCC | AGCGCGGATC | ATCGGTCAGA | CGATTCATTG | GCACCATGCC | GTGGGTTTCA | 2160 |
| ATATTGGCTT | CATCCACCAC | ATACAGGCCG | TAGCGGTCGC | ACAGCGTGTA | CCACAGCGGA | 2220 |
| TGGTTCGGAT | AATGCGAACA | GCGCACGGCG | TTAAAGTTGT | TCTGCTTCAT | CAGCAGGATA | 2280 |
| TCCTGCACCA | TCGTCTGCTC | ATCCATGACC | TGACCATGCA | GAGGATGATG | CTCGTGACGG | 2340 |
| TTAACGCCTC | GAATCAGCAA | CGGCTTGCCG | TTCAGCAGCA | GCAGACCATT | TTCAATCCGC | 2400 |
| ACCTCGCGGA | AACCGACATC | GCAGGCTTCT | GCTTCAATCA | GCGTGCCGTC | GGCGGTGTGC | 2460 |
| AGTTCAACCA | CCGCACGATA | GAGATTCGGG | ATTTCGGCGC | TCCACAGTTT | CGGGTTTTCG | 2520 |
| ACGTTCAGAC | GTAGTGTGAC | GCGATCGGCA | TAACCACCAC | GCTCATCGAT | AATTTCACCG | 2580 |
| CCGAAAGGCG | CGGTGCCGCT | GGCGACCTGC | GTTTCACCCT | GCCATAAAGA | AACTGTTACC | 2640 |
| CGTAGGTAGT | CACGCAACTC | GCCGCACATC | TGAACTTCAG | CCTCCAGTAC | AGCGCGGCTG | 2700 |
| AAATCATCAT | TAAAGCGAGT | GGCAACATGG | AAATCGCTGA | TTTGTGTAGT | CGGTTTATGC | 2760 |
| AGCAACGAGA | CGTCACGGAA | AATGCCGCTC | ATCCGCCACA | TATCCTGATC | TTCCAGATAA | 2820 |
| CTGCCGTCAC | TCCAACGCAG | CACCATCACC | GCGAGGCGGT | TTTCTCCGGC | GCGTAAAAAT | 2880 |
| GCGCTCAGGT | CAAATTCAGA | CGGCAAACGA | CTGTCCTGGC | CGTAACCGAC | CCAGCGCCCG | 2940 |
| TTGCACCACA | GATGAAACGC | CGAGTTAACG | CCATCAAAAA | TAATTCGCGT | CTGGCCTTCC | 3000 |
| TGTAGCCAGC | TTTCATCAAC | ATTAAATGTG | AGCGAGTAAC | AACCCGTCGG | ATTCTCCGTG | 3060 |
| GGAACAAACG | GCGGATTGAC | CGTAATGGGA | TAGGTTACGT | TGGTGTAGAT | GGGCGCATCG | 3120 |
| TAACCGTGCA | TCTGCCAGTT | TGAGGGGACG | ACGACAGTAT | CGGCCTCAGG | AAGATCGCAC | 3180 |
| TCCAGCCAGC | TTTCCGGCAC | CGCTTCTGGT | GCCGGAAACC | AGGCAAAGCG | CCATTCGCCA | 3240 |
| TTCAGGCTGC | GCAACTGTTG | GGAAGGGCGA | TCGGTGCGGG | CCTCTTCGCT | ATTACGCCAG | 3300 |
| CTGGCGAAAG | GGGGATGTGC | TGCAAGGCGA | TTAAGTTGGG | TAACGCCAGG | GTTTTCCCAG | 3360 |
| TCACGACGTT | GTAAAACGAC | GGCCAGTGCC | AAGCTTGGAC | TCAAAAAACT | TAGCAATTCT | 3420 |
| GAAGGAAAGT | CCTTGGGGTC | TTCTACCTTT | CTCTTCTTTT | TTGCGGAATT | CCGGAAAACT | 3480 |
| TTATCCATCT | TTGCAAAGCT | TGGGTCTCCC | TATAGTGAGT | CGTATTAATT | TCGATAAGCC | 3540 |
| AGTAAGCAGT | GGGTTCTCTA | GTTAGCCAGA | GAGCTCTGCT | TATATAGACC | TCCCACCGTA | 3600 |

-continued

| | | | | | | |
|---|---|---|---|---|---|---|
| CACGCCTACC | GCCCATTTGC | GTCAATGGGG | CGGAGTTGTT | ACGACATTTT | GGAAAGTCCC | 3660 |
| GTTGATTTTG | GTGCCAAAAC | AAACTCCCAT | TGACGTCAAT | GGGGTGGAGA | CTTGGAAATC | 3720 |
| CCCGTGAGTC | AAACCGCTAT | CCACGCCCAT | TGATGTACTG | CCAAAACCGC | ATCACCATGG | 3780 |
| TAATAGCGAT | GACTAATACG | TAGATGTACT | GCCAAGTAGG | AAAGTCCCAT | AAGGTCATGT | 3840 |
| ACTGGGCATA | ATGCCAGGCG | GGCCATTTAC | CGTCATTGAC | GTCAATAGGG | GGCGTACTTG | 3900 |
| GCATATGATA | CACTTGATGT | ACTGCCAAGT | GGGCAGTTTA | CCGTAAATAG | TCCACCCATT | 3960 |
| GACGTCAATG | GAAAGTCCCT | ATTGGCGTTA | CTATGGGAAC | ATACGTCATT | ATTGACGTCA | 4020 |
| ATGGGCGGGG | GTCGTTGGGC | GGTCAGCCAG | GCGGGCCATT | TACCGTAAGT | TATGTAACGC | 4080 |
| GGAACTCCAT | ATATGGGCTA | TGAACTAATG | ACCCCGTAAT | TGATTACTAT | TAATAACTAG | 4140 |
| TCAATAATCA | ATGTCAACGC | GTATATCTGG | CCCGTACATC | GCGAAGCAGC | GCAAAACGCC | 4200 |
| TAACCCCGGG | CCAGATCTGA | CATCGATTAC | GCCAAGCTTG | CATGCCTGCA | GGTTTAAACA | 4260 |
| GTCGACTCTA | GACTTAATTA | AGGATCTGGA | AGGTGCTGAG | GTACGATGAG | ACCCGCACCA | 4320 |
| GGTGCAGACC | CTGCGAGTGT | GGCGGTAAAC | ATATTAGGAA | CCAGCCTGTG | ATGCTGGATG | 4380 |
| TGACCGAGGA | GCTGAGGCCC | GATCACTTGG | TGCTGGCCTG | CACCCGCGCT | GAGTTTGGCT | 4440 |
| CTAGCGATGA | AGATACAGAT | TGAGGTACTG | AAATGTGTGG | GCGTGGCTTA | AGGGTGGGAA | 4500 |
| AGAATATATA | AGGTGGGGGT | CTTATGTAGT | TTTGTATCTG | TTTTGCAGCA | GCCGCCGCCG | 4560 |
| CCATGAGCAC | CAACTCGTTT | GATGGAAGCA | TTGTGAGCTC | ATATTTGACA | ACGCGCATGC | 4620 |
| CCCCATGGGC | CGGGGTGCGT | CAGAATGTGA | TGGGCTCCAG | CATTGATGGT | CGCCCCGTCC | 4680 |
| TGCCCGCAAA | CTCTACTACC | TTGACCTACG | AGACCGTGTC | TGGAACGCCG | TTGGAGACTG | 4740 |
| CAGCCTCCGC | CGCCGCTTCA | GCCGCTGCAG | CCACCGCCCG | CGGGATTGTG | ACTGACTTTG | 4800 |
| CTTTCCTGAG | CCCGCTTGCA | AGCAGTGCAG | CTTCCCGTTC | ATCCGCCCGC | GATGACAAGT | 4860 |
| TGACGGCTCT | TTTGGCACAA | TTGGATTCTT | TGACCCGGGA | ACTTAATGTC | GTTTCTCAGC | 4920 |
| AGCTGTTGGA | TCTGCGCCAG | CAGGTTTCTG | CCCTGAAGGC | TTCCTCCCCT | CCCAATGCGG | 4980 |
| TTTAAAACAT | AAATAAAAAA | CCAGACTCTG | TTTGGATTTG | GATCAAGCAA | GTGTCTTGCT | 5040 |
| GTCTTTATTT | AGGGGTTTTG | CGCGCGCGGT | AGGCCCGGGA | CCAGCGGTCT | CGGTCGTTGA | 5100 |
| GGGTCCTGTG | TATTTTTTCC | AGGACGTGGT | AAAGGTGACT | CTGGATGTTC | AGATACATGG | 5160 |
| GCATAAGCCC | GTCTCTGGGG | TGGAGGTAGC | ACCACTGCAG | AGCTTCATGC | TGCGGGGTGG | 5220 |
| TGTTGTAGAT | GATCCAGTCG | TAGCAGGAGC | GCTGGGCGTG | GTGCCTAAAA | ATGTCTTTCA | 5280 |
| GGTGTAAGTG | TTTACAAAGC | GGTTAAGCTG | GGATGGGTGC | ATACGTGGGG | ATATGAGATG | 5340 |
| CATCTTGGAC | TGTATTTTTA | GGTTGGCTAT | GTTCCCAGCC | ATATCCCTCC | GGGGATTCAT | 5400 |
| GTTGTGCAGA | ACCACCAGCA | CAGTGTATCC | GGTGCACTTG | GAAATTTGT | CATGTAGCTT | 5460 |
| AGAAGGAAAT | GCGTGGAAGA | ACTTGGAGAC | GCCCTTGTGA | CCTCCAAGAT | TTTCCATGCA | 5520 |
| TTCGTCCATA | ATGATGGCAA | TGGGCCCACG | GGCGGCGGCC | TGGGCGAAGA | TATTTCTGGG | 5580 |
| ATCACTAACG | TCATAGTTGT | GTTCCAGGAT | GAGATCGTCA | TAGGCCATTT | TTACAAAGCG | 5640 |
| CGGGCGGAGG | GTGCCAGACT | GCGGTATAAT | GGTTCCATCC | GGCCCAGGGG | CGTAGTTACC | 5700 |
| CTCACAGATT | TGCATTTCCC | ACGCTTTGAG | TTCAGATGGG | GGATCATGT | CTACCTGCGG | 5760 |
| GGCGATGAAG | AAAACGGTTT | CCGGGGTAGG | GGAGATCAGC | TGGAAGAAA | GCAGGTTCCT | 5820 |
| GAGCAGCTGC | GACTTACCGC | AGCCGGTGGG | CCCGTAAATC | ACACCTATTA | CCGGGTGCAA | 5880 |
| CTGGTAGTTA | AGAGAGCTGC | AGCTGCCGTC | ATCCCTGAGC | AGGGGGCCA | CTTCGTTAAG | 5940 |
| CATGTCCCTG | ACTCGCATGT | TTTCCCTGAC | CAAATCCGCC | AGAAGGCGCT | CGCCGCCCAG | 6000 |

-continued

| | | | | | |
|---|---|---|---|---|---|
| CGATAGCAGT | TCTTGCAAGG | AAGCAAAGTT | TTTCAACGGT | TTGAGACCGT | CCGCCGTAGG | 6060 |
| CATGCTTTTG | AGCGTTTGAC | CAAGCAGTTC | CAGGCGGTCC | CACAGCTCGG | TCACCTGCTC | 6120 |
| TACGGCATCT | CGATCCAGCA | TATCTCCTCG | TTTCGCGGGT | TGGGGCGGCT | TTCGCTGTAC | 6180 |
| GGCAGTAGTC | GGTGCTCGTC | CAGACGGGCC | AGGGTCATGT | CTTTCCACGG | GCGCAGGGTC | 6240 |
| CTCGTCAGCG | TAGTCTGGGT | CACGGTGAAG | GGGTGCGCTC | CGGGCTGCGC | GCTGGCCAGG | 6300 |
| GTGCGCTTGA | GGCTGGTCCT | GCTGGTGCTG | AAGCGCTGCC | GGTCTTCGCC | CTGCGCGTCG | 6360 |
| GCCAGGTAGC | ATTTGACCAT | GGTGTCATAG | TCCAGCCCCT | CCGCGGCGTG | GCCCTTGGCG | 6420 |
| CGCAGCTTGC | CCTTGGAGGA | GGCGCCGCAC | GAGGGGCAGT | GCAGACTTTT | GAGGGCGTAG | 6480 |
| AGCTTGGGCG | CGAGAAATAC | CGATTCCGGG | GAGTAGGCAT | CCGCGCCGCA | GGCCCCGCAG | 6540 |
| ACGGTCTCGC | ATTCCACGAG | CCAGGTGAGC | TCTGGCCGTT | CGGGGTCAAA | AACCAGGTTT | 6600 |
| CCCCCATGCT | TTTTGATGCG | TTTCTTACCT | CTGGTTTCCA | TGAGCCGGTG | TCCACGCTCG | 6660 |
| GTGACGAAAA | GGCTGTCCGT | GTCCCCGTAT | ACAGACTTGA | GAGGCCTGTC | CTCGAGCGGT | 6720 |
| GTTCCGCGGT | CCTCCTCGTA | TAGAAACTCG | GACCACTCTG | AGACAAGGC | TCGCGTCCAG | 6780 |
| GCCAGCACGA | AGGAGGCTAA | GTGGGAGGGG | TAGCGGTCGT | TGTCCACTAG | GGGGTCCACT | 6840 |
| CGCTCCAGGG | TGTGAAGACA | CATGTCGCCC | TCTTCGGCAT | CAAGGAAGGT | GATTGGTTTG | 6900 |
| TAGGTGTAGG | CCACGTGACC | GGGTGTTCCT | GAAGGGGGC | TATAAAAGGG | GGTGGGGGCG | 6960 |
| CGTTCGTCCT | CACTCTCTTC | CGCATCGCTG | TCTGCGAGGG | CCAGCTGTTG | GGGTGAGTAC | 7020 |
| TCCCTCTGAA | AAGCGGGCAT | GACTTCTGCG | CTAAGATTGT | CAGTTTCCAA | AAACGAGGAG | 7080 |
| GATTTGATAT | TCACCTGGCC | CGCGGTGATG | CCTTTGAGGG | TGGCCGCATC | CATCTGGTCA | 7140 |
| GAAAAGACAA | TCTTTTTGTT | GTCAAGCTTG | GTGGCAAACG | ACCCGTAGAG | GGCGTTGGAC | 7200 |
| AGCAACTTGG | CGATGGAGCG | CAGGGTTTGG | TTTTTGTCGC | GATCGGCGCG | CTCCTTGGCC | 7260 |
| GCGATGTTTA | GCTGCACGTA | TTCGCGCGCA | ACGCACCGCC | ATTCGGGAAA | GACGGTGGTG | 7320 |
| CGCTCGTCGG | GCACCAGGTG | CACGCGCCAA | CCGCGGTTGT | GCAGGGTGAC | AAGGTCAACG | 7380 |
| CTGGTGGCTA | CCTCTCCGCG | TAGGCGCTCG | TTGGTCCAGC | AGAGGCGGCC | GCCCTTGCGC | 7440 |
| GAGCAGAATG | GCGGTAGGGG | GTCTAGCTGC | GTCTCGTCCG | GGGGTCTGC | GTCCACGGTA | 7500 |
| AAGACCCCGG | GCAGCAGGCG | CGCGTCGAAG | TAGTCTATCT | TGCATCCTTG | CAAGTCTAGC | 7560 |
| GCCTGCTGCC | ATGCGCGGGC | GGCAAGCGCG | CGCTCGTATG | GGTTGAGTGG | GGGACCCCAT | 7620 |
| GGCATGGGT | GGGTGAGCGC | GGAGGCGTAC | ATGCCGCAAA | TGTCGTAAAC | GTAGAGGGGC | 7680 |
| TCTCTGAGTA | TTCCAAGATA | TGTAGGGTAG | CATCTTCCAC | CGCGGATGCT | GGCGCGCACG | 7740 |
| TAATCGTATA | GTTCGTGCGA | GGGAGCGAGG | AGGTCGGGAC | CGAGGTTGCT | ACGGGCGGGC | 7800 |
| TGCTCTGCTC | GGAAGACTAT | CTGCCTGAAG | ATGGCATGTG | AGTTGGATGA | TATGGTTGGA | 7860 |
| CGCTGGAAGA | CGTTGAAGCT | GGCGTCTGTG | AGACCTACCG | CGTCACGCAC | GAAGGAGGCG | 7920 |
| TAGGAGTCGC | GCAGCTTGTT | GACCAGCTCG | GCGGTGACCT | GCACGTCTAG | GGCGCAGTAG | 7980 |
| TCCAGGGTTT | CCTTGATGAT | GTCATACTTA | TCCTGTCCCT | TTTTTTTCCA | CAGCTCGCGG | 8040 |
| TTGAGGACAA | ACTCTTCGCG | GTCTTTCCAG | TACTCTTGGA | TCGGAAACCC | GTCGGCCTCC | 8100 |
| GAACGGTAAG | AGCCTAGCAT | GTAGAACTGG | TTGACGGCCT | GGTAGGCGCA | GCATCCCTTT | 8160 |
| TCTACGGGTA | GCGCGTATGC | CTGCGCGGCC | TTCCGGAGCG | AGGTGTGGGT | GAGCGCAAAG | 8220 |
| GTGTCCCTGA | CCATGACTTT | GAGGTACTGG | TATTTGAAGT | CAGTGTCGTC | GCATCCGCCC | 8280 |
| TGCTCCCAGA | GCAAAAAGTC | CGTGCGCTTT | TTGGAACGCG | GATTGGCAG | GGCGAAGGTG | 8340 |
| ACATCGTTGA | AGAGTATCTT | TCCCGCGCGA | GGCATAAAGT | TGCGTGTGAT | GCGGAAGGGT | 8400 |

| | | | | | | |
|---|---|---|---|---|---|---|
| CCCGGCACCT | CGGAACGGTT | GTTAATTACC | TGGGCGGCGA | GCACGATCTC | GTCAAAGCCG | 8460 |
| TTGATGTTGT | GGCCCACAAT | GTAAAGTTCC | AAGAAGCGCG | GGATGCCCTT | GATGGAAGGC | 8520 |
| AATTTTTTAA | GTTCCTCGTA | GGTGAGCTCT | TCAGGGGAGC | TGAGCCCGTG | CTCTGAAAGG | 8580 |
| GCCCAGTCTG | CAAGATGAGG | GTTGGAAGCG | ACGAATGAGC | TCCACAGGTC | ACGGGCCATT | 8640 |
| AGCATTTGCA | GGTGGTCGCG | AAAGGTCCTA | AACTGGCGAC | CTATGGCCAT | TTTTTCTGGG | 8700 |
| GTGATGCAGT | AGAAGGTAAG | CGGGTCTTGT | TCCCAGCGGT | CCCATCCAAG | GTTCGCGGCT | 8760 |
| AGGTCTCGCG | CGGCAGTCAC | TAGAGGCTCA | TCTCCGCCGA | ACTTCATGAC | CAGCATGAAG | 8820 |
| GGCACGAGCT | GCTTCCCAAA | GGCCCCCATC | CAAGTATAGG | TCTCTACATC | GTAGGTGACA | 8880 |
| AAGAGACGCT | CGGTGCGAGG | ATGCGAGCCG | ATCGGGAAGA | ACTGGATCTC | CCGCCACCAA | 8940 |
| TTGGAGGAGT | GGCTATTGAT | GTGGTGAAAG | TAGAAGTCCC | TGCGACGGGC | CGAACACTCG | 9000 |
| TGCTGGCTTT | TGTAAAAACG | TGCGCAGTAC | TGGCAGCGGT | GCACGGGCTG | TACATCCTGC | 9060 |
| ACGAGGTTGA | CCTGACGACC | GCGCACAAGG | AAGCAGAGTG | GGAATTTGAG | CCCCTCGCCT | 9120 |
| GGCGGGTTTG | GCTGGTGGTC | TTCTACTTCG | GCTGCTTGTC | CTTGACCGTC | TGGCTGCTCG | 9180 |
| AGGGGAGTTA | CGGTGGATCG | GACCACCACG | CCGCGCGAGC | CCAAAGTCCA | GATGTCCGCG | 9240 |
| CGCGGCGGTC | GGAGCTTGAT | GACAACATCG | CGCAGATGGG | AGCTGTCCAT | GGTCTGGAGC | 9300 |
| TCCCGCGGCG | TCAGGTCAGG | CGGGAGCTCC | TGCAGGTTTA | CCTCGCATAG | ACGGGTCAGG | 9360 |
| GCGCGGGCTA | GATCCAGGTG | ATACCTAATT | TCCAGGGGCT | GGTTGGTGGC | GGCGTCGATG | 9420 |
| GCTTGCAAGA | GGCCGCATCC | CCGCGGCGCG | ACTACGGTAC | CGCGCGGCGG | GCGGTGGGCC | 9480 |
| GCGGGGGTGT | CCTTGGATGA | TGCATCTAAA | AGCGGTGACG | CGGGCGAGCC | CCCGGAGGTA | 9540 |
| GGGGGGGCTC | CGGACCCGCC | GGGAGAGGGG | GCAGGGGCAC | GTCGGCGCCG | CGCGCGGGCA | 9600 |
| GGAGCTGGTG | CTGCGCGCGT | AGGTTGCTGG | CGAACGCGAC | GACGCGGCGG | TTGATCTCCT | 9660 |
| GAATCTGGCG | CCTCTGCGTG | AAGACGACGG | GCCCGGTGAG | CTTGAGCCTG | AAAGAGAGTT | 9720 |
| CGACAGAATC | AATTTCGGTG | TCGTTGACGG | CGGCCTGGCG | CAAAATCTCC | TGCACGTCTC | 9780 |
| CTGAGTTGTC | TTGATAGGCG | ATCTCGGCCA | TGAACTGCTC | GATCTCTTCC | TCCTGGAGAT | 9840 |
| CTCCGCGTCC | GGCTCGCTCC | ACGGTGGCGG | CGAGGTCGTT | GGAAATGCGG | CCATGAGCT | 9900 |
| GCGAGAAGGC | GTTGAGGCCT | CCCTCGTTCC | AGACGCGGCT | GTAGACCACG | CCCCCTTCGG | 9960 |
| CATCGCGGGC | GCGCATGACC | ACCTGCGCGA | GATTGAGCTC | CACGTGCCGG | GCGAAGACGG | 10020 |
| CGTAGTTTCG | CAGGCGCTGA | AAGAGGTAGT | TGAGGGTGGT | GGCGGTGTGT | TCTGCCACGA | 10080 |
| AGAAGTACAT | AACCCAGCGT | CGCAACGTGG | ATTCGTTGAT | ATCCCCAAG | GCCTCAAGGC | 10140 |
| GCTCCATGGC | CTCGTAGAAG | TCCACGGCGA | AGTTGAAAAA | CTGGGAGTTG | CGCGCCGACA | 10200 |
| CGGTTAACTC | CTCCTCCAGA | AGACGGATGA | GCTCGGCGAC | AGTGTCGCGC | ACCTCGCGCT | 10260 |
| CAAAGGCTAC | AGGGGCCTCT | TCTTCTTCTT | CAATCTCCTC | TTCCATAAGG | GCCTCCCCTT | 10320 |
| CTTCTTCTTC | TGGCGGCGGT | GGGGGAGGGG | GGACACGGCG | GCGACGACGG | CGCACCGGGA | 10380 |
| GGCGGTCGAC | AAAGCGCTCG | ATCATCTCCC | CGCGGCGACG | GCGCATGGTC | TCGGTGACGG | 10440 |
| CGCGGCCGTT | CTCGCGGGGG | CGCAGTTGGA | AGACGCCGCC | CGTCATGTCC | CGGTTATGGG | 10500 |
| TTGGCGGGGG | GCTGCCATGC | GGCAGGGATA | CGGCGCTAAC | GATGCATCTC | AACAATTGTT | 10560 |
| GTGTAGGTAC | TCCGCCGCCG | AGGGACCTGA | GCGAGTCCGC | ATCGACCGGA | TCGGAAAACC | 10620 |
| TCTCGAGAAA | GGCGTCTAAC | CAGTCACAGT | CGCAAGGTAG | GCTGAGCACC | GTGGCGGGCG | 10680 |
| GCAGCGGGCG | GCGGTCGGGG | TTGTTTCTGG | CGGAGGTGCT | GCTGATGATG | TAATTAAAGT | 10740 |
| AGGCGGTCTT | GAGACGGCGG | ATGGTCGACA | GAAGCACCAT | GTCCTTGGGT | CCGGCCTGCT | 10800 |

-continued

| | | | | | |
|---|---|---|---|---|---|
| GAATGCGCAG | GCGGTCGGCC | ATGCCCCAGG | CTTCGTTTTG | ACATCGGCGC | AGGTCTTTGT | 10860 |
| AGTAGTCTTG | CATGAGCCTT | TCTACCGGCA | CTTCTTCTTC | TCCTTCCTCT | TGTCCTGCAT | 10920 |
| CTCTTGCATC | TATCGCTGCG | GCGGCGGCGG | AGTTTGGCCG | TAGGTGGCGC | CCTCTTCCTC | 10980 |
| CCATGCGTGT | GACCCCGAAG | CCCCTCATCG | GCTGAAGCAG | GGCTAGGTCG | GCGACAACGC | 11040 |
| GCTCGGCTAA | TATGGCCTGC | TGCACCTGCG | TGAGGGTAGA | CTGGAAGTCA | TCCATGTCCA | 11100 |
| CAAAGCGGTG | GTATGCGCCC | GTGTTGATGG | TGTAAGTGCA | GTTGGCCATA | ACGGACCAGT | 11160 |
| TAACGGTCTG | GTGACCCGGC | TGCGAGAGCT | CGGTGTACCT | GAGACGCGAG | TAAGCCCTCG | 11220 |
| AGTCAAATAC | GTAGTCGTTG | CAAGTCCGCA | CCAGGTACTG | GTATCCCACC | AAAAAGTGCG | 11280 |
| GCGGCGGCTG | GCGGTAGAGG | GGCCAGCGTA | GGGTGGCCGG | GGCTCCGGGG | GCGAGATCTT | 11340 |
| CCAACATAAG | GCGATGATAT | CCGTAGATGT | ACCTGGACAT | CCAGGTGATG | CCGGCGGCGG | 11400 |
| TGGTGGAGGC | GCGCGGAAAG | TCGCGGACGC | GGTTCCAGAT | GTTGCGCAGC | GGCAAAAAGT | 11460 |
| GCTCCATGGT | CGGGACGCTC | TGGCCGGTCA | GGCGCGCGCA | ATCGTTGACG | CACTAGACCG | 11520 |
| TGCAAAAGGA | GAGCCTGTAA | GCGGGCACTC | TTCCGTGGTC | TGGTGGATAA | ATTCGCAAGG | 11580 |
| GTATCATGGC | GGACGACCGG | GGTTCGAGCC | CCGTATCCGG | CCGTCCGCCG | TGATCCATGC | 11640 |
| GGTTACCGCC | CGCGTGTCGA | ACCCAGGTGT | GCGACGTCAG | ACAACGGGGG | AGTGCTCCTT | 11700 |
| TTGGCTTCCT | TCCAGGCGCG | GCGGCTGCTG | CGCTAGCTTT | TTTGGCCACT | GGCCGCGCGC | 11760 |
| AGCGTAAGCG | GTTAGGCTGG | AAAGCGAAAG | CATTAAGTGG | CTCGCTCCCT | GTAGCCGGAG | 11820 |
| GGTTATTTTC | CAAGGGTTGA | GTCGCGGGAC | CCCCGGTTCG | AGTCTCGGAC | CGGCCGGACT | 11880 |
| GCGGCGAACG | GGGGTTTGCC | TCCCCGTCAT | GCAAGACCCC | GCTTGCAAAT | TCCTCCGGAA | 11940 |
| ACAGGGACGA | GCCCCTTTTT | TGCTTTTCCC | AGATGCATCC | GGTGCTGCGG | CAGATGCGCC | 12000 |
| CCCCTCCTCA | GCAGCGGCAA | GAGCAAGAGC | AGCGGCAGAC | ATGCAGGGCA | CCCTCCCCTC | 12060 |
| CTCCTACCGC | GTCAGGAGGG | GCGACATCCG | CGGTTGACGC | GGCAGCAGAT | GGTGATTACG | 12120 |
| AACCCCCGCG | GCGCCGGGCC | CGGCACTACC | TGGACTTGGA | GGAGGGCGAG | GGCCTGGCGC | 12180 |
| GGCTAGGAGC | GCCCTCTCCT | GAGCGGTACC | CAAGGGTGCA | GCTGAAGCGT | GATACGCGTG | 12240 |
| AGGCGTACGT | GCCGCGGCAG | AACCTGTTTC | GCGACCGCGA | GGGAGAGGAG | CCCGAGGAGA | 12300 |
| TGCGGGATCG | AAAGTTCCAC | GCAGGGCGCG | AGCTGCGGCA | TGGCCTGAAT | CGCGAGCGGT | 12360 |
| TGCTGCGCGA | GGAGGACTTT | GAGCCCGACG | CGCGAACCGG | GATTAGTCCC | GCGCGCGCAC | 12420 |
| ACGTGGCGGC | CGCCGACCTG | GTAACCGCAT | ACGAGCAGAC | GGTGAACCAG | GAGATTAACT | 12480 |
| TTCAAAAAAG | CTTTAACAAC | CACGTGCGTA | CGCTTGTGGC | GCGCGAGGAG | GTGGCTATAG | 12540 |
| GACTGATGCA | TCTGTGGGAC | TTTGTAAGCG | CGCTGGAGCA | AAACCCAAAT | AGCAAGCCGC | 12600 |
| TCATGGCGCA | GCTGTTCCTT | ATAGTGCAGC | ACAGCAGGGA | CAACGAGGCA | TTCAGGGATG | 12660 |
| CGCTGCTAAA | CATAGTAGAG | CCCGAGGGCC | GCTGGCTGCT | CGATTTGATA | AACATCCTGC | 12720 |
| AGAGCATAGT | GGTGCAGGAG | CGCAGCTTGA | GCCTGGCTGA | CAAGGTGGCC | GCCATCAACT | 12780 |
| ATTCCATGCT | TAGCCTGGGC | AAGTTTTACG | CCCGCAAGAT | ATACCATACC | CCTTACGTTC | 12840 |
| CCATAGACAA | GGAGGTAAAG | ATCGAGGGGT | TCTACATGCG | CATGGCGCTG | AAGGTGCTTA | 12900 |
| CCTTGAGCGA | CGACCTGGGC | GTTTATCGCA | ACGAGCGCAT | CCACAAGGCC | GTGAGCGTGA | 12960 |
| GCCGGCGGCG | CGAGCTCAGC | GACCGCGAGC | TGATGCACAG | CCTGCAAAGG | GCCCTGGCTG | 13020 |
| GCACGGGCAG | CGGCGATAGA | GAGGCCGAGT | CCTACTTTGA | CGCGGGCGCT | GACCTGCGCT | 13080 |
| GGGCCCCAAG | CCGACGCGCC | CTGGAGGCAG | CTGGGGCCGG | ACCTGGGCTG | GCGGTGGCAC | 13140 |
| CCGCGCGCGC | TGGCAACGTC | GGCGGCGTGG | AGGAATATGA | CGAGGACGAT | GAGTACGAGC | 13200 |

| | | | | | | |
|---|---|---|---|---|---|---|
| CAGAGGACGG | CGAGTACTAA | GCGGTGATGT | TTCTGATCAG | ATGATGCAAG | ACGCAACGGA | 13260 |
| CCCGGCGGTG | CGGGCGGCGC | TGCAGAGCCA | GCCGTCCGGC | CTTAACTCCA | CGGACGACTG | 13320 |
| GCGCCAGGTC | ATGGACCGCA | TCATGTCGCT | GACTGCGCGC | AATCCTGACG | CGTTCCGGCA | 13380 |
| GCAGCCGCAG | GCCAACCGGC | TCTCCGCAAT | TCTGGAAGCG | GTGGTCCCGG | CGCGCGCAAA | 13440 |
| CCCCACGCAC | GAGAAGGTGC | TGGCGATCGT | AAACGCGCTG | GCCGAAAACA | GGGCCATCCG | 13500 |
| GCCCGACGAG | GCCGGCCTGG | TCTACGACGC | GCTGCTTCAG | CGCGTGGCTC | GTTACAACAG | 13560 |
| CGGCAACGTG | CAGACCAACC | TGGACCGGCT | GGTGGGGGAT | GTGCGCGAGG | CCGTGGCGCA | 13620 |
| GCGTGAGCGC | GCGCAGCAGC | AGGGCAACCT | GGGCTCCATG | GTTGCACTAA | ACGCCTTCCT | 13680 |
| GAGTACACAG | CCCGCCAACG | TGCCGCGGGG | ACAGGAGGAC | TACACCAACT | TTGTGAGCGC | 13740 |
| ACTGCGGCTA | ATGGTGACTG | AGACACCGCA | AAGTGAGGTG | TACCAGTCTG | GCCAGACTA | 13800 |
| TTTTTTCCAG | ACCAGTAGAC | AAGGCCTGCA | GACCGTAAAC | CTGAGCCAGG | CTTTCAAAAA | 13860 |
| CTTGCAGGGG | CTGTGGGGGG | TGCGGGCTCC | CACAGGCGAC | CGCGCGACCG | TGTCTAGCTT | 13920 |
| GCTGACGCCC | AACTCGCGCC | TGTTGCTGCT | GCTAATAGCG | CCCTTCACGG | ACAGTGGCAG | 13980 |
| CGTGTCCCGG | GACACATACC | TAGGTCACTT | GCTGACACTG | TACCGCGAGG | CCATAGGTCA | 14040 |
| GGCGCATGTG | GACGAGCATA | CTTTCCAGGA | GATTACAAGT | GTCAGCCGCG | CGCTGGGGCA | 14100 |
| GGAGGACACG | GGCAGCCTGG | AGGCAACCCT | AAACTACCTG | CTGACCAACC | GGCGGCAGAA | 14160 |
| GATCCCCTCG | TTGCACAGTT | TAAACAGCGA | GGAGGAGCGC | ATTTGCGCT | ACGTGCAGCA | 14220 |
| GAGCGTGAGC | CTTAACCTGA | TGCGCGACGG | GGTAACGCCC | AGCGTGGCGC | TGGACATGAC | 14280 |
| CGCGCGCAAC | ATGGAACCGG | GCATGTATGC | CTCAAACCGG | CCGTTTATCA | ACCGCCTAAT | 14340 |
| GGACTACTTG | CATCGCGCGG | CCGCCGTGAA | CCCCGAGTAT | TTCACCAATG | CCATCTTGAA | 14400 |
| CCCGCACTGG | CTACCGCCCC | CTGGTTTCTA | CACCGGGGGA | TTCGAGGTGC | CCGAGGGTAA | 14460 |
| CGATGGATTC | CTCTGGGACG | ACATAGACGA | CAGCGTGTTT | TCCCCGCAAC | CGCAGACCCT | 14520 |
| GCTAGAGTTG | CAACAGCGCG | AGCAGGCAGA | GGCGGCGCTG | CGAAAGGAAA | GCTTCCGCAG | 14580 |
| GCCAAGCAGC | TTGTCCGATC | TAGGCGCTGC | GGCCCCGCGG | TCAGATGCTA | GTAGCCCATT | 14640 |
| TCCAAGCTTG | ATAGGGTCTC | TTACCAGCAC | TCGCACCACC | CGCCCGCGCC | TGCTGGGCGA | 14700 |
| GGAGGAGTAC | CTAAACAACT | CGCTGCTGCA | GCCGCAGCGC | GAAAAAAACC | TGCCTCCGGC | 14760 |
| ATTTCCCAAC | AACGGGATAG | AGAGCCTAGT | GGACAAGATG | AGTAGATGGA | AGACGTACGC | 14820 |
| GCAGGAGCAC | AGGGACGTGC | CAGGCCCGCG | CCCGCCCACC | CGTCGTCAAA | GGCACGACCG | 14880 |
| TCAGCGGGGT | CTGGTGTGGG | AGGACGATGA | CTCGGCAGAC | GACAGCAGCG | TCCTGGATTT | 14940 |
| GGGAGGGAGT | GGCAACCCGT | TTGCGCACCT | TCGCCCCAGG | CTGGGGAGAA | TGTTTTAAAA | 15000 |
| AAAAAAAGC | ATGATGCAAA | ATAAAAAACT | CACCAAGGCC | ATGGCACCGA | GCGTTGGTTT | 15060 |
| TCTTGTATTC | CCCTTAGTAT | GCGGCGCGCG | GCGATGTATG | AGGAAGGTCC | TCCTCCCTCC | 15120 |
| TACGAGAGTG | TGGTGAGCGC | GGCGCCAGTG | GCGGCGGCGC | TGGGTTCTCC | CTTCGATGCT | 15180 |
| CCCCTGGACC | CGCCGTTTGT | GCCTCCGCGG | TACCTGCGGC | CTACCGGGGG | GAGAAACAGC | 15240 |
| ATCCGTTACT | CTGAGTTGGC | ACCCCTATTC | GACACCACCC | GTGTGTACCT | GGTGGACAAC | 15300 |
| AAGTCAACGG | ATGTGGCATC | CCTGAACTAC | CAGAACGACC | ACAGCAACTT | TCTGACCACG | 15360 |
| GTCATTCAAA | ACAATGACTA | CAGCCCGGGG | GAGGCAAGCA | CACAGACCAT | CAATCTTGAC | 15420 |
| GACCGGTCGC | ACTGGGGCGG | CGACCTGAAA | ACCATCCTGC | ATACCAACAT | GCCAAATGTG | 15480 |
| AACGAGTTCA | TGTTTACCAA | TAAGTTTAAG | GCGCGGGTGA | TGGTGTCGCG | CTTGCCTACT | 15540 |
| AAGGACAATC | AGGTGGAGCT | GAAATACGAG | TGGGTGGAGT | TCACGCTGCC | CGAGGGCAAC | 15600 |

```
TACTCCGAGA  CCATGACCAT  AGACCTTATG  AACAACGCGA  TCGTGGAGCA  CTACTTGAAA  15660
GTGGGCAGAC  AGAACGGGGT  TCTGGAAAGC  GACATCGGGG  TAAAGTTTGA  CACCCGCAAC  15720
TTCAGACTGG  GGTTTGACCC  CGTCACTGGT  CTTGTCATGC  CTGGGGTATA  TACAAACGAA  15780
GCCTTCCATC  CAGACATCAT  TTTGCTGCCA  GGATGCGGGG  TGGACTTCAC  CCACAGCCGC  15840
CTGAGCAACT  TGTTGGGCAT  CCGCAAGCGG  CAACCCTTCC  AGGAGGGCTT  TAGGATCACC  15900
TACGATGATC  TGGAGGGTGG  TAACATTCCC  GCACTGTTGG  ATGTGGACGC  CTACCAGGCG  15960
AGCTTGAAAG  ATGACACCGA  ACAGGGCGGG  GGTGGCGCAG  GCGGCAGCAA  CAGCAGTGGC  16020
AGCGGCGCGG  AAGAGAACTC  CAACGCGGCA  GCCGCGGCAA  TGCAGCCGGT  GGAGGACATG  16080
AACGATCATG  CCATTCGCGG  CGACACCTTT  GCCACACGGG  CTGAGGAGAA  GCGCGCTGAG  16140
GCCGAAGCAG  CGGCCGAAGC  TGCCGCCCCC  GCTGCGCAAC  CCGAGGTCGA  GAAGCCTCAG  16200
AAGAAACCGG  TGATCAAACC  CCTGACAGAG  GACAGCAAGA  AACGCAGTTA  CAACCTAATA  16260
AGCAATGACA  GCACCTTCAC  CCAGTACCGC  AGCTGGTACC  TTGCATACAA  CTACGGCGAC  16320
CCTCAGACCG  GAATCCGCTC  ATGGACCCTG  CTTTGCACTC  CTGACGTAAC  CTGCGGCTCG  16380
GAGCAGGTCT  ACTGGTCGTT  GCCAGACATG  ATGCAAGACC  CCGTGACCTT  CCGCTCCACG  16440
CGCCAGATCA  GCAACTTTCC  GGTGGTGGGC  GCCGAGCTGT  TGCCCGTGCA  CTCCAAGAGC  16500
TTCTACAACG  ACCAGGCCGT  CTACTCCCAA  CTCATCCGCC  AGTTTACCTC  TCTGACCCAC  16560
GTGTTCAATC  GCTTTCCCGA  GAACCAGATT  TTGGCGCGCC  CGCCAGCCCC  CACCATCACC  16620
ACCGTCAGTG  AAAACGTTCC  TGCTCTCACA  GATCACGGGA  CGCTACCGCT  GCGCAACAGC  16680
ATCGGAGGAG  TCCAGCGAGT  GACCATTACT  GACGCCAGAC  GCCGCACCTG  CCCCTACGTT  16740
TACAAGGCCC  TGGGCATAGT  CTCGCCGCGC  GTCCTATCGA  GCCGCACTTT  TTGAGCAAGC  16800
ATGTCCATCC  TTATATCGCC  CAGCAATAAC  ACAGGCTGGG  GCCTGCGCTT  CCCAAGCAAG  16860
ATGTTTGGCG  GGGCCAAGAA  GCGCTCCGAC  CAACACCCAG  TGCGCGTGCG  CGGGCACTAC  16920
CGCGCGCCCT  GGGGCGCGCA  CAAACGCGGC  CGCACTGGGC  GCACCACCGT  CGATGACGCC  16980
ATCGACGCGG  TGGTGGAGGA  GGCGCGCAAC  TACACGCCCA  CGCCGCCACC  AGTGTCCACA  17040
GTGGACGCGG  CCATTCAGAC  CGTGGTGCGC  GGAGCCCGGC  GCTATGCTAA  AATGAAGAGA  17100
CGGCGGAGGC  GCGTAGCACG  TCGCCACCGC  CGCCGACCCG  GCACTGCCGC  CAACGCGCG   17160
GCGGCGGCCC  TGCTTAACCG  CGCACGTCGC  ACCGGCCGAC  GGGCGGCCAT  GCGGGCCGCT  17220
CGAAGGCTGG  CCGCGGGTAT  TGTCACTGTG  CCCCCCAGGT  CCAGGCGACG  AGCGGCCGCC  17280
GCAGCAGCCG  CGGCCATTAG  TGCTATGACT  CAGGGTCGCA  GGGGCAACGT  GTATTGGGTG  17340
CGCGACTCGG  TTAGCGGCCT  GCGCGTGCCC  GTGCGCACCC  GCCCCCCGCG  CAACTAGATT  17400
GCAAGAAAAA  ACTACTTAGA  CTCGTACTGT  TGTATGTATC  CAGCGGCGGC  GGCGCGCAAC  17460
GAAGCTATGT  CCAAGCGCAA  AATCAAAGAA  GAGATGCTCC  AGGTCATCGC  GCCGGAGATC  17520
TATGGCCCCC  CGAAGAAGGA  AGAGCAGGAT  TACAAGCCCC  GAAAGCTAAA  GCGGGTCAAA  17580
AAGAAAAAGA  AAGATGATGA  TGATGAACTT  GACGACGAGG  TGGAACTGCT  GCACGCTACC  17640
GCGCCCAGGC  GACGGGTACA  GTGGAAAGGT  CGACGCGTAA  AACGTGTTTT  GCGACCCGGC  17700
ACCACCGTAG  TCTTTACGCC  CGGTGAGCGC  TCCACCCGCA  CCTACAAGCG  CGTGTATGAT  17760
GAGGTGTACG  GCGACGAGGA  CCTGCTTGAG  CAGGCCAACG  AGCGCCTCGG  GGAGTTTGCC  17820
TACGGAAAGC  GGCATAAGGA  CATGCTGGCG  TTGCCGCTGG  ACGAGGGCAA  CCCAACACCT  17880
AGCCTAAAGC  CCGTAACACT  GCAGCAGGTG  CTGCCCGCGC  TTGCACCGTC  CGAAGAAAAG  17940
CGCGGCCTAA  AGCGCGAGTC  TGGTGACTTG  GCACCCACCG  TGCAGCTGAT  GGTACCCAAG  18000
```

| | | | | | | |
|---|---|---|---|---|---|---|
| CGCCAGCGAC | TGGAAGATGT | CTTGGAAAAA | ATGACCGTGG | AACCTGGGCT | GGAGCCCGAG | 18060 |
| GTCCGCGTGC | GGCCAATCAA | GCAGGTGGCG | CCGGGACTGG | GCGTGCAGAC | CGTGGACGTT | 18120 |
| CAGATACCCA | CTACCAGTAG | CACCAGTATT | GCCACCGCCA | CAGAGGGCAT | GGAGACACAA | 18180 |
| ACGTCCCCGG | TTGCCTCAGC | GGTGGCGGAT | GCCGCGGTGC | AGGCGGTCGC | TGCGGCCGCG | 18240 |
| TCCAAGACCT | CTACGGAGGT | GCAAACGGAC | CCGTGGATGT | TTCGCGTTTC | AGCCCCCGG | 18300 |
| CGCCCGCGCG | GTTCGAGGAA | GTACGGCGCC | GCCAGCGCGC | TACTGCCCGA | ATATGCCCTA | 18360 |
| CATCCTTCCA | TTGCGCCTAC | CCCCGGCTAT | CGTGGCTACA | CCTACCGCCC | CAGAAGACGA | 18420 |
| GCAACTACCC | GACGCCGAAC | CACCACTGGA | ACCCGCCGCC | GCCGTCGCCG | TCGCCAGCCC | 18480 |
| GTGCTGGCCC | CGATTTCCGT | GCGCAGGGTG | GCTCGCGAAG | GAGGCAGGAC | CCTGGTGCTG | 18540 |
| CCAACAGCGC | GCTACCACCC | CAGCATCGTT | TAAAAGCCGG | TCTTTGTGGT | TCTTGCAGAT | 18600 |
| ATGGCCCTCA | CCTGCCGCCT | CCGTTTCCCG | GTGCCGGGAT | TCCGAGGAAG | AATGCACCGT | 18660 |
| AGGAGGGGCA | TGGCCGGCCA | CGGCCTGACG | GGCGGCATGC | GTCGTGCGCA | CCACCGGCGG | 18720 |
| CGGCGCGCGT | CGCACCGTCG | CATGCGCGGC | GGTATCCTGC | CCCTCCTTAT | TCCACTGATC | 18780 |
| GCCGCGGCGA | TTGGCGCCGT | GCCCGGAATT | GCATCCGTGG | CCTTGCAGGC | GCAGAGACAC | 18840 |
| TGATTAAAAA | CAAGTTGCAT | GTGGAAAAAT | CAAAATAAAA | AGTCTGGACT | CTCACGCTCG | 18900 |
| CTTGGTCCTG | TAACTATTTT | GTAGAATGGA | AGACATCAAC | TTTGCGTCTC | TGGCCCCGCG | 18960 |
| ACACGGCTCG | CGCCCGTTCA | TGGGAAACTG | GCAAGATATC | GGCACCAGCA | ATATGAGCGG | 19020 |
| TGGCGCCTTC | AGCTGGGGCT | CGCTGTGGAG | CGGCATTAAA | AATTTCGGTT | CCACCGTTAA | 19080 |
| GAACTATGGC | AGCAAGGCCT | GGAACAGCAG | CACAGGCCAG | ATGCTGAGGG | ATAAGTTGAA | 19140 |
| AGAGCAAAAT | TTCCAACAAA | AGGTGGTAGA | TGGCCTGGCC | TCTGGCATTA | GCGGGGTGGT | 19200 |
| GGACCTGGCC | AACCAGGCAG | TGCAAAATAA | GATTAACAGT | AAGCTTGATC | CCCGCCCTCC | 19260 |
| CGTAGAGGAG | CCTCCACCGG | CCGTGGAGAC | AGTGTCTCCA | GAGGGGCGTG | GCGAAAAGCG | 19320 |
| TCCGCGCCCC | GACAGGGAAG | AAACTCTGGT | GACGCAAATA | GACGAGCCTC | CCTCGTACGA | 19380 |
| GGAGGCACTA | AAGCAAGGCC | TGCCCACCAC | CCGTCCCATC | GCGCCCATGG | CTACCGGAGT | 19440 |
| GCTGGGCCAG | CACACACCCG | TAACGCTGGA | CCTGCCTCCC | CCGCCGACA | CCCAGCAGAA | 19500 |
| ACCTGTGCTG | CCAGGCCCGA | CCGCCGTTGT | TGTAACCCGT | CCTAGCCGCG | CGTCCCTGCG | 19560 |
| CCGCGCCGCC | AGCGGTCCGC | GATCGTTGCG | GCCCGTAGCC | AGTGGCAACT | GGCAAAGCAC | 19620 |
| ACTGAACAGC | ATCGTGGGTC | TGGGGGTGCA | ATCCCTGAAG | CGCCGACGAT | GCTTCTGAAT | 19680 |
| AGCTAACGTG | TCGTATGTGT | GTCATGTATG | CGTCCATGTC | GCCGCCAGAG | GAGCTGCTGA | 19740 |
| GCCGCCGCGC | GCCCGCTTTC | CAAGATGGCT | ACCCCTTCGA | TGATGCCGCA | GTGGTCTTAC | 19800 |
| ATGCACATCT | CGGGCCAGGA | CGCCTCGGAG | TACCTGAGCC | CCGGGCTGGT | GCAGTTTGCC | 19860 |
| CGCGCCACCG | AGACGTACTT | CAGCCTGAAT | AACAAGTTTA | GAAACCCCAC | GGTGGCGCCT | 19920 |
| ACGCACGACG | TGACCACAGA | CCGGTCCCAG | CGTTTGACGC | TGCGGTTCAT | CCCTGTGGAC | 19980 |
| CGTGAGGATA | CTGCGTACTC | GTACAAGGCG | CGGTTCACCC | TAGCTGTGGG | TGATAACCGT | 20040 |
| GTGCTGGACA | TGGCTTCCAC | GTACTTTGAC | ATCCGCGGCG | TGCTGGACAG | GGGCCCTACT | 20100 |
| TTTAAGCCCT | ACTCTGGCAC | TGCCTACAAC | GCCCTGGCTC | CAAGGGTGC | CCCAAATCCT | 20160 |
| TGCGAATGGG | ATGAAGCTGC | TACTGCTCTT | GAAATAAACC | TAGAAGAAGA | GGACGATGAC | 20220 |
| AACGAAGACG | AAGTAGACGA | GCAAGCTGAG | CAGCAAAAAA | CTCACGTATT | TGGGCAGGCG | 20280 |
| CCTTATTCTG | GTATAAATAT | TACAAAGGAG | GGTATTCAAA | TAGGTGTCGA | AGGTCAAACA | 20340 |
| CCTAAATATG | CCGATAAAAC | ATTTCAACCT | GAACCTCAAA | TAGGAGAATC | TCAGTGGTAC | 20400 |

| | | | | | | |
|---|---|---|---|---|---|---|
| GAAACTGAAA | TTAATCATGC | AGCTGGGAGA | GTCCTTAAAA | AGACTACCCC | AATGAAACCA | 20460 |
| TGTTACGGTT | CATATGCAAA | ACCCACAAAT | GAAATGGAG | GGCAAGGCAT | TCTTGTAAAG | 20520 |
| CAACAAAATG | GAAAGCTAGA | AAGTCAAGTG | GAAATGCAAT | TTTTCTCAAC | TACTGAGGCG | 20580 |
| ACCGCAGGCA | ATGGTGATAA | CTTGACTCCT | AAAGTGGTAT | TGTACAGTGA | AGATGTAGAT | 20640 |
| ATAGAAACCC | CAGACACTCA | TATTTCTTAC | ATGCCCACTA | TTAAGGAAGG | TAACTCACGA | 20700 |
| GAACTAATGG | GCCAACAATC | TATGCCCAAC | AGGCCTAATT | ACATTGCTTT | TAGGGACAAT | 20760 |
| TTTATTGGTC | TAATGTATTA | CAACAGCACG | GGTAATATGG | GTGTTCTGGC | GGGCCAAGCA | 20820 |
| TCGCAGTTGA | ATGCTGTTGT | AGATTTGCAA | GACAGAAACA | CAGAGCTTTC | ATACCAGCTT | 20880 |
| TTGCTTGATT | CCATTGGTGA | TAGAACCAGG | TACTTTTCTA | TGTGGAATCA | GGCTGTTGAC | 20940 |
| AGCTATGATC | CAGATGTTAG | AATTATTGAA | AATCATGGAA | CTGAAGATGA | ACTTCCAAAT | 21000 |
| TACTGCTTTC | CACTGGGAGG | TGTGATTAAT | ACAGAGACTC | TTACCAAGGT | AAAACCTAAA | 21060 |
| ACAGGTCAGG | AAAATGGATG | GGAAAAAGAT | GCTACAGAAT | TTTCAGATAA | AAATGAAATA | 21120 |
| AGAGTTGGAA | ATAATTTTGC | CATGGAAATC | AATCTAAATG | CCAACCTGTG | GAGAAATTTC | 21180 |
| CTGTACTCCA | ACATAGCGCT | GTATTTGCCC | GACAAGCTAA | AGTACAGTCC | TTCCAACGTA | 21240 |
| AAAATTTCTG | ATAACCCAAA | CACCTACGAC | TACATGAACA | AGCGAGTGGT | GGCTCCCGGG | 21300 |
| TTAGTGGACT | GCTACATTAA | CCTTGGAGCA | CGCTGGTCCC | TTGACTATAT | GGACAACGTC | 21360 |
| AACCCATTTA | ACCACCACCG | CAATGCTGGC | CTGCGCTACC | GCTCAATGTT | GCTGGGCAAT | 21420 |
| GGTCGCTATG | TGCCCTTCCA | CATCCAGGTG | CCTCAGAAGT | TCTTTGCCAT | TAAAAACCTC | 21480 |
| CTTCTCCTGC | CGGGCTCATA | CACCTACGAG | TGGAACTTCA | GGAAGGATGT | TAACATGGTT | 21540 |
| CTGCAGAGCT | CCCTAGGAAA | TGACCTAAGG | GTTGACGGAG | CCAGCATTAA | GTTTGATAGC | 21600 |
| ATTTGCCTTT | ACGCCACCTT | CTTCCCCATG | GCCCACAACA | CCGCCTCCAC | GCTTGAGGCC | 21660 |
| ATGCTTAGAA | ACGACACCAA | CGACCAGTCC | TTTAACGACT | ATCTCTCCGC | CGCCAACATG | 21720 |
| CTCTACCCTA | TACCCGCCAA | CGCTACCAAC | GTGCCCATAT | CCATCCCCTC | CCGCAACTGG | 21780 |
| GCGGCTTTCC | GCGGCTGGGC | CTTCACGCGC | CTTAAGACTA | AGGAAACCCC | ATCACTGGGC | 21840 |
| TCGGGCTACG | ACCCTTATTA | CACCTACTCT | GGCTCTATAC | CCTACCTAGA | TGGAACCTTT | 21900 |
| TACCTCAACC | ACACCTTTAA | GAAGGTGGCC | ATTACCTTTG | ACTCTTCTGT | CAGCTGGCCT | 21960 |
| GGCAATGACC | GCCTGCTTAC | CCCCAACGAG | TTTGAAATTA | AGCGCTCAGT | TGACGGGGAG | 22020 |
| GGTTACAACG | TTGCCCAGTG | TAACATGACC | AAAGACTGGT | TCCTGGTACA | AATGCTAGCT | 22080 |
| AACTACAACA | TTGGCTACCA | GGGCTTCTAT | ATCCCAGAGA | GCTACAAGGA | CCGCATGTAC | 22140 |
| TCCTTCTTTA | GAAACTTCCA | GCCCATGAGC | CGTCAGGTGG | TGGATGATAC | TAAATACAAG | 22200 |
| GACTACCAAC | AGGTGGGCAT | CCTACACCAA | CACAACAACT | CTGGATTTGT | TGGCTACCTT | 22260 |
| GCCCCCACCA | TGCGCGAAGG | ACAGGCCTAC | CCTGCTAACT | TCCCCTATCC | GCTTATAGGC | 22320 |
| AAGACCGCAG | TTGACAGCAT | TACCCAGAAA | AAGTTTCTTT | GCGATCGCAC | CCTTTGGCGC | 22380 |
| ATCCCATTCT | CCAGTAACTT | TATGTCCATG | GGCGCACTCA | CAGACCTGGG | CCAAAACCTT | 22440 |
| CTCTACGCCA | ACTCCGCCCA | CGCGCTAGAC | ATGACTTTTG | AGGTGGATCC | CATGGACGAG | 22500 |
| CCCACCCTTC | TTTATGTTTT | GTTTGAAGTC | TTTGACGTGG | TCCGTGTGCA | CCGGCCGCAC | 22560 |
| CGCGGCGTCA | TCGAAACCGT | GTACCTGCGC | ACGCCCTTCT | CGGCCGGCAA | CGCCACAACA | 22620 |
| TAAAGAAGCA | AGCAACATCA | ACAACAGCTG | CCGCCATGGG | CTCCAGTGAG | CAGGAACTGA | 22680 |
| AAGCCATTGT | CAAAGATCTT | GGTTGTGGGC | CATATTTTTT | GGGCACCTAT | GACAAGCGCT | 22740 |
| TTCCAGGCTT | TGTTTCTCCA | CACAAGCTCG | CCTGCGCCAT | AGTCAATACG | GCCGGTCGCG | 22800 |

| | | | | | | |
|---|---|---|---|---|---|---|
| AGACTGGGGG | CGTACACTGG | ATGGCCTTTG | CCTGGAACCC | GCACTCAAAA | ACATGCTACC | 22860 |
| TCTTTGAGCC | CTTTGGCTTT | TCTGACCAGC | GACTCAAGCA | GGTTTACCAG | TTTGAGTACG | 22920 |
| AGTCACTCCT | GCGCCGTAGC | GCCATTGCTT | CTTCCCCCGA | CCGCTGTATA | ACGCTGGAAA | 22980 |
| AGTCCACCCA | AAGCGTACAG | GGGCCCAACT | CGGCCGCCTG | TGGACTATTC | TGCTGCATGT | 23040 |
| TTCTCCACGC | CTTTGCCAAC | TGGCCCCAAA | CTCCATGGA | TCACAACCCC | ACCATGAACC | 23100 |
| TTATTACCGG | GGTACCCAAC | TCCATGCTCA | ACAGTCCCA | GGTACAGCCC | ACCCTGCGTC | 23160 |
| GCAACCAGGA | ACAGCTCTAC | AGCTTCCTGG | AGCGCCACTC | GCCCTACTTC | CGCAGCCACA | 23220 |
| GTGCGCAGAT | TAGGAGCGCC | ACTTCTTTTT | GTCACTTGAA | AAACATGTAA | AAATAATGTA | 23280 |
| CTAGAGACAC | TTTCAATAAA | GGCAAATGCT | TTTATTTGTA | CACTCTCGGG | TGATTATTTA | 23340 |
| CCCCCACCCT | TGCCGTCTGC | GCCGTTTAAA | AATCAAAGGG | GTTCTGCCGC | GCATCGCTAT | 23400 |
| GCGCCACTGG | CAGGGACACG | TTGCGATACT | GGTGTTTAGT | GCTCCACTTA | AACTCAGGCA | 23460 |
| CAACCATCCG | CGGCAGCTCG | GTGAAGTTTT | CACTCCACAG | GCTGCGCACC | ATCACCAACG | 23520 |
| CGTTTAGCAG | GTCGGGCGCC | GATATCTTGA | AGTCGCAGTT | GGGGCCTCCG | CCCTGCGCGC | 23580 |
| GCGAGTTGCG | ATACACAGGG | TTGCAGCACT | GGAACACTAT | CAGCGCCGGG | TGGTGCACGC | 23640 |
| TGGCCAGCAC | GCTCTTGTCG | GAGATCAGAT | CCGCGTCCAG | GTCCTCCGCG | TTGCTCAGGG | 23700 |
| CGAACGGAGT | CAACTTTGGT | AGCTGCCTTC | CCAAAAGGG | CGCGTGCCCA | GGCTTTGAGT | 23760 |
| TGCACTCGCA | CCGTAGTGGC | ATCAAAAGGT | GACCGTGCCC | GGTCTGGGCG | TTAGGATACA | 23820 |
| GCGCCTGCAT | AAAAGCCTTG | ATCTGCTTAA | AAGCCACCTG | AGCCTTTGCG | CCTTCAGAGA | 23880 |
| AGAACATGCC | GCAAGACTTG | CCGGAAAACT | GATTGGCCGG | ACAGGCCGCG | TCGTGCACGC | 23940 |
| AGCACCTTGC | GTCGGTGTTG | GAGATCTGCA | CCACATTTCG | GCCCCACCGG | TTCTTCACGA | 24000 |
| TCTTGGCCTT | GCTAGACTGC | TCCTTCAGCG | CGCGCTGCCC | GTTTTCGCTC | GTCACATCCA | 24060 |
| TTTCAATCAC | GTGCTCCTTA | TTTATCATAA | TGCTTCCGTG | TAGACACTTA | AGCTCGCCTT | 24120 |
| CGATCTCAGC | GCAGCGGTGC | AGCCACAACG | CGCAGCCCGT | GGGCTCGTGA | TGCTTGTAGG | 24180 |
| TCACCTCTGC | AAACGACTGC | AGGTACGCCT | GCAGGAATCG | CCCCATCATC | GTCACAAAGG | 24240 |
| TCTTGTTGCT | GGTGAAGGTC | AGCTGCAACC | CGCGGTGCTC | CTCGTTCAGC | CAGGTCTTGC | 24300 |
| ATACGGCCGC | CAGAGCTTCC | ACTTGGTCAG | GCAGTAGTTT | GAAGTTCGCC | TTTAGATCGT | 24360 |
| TATCCACGTG | GTACTTGTCC | ATCAGCGCGC | GCGCAGCCTC | CATGCCCTTC | TCCCACGCAG | 24420 |
| ACACGATCGG | CACACTCAGC | GGGTTCATCA | CCGTAATTTC | ACTTTCCGCT | TCGCTGGGCT | 24480 |
| CTTCCTCTTC | CTCTTGCGTC | CGCATACCAC | GCGCCACTGG | GTCGTCTTCA | TTCAGCCGCC | 24540 |
| GCACTGTGCG | CTTACCTCCT | TTGCCATGCT | TGATTAGCAC | CGGTGGGTTG | CTGAAACCCA | 24600 |
| CCATTTGTAG | CGCCACATCT | TCTCTTTCTT | CCTCGCTGTC | CACGATTACC | TCTGGTGATG | 24660 |
| GCGGGCGCTC | GGGCTTGGGA | GAAGGGCGCT | TCTTTTTCTT | CTTGGGCGCA | ATGGCCAAAT | 24720 |
| CCGCCGCCGA | GGTCGATGGC | CGCGGGCTGG | GTGTGCGCGG | CACCAGCGCG | TCTTGTGATG | 24780 |
| AGTCTTCCTC | GTCCTCGGAC | TCGATACGCC | GCCTCATCCG | CTTTTTGGG | GGCGCCCGGG | 24840 |
| GAGGCGGCGG | CGACGGGGAC | GGGGACGACA | CGTCCTCCAT | GGTTGGGGGA | CGTCGCGCCG | 24900 |
| CACCGCGTCC | GCGCTCGGGG | GTGGTTTCGC | GCTGCTCCTC | TTCCCGACTG | GCCATTTCCT | 24960 |
| TCTCCTATAG | GCAGAAAAAG | ATCATGGAGT | CAGTCGAGAA | GAAGGACAGC | CTAACCGCCC | 25020 |
| CCTCTGAGTT | CGCCACCACC | GCCTCCACCG | ATGCCGCCAA | CGCGCCTACC | ACCTTCCCCG | 25080 |
| TCGAGGCACC | CCCGCTTGAG | GAGGAGGAAG | TGATTATCGA | GCAGGACCCA | GGTTTTGTAA | 25140 |
| GCGAAGACGA | CGAGGACCGC | TCAGTACCAA | CAGAGGATAA | AAAGCAAGAC | CAGGACAACG | 25200 |

-continued

| | | | | | | |
|---|---|---|---|---|---|---|
|CAGAGGCAAA|CGAGGAACAA|GTCGGGCGGG|GGGACGAAAG|GCATGGCGAC|TACCTAGATG|25260|
|TGGGAGACGA|CGTGCTGTTG|AAGCATCTGC|AGCGCCAGTG|CGCCATTATC|TGCGACGCGT|25320|
|TGCAAGAGCG|CAGCGATGTG|CCCCTCGCCA|TAGCGGATGT|CAGCCTTGCC|TACGAACGCC|25380|
|ACCTATTCTC|ACCGCGCGTA|CCCCCCAAAC|GCCAAGAAAA|CGGCACATGC|GAGCCCAACC|25440|
|CGCGCCTCAA|CTTCTACCCC|GTATTGCCG|TGCCAGAGGT|GCTTGCCACC|TATCACATCT|25500|
|TTTTCCAAAA|CTGCAAGATA|CCCCTATCCT|GCCGTGCCAA|CCGCAGCCGA|GCGGACAAGC|25560|
|AGCTGGCCTT|GCGGCAGGGC|GCTGTCATAC|CTGATATCGC|CTCGCTCAAC|GAAGTGCCAA|25620|
|AAATCTTTGA|GGGTCTTGGA|CGCGACGAGA|AGCGCGCGGC|AAACGCTCTG|CAACAGGAAA|25680|
|ACAGCGAAAA|TGAAAGTCAC|TCTGGAGTGT|TGGTGGAACT|CGAGGGTGAC|AACGCGCGCC|25740|
|TAGCCGTACT|AAAACGCAGC|ATCGAGGTCA|CCCACTTTGC|CTACCCGGCA|CTTAACCTAC|25800|
|CCCCCAAGGT|CATGAGCACA|GTCATGAGTG|AGCTGATCGT|GCGCCGTGCG|CAGCCCCTGG|25860|
|AGAGGGATGC|AAATTTGCAA|GAACAAACAG|AGGAGGGCCT|ACCCGCAGTT|GGCGACGAGC|25920|
|AGCTAGCGCG|CTGGCTTCAA|ACGCGCGAGC|CTGCCGACTT|GGAGGAGCGA|CGCAAACTAA|25980|
|TGATGGCCGC|AGTGCTCGTT|ACCGTGGAGC|TTGAGTGCAT|GCAGCGGTTC|TTTGCTGACC|26040|
|CGGAGATGCA|GCGCAAGCTA|GAGGAAACAT|TGCACTACAC|CTTTCGACAG|GGCTACGTAC|26100|
|GCCAGGCCTG|CAAGATCTCC|AACGTGGAGC|TCTGCAACCT|GGTCTCCTAC|CTTGGAATTT|26160|
|TGCACGAAAA|CCGCCTTGGG|CAAAACGTGC|TTCATTCCAC|GCTCAAGGGC|GAGGCGCGCC|26220|
|GCGACTACGT|CCGCGACTGC|GTTTACTTAT|TTCTATGCTA|CACCTGGCAG|ACGGCCATGG|26280|
|GCGTTTGGCA|GCAGTGCTTG|GAGGAGTGCA|ACCTCAAGGA|GCTGCAGAAA|CTGCTAAAGC|26340|
|AAAACTTGAA|GGACCTATGG|ACGGCCTTCA|ACGAGCGCTC|CGTGGCCGCG|CACCTGGCGG|26400|
|ACATCATTTT|CCCCGAACGC|CTGCTTAAAA|CCCTGCAACA|GGGTCTGCCA|GACTTCACCA|26460|
|GTCAAAGCAT|GTTGCAGAAC|TTTAGGAACT|TTATCCTAGA|GCGCTCAGGA|ATCTTGCCCG|26520|
|CCACCTGCTG|TGCACTTCCT|AGCGACTTTG|TGCCCATTAA|GTACCGCGAA|TGCCCTCCGC|26580|
|CGCTTTGGGG|CCACTGCTAC|CTTCTGCAGC|TAGCCAACTA|CCTTGCCTAC|CACTCTGACA|26640|
|TAATGGAAGA|CGTGAGCGGT|GACGGTCTAC|TGGAGTGTCA|CTGTCGCTGC|AACCTATGCA|26700|
|CCCCGCACCG|CTCCCTGGTT|TGCAATTCGC|AGCTGCTTAA|CGAAAGTCAA|ATTATCGGTA|26760|
|CCTTTGAGCT|GCAGGGTCCC|TCGCCTGACG|AAAAGTCCGC|GGCTCCGGGG|TTGAAACTCA|26820|
|CTCCGGGGCT|GTGGACGTCG|GCTTACCTTC|GCAAATTTGT|ACCTGAGGAC|TACCACGCCC|26880|
|ACGAGATTAG|GTTCTACGAA|GACCAATCCC|GCCCGCCAAA|TGCGGAGCTT|ACCGCCTGCG|26940|
|TCATTACCCA|GGGCCACATT|CTTGGCCAAT|TGCAAGCCAT|CAACAAAGCC|CGCCAAGAGT|27000|
|TTCTGCTACG|AAAGGGACGG|GGGGTTTACT|TGGACCCCCA|GTCCGGCGAG|GAGCTCAACC|27060|
|CAATCCCCCC|GCCGCCGCAG|CCCTATCAGC|AGCAGCCGCG|GGCCCTTGCT|TCCCAGGATG|27120|
|GCACCCAAAA|AGAAGCTGCA|GCTGCCGCCG|CCACCCACGG|ACGAGGAGGA|ATACTGGGAC|27180|
|AGTCAGGCAG|AGGAGGTTTT|GGACGAGGAG|GAGGAGGACA|TGATGGAAGA|CTGGGAGAGC|27240|
|CTAGACGAGG|AAGCTTCCGA|GGTCGAAGAG|GTGTCAGACG|AAACACCGTC|ACCCTCGGTC|27300|
|GCATTCCCCT|CGCCGGCGCC|CCAGAAATCG|GCAACCGGTT|CCAGCATGGC|TACAACCTCC|27360|
|GCTCCTCAGG|CGCCGCCGGC|ACTGCCCGTT|CGCCGACCCA|ACCGTAGATG|GGACACCACT|27420|
|GGAACCAGGG|CCGGTAAGTC|CAAGCAGCCG|CCGCCGTTAG|CCCAAGAGCA|ACAACAGCGC|27480|
|CAAGGCTACC|GCTCATGGCG|CGGGCACAAG|AACGCCATAG|TTGCTTGCTT|GCAAGACTGT|27540|
|GGGGGCAACA|TCTCCTTCGC|CCGCCGCTTT|CTTCTCTACC|ATCACGGCGT|GGCCTTCCCC|27600|

| | | | | | | |
|---|---|---|---|---|---|---|
| CGTAACATCC | TGCATTACTA | CCGTCATCTC | TACAGCCCAT | ACTGCACCGG | CGGCAGCGGC | 27660 |
| AGCGGCAGCA | ACAGCAGCGG | CCACACAGAA | GCAAAGGCGA | CCGGATAGCA | AGACTCTGAC | 27720 |
| AAAGCCCAAG | AAATCCACAG | CGGCGGCAGC | AGCAGGAGGA | GGAGCGCTGC | GTCTGGCGCC | 27780 |
| CAACGAACCC | GTATCGACCC | GCGAGCTTAG | AAACAGGATT | TTTCCCACTC | TGTATGCTAT | 27840 |
| ATTTCAACAG | AGCAGGGGCC | AAGAACAAGA | GCTGAAAATA | AAAAACAGGT | CTCTGCGATC | 27900 |
| CCTCACCCGC | AGCTGCCTGT | ATCACAAAAG | CGAAGATCAG | CTTCGGCGCA | CGCTGGAAGA | 27960 |
| CGCGGAGGCT | CTCTTCAGTA | AATACTGCGC | GCTGACTCTT | AAGGACTAGT | TTCGCGCCCT | 28020 |
| TTCTCAAATT | TAAGCGCGAA | AACTACGTCA | TCTCCAGCGG | CCACACCCGG | CGCCAGCACC | 28080 |
| TGTCGTCAGC | GCCATTATGA | GCAAGGAAAT | TCCCACGCCC | TACATGTGGA | GTTACCAGCC | 28140 |
| ACAAATGGGA | CTTGCGGCTG | GAGCTGCCCA | AGACTACTCA | ACCCGAATAA | ACTACATGAG | 28200 |
| CGCGGGACCC | CACATGATAT | CCCGGGTCAA | CGGAATCCGC | GCCCACCGAA | ACCGAATTCT | 28260 |
| CTTGGAACAG | GCGGCTATTA | CCACCACACC | TCGTAATAAC | CTTAATCCCC | GTAGTTGGCC | 28320 |
| CGCTGCCCTG | GTGTACCAGG | AAAGTCCCGC | TCCCACCACT | GTGGTACTTC | CCAGAGACGC | 28380 |
| CCAGGCCGAA | GTTCAGATGA | CTAACTCAGG | GGCGCAGCTT | GCGGGCGGCT | TTCGTCACAG | 28440 |
| GGTGCGGTCG | CCCGGGCAGG | GTATAACTCA | CCTGACAATC | AGAGGGCGAG | GTATTCAGCT | 28500 |
| CAACGACGAG | TCGGTGAGCT | CCTCGCTTGG | TCTCCGTCCG | GACGGGACAT | TTCAGATCGG | 28560 |
| CGGCGCCGGC | CGTCCTTCAT | TCACGCCTCG | TCAGGCAATC | CTAACTCTGC | AGACCTCGTC | 28620 |
| CTCTGAGCCG | CGCTCTGGAG | GCATTGGAAC | TCTGCAATTT | ATTGAGGAGT | TTGTGCCATC | 28680 |
| GGTCTACTTT | AACCCCTTCT | CGGGACCTCC | CGGCCACTAT | CCGGATCAAT | TTATTCCTAA | 28740 |
| CTTTGACGCG | GTAAAGGACT | CGGCGGACGG | CTACGACTGA | ATGTTAAGTG | GAGAGGCAGA | 28800 |
| GCAACTGCGC | CTGAAACACC | TGGTCCACTG | TCGCCGCCAC | AAGTGCTTTG | CCCGCGACTC | 28860 |
| CGGTGAGTTT | TGCTACTTTG | AATTGCCCGA | GGATCATATC | GAGGGCCCGG | CGCACGGCGT | 28920 |
| CCGGCTTACC | GCCCAGGGAG | AGCTTGCCCG | TAGCCTGATT | CGGGAGTTTA | CCCAGCGCCC | 28980 |
| CCTGCTAGTT | GAGCGGGACA | GGGGACCCTG | TGTTCTCACT | GTGATTTGCA | ACTGTCCTAA | 29040 |
| CCTTGGATTA | CATCAAGATC | TTTGTTGCCA | TCTCTGTGCT | GAGTATAATA | AATACAGAAA | 29100 |
| TTAAAATATA | CTGGGGCTCC | TATCGCCATC | CTGTAAACGC | CACCGTCTTC | ACCCGCCCAA | 29160 |
| GCAAACCAAG | GCTTCGAATC | GCGACGCGTC | AGTTTCCTCC | TGTTCCTGTC | CATCCGCACC | 29220 |
| CACTATCTTC | ATGTTGTTGC | AGATGAAGCG | CGCAAGACCG | TCTGAAGATA | CCTTCAACCC | 29280 |
| CGTGTATCCA | TATGACACGG | AAACCGGTCC | TCCAACTGTG | CCTTTTCTTA | CTCCTCCCTT | 29340 |
| TGTATCCCCC | AATGGGTTTC | AAGAGAGTCC | CCCTGGGGTA | CTCTCTTTGC | GCCTATCCGA | 29400 |
| ACCTCTAGTT | ACCTCCAATG | GCATGCTTGC | GCTCAAAATG | GGCAACGGCC | TCTCTCTGGA | 29460 |
| CGAGGCCGGC | AACCTTACCT | CCCAAAATGT | AACCACTGTG | AGCCCACCTC | TCAAAAAAAC | 29520 |
| CAAGTCAAAC | ATAAACCTGG | AAATATCTGC | ACCCCTCACA | GTTACCTCAG | AAGCCCTAAC | 29580 |
| TGTGGCTGCC | GCCGCACCTC | TAATGGTCGC | GGGCAACACA | CTCACCATGC | AATCACAGGC | 29640 |
| CCCGCTAACC | GTGCACGACT | CCAAACTTAG | CATTGCCACC | CAAGGACCCC | TCACAGTGTC | 29700 |
| AGAAGGAAAG | CTAGCCCTGC | AAACATCAGG | CCCCCTCACC | ACCACCGATA | GCAGTACCCT | 29760 |
| TACTATCACT | GCCTCACCCC | CTCTAACTAC | TGCCACTGGT | AGCTTGGGCA | TTGACTTGAA | 29820 |
| AGAGCCCATT | TATACACAAA | ATGGAAAACT | AGGACTAAAG | TACGGGGCTC | CTTTGCATGT | 29880 |
| AACAGACGAC | CTAAACACTT | TGACCGTAGC | AACTGGTCCA | GGTGTGACTA | TTAATAATAC | 29940 |
| TTCCTTGCAA | ACTAAAGTTA | CTGGAGCCTT | GGGTTTTGAT | TCACAAGGCA | ATATGCAACT | 30000 |

| | | | | | | |
|---|---|---|---|---|---|---|
| TAATGTAGCA | GGAGGACTAA | GGATTGATTC | TCAAAACAGA | CGCCTTATAC | TTGATGTTAG | 30060 |
| TTATCCGTTT | GATGCTCAAA | ACCAACTAAA | TCTAAGACTA | GGACAGGGCC | CTCTTTTTAT | 30120 |
| AAACTCAGCC | CACAACTTGG | ATATTAACTA | CAACAAAGGC | CTTTACTTGT | TTACAGCTTC | 30180 |
| AAACAATTCC | AAAAAGCTTG | AGGTTAACCT | AAGCACTGCC | AAGGGGTTGA | TGTTTGACGC | 30240 |
| TACAGCCATA | GCCATTAATG | CAGGAGATGG | GCTTGAATTT | GGTTCACCTA | ATGCACCAAA | 30300 |
| CACAAATCCC | CTCAAAACAA | AAATTGGCCA | TGGCCTAGAA | TTTGATTCAA | ACAAGGCTAT | 30360 |
| GGTTCCTAAA | CTAGGAACTG | GCCTTAGTTT | TGACAGCACA | GGTGCCATTA | CAGTAGGAAA | 30420 |
| CAAAATAAT | GATAAGCTAA | CTTTGTGGAC | CACACCAGCT | CCATCTCCTA | ACTGTAGACT | 30480 |
| AAATGCAGAG | AAAGATGCTA | AACTCACTTT | GGTCTTAACA | AAATGTGGCA | GTCAAATACT | 30540 |
| TGCTACAGTT | TCAGTTTTGG | CTGTTAAAGG | CAGTTTGGCT | CCAATATCTG | GAACAGTTCA | 30600 |
| AAGTGCTCAT | CTTATTATAA | GATTTGACGA | AAATGGAGTG | CTACTAAACA | ATTCCTTCCT | 30660 |
| GGACCCAGAA | TATTGGAACT | TTAGAAATGG | AGATCTTACT | GAAGGCACAG | CCTATACAAA | 30720 |
| CGCTGTTGGA | TTTATGCCTA | ACCTATCAGC | TTATCCAAAA | TCTCACGGTA | AAACTGCCAA | 30780 |
| AAGTAACATT | GTCAGTCAAG | TTTACTTAAA | CGGAGACAAA | ACTAAACCTG | TAACACTAAC | 30840 |
| CATTACACTA | AACGGTACAC | AGGAAACAGG | AGACACAACT | CCAAGTGCAT | ACTCTATGTC | 30900 |
| ATTTTCATGG | GACTGGTCTG | GCCACAACTA | CATTAATGAA | ATATTTGCCA | CATCCTCTTA | 30960 |
| CACTTTTTCA | TACATTGCCC | AAGAATAAAG | AATCGTTTGT | GTTATGTTTC | AACGTGTTTA | 31020 |
| TTTTTCAATT | GCAGAAAATT | TCAAGTCATT | TTTCATTCAG | TAGTATAGCC | CCACCACCAC | 31080 |
| ATAGCTTATA | CAGATCACCG | TACCTTAATC | AAACTCACAG | AACCCTAGTA | TTCAACCTGC | 31140 |
| CACCTCCCTC | CCAACACACA | GAGTACACAG | TCCTTTCTCC | CCGGCTGGCC | TTAAAAAGCA | 31200 |
| TCATATCATG | GGTAACAGAC | ATATTCTTAG | GTGTTATATT | CCACACGGTT | TCCTGTCGAG | 31260 |
| CCAAACGCTC | ATCAGTGATA | TTAATAAACT | CCCCGGGCAG | CTCACTTAAG | TTCATGTCGC | 31320 |
| TGTCCAGCTG | CTGAGCCACA | GGCTGCTGTC | CAACTTGCGG | TTGCTTAACG | GCGGCGAAG | 31380 |
| GAGAAGTCCA | CGCCTACATG | GGGGTAGAGT | CATAATCGTG | CATCAGGATA | GGGCGGTGGT | 31440 |
| GCTGCAGCAG | CGCGCGAATA | AACTGCTGCC | GCCGCCGCTC | CGTCCTGCAG | GAATACAACA | 31500 |
| TGGCAGTGGT | CTCCTCAGCG | ATGATTCGCA | CCGCCGCAG | CATAAGGCGC | CTTGTCCTCC | 31560 |
| GGGCACAGCA | GCGCACCCTG | ATCTCACTTA | AATCAGCACA | GTAACTGCAG | CACAGCACCA | 31620 |
| CAATATTGTT | CAAAATCCCA | CAGTGCAAGG | CGCTGTATCC | AAAGCTCATG | GCGGGGACCA | 31680 |
| CAGAACCCAC | GTGGCCATCA | TACCACAAGC | GCAGGTAGAT | TAAGTGGCGA | CCCCTCATAA | 31740 |
| ACACGCTGGA | CATAAACATT | ACCTCTTTTG | GCATGTTGTA | ATTCACCACC | TCCCGGTACC | 31800 |
| ATATAAACCT | CTGATTAAAC | ATGGCGCCAT | CCACCACCAT | CCTAAACCAG | CTGGCCAAAA | 31860 |
| CCTGCCCGCC | GGCTATACAC | TGCAGGGAAC | CGGGACTGGA | ACAATGACAG | TGGAGAGCCC | 31920 |
| AGGACTCGTA | ACCATGGATC | ATCATGCTCG | TCATGATATC | AATGTTGGCA | CAACACAGGC | 31980 |
| ACACGTGCAT | ACACTTCCTC | AGGATTACAA | GCTCCTCCCG | CGTTAGAACC | ATATCCCAGG | 32040 |
| GAACAACCCA | TTCCTGAATC | AGCGTAAATC | CCACACTGCA | GGGAAGACCT | CGCACGTAAC | 32100 |
| TCACGTTGTG | CATTGTCAAA | GTGTTACATT | CGGGCAGCAG | CGGATGATCC | TCCAGTATGG | 32160 |
| TAGCGCGGGT | TTCTGTCTCA | AAAGGAGGTA | GACGATCCCT | ACTGTACGGA | GTGCGCCGAG | 32220 |
| ACAACCGAGA | TCGTGTTGGT | CGTAGTGTCA | TGCCAAATGG | AACGCCGGAC | GTAGTCATAT | 32280 |
| TTCCTGAAGC | AAAACCAGGT | GCGGGCGTGA | CAAACAGATC | TGCGTCTCCG | GTCTCGCCGC | 32340 |
| TTAGATCGCT | CTGTGTAGTA | GTTGTAGTAT | ATCCACTCTC | TCAAAGCATC | CAGGCGCCCC | 32400 |

-continued

| | | | | | | |
|---|---|---|---|---|---|---|
| CTGGCTTCGG | GTTCTATGTA | AACTCCTTCA | TGCGCCGCTG | CCCTGATAAC | ATCCACCACC | 32460 |
| GCAGAATAAG | CCACACCCAG | CCAACCTACA | CATTCGTTCT | GCGAGTCACA | CACGGGAGGA | 32520 |
| GCGGAAGAG | CTGGAAGAAC | CATGTTTTT | TTTTTATTCC | AAAAGATTAT | CCAAAACCTC | 32580 |
| AAAATGAAGA | TCTATTAAGT | GAACGCGCTC | CCCTCCGGTG | GCGTGGTCAA | ACTCTACAGC | 32640 |
| CAAAGAACAG | ATAATGGCAT | TTGTAAGATG | TTGCACAATG | GCTTCCAAAA | GGCAAACGGC | 32700 |
| CCTCACGTCC | AAGTGGACGT | AAAGGCTAAA | CCCTTCAGGG | TGAATCTCCT | CTATAAACAT | 32760 |
| TCCAGCACCT | TCAACCATGC | CCAAATAATT | CTCATCTCGC | CACCTTCTCA | ATATATCTCT | 32820 |
| AAGCAAATCC | CGAATATTAA | GTCCGGCCAT | TGTAAAATC | TGCTCCAGAG | CGCCCTCCAC | 32880 |
| CTTCAGCCTC | AAGCAGCGAA | TCATGATTGC | AAAAATTCAG | GTTCCTCACA | GACCTGTATA | 32940 |
| AGATTCAAAA | GCGGAACATT | AACAAAATA | CCGCGATCCC | GTAGGTCCCT | TCGCAGGGCC | 33000 |
| AGCTGAACAT | AATCGTGCAG | GTCTGCACGG | ACCAGCGCGG | CCACTTCCCC | GCCAGGAACC | 33060 |
| TTGACAAAAG | AACCCACACT | GATTATGACA | CGCATACTCG | GAGCTATGCT | AACCAGCGTA | 33120 |
| GCCCCGATGT | AAGCTTTGTT | GCATGGGCGG | CGATATAAAA | TGCAAGGTGC | TGCTCAAAAA | 33180 |
| ATCAGGCAAA | GCCTCGCGCA | AAAAGAAAG | CACATCGTAG | TCATGCTCAT | GCAGATAAAG | 33240 |
| GCAGGTAAGC | TCCGGAACCA | CCACAGAAAA | AGACACCATT | TTTCTCTCAA | ACATGTCTGC | 33300 |
| GGGTTTCTGC | ATAAACACAA | AATAAATAA | CAAAAAACA | TTTAAACATT | AGAAGCCTGT | 33360 |
| CTTACAACAG | GAAAAACAAC | CCTTATAAGC | ATAAGACGGA | CTACGGCCAT | GCCGGCGTGA | 33420 |
| CCGTAAAAAA | ACTGGTCACC | GTGATTAAAA | AGCACCACCG | ACAGCTCCTC | GGTCATGTCC | 33480 |
| GGAGTCATAA | TGTAAGACTC | GGTAAACACA | TCAGGTTGAT | TCATCGGTCA | GTGCTAAAAA | 33540 |
| GCGACCGAAA | TAGCCCGGGG | GAATACATAC | CCGCAGGCGT | AGAGACAACA | TTACAGCCCC | 33600 |
| CATAGGAGGT | ATAACAAAAT | TAATAGGAGA | GAAAAACACA | TAAACACCTG | AAAAACCCTC | 33660 |
| CTGCCTAGGC | AAAATAGCAC | CCTCCCGCTC | CAGAACAACA | TACAGCGCTT | CACAGCGGCA | 33720 |
| GCCTAACAGT | CAGCCTTACC | AGTAAAAAAG | AAAACCTATT | AAAAAAACAC | CACTCGACAC | 33780 |
| GGCACCAGCT | CAATCAGTCA | CAGTGTAAAA | AAGGGCCAAG | TGCAGAGCGA | GTATATATAG | 33840 |
| GACTAAAAAA | TGACGTAACG | GTTAAAGTCC | ACAAAAAACA | CCCAGAAAAC | CGCACGCGAA | 33900 |
| CCTACGCCCA | GAAACGAAAG | CCAAAAAACC | CACAACTTCC | TCAAATCGTC | ACTTCCGTTT | 33960 |
| TCCCACGTTA | CGTAACTTCC | CATTTTAAGA | AAACTACAAT | TCCAACACA | TACAAGTTAC | 34020 |
| TCCGCCCTAA | ACTAGACAAA | TATTACGCGC | TATGAGTAAC | ACAAAATTAT | TCAGATTTCA | 34080 |
| CTTCCTCTTA | TTCAGTTTTC | CCGCGAAAAT | GGCCAAATCT | TACTCGGTTA | CGCCCAAATT | 34140 |
| TACTACAACA | TCCGCCTAAA | ACCGCGCGAA | AATTGTCACT | TCCTGTGTAC | ACCGGCGCAC | 34200 |
| ACCAAAAACG | TCACTTTTGC | CACATCCGTC | GCTTACATGT | GTTCCGCCAC | ACTTGCAACA | 34260 |
| TCACACTTCC | GCCACACTAC | TACGTCACCC | GCCCCGTTCC | CACGCCCCGC | GCCACGTCAC | 34320 |
| AAACTCCACC | CCCTCATTAT | CATATTGGCT | TCAATCCAAA | ATAAGGTATA | TTATTGATGA | 34380 |
| TG | | | | | | 34382 |

( 2 ) INFORMATION FOR SEQ ID NO:7:

( i ) SEQUENCE CHARACTERISTICS:
        ( A ) LENGTH: 1015 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

-continued

```
Lys  Gln  Cys  Trp  Val  Leu  Gln  Tyr  His  Tyr  Arg  Gly  Ala  Ser  Leu  Gln
 1              5                        10                       15

Phe  Glu  Ala  Ser  Val  Ser  Pro  Ser  Trp  Ser  Asp  Asp  Gly  Gly  Ile  Gly
               20                   25                        30

Met  His  Phe  Gly  Asp  Ile  Asn  Leu  Trp  Thr  Gly  Glu  Glu  Ala  His  Leu
          35                        40                   45

Leu  His  Arg  His  Ser  Thr  Glu  Met  Leu  Gln  Gln  Gln  Ser  Tyr  Arg  Ser
     50                        55                             60

Ile  Asn  Phe  Gln  Phe  Asp  Gly  Arg  Trp  Gln  His  Pro  Gly  Tyr  Asn  Leu
 65                      70                        75                        80

Glu  Arg  Thr  Gly  Cys  Arg  Leu  Gly  Asn  Glu  Ser  Pro  Phe  Val  Tyr  Pro
                    85                        90                        95

Thr  Tyr  Met  Asp  Ser  Leu  Pro  Leu  Asp  Trp  Arg  Asp  Phe  Cys  Ala  Ala
               100                       105                      110

Thr  Leu  Arg  Asp  Pro  Tyr  Asn  Glu  Gln  Pro  Gly  Leu  Gly  Leu  Trp  Xaa
          115                      120                      125

Xaa  Xaa  Xaa  Xaa  Xaa  Xaa  Xaa  Xaa  Xaa  Xaa  Xaa  Xaa  Xaa  Xaa  Xaa  Ala
          130                      135                      140

Pro  His  Pro  Thr  Asp  Ser  Ala  Val  Glu  Val  Asp  Val  Thr  Ile  Ala  Met
145                           150                      155                      160

Gln  Gly  Ser  Gly  Asp  Ile  Arg  Tyr  Thr  Lys  Arg  Ser  Ile  Phe  Leu  Thr
                    165                      170                      175

Lys  Gly  Gln  His  Gln  Trp  Ala  His  Ala  Thr  Thr  Ile  Leu  Val  Ala  Asp
               180                      185                      190

Ala  Leu  Thr  Asp  Ala  Thr  Cys  Gln  Leu  Leu  Ala  Ala  Glu  Ala  Gln  Tyr
          195                      200                      205

His  Gly  Ala  Ala  Lys  Trp  Arg  Glu  Val  Trp  Ala  Asn  Pro  Asp  Ile  Arg
     210                      215                      220

Thr  Ala  Glu  Ser  Val  Gly  Ile  Asp  Asn  Asp  Leu  Pro  Ala  Arg  Thr  Phe
225                           230                      235                      240

Gln  Asp  Arg  Leu  Pro  Thr  Leu  Leu  Gln  Lys  Lys  Asp  Gly  Ile  Trp  Met
                    245                      250                      255

Gln  Ser  Leu  Phe  Gly  Ser  Gln  Arg  Asn  Phe  Gln  Trp  Arg  Lys  Asn  Gly
               260                      265                      270

Leu  Glu  Ile  Cys  Phe  Asp  Met  Glu  Ser  Thr  Thr  Leu  His  Pro  Ile  Ala
          275                      280                      285

His  Ser  Ala  Ala  Pro  Leu  Thr  Val  Ser  Leu  Asn  Glu  Ala  Leu  Arg  Trp
     290                      295                      300

Gln  Gln  Trp  Ala  Ser  Ile  His  Gly  Ala  Glu  Ser  Trp  Ala  Thr  Ala  Asn
305                           310                      315                      320

Pro  Gln  Val  Val  Arg  Val  Thr  Leu  Trp  Leu  Gln  Gly  Ala  Ser  Glu  Pro
                    325                      330                      335

Gln  Pro  Leu  Glu  Pro  Leu  Glu  Ile  Leu  Gln  Lys  Gly  Gln  Pro  Ala  Val
               340                      345                      350

Asp  Leu  Pro  Val  Glu  Gly  Ser  Ala  Leu  Pro  Lys  Gly  Asp  Leu  Ala  Val
          355                      360                      365

Met  Trp  His  Leu  Leu  Glu  Asn  Asp  Ser  His  Arg  Phe  Leu  Tyr  Glu  Ser
     370                      375                      380

Thr  Val  Glu  Ile  Thr  Gln  Gly  Ser  Leu  Arg  Phe  Gln  Phe  Gln  Gln  Gln
385                           390                      395                      400

Gln  His  Lys  Ala  Glu  Thr  Leu  Ala  Pro  His  Pro  Thr  Arg  Asp  Ala  Phe
                    405                      410                      415

Val  Leu  Gly  Asn  Met  Cys  Phe  Gln  Arg  Asp  Asn  Pro  Thr  Asp  Gly  Phe
```

-continued

|     |     |     | 420 |     |     |     | 425 |     |     |     | 430 |     |     |     |
|-----|-----|-----|-----|-----|-----|-----|-----|-----|-----|-----|-----|-----|-----|-----|
| Asp | Gly | Gly | Tyr | Ala | Ser | Trp | Pro | Asn | Gly | Asn | Glu | Asp | Tyr | Lys | Ile |
|     |     | 435 |     |     |     |     | 440 |     |     |     | 445 |     |     |     |
| Leu | Ser | Gln | Asp | Val | Trp | Asp | Trp | Val | Phe | Gly | Gly | Gln | Leu | Arg | Pro |
|     | 450 |     |     |     |     | 455 |     |     |     | 460 |     |     |     |     |
| Tyr | Gln | Arg | Phe | Ala | Gln | Trp | Tyr | Lys | Ala | Phe | Gly | Gly | Leu | Ser | Asn |
| 465 |     |     |     |     | 470 |     |     |     |     | 475 |     |     |     |     | 480 |
| Gly | Met | Ala | His | Ala | Tyr | Glu | Cys | Leu | Ile | Leu | Pro | Arg | Thr | Glu | Gly |
|     |     |     |     | 485 |     |     |     |     | 490 |     |     |     |     | 495 |     |
| Pro | Leu | Ser | Leu | Trp | Lys | Lys | Ile | Ser | Trp | Lys | Pro | Val | Ala | Pro | Phe |
|     |     |     |     | 500 |     |     |     |     | 505 |     |     |     | 510 |     |     |
| Pro | Gln | Asp | Glu | Asp | Val | Arg | Ala | Tyr | Met | Pro | Cys | Ile | Ile | Asp | Thr |
|     |     | 515 |     |     |     |     | 520 |     |     |     |     | 525 |     |     |     |
| Ala | Thr | Thr | Asp | Ala | Gly | Gly | Gly | Glu | Tyr | Gln | Val | Pro | Arg | Ser | Pro |
|     | 530 |     |     |     |     | 535 |     |     |     |     | 540 |     |     |     |     |
| Asp | Val | Ser | Lys | Ile | Trp | Arg | Tyr | Leu | Ala | Asp | His | Asn | Ala | Gly | His |
| 545 |     |     |     |     | 550 |     |     |     |     | 555 |     |     |     |     | 560 |
| Gly | Ser | Glu | Asn | Gly | Leu | Ser | Trp | Ile | Ile | Val | Ser | Pro | His | Asn | Arg |
|     |     |     |     | 565 |     |     |     |     | 570 |     |     |     | 575 |     |     |
| Asp | Arg | Gln | Val | Met | Arg | Thr | Val | Arg | Glu | Ser | Met | Ala | Pro | Leu | Trp |
|     |     |     | 580 |     |     |     |     | 585 |     |     |     |     | 590 |     |     |
| Arg | Pro | Asp | Asp | Thr | Leu | Arg | Asn | Met | Pro | Val | Met | Gly | His | Thr | Glu |
|     |     | 595 |     |     |     |     | 600 |     |     |     |     | 605 |     |     |     |
| Ile | Asn | Ala | Glu | Asp | Val | Val | Tyr | Leu | Gly | Tyr | Arg | Asp | Cys | Leu | Thr |
|     | 610 |     |     |     |     | 615 |     |     |     |     | 620 |     |     |     |     |
| Tyr | Trp | Leu | Pro | His | Asn | Pro | Tyr | His | Ser | Cys | Arg | Val | Ala | Asn | Phe |
| 625 |     |     |     |     | 630 |     |     |     |     | 635 |     |     |     |     | 640 |
| Asn | Asn | Gln | Lys | Met | Leu | Leu | Ile | Asp | Gln | Val | Met | Thr | Gln | Glu | Asp |
|     |     |     |     | 645 |     |     |     |     | 650 |     |     |     | 655 |     |     |
| Met | Val | Gln | Gly | His | Leu | Pro | His | His | Glu | His | Arg | Asn | Val | Gly | Arg |
|     |     |     |     | 660 |     |     |     | 665 |     |     |     |     | 670 |     |     |
| Ile | Leu | Leu | Pro | Lys | Gly | Asn | Leu | Leu | Leu | Gly | Asn | Glu | Ile | Arg |
|     |     | 675 |     |     |     |     | 680 |     |     |     | 685 |     |     |     |
| Val | Glu | Arg | Phe | Gly | Val | Asp | Cys | Ala | Glu | Ala | Glu | Ile | Leu | Thr | Gly |
|     | 690 |     |     |     |     | 695 |     |     |     | 700 |     |     |     |     |     |
| Asp | Ala | Thr | His | Leu | Glu | Val | Val | Ala | Arg | Tyr | Leu | Asn | Pro | Ile | Glu |
| 705 |     |     |     |     | 710 |     |     |     |     | 715 |     |     |     |     | 720 |
| Ala | Ser | Trp | Leu | Lys | Pro | Asn | Glu | Val | Asn | Leu | Arg | Leu | Thr | Val | Arg |
|     |     |     |     | 725 |     |     |     |     | 730 |     |     |     |     | 735 |     |
| Asp | Ala | Tyr | Gly | Gly | Arg | Glu | Asp | Ile | Ile | Glu | Gly | Gly | Phe | Pro | Ala |
|     |     |     | 740 |     |     |     |     | 745 |     |     |     |     | 750 |     |     |
| Thr | Gly | Ser | Ala | Val | Gln | Thr | Glu | Gly | Gln | Trp | Leu | Ser | Val | Thr | Val |
|     |     | 755 |     |     |     |     | 760 |     |     |     |     | 765 |     |     |     |
| Arg | Leu | Tyr | Asp | Arg | Leu | Glu | Gly | Cys | Met | Gln | Val | Glu | Ala | Glu | Leu |
|     | 770 |     |     |     |     | 775 |     |     |     |     | 780 |     |     |     |     |
| Val | Ala | Arg | Ser | Phe | Asp | Asp | Asn | Phe | Arg | Thr | Ala | Val | His | Phe | Asp |
| 785 |     |     |     |     | 790 |     |     |     |     | 795 |     |     |     |     | 800 |
| Ser | Ile | Gln | Thr | Thr | Pro | Lys | His | Leu | Leu | Ser | Val | Asp | Arg | Phe | Ile |
|     |     |     |     | 805 |     |     |     |     | 810 |     |     |     |     | 815 |     |
| Gly | Ser | Met | Arg | Trp | Met | Asp | Gln | Asp | Glu | Leu | Tyr | Ser | Gly | Asp | Ser |
|     |     |     | 820 |     |     |     |     | 825 |     |     |     |     | 830 |     |     |
| Trp | Arg | Leu | Val | Met | Val | Ala | Leu | Arg | Asn | Glu | Gly | Ala | Arg | Leu | Phe |
|     |     | 835 |     |     |     |     | 840 |     |     |     |     | 845 |     |     |     |

-continued

| | | | | | | | | | | | | | | |
|---|---|---|---|---|---|---|---|---|---|---|---|---|---|---|
| Ala | Ser 850 | Leu | Asp | Phe | Glu | Ser 855 | Pro | Leu | Arg | Ser | Asp 860 | Gln | Gly | Tyr | Gly |
| Val 865 | Trp | Arg | Gly | Asn | Cys 870 | Trp | Leu | His | Phe | Ala 875 | Ser | Asn | Val | Gly | Asp 880 |
| Phe | Ile | Ile | Arg | Thr 885 | Gln | Gly | Glu | Gln | Leu | Trp 890 | Ser | Glu | Asp | Val 895 | Asn |
| Phe | Thr | Leu | Ser 900 | Tyr | Cys | Gly | Thr | Pro 905 | Asn | Glu | Thr | Pro | Val 910 | Phe | Pro |
| Pro | Asn | Val 915 | Thr | Ile | Pro | Tyr | Thr 920 | Val | Asn | Thr | Tyr | Ile 925 | Pro | Ala | Asp |
| Tyr | Gly 930 | His | Met | Gln | Trp | Asn 935 | Ser | Pro | Val | Val | Val 940 | Thr | Asp | Ala | Glu |
| Pro 945 | Leu | Asp | Cys | Glu | Leu 950 | Trp | Ser | Glu | Pro | Val 955 | Ala | Glu | Pro | Ala | Pro 960 |
| Phe | Trp | Ala | Phe | Arg 965 | Trp | Glu | Gly | Asn | Leu 970 | Ser | Arg | Leu | Gln | Gln 975 | Ser |
| Pro | Arg | Asp | Thr 980 | Arg | Ala | Glu | Glu | Ser 985 | Asn | Arg | Trp | Ser | Ala 990 | Phe | Pro |
| Pro | His | Ala 995 | Ala | Leu | Arg | Asn | Leu 1000 | Gln | Thr | Val | Gly | Pro 1005 | Asn | Glu | Trp |
| Asp | Arg 1010 | Arg | Gln | Leu | Val | Val 1015 | | | | | | | | | |

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGGGACTGGA ACAATGA                                17

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GAATGGATCC ATCATCAATA ATATACCTTA TTTTGG                36

ADENOVIRAL VECTOR SYSTEM

FIELD OF THE INVENTION

The present invention relates, in general, to a gene transfer system and, in particular, to an adenoviral vector system suitable for use in gene transfer and gene therapy.

BACKGROUND

Gene delivery using recombinant adenoviral vectors is over a decade old (Berkner, Biotechniques 6:616–628 (1988)). There are three primary methods of generating such vectors. First, overlap recombination can be effected in the 293 helper cell line between a restriction digested adenovirus and a plasmid containing adenoviral sequences (see, for example, Hearing and Shenk, Cell 33:695–703 (1983)). Alternatively, overlap recombination can be effected in 293 cells between a 40 kb plasmid that contains the majority of the adenoviral genome and a smaller plasmid containing certain adenoviral sequences (Ghosh-Chaudhury et al, Gene 50:161–171 (1986)). Finally, a segment of DNA containing adenoviral sequences can be ligated with a restriction-digested adenovirus (Stratford Perricaudet et al, J. Clin. Invest. 90:626–630 (1992)).

In the foregoing methods, the adenoviral sequences referred to are the viral terminal repeat, which is the adenoviral DNA polymerase binding site necessary for replication, and the E1a enhancer/packaging signal that is necessary for viral assembly. The first two of the foregoing methods require additional adenoviral sequences for overlap recombination to occur in the 293 cell line.

There are problems inherent in each of the existing methods. First, none of the methods described above has a screening capacity built into it for determining the success of a particular recombination or ligation event. Further, the first and last of the methods described above use wild type virus to generate the vector backbone. The wild type virus is hazardous to use as it is replication efficient which gives it a distinct growth advantage over recombinant virions, especially large recombinant virions (Graham and Prevec, Gene Transfer and Expression Protocols, Methods in Molecular Biology 7:109–128, Humana Press (1991)). This latter problem manifests itself when an effort is made to generate recombinant virions and the restriction digestion of the viral DNA is less than complete. Even at a 99.99% complete digestion of 1 µg of viral DNA, approximately 4×10$^6$ copies of uncut wild-type viral DNA is present that could infect cells. This problem would hopelessly confound the isolation of recombinant virions.

The present invention provides an adenoviral vector system that is free of the problems of the systems of the art. The present system simplifies the cloning of genes into plasmid vectors, it makes possible the use of either ligation or overlap recombination in the generation of a recombinant virus and it eliminates the use of cell replication efficient viral forms.

OBJECTS AND SUMMARY OF THE INVENTION

It is a general object of the invention to provide an adenoviral vector system that can be used in gene transfer.

It is a specific object of the invention to provide a vector system that, in use, results in levels of gene expression superior to those of existing vectors.

It is another object of the invention to provide a vector system that can be used at titers significantly lower than those required for existing systems thereby reducing/eliminating the potential for adverse (eg cytotoxic or inflammatory) effects.

It is a further object of the present invention to provide a vector system that is replication deficient.

In one embodiment, the present invention relates to adenoviruses bearing E1a and E3 deletions and comprising, at the 3' end thereof, E1a enhancer and packaging signal sequences. Specific embodiments are Ad:Pac-βGal or Ad:Pac-βGal/gfp.

In another embodiment, the invention relates to plasmids devoid of adenoviral E1a enhancer and packaging signal sequences that are replicable and selectable, for example, in *E. coli*, comprising an adenoviral terminal repeat (eg bp 1 to 105), a promoter/multiple cloning site (MCS)/poly A and intron unit, and an adenoviral recombination sequence (that is, a sequence that overlaps with restricted virus that is sufficient in length for recombination). The terminal repeat is located in the plasmid 5' to the promoter/MCS/poly A and intron unit and the promoter/MCS/poly A and intron unit is located 5' to the recombination sequence. Plasmid pGEM Age I CMV new and plasmid pGEM Cla CMV(+) Pac, optionally comprising, in operable linkage, a non-adenoviral encoding sequence, are specific embodiments of the invention.

The invention also relates to a replication deficient adenovirus that is a recombination or ligation product of the above-described adenovirus and the above-described plasmid comprising, in operable linkage, an insert encoding a therapeutically active molecule.

In a further embodiment, the invention relates to a method of producing in a cell a therapeutically active molecule comprising introducing into the cell the above-described replication deficient recombinant adenovirus under conditions such that the insert is expressed and the molecule thereby produced.

Further objects and advantages of the invention will be clear from the description that follows.

BRIEF DESCRIPTION OF THE DRAWINGS

FIGS. 7–27. pGEM CMV NEW (+) enzyme cutters and sequence.

FIGS. 29–46. pGEM Age PacβGal sequence.

FIGS. 49–100. Ad:Pac-βGal sequence.

FIG. 104A. Structure of the AdE2F1 recombinant adenovirus. Adenovirus sequences from 191 to 3325 have been replaced with a CMV expression cassette containing the E2F1 cDNA. FIG. 104B. E2F1 protein accumulation following infection with the AdE2F1 recombinant virus. Mv1Lu cells were infected with the AdE2F1 recombinant virus or the MbAd2 vector virus. Extracts were prepared at the indicated time, proteins were separated by SDS gel electrophoresis, a Western blot prepared, and then the E2F1 polypeptide detected with a specific antibody.

FIGS. 107A and 107B. Comparison of level of gene expression. Meidell vector (FIG. 107A). Present vector (FIG. 107B). $1 \times 10^8$ pfu/ml (50 pfu/cell), 30 min. infections.

DETAILED DESCRIPTION OF THE INVENTION

Figure 1:
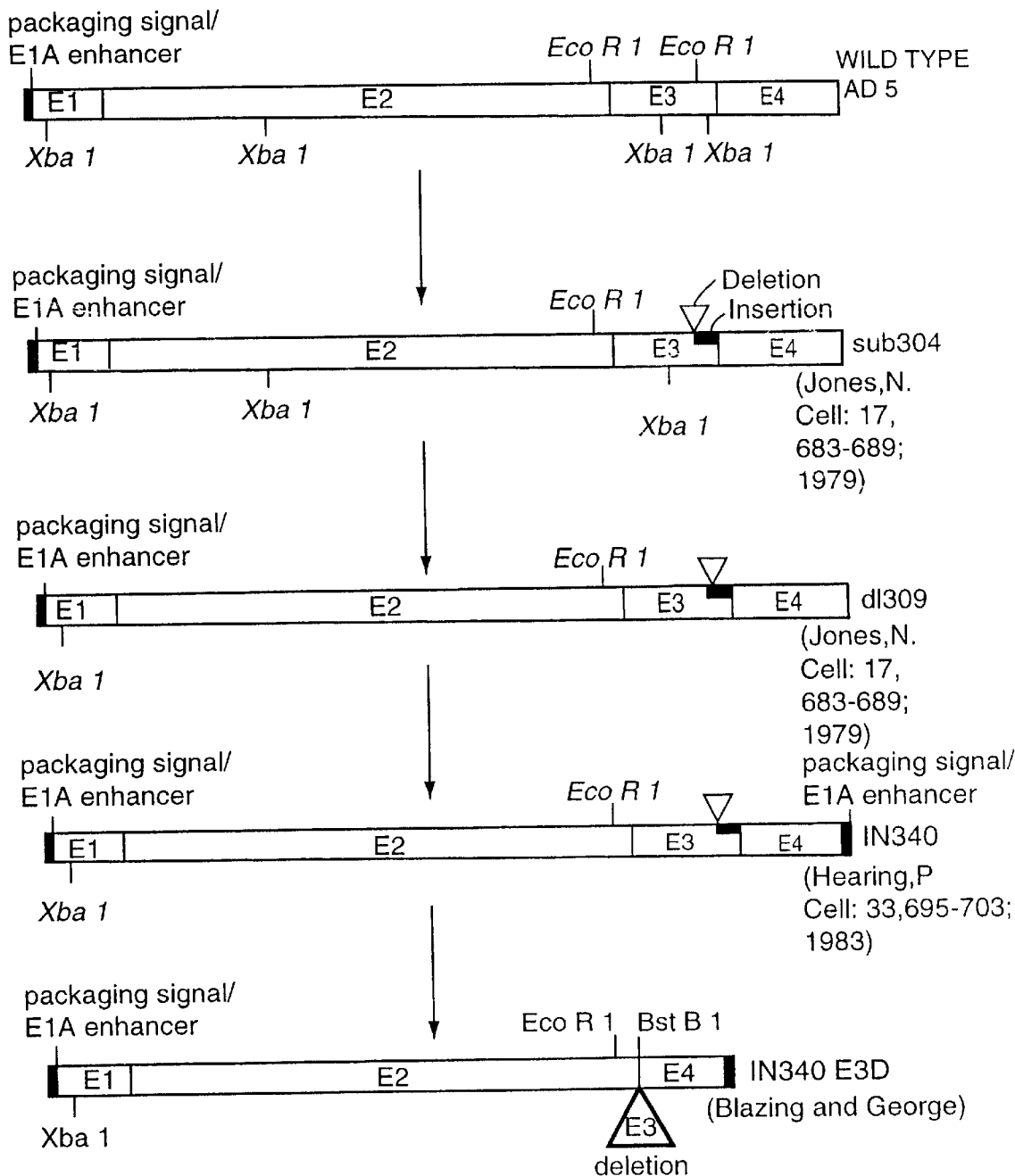
FIG. 1. Origins of the E3 deleted In340 adenovirus.

The present invention relates to a replication deficient adenoviral vector system that is suitable for use in effecting gene transfer in gene therapy. The system is fundamentally different from and represents a substantial improvement over existing systems from the standpoints of safety, ease of use and gene transfer properties.

The vector system of the invention represents an extensively modified version of the gene delivery system of Friedman et al, Mol. Cell. Biol. 6:3791–3797(1986); Babiss Mol. Cell. Biol. 6:3798 (1986)). To arrive at the present invention, modifications were made in the In340 adenovirus itself and in the plasmid that harbors target DNA sequences and sequences from the 5' end of the virus.

The viral modifications that resulted in a vector system of the present invention included deletion from the In340 virus of the E3 region. The E3 region of the Adγ adenovirus strain is nonessential for replication and viability. The E3 gene product enables the virus to escape human immune surveillance. Deletion of this region was effected by using polymerase chain reaction (PCR) to copy, amplify and modify the far right end of In340 (see FIGS. 2A and 2B). The native right end of In340 was then removed by restricting with EcoRI. The remaining 27000 bp of the left end was ligated to a new E3-deleted right end (yielding In340 E3D). The ligated mixture was transfected into 293 cells using the calcium phosphate method. Virus was isolated and plaque purified (Graham and Prevec, Gene Transfer and Expression Protocols, Methods in Molecular Biology 7:109–128, Humana Press (1991)). Restriction digests proved that In340 E3D is devoid of the E3 region. The details of the construction are set forth in Example 1.

The plasmid modifications that yielded a system of the invention included the modification of the plasmid pGEM Ad60.1 so as to render it suitable for intracellular recombination and for direct ligation. For intracellular recombination, the multiple cloning site of pGEM Ad60.1 was removed between the Bam HI and Hind III sites (resulting in pGEM Ad60.1 (MCS(−)). To create unique sites for plasmid linearization, fragments of luciferase cDNA were PCR modified (the addition of an EcoRI site and either an AgeI site or ClaI site) and inserted into the EcoRI site of pGEM Ad60.1. A CMV promoter, multiple cloning site and intron/polyadenylation signal were then introduced into the unique Bgl II site of pGEM Ad60.1 MSC(−) to generate pGEM AgeI CMV new. Details of the modification are provided in Example 1.

The foregoing plasmids were designed for cotransfection with In340 E3D. Cotransfection can be carried out by:

(1) linearizing the plasmid (eg with Age I or Cla I) and restricting the adenoviral DNA with Xba I and/or Cla I, the larger (approximately 25 kb, more specifically, about 31–32 kb) dsDNA fragment being isolated and purified; and (2) cotransfecting the plasmid and adenoviral DNA into 293 cells using standard techniques.

Upon recombination, replication deficient adenoviral virions are produced that can harbor a gene of interest. Successful recombination of the plasmid and the adenoviral DNA results in the generation of a full adenoviral genome (minus, for example, base pairs 193–3327 (an E1-deletion) and E3), with the gene(s) of interest cloned into the E1 and/or E3 deleted regions. The recombinant virions are replication deficient because they lack essential E1 adenoviral gene sequences. However, the 293 cell line is stably transfected with the E1a gene, thus supplying its essential function in trans. The replication deficient recombinant adenovirus is thus replication efficient in 293 cells, producing cell lysis and virion production. The virions that are produced do not produce lytic infections in other cell types, but they can and do express the gene of interest.

The invention also relates to plasmids designed for direct in vitro ligation. Ligation is advantageous as it simplifies the production of recombinant virions and significantly shortens the time to produce them. Isolating recombinant virions produced by intracellular recombination takes about 10 days whereas direct ligation can be carried out at 16° C. overnight or a few hours at room temperature. The plasmid modifications necessary to produce plasmid pGEM Cla CMV(+)Pac, which allows direct in vitro ligation, are detailed in Example 1.

Figure 101:
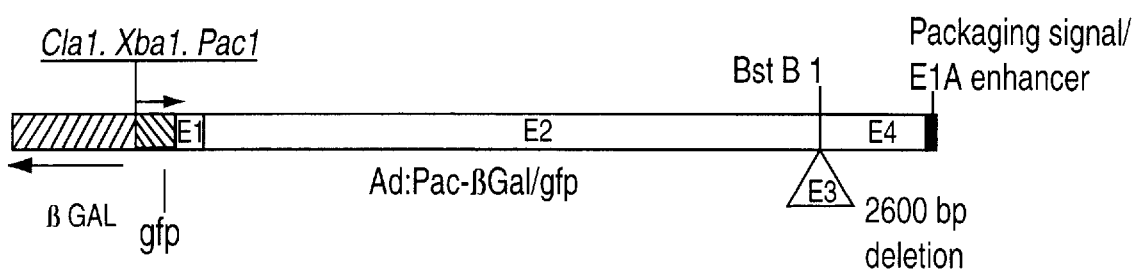
FIG. 101. Recombinant adenovirus Ad:Pac-βGal/gfp.

A preferred embodiment of the present invention is the virus Ad:Pac-βGal (see FIG. 48), and modified forms thereof (see, for example, Ad:Pac-βGal/gfp shown in FIG. 101). This replication deficient virus (produced using the methods described herein) contains a nuclear localizing β-galactosidase gene cloned into the E1-deleted site. Ad:Pac-βGal maintains 2 unique restriction sites for cutting in preparing viral vector which has the advantage of reducing the possibility of contamination with uncut virus. Ad:Pac-βGal has a cloning capacity of 8 kDa. Ad:Pac-βGal can be used with either pGEM AgeI CMV new or pGEM Cla CMV(+)Pac to generate further recombinant virions.

Included within the scope of the present invention are viruses sharing the major structural features of Ad:Pac-βGal. That is, the invention includes replication deficient E1-, E3-deleted adenoviruses comprising E1a enhancer/packaging signals at the 3' end. The viruses can have in the E1 deletion site a non-adenoviral encoding sequence operably linked to a promoter. The non-adenoviral encoding sequence can be a marker gene (such as the nuclear localizing β-Gal gene, the luciferase gene, the bovine growth hormone gene, etc). The encoding sequence can also be a gene encoding a therapeutically active molecule (examples of which are set forth below). The promoter to which the encoding sequence is operably linked can be, for example, a strong viral promoter, such as the CMV promoter/enhancer or the respiratory syncytial virus (RSV) promoter, a tissue specific promoter, or an inducible promoter (eg the metallothionine promoter). The adenovirus can include, 3' to the above-described non-adenoviral encoding sequence and promoter/enhancer and within the E1 deletion site, one or more endonuclease cleavage sites, eg restriction sites unique to the adenovirus. Various sites can be used, preferably, however, the sequence recognized by the endonuclease is at least 6 bases in length, more preferably, at least 8. Downstream from the cleavage site(s), the virus includes that portion of E1b (eg from wild type Adγ) that includes the protein 9 promoter and the protein 9 encoding sequence. E2 is downstream from E1b and 3' to E2 is the E3 deletion site. An endonuclease cleavage site can be present at the E3-deletion site. A cleavage site unique to the adenovirus is a preferred cloning site for a marker gene or a gene encoding a therapeutically active molecule, and its associated regulatory elements (selected, for example, from those described above). A fiber peptide encoding sequence can be located 3' to the E3 deletion site, 3' to which is E4 with the packaging signal/E1a enhancer being present at the 3' end of the virus.

Ad:Pac-βGal, and modifications thereof as described above, can be used in a negative screening protocol, as described in Example 1. Ad:Pac-βGal/gfp (which contains the green fluorescent protein (gfp) gene) can be used for positive screening, also as described in Example 1. As shown in FIG. 101, restriction sites are present in Ad:Pac-βGal/gfp such that only those virions that are successfully ligated and copied have the capacity to express gfp (visualized as a green color under UV light). Each cell transfected with Ad:Pac-βGal/gfp expresses both gfp and the gene of interest. Thus, transfection efficiency can be determined by irradiating the cells/tissues with UV light. Although the positive screening protocol is described with reference to Ad:Pac-βGal/gfp, variations of this virus that include different markers, restriction sites, promoters, etc (see alternatives described above with reference to Ad:Pac-βGal) can also be used.

The replication deficient viral vectors of the present invention can be used in gene therapy regimens to effect the transfer of genes encoding molecules of therapeutic importance (Kozarsky et al, Current Opin. Genetc. Develop. 3:499–503 (1993); Rosenfeld et al, Cell 68:143–155 (1992); Rogot et al, Nature 361:647–650 (1993); Ishibashi et al, J. Clin. Invest. 92:883–893 (1993); Tripathy et al, Proc. Natl. Acad. Sci. USA 91:11557–11561 (1994)). Such genes include isoforms of the nitric oxide synthase(NOS)gene (eg brain NOS (bNOS), endothelial NOS (eNOS) and microphage NOS (mNOS)), the cystic fibrosis chloride channel (CFTR) gene, the dystrophin gene, the LDL receptor gene, and erythropoietin gene.

Protocols suitable for use in administering the vectors of the invention include direct administration (eg by injection) to target tissue, intravascular administration, and catheter-based administration, for example, when the target is vascular tissue. Tissue specific expression of the gene transferred can be facilitated using tissue specific promoters.

With the present vectors, titers of $10^8$–$10^9$ pfu/ml can be used to obtain gene expression in at least 85% of exposed cells. This is in contrast with currently available adenoviral vectors, in which case titers of about $10^{10}$–$10^{11}$ pfu/ml are typically used. Such titers are sufficiently high to induce inflammation (French et al, Circulation 90:2414 (1994); Zahmer et al, Cell 75:207 (1993)). The present vector is also characterized by gene expression superior to that of existing vectors. When compared to the vector of Meidell et al (Circulation 89:2190 (1994)), 80-fold more β-gal was observed (see FIG. 11).

As indicated above, the vectors of the present invention can be used to effect expression of specific isoforms of NOS in various tissues, including vascular tissue, tumor tissue, tissue of the nervous system, including brain, and lung tissue. The particular isoform used can be selected for optimum results. For example, bNOS and eNOS can be used in vascular applications and mNOS can be used in cancer therapy. Expression of the NOS gene product is desirable where nitric oxide (NO) production is advantageous. (NO is a signaling molecule having a broad range of effects. For example, NO is neurotransmitter and a vasodialator, it is a tumoricidal agent as well as a bacteriocidal agent.)

By way of example, the adenoviruses of the invention can be used to introduce the NOS gene into vein grafts prior to their use as coronary artery bypass grafts. Vein graft failure is the major limiting problem with coronary artery surgery. Treatment of vein grafts with NOS-producing adenoviruses can substantially enhance long-term patency of the grafts. Treatment can be effected by infusing and expanding the vein segment to be grafted with a solution (eg saline solution) containing the NOS adenovirus (eg for approximately 15–30 minutes) prior to grafting.

An NOS-containing adenovirus can also be used following coronary angioplasty to prevent restenosis. Although coronary angioplasty has an initial success rate of 95%, renarrowing of the dilated segment produces recurrent symptoms in over one-third of cases. An NOS-containing adenovirus can be used to promote reendothelialization of the injured segment, and thereby prevent restenosis. For this purpose, administration can be effected via a catheter (eg a balloon-tipped catheter) or, for example, via a stent. (See, for example, Chapman, Cir. Res. 71:27–33 (1992); Restenosis Summit V, E.G. Topol Ed., Cleveland Clinic Heart Center (1993).)

In addition to the above, the NOS-adenovirus can also be used in the treatment of atherosclerotic arteries. Endothelial dysfunction is an early event in atherosclerosis. Introduction of an NOS-containing adenovirus at a lesion site can be used to prevent progression to complex lesions, as well as to promote healing once developed. Administration can be effected as described above (eg by catheter or by stent).

The NOS-adenoviruses of the invention can also be used in anti-cancer therapy. NO can be used to promote cell death. Accordingly, the NOS-adenoviruses of the invention delivered to well vascularized tumors can be used to effect the generation of cytotoxic levels of NO. Administration can be effected by direct injection or implantation into the tumor tissue or, for example, by intravascular injection.

In addition to its cytotoxic and growth inhibiting effect, NO reacts with superoxide and other oxygen free radicals to produce highly toxic radicals such as peroxynitrite. Radiotherapy induces the formation of oxygen free radicals as a major part of its therapeutic effect. In the presence of the NOS adenovirus construct of the invention, radiotherapy is far more potent. Thus significantly lower radiation doses can be used. Again, administration can be effected, for example, by direct injection or intravascular injection.

Ectopic NO production may be limited by the lack of available co-factors, such as tetrahydrobiopterin. One of the advantages of the invention is the fact that two encoding sequences (eg cDNAs) can be introduced into the same adenovirus. A cDNA for GTP cyclohydrolase can be cloned into this additional site of the instant NOS-adenovirus and expression of the two cDNAs obtained. The result is the increased production of the co-factor tetrahydrobiopterin, and therefore increased nitric oxide production. Alternatively, two adenoviruses can be constructed, one containing the appropriate NOS isoform and the other containing the cyclohydrolase gene, and co-infected.

An alternative form of the invention involves genetic engineering and mutagenesis of the NOS isoforms. For example, calcium-calmodulin independent forms of eNOS or bNOS can be engineered, for example, by substituting the calmodulin binding region of mNOS into the corresponding regions of bNOS and eNOS. The genetically engineered NOS isoforms are constituitively active and thus more effective in the treatment of vascular disease or cancer.

Certain aspects of the invention are described in greater detail in the non-limiting Examples that follow.

EXAMPLE 1

Preparation of Adenoviral Vector System

E3 Deletion from In340 Virus

Figure 2A:
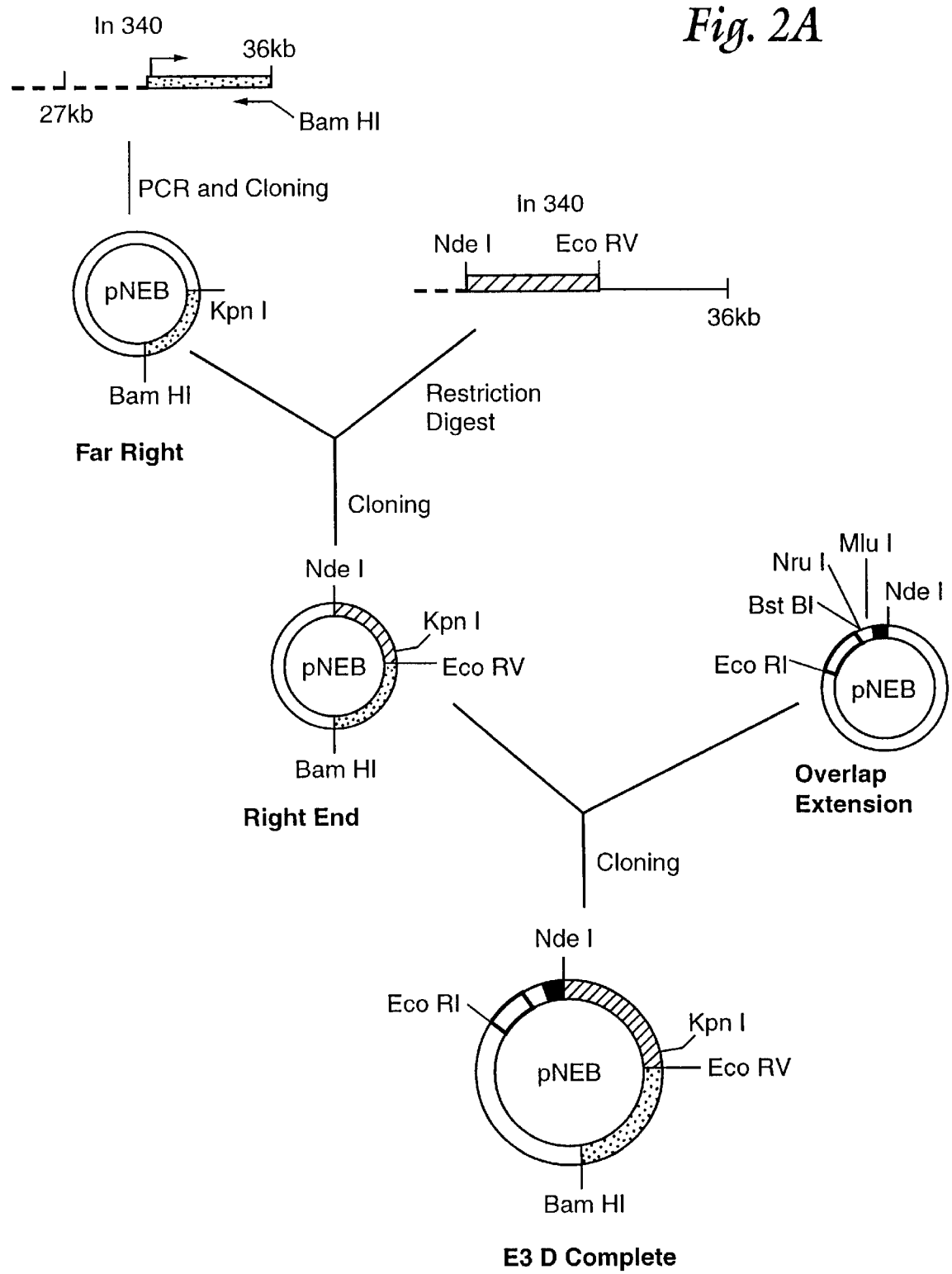
FIG. 2. Generation of the E3 deletion.
Figure 2B:
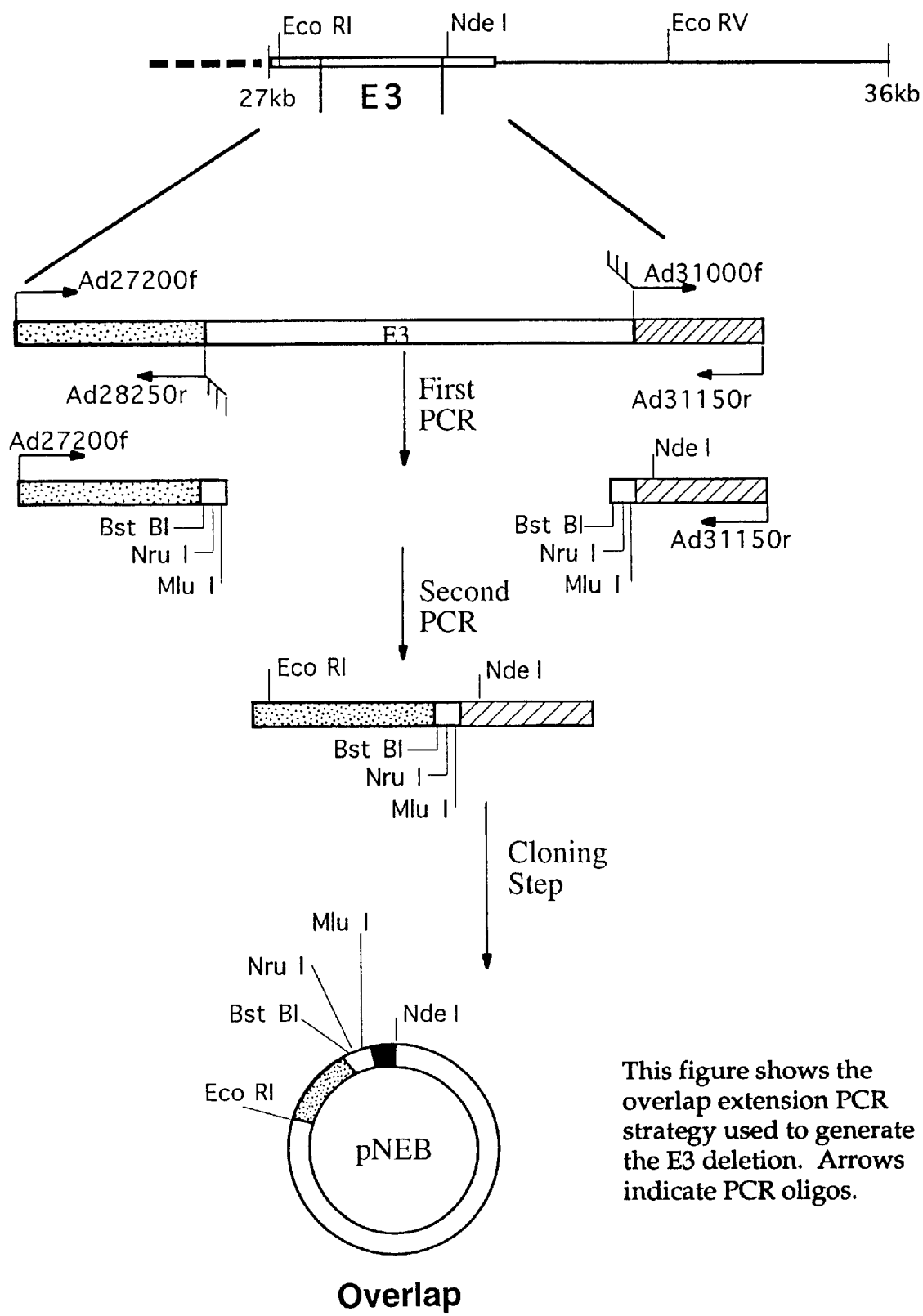

The E3 region was deleted using overlap restriction PCR as shown in FIGS. 2A and 2B. With reference to FIG. 2A, the forward oligonucleotide used was CGGGACTGGAA-CAATGA (SEQ ID NO: 8) and the reverse oligonucleotide was GAATGGATCCATCATCAATAATATACCT-TATTTTGG (SEQ ID NO: 9). The product was approximately 2500 bp and had a unique Kpn I site and a unique Bam HI site (the latter was engineered into the reverse oligonucleotide). This PCR fragment was cloned into the New England Biolabs plasmid pNEB193 Kpn I to Bam HI. The new plasmid was called E3D far right. The adenoviral E4 region segment that lies between an Nde I site and the Kpn I site (approximately 2500 bp) was then restriction digested and cloned into the E3D far right plasmid Nde I to Kpn I. This step required the use of *Epicurian Coli* SURE cells from Stratagene. The new plasmid was called E3D Nde to end plasmid.

With reference to FIG. 2B, fragment 1 runs from 5' to the unique Eco RI restriction site of In340 to about 50 bp into the E3 region. Fragment 2 runs from about 50 bp inside the 3' border of the E3 region to just beyond the unique Nde I site in the E4 region. The reverse oligonucleotide primer for fragment 1 and forward oligonucleotide primer for fragment 2 had 16 overlapping nucleotides for reannealing at the second PCR. This overlapping fragment inserts 3 new restriction sites into this region, Bst BI, Nru I, and Mlu I. The Bst BI site is unique to the virus. After the second PCR, the new PCR product was restriction digested with Eco RI and Age I and cloned into pNEB 193 plasmid Eco RI to Xma I (which is compatible with Age I). This new plasmid was called pNEB OE Eco RI to Age I/Xma I. This fragment was restriction digested with Nde I and cloned into the E3D Nde to end plasmid (FIG. 2A) which had been cut with Nde I. The resulting plasmid called E3D RE complete (FIG. 2A) had the completed E3 deleted right end of In340 within it.

The now complete right end was digested with Bam HI, blunted with Klenow fragment then digested with Eco RI. This was ligated to a previously Eco RI digested and purified 27000 bp left end In340 fragment. The ligated DNA was transfected into 293 cells using the calcium phosphate method. The resulting virus was purified by selecting well-isolated plaques (Graham and Prevec, Gene Transfer and Expression Protocols, Methods in Molecular Biology 7:109–128, Humana Press. (1991)). The E3 deletion was confirmed with restriction digests.

Plasmid Modification

Figure 3:
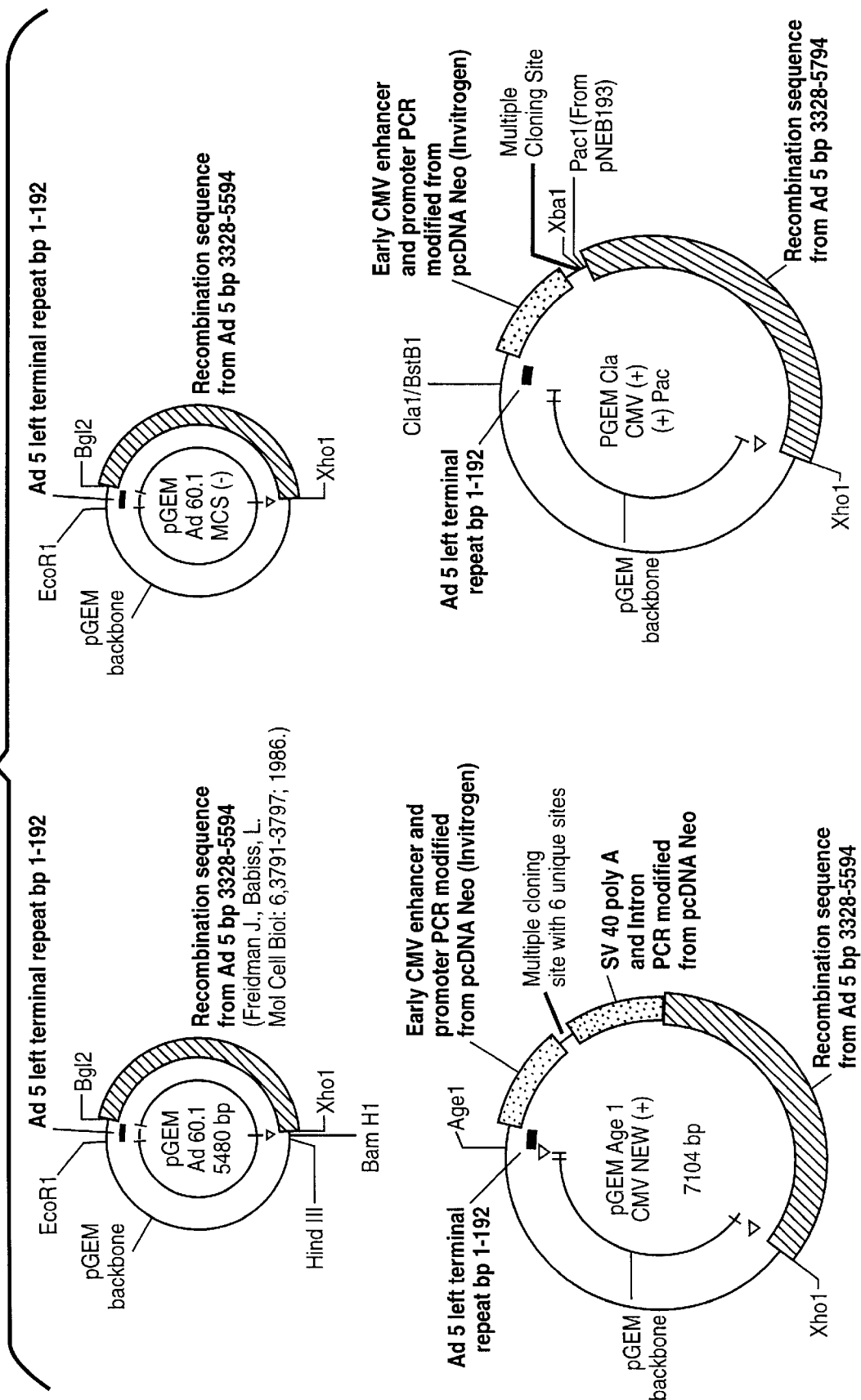
FIG. 3. Plasmids designed for intracellular recombination and for direct ligation.
Figure 4:
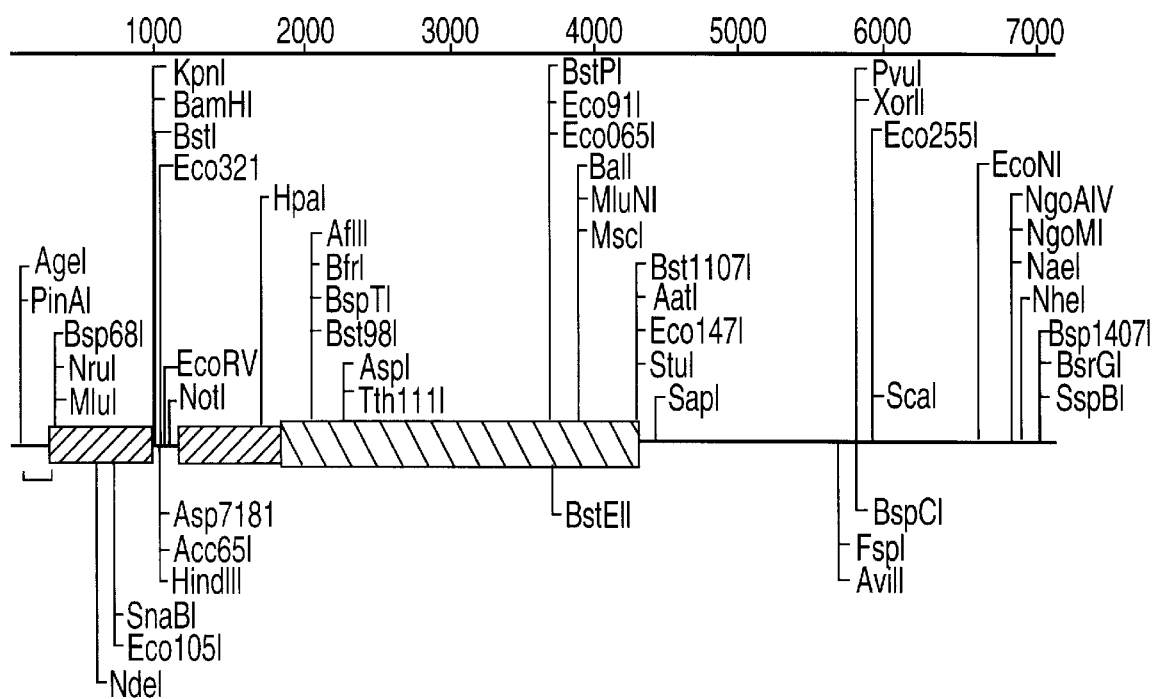
FIGS. 4 and 5. pGEM CMV NEW (+) cut site map.
Figure 5:
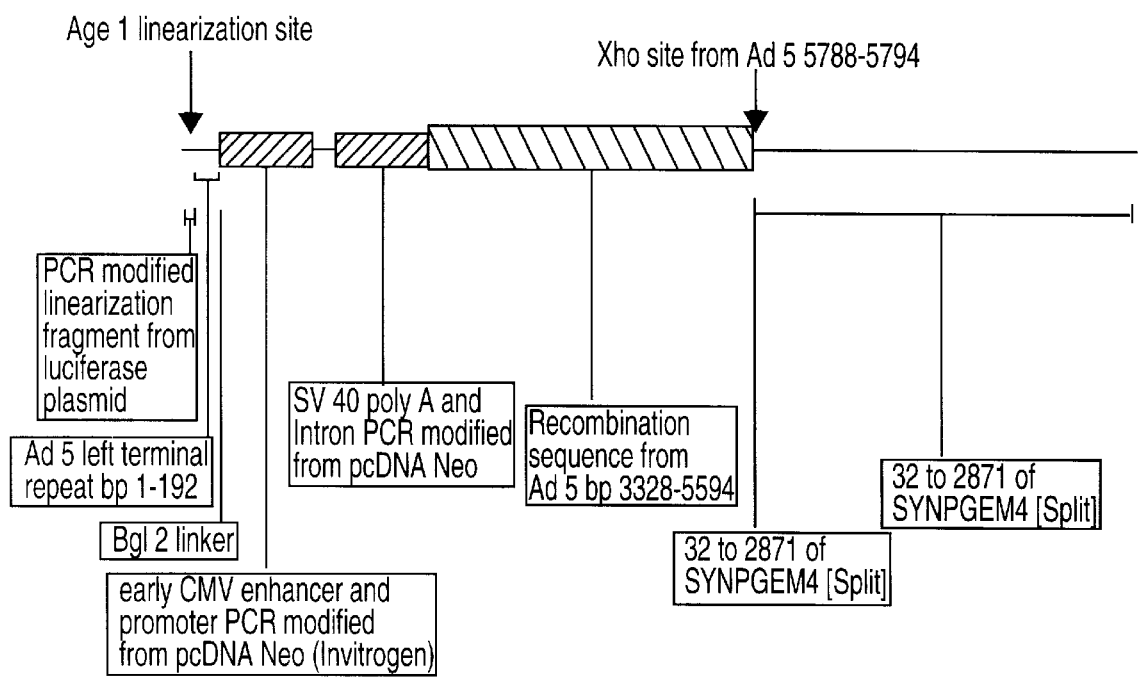
Figure 6:
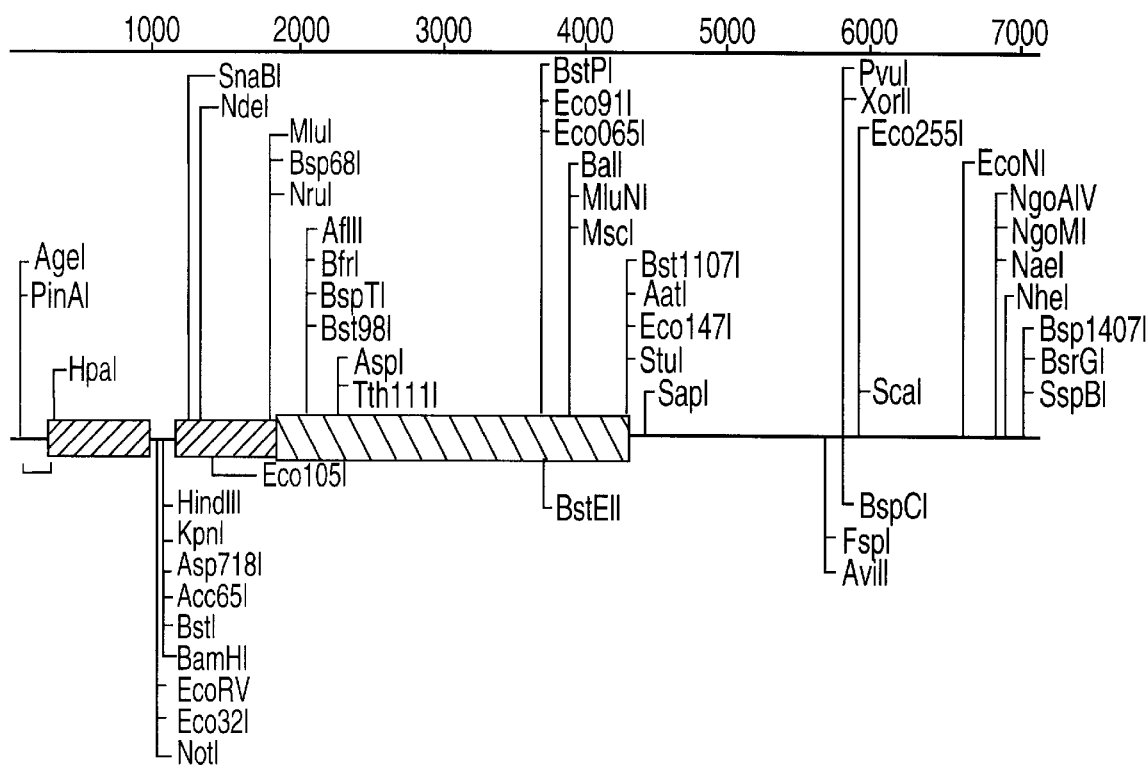
FIG. 6. pGEM CMV NEW (−) cut site map.
Figure 28:
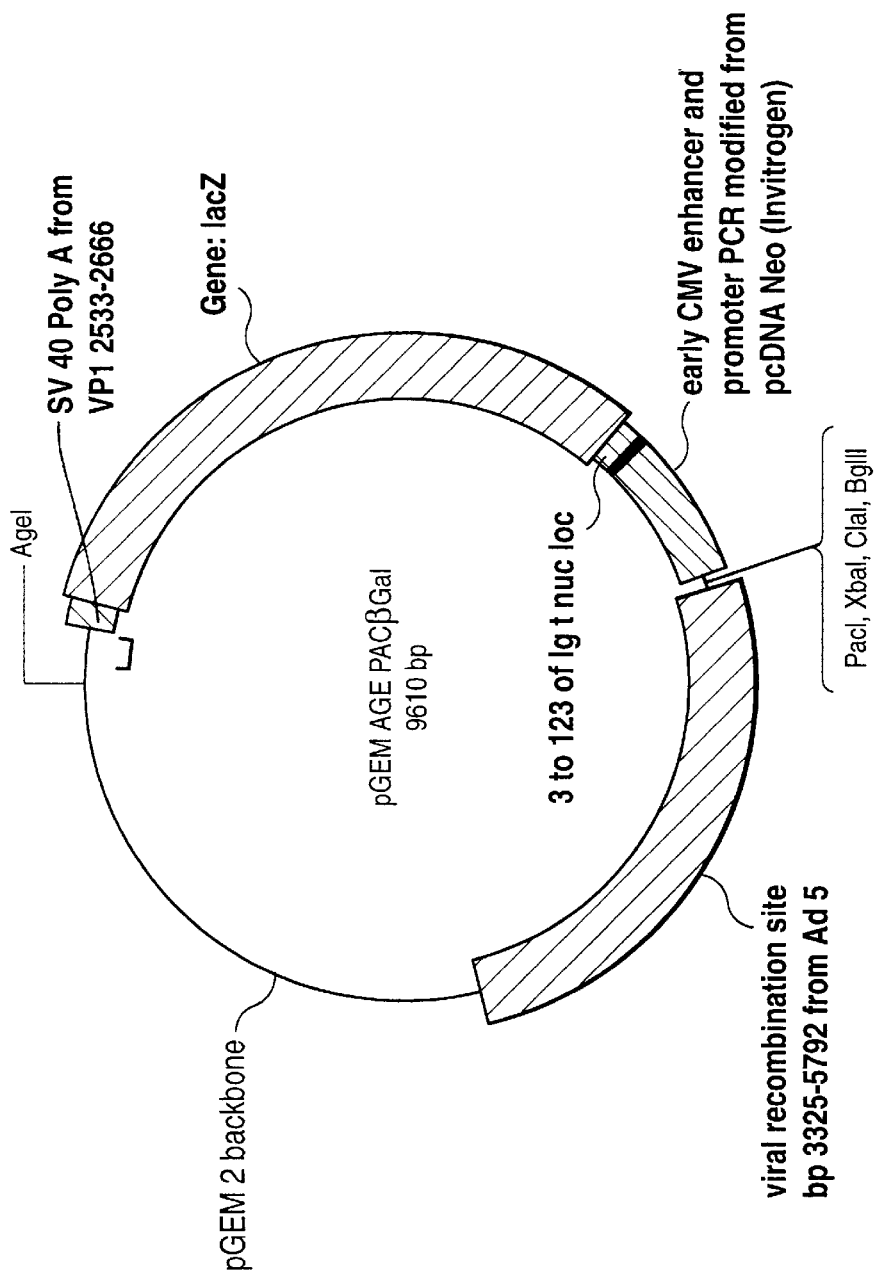
FIG. 28 pGEM Age PacβGal.

Plasmids designed for intracellular recombination:

The base plasmid is pGEM Ad60, 1 (provided by Lee Babiss (see Babiss, Mol. Cell. Biol. 6:3798 (1986) and Brunet, Mol. Cell. Biol. 7:1091–1100 (1987)). It is a modification of pMLP6 (Friedman et al, Mol. Cell. Biol. 6:3798 (1986)). The backbone of this plasmid, pGEM, is obtained from Promega. Restriction enzyme cutting and blunting with the Klenow fragment of *E. coli* were used to remove the multiple cloning site of this plasmid between the Bam HI and Hind III sites. This new plasmid is pGEM Ad 60.1 MCS(−)(see FIG. 3) PCR with mutagenic oligonucleotides was then used to create a small 100 bp fragment from luciferase cDNA for insertion into the Eco RI site of this plasmid. This 100 bp segment, of which there are two—Age I and Cla I—provides a unique restriction enzyme site for linearizing the plasmid. Linearization increases the efficiency of recombinant generation (Tamanoi and Stillman, Proc. Natl. Acad. Sci. USA 79:2221–2225 (1982)).

The CMV promoter, multiple cloning site and intron/polyadenylation signal sequence of DNA from the Invitrogen plasmid pcDNA NEO were next inserted into this plasmid. This provides a promoter and enhancer to drive expression, ease of cloning, and RNA processing signals to increase the efficiency of translation. The Eco RI site was first deleted in the multiple cloning site of pcDNA NEO by restriction digesting, blunting with the Klenow fragment of *E coli* and religating. PCR was then used to modify the 5' and 3' ends of this segment of DNA to insert unique cloning sites (Bgl II and Sma I at the 5' end and Xba I and Bgl II at the 3' end). This PCR modified segment was inserted into the unique Bgl II site pGEM Ad 60.1 MCS (−) to generate the overlap recombination plasmid pGEM Age 1 CMV new (see FIG. 3). This 1500 bp segment of DNA has been inserted into plasmids in both the (+) and (−) directions to allow for a choice of the direction of transcription.

Plasmids designed for direct ligation:

This plasmid has been further modified to increase the sites for ligation by adding a unique Pac I site to the plasmid and removing the intron/poly A segment. Pac I has an 8-base recognition sequence, and is therefore a rare cutter; there are no other Pac I sites in the adenoviral genome. With the ligation plasmid, it is possible to use either ligation or recombination to generate recombinant virions.

The Pac I site was inserted as follows: 1) PCR and a mutagenic oligonucleotide primer were used to modify the sequence of pNEB 193 3' to the multiple cloning site. The modifications were to add a Cla I site and a Bgl II site; 2) the PCR fragment that was generated was cloned into the Bgl II site of pGEM Ad 60.1 MCS (−) Bam HI to Bgl II. This added the Pac I site which is next to a Xba I site; and 3) the CMV promoter and multiple cloning site from pGEM Age I CMV New were excised Bgl II to Xba I and cloned into the interim plasmid resulting in the final recombination plasmid pGEM Cla CMV (+) Pac (see FIG. 3).

Nuclear Localizing β-Galactosidase Virus

Figure 47:
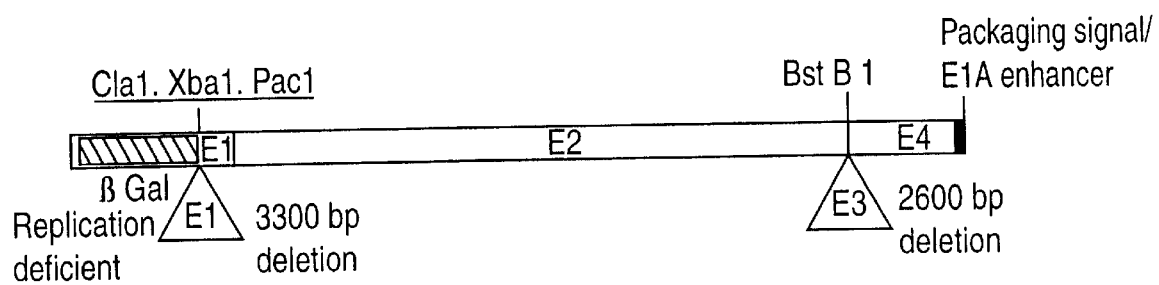
FIGS. 47 and 48. Recombinant adenovirus Ad:Pac-βGal ■=Terminal repeat.

The nuclear-localizing β-galactosidase gene used was originally from Integrated Genetics. It contains the SV40 nuclear localization signal, the SV40 polyadenylation signal and the *E coli* β-galactosidase gene. It was cloned into the pGEM CMV (−) new vector. The SV40 poly A/intron sequence from this vector was excised to prevent possible annealing problems with the duplicated sequences. The same modified pNEB fragment containing Pac I and Cla I described above was placed into the Bgl II site located next to the CMV promoter of this construct. Upon generating the recombinant virus Ad:Pac-βGal (see FIG. 47 and FIG. 48), this placed three unique sites-Cla I, Xba I and Pac I-within 50 bp of the border of the E1 deletion, which permits the maximal cloning capacity of 8000 bp to be achieved by ligation in the E1 region.

Negative screening:

Ad:Pac-βGal (see FIG. 47 and FIG. 48) allows negative screening. The virus is cut with Cla I, Xba I, or Pac I, removing the βgal cDNA. The virus is then either cotransfected or directly ligated with an appropriate plasmid containing the gene of interest. A successful recombination (or direct ligation) event produces white plaques in 293 cells stained with X-gal (0.25 mg/plate added to the last overlay); uncut parental virus produces blue plaques.

Figure 102A:
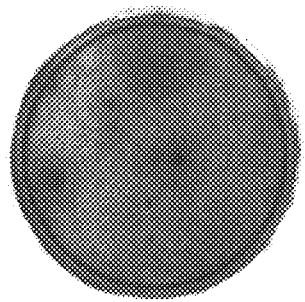
FIGS. 102A to 102C. X-Gal staining of recombinant viral plaques (FIG. 102A). Infection of smooth muscle cells (SMCs) with Ad:Pac-βGal, primary rabbit SMCs (70×)—FIG. 102B; rat A10 SMC line (15×)—FIG. 102C.

By way of example, a lysate of infected cells is placed on confluent plates of 293 cells at various dilutions for one hour. The virus is removed and the plates overlaid with a nutrient agar medium (DMEM/2% FCS/0.8%) at 37° C. When plaques appear (usually 8–10 days), they are overlaid with 3 ml of nutrient agar containing 0.01% neutral red and 0.25 mg of X-gal and incubated overnight. For the Ad:Pac-βGal virus, plaques were picked and taken through a second round of purification. Viral titers were determined using this plaque assay. For all other recombinant virions, white plaques are picked (see FIG. 102A).

Figure 102B:
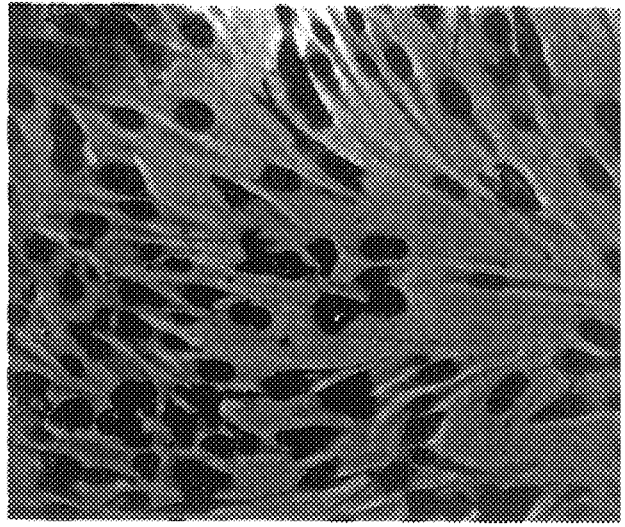
Figure 102C:
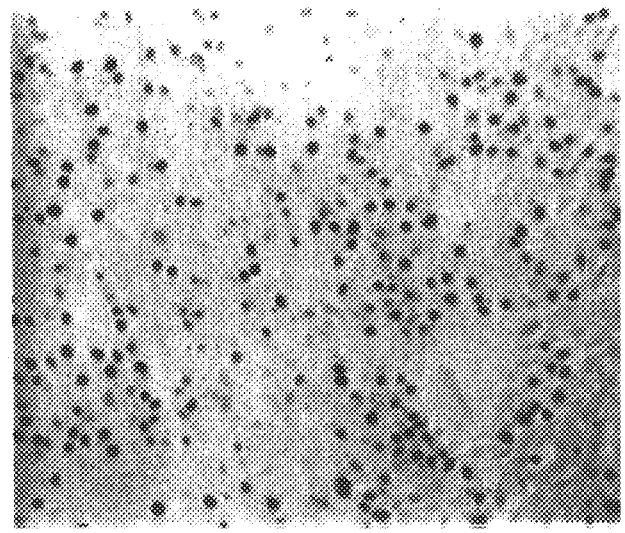
Figure 103A:
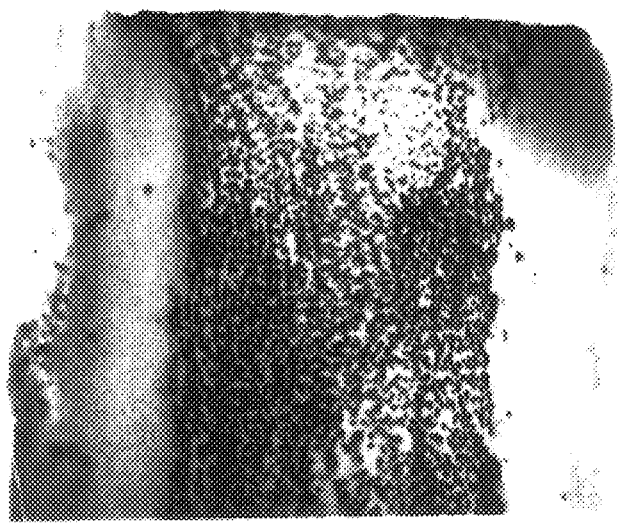
FIGS. 103A and 103B. Infection of rabbit carotid artery segments with Ad:Pac-βGal. Longitudinal view (FIG. 103A). Cross-sectional view (FIG. 103B) (12.5×).
Figure 103B:
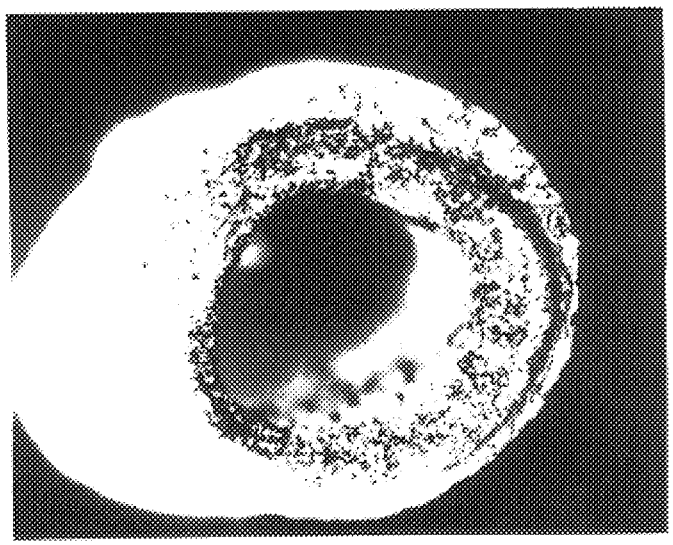

Smooth muscle cells were also infected with Ad:Pac-βGal. Infections were for 1 hour with $1 \times 10^8$ pfu/ml (see FIGS. 102B and 102C). Rabbit carotid artery segments were also infected with Ad:Pac-βGal. Infection was for 1 hour in serum free medium at a titer of $5 \times 10^8$ pfu/ml. The arteries were strained after 48 hours with X-gal. (See FIGS. 103A and 103B).

Positive screening:

This method uses the green fluorescent protein (gfp) of Prasher (Science 263:802–805 (1994)). The approximately 750 bp cDNA is cloned into the Ad:Pac-βGal virus as shown in FIG. 101 to generate a virus named Ad:Pac-βgal/gfp. Ad:Pac-βGal/gfp contains a cDNA for gfp (cloned in left to right orientation), and a promoter and cDNA for βGal (cloned right to left). The plasmid, which must be directly ligated to the restricted virus, is designed to contain the cDNA of interest (oriented right to left), and a promoter for gfp (oriented left to right). Since transcription from adenoviral DNA is bidirectional, both cDNAs would be expressed. Positive screening works because gfp will be expressed if and only if the recombinant virus results from ligation of the plasmid to the restricted virus. A plaque that is white under visible light, and green under UV light, represents a successful recombination event.

EXAMPLE 2

Over Expression of E2F1 from E2F1 Recombinant Adenovirus

Experimental Protocols:

Cell culture: Mink lung epithelial cells (Mv1Lu) and 293 cells were obtained from the ATCC. REF-52 cells were obtained from Keith Burridge at University of North Carolina. Mink lung epithelial cells were maintained in DMEM containing non-essential amino acids together with 10% fetal calf serum.

Generation of recombinant adenoviruses: The overlap recombination procedure was used to introduce the E2F1 gene, under the control of a CMV promoter, into the adenovirus genome (Friedman et al, Mol. Cell. Biol. 6:3791 (1986)). The E2F1 cDNA was cloned into the BamHI site of the adenovirus recombination plasmid pGEM-CMV. This places the cDNA downstream from a CMV promoter. Downstream of the cDNA are sequences containing an SV40 splice donor/acceptor and an SV40 polyadenylation site. Flanking the inserted sequences are adenovirus sequences from genome position 1–194 and 3325–5788 nucleotides which provide the adenovirus left terminus and sequences for overlap recombination. The plasmid contains a unique AgeI site that is used for linearization. DNA was prepared from the Ad5 virus In340 (Hearing and Shenk, Cell 33:695 (1983)) and digested to completion with XbaI and ClaI, each of which cuts the viral DNA only once. (Note that In340 was used rather than the E3-deleted form described in Example 1). This digested DNA was then transfected into 293 cells along with a linearized plasmid containing the E2F1 construct. An identical construct that did not contain the cDNA sequence was processed in parallel. Five days after transfection, lysates were prepared and potential recombinant viruses were isolated by plaque assays on 293 cells. After plaque purification, recombinants were detected by isolation of viral DNA and analyzed by restriction digestion and Southern hybridization. Viral stocks were obtained by infection of monolayer cultures of 293 cells and crude cellular lysates prepared by repeated cycles of freezing and thawing. Titers of viral stocks were determined by plaque assay on 293 cells. After plaque purification, recombinants were detected by restriction digestion and Southern hybridization. The E2F1 recombinant virus was termed AdE2F1 and the control virus containing only the vector and no cDNA insert was termed MbAd2.

Virus infection: All infections were performed at an input multiplicity of 100 pfu/cell. Cells were infected in media containing reduced serum (0.2%) for 2 hr at 37° C. For infection of TGF-γ treated cells, TGF-β was maintained in the medium during the infection procedure. The AdE1A$_{12S}$ virus contains the 12S cDNA in place of E1A genomic sequences (Moran et al, J. Virol. 57:765 (1986)) and was provided by E. Moran.

Western blot assays for E2F1: Mv1Lu cells were treated with TGF-β and infected with the MbAd2 control virus or the AdE2F1 virus. Whole cell lysates were prepared from the infected cells at various times following infection and 50 μg of protein was loaded onto a 10% SDS polyacrylamide gel. Separated proteins were transferred to nitrocellulose and probed with an E2F1-specific monoclonal antibody (Santa Cruz) at a 1:1000 dilution. Secondary antibody detection was performed by the ECL protocol (Amersham).

TGF-β growth arrest assay: Mink lung epithelial cells were placed into 12 well plates at a density of $2 \times 10^4$ cells per well, grown overnight, and then placed in DMEM containing 0.2% fetal calf serum. Cells were incubated for 24 hr in 100 pM TGF-β2 and either infected with the adenovirus vectors or washed and placed into DMEM containing 10% fetal calf serum. Infected cells were continually incubated in the presence of TGF-β2. Cultures were grown for 22, 26, or 30 hr and during the last 2 hr, labeled with 4 μCi/ml $^3$H-thymidine. Cells were lysed and the amount of $^3$H-thymidine incorporation into the DNA was quantitated using a scintillation counter. For BrdU assays, cells were labeled with 10 μM BrdU for the indicated time period, fixed, and then stained with BrdU specific antibody as described previously (Johnson et al, Nature 365:349 (1993)).

CsCl density gradient analysis of viral and cellular DNA: Adenoviral and cellular DNA were separated by bouyant density centrifugation as described previously (Spindler et al, J. Virol. 53:742 (1985)). Mv1Lu cells were treated with TGF-β for 24 hr. As in other experiments, the cells were either washed free of TGF-β and the media replaced with media containing 10% serum or the cells were infected. At 20 hr post infection, the cells were labeled with 2 μCi/ml of $^3$H-thymidine for 4 hr. The cells were then washed and total DNA was prepared using SDS/proteinase K digestion as described. A sample of each lysate (0.5 ml) was mixed with 9.5 ml of a CsCl solution of density 1.70348 g/ml in 10 mM Tris (pH 8.5), 1 mM EDTA, 0.1% sarcosyl and centrifuged at 18° C. for 15 hr at 55,000 rpm in a VTi 65 rotor. In addition, $5 \times 10^5$ cpm of $^{32}$P-labeled adenovirus DNA (labeled by nick translation) was added to each sample prior to centrifugation as an internal marker. Fractions of 0.2 ml were collected and 50 μl of each was TCA precipitated and counted in a liquid scintillation counter.

Phosphorylation of Rb: Mink lung epithelial cells were plated into 10 cm plates (approximately 50% confluent), grown overnight, and then placed in DMEM containing 0.2% fetal calf serum. The cells were incubated with 100 pM TGF-β2 for 24 hr and then either infected with the adenovirus E2F1 vector or washed and placed into DMEM containing 10% fetal calf serum. Infected cultures were maintained in the presence of 100 pM TGF-β2. The cultures were grown for 27.5 hr, starved for methionine for 30 min, and then labeled for 3 hr with 0.5 mCi of $^{35}$S-methionine in 3 mol of methionine-free medium containing 5% dialyzed fetal calf serum. Cells were washed three times with cold PBS and lysed for 15 min on ice in 1 ml of 50 mM Tris-HCl (pH 8.0), 200 mM NaCl, 0.5% NP40, containing 50 μg/ml phenylmethylsulfonyl fluoride, 10 μg/ml aprotonin, 10 μg/ml leupeptin, 20 mM NaF, 20 mM potassium phosphate, and 0.1 mM sodium orthovanadate. Lysates were precleared with protein A-Sepharose for 1 hr at 4° C. and a mixture of the Rb monoclonal antibodies XZ77 and XZ91 (Hu et al, Mol. Cell Biol. 11:5792 (1991)) was added for 2 hr at 4° C. The phosphorylation state of Rb was assessed by gel electrophoresis of the immunoprecipitated proteins followed by fluorography.

Figure 104A:
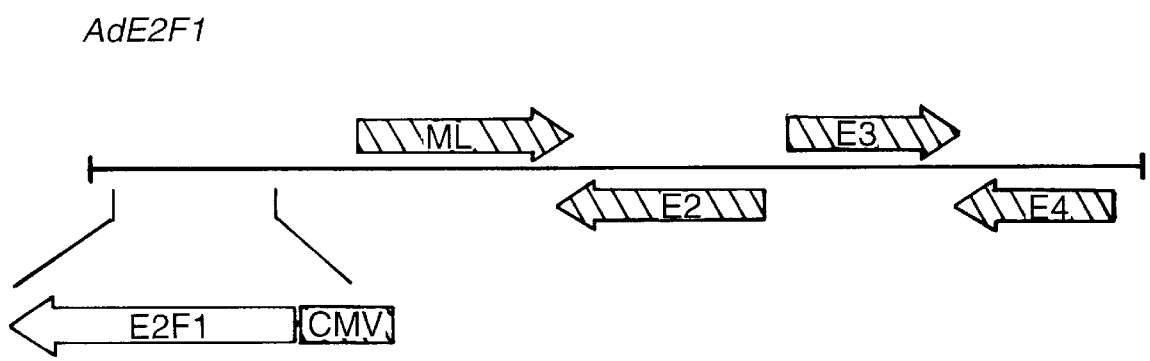
FIGS. 104A and 104B. Overexpression of E2F1 from an E2F1 recombinant adenovirus.
Figure 104B:
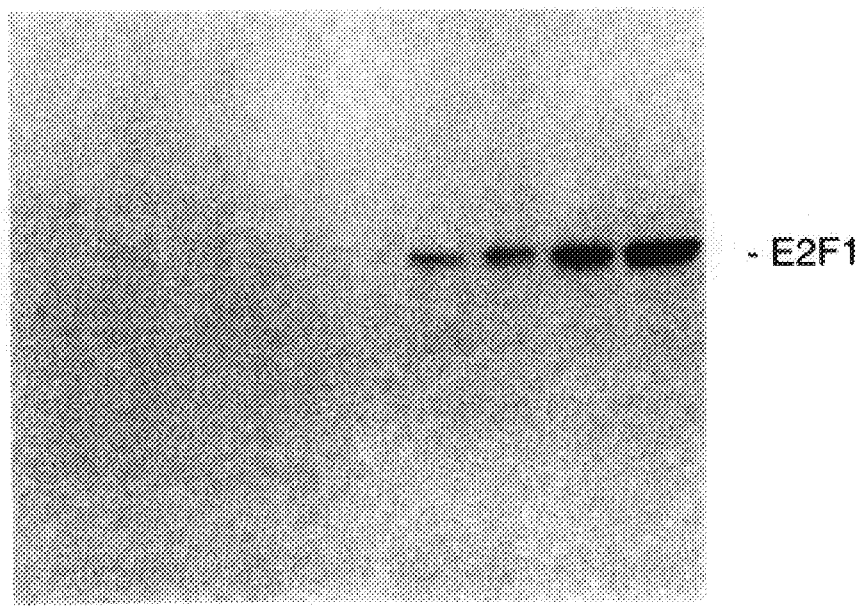

Results:

Construction of an adenovirus E2F1 expression vector: In order to achieve efficient expression of the E2F1 gene product in quiescent cells, an adenovirus expression vector was constructed in which the adenovirus E1 region was replaced by the human E2F1 cDNA (Helin et al, Cell 70:337 (1992), Kaelin et al, Cell 70:351 (1992), Shan et al, Mol. Cell Biol. 12:5620 (1992)) under the control of the CMV immediate early promoter (FIG. 104A). As shown in FIG. 104B, large amounts of the E2F1 protein are expressed in Mv1Lu cells following infection with the recombinant virus AdE2F1 in contrast to the infection of cells with a virus lacking the E2F1 insert, MbAd2.

Recent experiments have shown that E2F1 overexpression can induce quiescent cells to enter S phase (Johnson et al, Nature 365:349 (1993)). The ability of the virus to induce S-phase in quiescent REF-52 cells was tested. REF-52 cells were incubated in 0.2% serum for 48 hours and then either mock infected, infected with the E2F1 expression virus or the control virus. BrdU was added to the media after infection and the cells were maintained in 0.2% serum for 30 hours. The cells were then fixed and stained for BrdU incorporation. Approximately 25% of the cells infected with the AdE2F1 vector were positive for BrdU incorporation. This is a similar efficiency as observed previously for the ability of a microinjected E2F1 cDNA to induce S phase (Johnson et al, Nature 365:349 (1993)). Thus, presumably as a consequence of overexpression of E2F1, this virus vector is able to induce the quiescent cells to enter S-phase following infection and expression of E2F1.

TGF-β induced cell cycle arrest is overcome by E2F1 overexpression: Given the data which suggests that E2F activation is an important event of late G1 progression as well as the data showing control of E2F1 RNA levels by TGF-β, it was determined whether E2F1 overexpression can overcome a TGF-β induced cell cycle arrest. Two approaches to this general question were taken. First, the question was asked whether E2F1 overexpression could prevent cells from leaving the cell cycle as a result of TGF-β treatment. In this experiment, mink lung epithelial cells were infected with AdE2F1 or the control virus MbAd2 and then treated with TGF-β for 36 hr. At this time, BrdU was added, incubation continued for another 12 hr and then BrdU incorporation was measured by indirect immunofluorescence. TGF-β treatment resulted in a 10-fold reduction in BrdU positive cells. Infection with the MbAd2 control virus did not alter this inhibition. In contrast, infection with the AdE2F1 virus, or an adenovirus that expresses the E1A$_{12S}$ product, prevented the inhibition.

Figure 48:
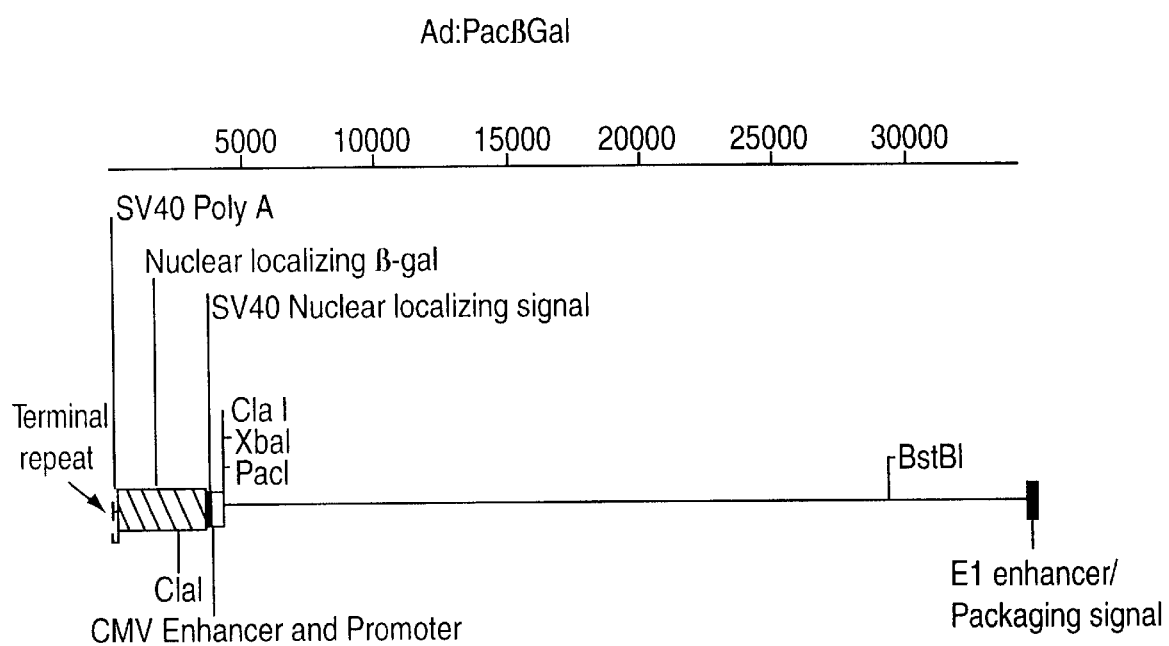

The second approach asked whether E2F1 overexpression could overcome a TGF-β mediated block of cell growth that had already taken place. Mink lung epithelial cells were arrested with TGF-β for 24 hours and then infected with AdE2F1 or MbAd2. In addition, cells were washed and the media replaced with media containing 10% serum. Thymidine incorporation was measured by pulse labeling for 2 hr beginning at 20, 24, and 28 hr after infection. As shown in FIG. 48, which is the average for three independent experiments, cells which were infected with the control virus remained arrested with no evidence of DNA synthesis whereas cells infected with the AdE2F1 virus exhibited a significant incorporation of $^3$H-thymidine, above that achieved by the addition of serum.

A possible complication of using adenoviral vectors in these experiments is that viral DNA replication may be occurring which would be measured as thymidine incorporation. This is not likely given that wild-type adenoviruses replicate inefficiently in rodent cells and these vectors lack E1A and E1B. Nevertheless, to investigate this possibility, $^3$H-thymidine labeled DNA was analyzed by CsCl density gradient centrifugation to separate viral DNA from cellular DNA. Only one peak of labeled DNA was observed with either the serum stimulated sample or the sample from an infection with the AdE2F1 virus and this peak is clearly separate from that of viral DNA which was added as an internal marker.

Phosphorylation state of Rb in E2F1 expressing cells: These experiments demonstrate that overexpression of E2F1 can induce S phase in cells which are growth arrested by TGF-β. Perhaps the simplest model of how this might be accomplished would be to suggest that while Rb remains in the underphosphorylated state as a result of G1 cyclin/kinase inhibition, E2F1 expression is sufficient to overwhelm the level of active Rb that is present. Alternatively, E2F1 expression might reactivate the G1 cyclin kinases resulting in the phosphorylation of Rb as well as other targets, thus allowing accumulation of E2F and S phase induction. To investigate these possibilities, the phosphorylation state of Rb was examined under the experimental conditions where E2F1 was inducing S-phase in TGF-β treated cells. Mink lung epithelial cells were arrested with TGF-β and then infected with MbAd2 or AdE2F1 or released from TGF-β as in previous experiments. The cells were labeled with $^{35}$S-methionine from 28–31 hours after infection and the phosphorylation state of Rb was assessed by gel electrophoresis after immunoprecipitation and fluorography. As expected, an increase in the ratio of hyperphosphorylated forms of Rb were observed in the cells that were released from TGF-β compared to those which are still growth arrested with TGF-β. TGF-β treated cells which were infected with AdE2F1 also show an increase in the hyperphosphorylated forms of Rb. Thus it would appear that G1 cyclin/kinase activity may be at least partially reactivated in AdE2F1 infected cells and that this may contribute to the induction of S phase in the presence of TGF-β.

EXAMPLE 3

Expression of Nitric Oxide Synthase Isoforms cDNAs were obtained for the brain isoform of nitric oxide synthase (bNOS) (Bredt et al, Nature 351:714 (1991)), the macrophage isoform (mNOS) (Lowenstein et al, Proc. Natl. Acad. Sci. USA 89:6771 (1992)), and the endothelial isoform (eNOS) (Sessa et al, J. Biol. Chem. 267:15247 (1992)). These DNAs were cloned into the plasmid pGEM CMV+ new (see Example 1). This plasmid contains the early CMV enhancer and promoter and SV40 poly A/intron, a recombination sequence from the Ad5 strain of adenovirus. A bNOS and a mNOS-containing adenovirus were generated by co-transfecting each plasmid with an E1–E3 deleted version of Ad5 In340 strain of adenovirus which had been digested with the appropriate restriction enzymes (see Example 1). The plasmid and virus were co-transfected into the 293 helper cell line and the bNOS containing virus was generated by overlap recombination. This virus was isolated and purified using previously-described techniques. In addition to the above constructs, NOS containing adenoviruses can also be generated that have a marker called green fluorescent protein (Chalfie et al, Science 263:802 (1994)) (see Example 1). Co-expression of GFP with NOS enables the detection of successfully transfected tissue in vitro and in vivo, without the necessity of fixing the tissue beforehand. Light of appropriate wavelength can simply be directed on the cells or transfected tissue (for example, via endoscopy or angioscopy).

Figure 105:
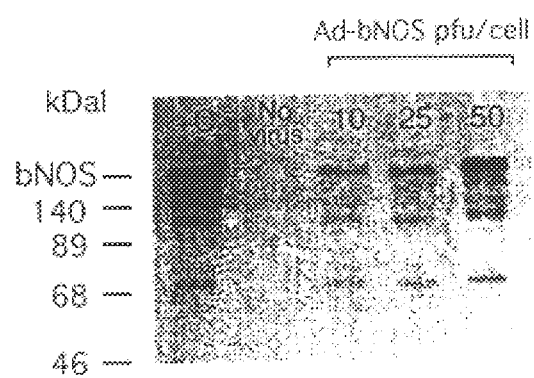
FIG. 105. Expression of bNos in Ad-bNOS infected vascular SMC. '+C' denotes a standard bNOS preparation purified from the 293 bNOS cell line; 'No virus' denotes an extract from mock-infected cells.

By way of example, rat A10 SMC ($10^6$ cells in 100 mm disk) were infected with Ad-bNOS at titers of 10, 25 or 50 pfu/cell for 1 hour. After 72 hours, expression of bNOS protein was determined in 2'–5' ADP-binding fractions of cell lysates by immunoblotting, using a monoclonal anti-bNOS antibody (see FIG. 105). The protein bands were visualized by chemiluminescence.

Figure 106:
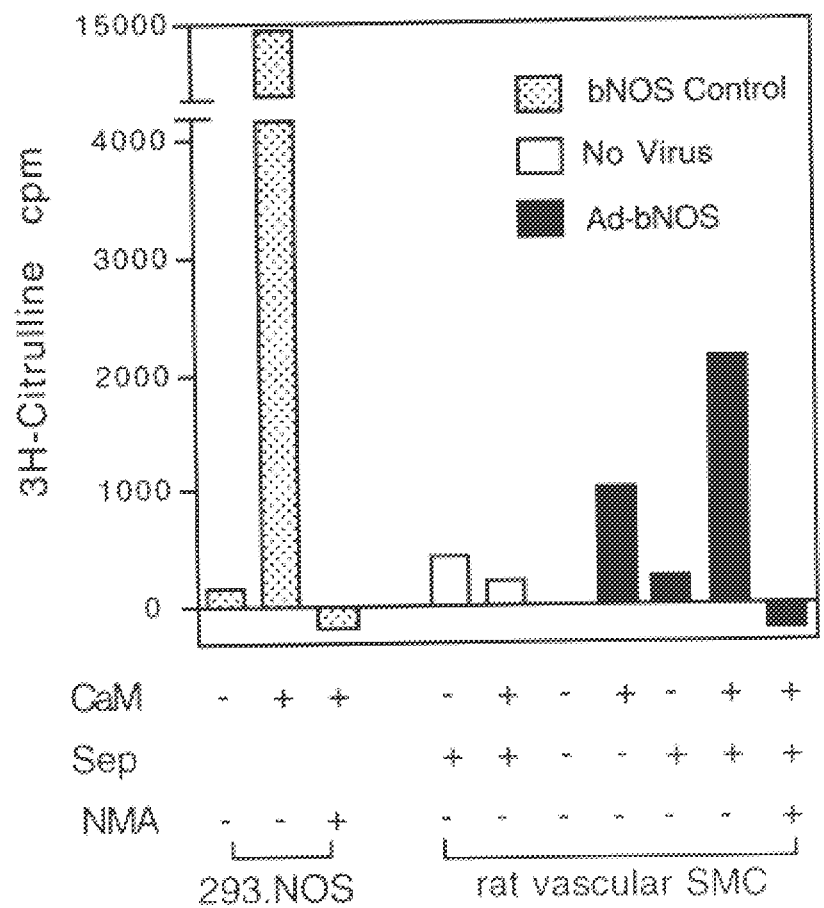
FIG. 106. bNOS activity in Ad-bNOS-infected SMC.

In addition, a 100 mm dish of rat A10 vascular SMC was infected with Ad-bNOS at a titer of 15 pfu/cell for 1 hour. After 72 hours to allow for expression, bNOS activity was measured in the 2'–5' ADP-binding fraction of cell lysates. bNOS activity was determined by conversion of 3H-arginine to 3H-citrulline (see FIG. 106). Cells were incubated in the presence or absence of the tetrahydrobiopterin precursor, L-sepiapterin (Sep). NOS assays were performed in the presence or absence of calmodulin (CaM) or of the NOS inhibitor, N-methyl arginine (NMA). The bNOS control is a 2'–5' ADP-binding fraction of a lysate from the 293.NOS cell line.

All documents cited above are hereby incorporated in their entirety by reference.

One skilled in the art will appreciate from a reading of this disclosure that various changes in form and detail can be made without departing from the true scope of the invention.

What is claimed is:

1. An adenovirus bearing deletions of the E1a an E3 regions and comprising a single packaging signal sequence and an E1a enhancer sequence, wherein said packaging signal sequence and said E1a enhancer sequence are at the 3' end of said adenovirus.

2. The adenovirus according to claim 1 further comprising, in the E1a-deleted region, at least one DNA endonuclease cleavage site.

3. The adenovirus according to claim 2 wherein said at least one cleavage site is unique to said adenovirus.

4. An adenovirus bearing deletions of the E1a and E3 regions and comprising, at the 3' end thereof, E1a enhancer and packaging signal sequences, wherein said adenovirus comprisers, in the E1a-delete region, at least one Pac1 cleavage site.

5. The adenovirus according to claim 2 wherein three cleavage sites are present in the E1a-deleted region.

6. An adenovirus bearing deletions of the E1a and E3 regions and comprising, at the 3' end thereof, E1a enhancer and packaging signal sequences, wherein said adenovirus comprisers, in the E1a-deleted region, Cla1, Xba1 and Pac1 cleavage sites.

7. The adenovirus according to claim 1 further comprising, in the E3-deleted region, a DNA endonuclease cleavage site.

8. The adenovirus according to claim 7 wherein said cleavage site is unique to said adenovirus.

9. An adenovirus bearing deletions of the E1a and E3 regions and comprising, at the 3' end thereof, E1a enhancer and packaging signal sequences, wherein said adenovirus comprisers, in the E1a-delete region, a BstB1 cleavage site.

10. The adenovirus according to claim 1 further comprising, in the E1a-deleted region, a non-adenoviral encoding sequence operably linked to a promoter.

11. The adenovirus according to claim 10 wherein the encoding sequence is a marker gene.

12. The adenovirus according to claim 11 wherein the marker gene is the nuclear localizing β-galactosidase (β-Gal) gene.

13. The adenovirus according to claim 10 wherein the encoding sequence encodes a NOS isoform.

14. The adenovirus according to claim 10 further comprising in said E1a-deleted region and 3' to said non-adenoviral encoding sequence, a sequence encoding a detectable molecule operably linked to a promoter.

15. The adenovirus according to claim 1 further comprising, in the E3-deleted region, a non-adenoviral encoding sequence operably linked to a promoter.

16. An adenovirus bearing deletions of the E1a and E3 regions and comprising, at the 3' end thereof, E1a enhancer and packaging signal sequences, wherein said adenovirus is Ad:Pac-βGal.

17. An adenovirus bearing deletions of the E1a and E3 regions and comprising, at the 3' end thereof, E1a enhancer and packaging signal sequences, wherein said adenovirus is Ad:Pac-βGal/gfp.

18. An adenovirus designated In340 E3D.

19. A plasmid designated pGEM Age I CMV new.

20. The plasmid according to claim 19 wherein said plasmid comprises, in operable linkage, a sequence encoding a selectable marker or other desired protein.

21. The plasmid according to claim 20 wherein said desired protein is a nitric oxide synthase (NOS) isoform.

22. A plasmid designated pGEM Cla CMV(+) Pac.

23. The plasmid according to claim 22 wherein said plasmid comprises, in operable linkage, a sequence encoding a selectable marker or other desired protein.

24. The plasmid according to claim 23 wherein said desired protein is a NOS isoform.

25. A replication deficient adenovirus comprising a recombination product of In340 E3D, Ad:Pac-βGal or Ad:Pac-βGal/gfp and plasmid pGEM Age I CMV new comprising, in operable linkage, a sequence encoding a selectable marker or other desired protein.

26. The adenovirus according to claim 25 wherein said desired protein is a NOS isoform.

27. A replication deficient adenovirus comprising a recombination or ligation product of In340 E3D, Ad:Pac-βGal or Ad:Pac-βGal/gfp and plasmid pGEM Cla CMV (+) Pac comprising, in operable linkage, a sequence encoding a selectable marker or other desired protein.

28. The adenovirus according to claim 27 wherein said desired protein is a NOS isoform.

29. A cell comprising the adenovirus according to claim 1.

30. A cell comprising the adenovirus according to claim 18.

31. A cell comprising the adenovirus according to claim 25.

32. A cell comprising the adenovirus according to claim 27.

33. A plasmid replicable and selectable in bacteria, devoid of adenoviral E1a enhancer and packaging signal sequences, comprising an adenoviral terminal repeat, a promoter/multiple cloning site (MCS)/poly A unit and an adenoviral recombination sequence, wherein said terminal repeat is 5' to said promoter/MCS/Poly A unit and said promoter/MCS/poly A unit is 5' to said recombination sequence, wherein said plasmid further comprises a restriction site unique to said plasmid that permits direct ligation of said plasmid with an adenovirus, wherein said unique restriction site is present in said plasmid 3' to said promoter/MCS/poly A unit and 5' to said recombination sequence.

34. The plasmid according to claim 33 wherein said unique restriction site is an Xba1, a Cla1, or a Pac1 site.

35. A plasmid replicable and selectable in bacteria, devoid of adenoviral E1a enhancer and packaging signal sequences, comprising an adenoviral terminal repeat, a promoter/multiple cloning site (MCS)/poly A unit and a restriction site unique to said plasmid that permits direct ligation of said plasmid with an adenovirus wherein said terminal repeat is 5' to said promoter/MCS/poly A unit and said promoter/MCS/poly A unit is 5' to said unique restriction site.

36. The plasmid according to claim 35 wherein said unique restriction site is a Xba1, a Cla1, or a Pac1 site.

* * * * *